US012618830B2

(12) United States Patent
Zernicka-Goetz et al.

(10) Patent No.: US 12,618,830 B2
(45) Date of Patent: May 5, 2026

(54) METHODS, CULTURE MEDIAS AND DEVICES FOR GENERATING EMBRYOS IN VITRO FROM STEM CELLS

(71) Applicants: California Institute of Technology, Pasadena, CA (US); Cambridge Enterprise Limited, Cambridge (GB)

(72) Inventors: Magdalena D. Zernicka-Goetz, Pasadena, CA (US); Gianluca Amadei, Cambridge (GB); Charlotte Handford, Cambridge (GB)

(73) Assignee: California Institute of Technology, Pasadena, CA (US)

( * ) Notice: Subject to any disclaimer, the term of this patent is extended or adjusted under 35 U.S.C. 154(b) by 559 days.

(21) Appl. No.: 18/065,480

(22) Filed: Dec. 13, 2022

(65) Prior Publication Data

US 2023/0236171 A1     Jul. 27, 2023

Related U.S. Application Data

(60) Provisional application No. 63/289,587, filed on Dec. 14, 2021.

(51) Int. Cl.
G01N 33/50          (2006.01)
C12N 5/073          (2010.01)
(Continued)

(52) U.S. Cl.
CPC ....... G01N 33/5088 (2013.01); C12N 5/0604 (2013.01); C12Q 1/6841 (2013.01); *C12N 2500/02* (2013.01); *C12N 2501/119* (2013.01); *C12N 2501/33* (2013.01); *C12N 2501/392* (2013.01); *C12N 2503/02* (2013.01); (Continued)

(58) Field of Classification Search
None
See application file for complete search history.

(56) References Cited

U.S. PATENT DOCUMENTS 5,322,770 A     6/1994   Gelfand
6,186,796 B1    2/2001   Wedge
(Continued)

FOREIGN PATENT DOCUMENTS

CN     109749987 A     5/2019
EP      0684315 A1    11/1995
(Continued)

OTHER PUBLICATIONS

Carpenedo, Richard L; et al; "Rotary Suspension Culture Enhances the Efficiency, Yield, and Homogeneity of Embryoid Body Differentiation" Stem Cells, 25,2224-2234, 2007 (Year: 2007).*
(Continued)

*Primary Examiner* — David W Berke-Schlessel
(74) *Attorney, Agent, or Firm* — Dickinson Wright PLLC

(57)          ABSTRACT

Disclosed herein include methods and compositions for culture medias for in vitro culture of synthetic embryos from mammalian pluripotent stem cells and extra-embryonic stem cells. The methods and compositions described herein can generate synthetic embryos at different developmental stage reaching early organogenesis and beyond. Disclosed herein also include an embryo culturing system and methods of using same.

27 Claims, 117 Drawing Sheets
(115 of 117 Drawing Sheet(s) Filed in Color)
Specification includes a Sequence Listing.

E0/ETiX0          E5.5/ETiX4          E6.5/ETiX5          E7.5/ETiX6          E8.0/ETiX7          E8.5/ETiX8

Static culture                                                                 Roller culture ⊚ ES–epiblast                              ○ AVE                          ⊛ Gut tube
○ TSC–trophectoderm–ExE–chorion           ● Primitive streak             ⊚ Allantois
○ tetO–GATA4 ESC–VE–yolk sac              ⊛ Neural folds–neural tube     ⊙ Heart

(51) Int. Cl.
*C12Q 1/6841* (2018.01)
*C12Q 1/6869* (2018.01)

(52) U.S. Cl.
CPC .... *C12N 2506/025* (2013.01); *C12N 2506/45*
(2013.01); *C12N 2513/00* (2013.01); *C12Q*
*1/6869* (2013.01); *C12Q 2600/158* (2013.01)

(56) References Cited

U.S. PATENT DOCUMENTS

| | | |
|---|---|---|
| 6,379,897 B1 | 4/2002 | Weidenhammer |
| 6,451,536 B1 | 9/2002 | Fodor |
| 6,548,257 B2 | 4/2003 | Lockhart |
| 6,618,679 B2 | 9/2003 | Loehrlein et al. |
| 6,664,377 B1 | 12/2003 | Xu |
| 7,084,246 B2 | 8/2006 | Coco |
| 8,247,531 B2 | 8/2012 | Cochran |
| 2003/0157485 A1 | 8/2003 | Bejanin |
| 2003/0215858 A1 | 11/2003 | Templeton |
| 2005/0112764 A1 | 5/2005 | Ivics et al. |
| 2018/0155789 A1 | 6/2018 | Maeder et al. |
| 2022/0308041 A1 | 9/2022 | Zernicka-Goetz |

FOREIGN PATENT DOCUMENTS

| | | | |
|---|---|---|---|
| KR | 10-2009-0050022 A | 5/2009 | |
| KR | 10-2010-0042649 A | 4/2010 | |
| WO | WO1993/022461 | 11/1993 | |
| WO | WO2010085699 | 7/2010 | |
| WO | WO2014174470 | 10/2014 | |
| WO | WO2016016894 | 2/2016 | |
| WO | WO-2018046929 A1 * | 3/2018 | ........... C12N 5/0604 |
| WO | WO2020069339 | 4/2020 | |
| WO | WO2020152686 | 7/2020 | |
| WO | WO2021067854 | 4/2021 | |
| WO | WO2021259909 | 12/2021 | |
| WO | WO2022195589 | 9/2022 | |
| WO | WO2023114754 | 6/2023 | |
| WO | WO2023170682 | 9/2023 | |

OTHER PUBLICATIONS

Abe, Koichiro, et al. "Endoderm-specific gene expression in embryonic stem cells differentiated to embryoid bodies." Experimental cell research 229.1 (1996): 27-34.

Aibar, Sara, et al. "SCENIC: single-cell regulatory network inference and clustering." Nature methods 14.11 (2017): 1083-1086.

Alsanie, Walaa F., et al. "Specification of murine ground state pluripotent stem cells to regional neuronal populations." Scientific Reports 7.1 (2017): 16001.

Altschuler, Steven J., and Lani F. Wu. "Cellular heterogeneity: do differences make a difference ?." Cell 141.4 (2010): 559-563.

Amack, Jeffrey D., and M. Lisa Manning. "Knowing the boundaries: extending the differential adhesion hypothesis in embryonic cell sorting." Science 338.6104 (2012): 212-215.

Anders, Simon, Paul Theodor Pyl, and Wolfgang Huber. "HTSeq—a Python framework to work with high-throughput sequencing data." bioinformatics 31.2 (2015): 166-169.

Arnold, Sebastian J., and Elizabeth J. Robertson. "Making a commitment: cell lineage allocation and axis patterning in the early mouse embryo." Nature reviews Molecular cell biology 10.2 (2009): 91-103.

Arslan, Feyza Nur, et al. "Holding it together: when cadherin meets cadherin." Biophysical Journal 120.19 (2021): 4182-4192.

Ashburner, Michael, et al. "Gene ontology: tool for the unification of biology." Nature genetics 25.1 (2000): 25-29.

Bao, Min, et al. "Stem cell-derived synthetic embryos self-assemble by exploiting cadherin codes and cortical tension." Nature Cell Biology 24.9 (2022): 1341-1349.

Bao, Zheng-Zheng, et al. "Regulation of chamber-specific gene expression in the developing heart by Irx4." Science 283.5405 (1999): 1161-1164.

Baran, Yael, et al. "MetaCell: analysis of single-cell RNA-seq data using K-nn graph partitions." Genome biology 20.1 (2019): 1-19.

Bardot, Evan S., and Anna-Katerina Hadjantonakis. "Mouse gastrulation: Coordination of tissue patterning, specification and diversification of cell fate." Mechanisms of development 163 (2020): 103617.

Bedzhov, Ivan, and Magdalena Zernicka-Goetz. "Self-organizing properties of mouse pluripotent cells initiate morphogenesis upon implantation." Cell 156.5 (2014): 1032-1044.

Bedzhov, Ivan, et al. "Developmental plasticity, cell fate specification and morphogenesis in the early mouse embryo." Philosophical Transactions of the Royal Society B: Biological Sciences 369.1657 (2014): 20130538.

Benchling "CRISPR Guide RNA Design Tool" available at: www.benchling.com/crispr last accessed on Oct. 26, 2023 Printed in 7 Pages.

Ben-Kiki, Oren, et al. "Metacell-2: a divide-and-conquer metacell algorithm for scalable scRNA-seq analysis." Genome biology 23.1 (2022): 1-18.

Bergmann, Sophie, et al. "Spatial profiling of early primate gastrulation in utero." Nature 609.7925 (2022): 136-143.

Biospherix, Oxystreamer, Cytocentric® O2 and CO2 Controller for Live Cell Microscopy, available at: https://biospherix.com/oxystreamer/ last accessed on Oct. 26, 2023 printed in 6 Pages.

Blakeley, Paul, et al. "Defining the three cell lineages of the human blastocyst by single-cell RNA-seq." Development 142.18 (2015): 3151-3165.

Blij, S., et al. "Cdx2 Efficiently Induces Trophoblast Stem-Like Cells in Naive, but Not Primed, Pluripotent Stem Cells." Stem Cells Dev 24.11 (2015): 1352-65.

Brassard, Jonathan A., and Matthias P. Lutolf. "Engineering stem cell self-organization to build better organoids." Cell stem cell 24.6 (2019): 860-876.

Bray, Nicolas L., et al. "Near-optimal probabilistic RNA-seq quantification." Nature biotechnology 34.5 (2016): 525-527.

Bredenkamp, Nicholas, et al. "Wnt inhibition facilitates RNA-mediated reprogramming of human somatic cells to naive pluripotency." Stem Cell Reports 13.6 (2019): 1083-1098.

Brodland, G. Wayne. "The differential interfacial tension hypothesis (DITH): a comprehensive theory for the self-rearrangement of embryonic cells and tissues." J. Biomech. Eng. 124.2 (2002): 188-197.

Cahan, Patrick, and George Q. Daley. "Origins and implications of pluripotent stem cell variability and heterogeneity." Nature reviews Molecular cell biology 14.6 (2013): 357-368.

Canty, Laura, et al. "Sorting at embryonic boundaries requires high heterotypic interfacial tension." Nature communications 8.1 (2017): 157.

Cao, Junyue, et al. "Comprehensive single-cell transcriptional profiling of a multicellular organism." Science 357.6352 (2017): 661-667.

Cao, Junyue, et al. "The single-cell transcriptional landscape of mammalian organogenesis." Nature 566.7745 (2019): 496-502.

Castillo-Venzor, Aracely, et al. "Origin and segregation of the human germline." Life Science Alliance 6.8 (2023).

Cerchiari, Alec E., et al. "A strategy for tissue self-organization that is robust to cellular heterogeneity and plasticity." Proceedings of the National Academy of Sciences 112.7 (2015): 2287-2292.

Chen, Di, et al. "Human primordial germ cells are specified from lineage-primed progenitors." Cell reports 29.13 (2019): 4568-4582.

Chen, Dong-Yuan, et al. "Extracellular matrix stiffness cues junctional remodeling for 3D tissue elongation." Nature communications 10.1 (2019): 3339.

Cheng, Saifeng, et al. "The intrinsic and extrinsic effects of TET proteins during gastrulation." Cell 185.17 (2022): 3169-3185.

Chhabra, Sapna, and Aryeh Warmflash. "BMP-treated human embryonic stem cells transcriptionally resemble amnion cells in the monkey embryo." Biology Open 10.9 (2021): bio058617.

Cindrova-Davies, Tereza, et al. "RNA-seq reveals conservation of function among the yolk sacs of human, mouse, and chicken." Proceedings of the National Academy of Sciences 114.24 (2017): E4753-E4761.

(56) References Cited

OTHER PUBLICATIONS

Clark, Amander T., et al. "Human embryo research, stem cell-derived embryo models and in vitro gametogenesis: Considerations leading to the revised ISSCR guidelines." Stem Cell Reports 16.6 (2021): 1416-1424.

Cockburn et al., "Making the blastocyst: lessons from the mouse," The Journal of Clinical Investigation 2010, 120(4), 995-1003.

Cross, James C., et al. "Trophoblast functions, angiogenesis and remodeling of the maternal vasculature in the placenta." Molecular and cellular endocrinology 187.1-2 (2002): 207-212.

Cullum Starr Ltd, "BTC Rotating Bottle Culture Unit" available at: http://www.cullumstarr.com/btc-engineering/rotating-bottle-culture-unit Printed in 2 Pages.

Deglincerti, Alessia, et al. "Self-organization of the in vitro attached human embryo." Nature 533.7602 (2016): 251-254.

Dobin, Alexander, et al. "Star: ultrafast universal RNA-seq aligner." Bioinformatics 29.1 (2013): 15-21.

Dobreva, Mariya P., et al. "Periostin as a biomarker of the amniotic membrane." Stem Cells International 2012 (2012).

Dohn, Tracy E., et al. "Nr2f-dependent allocation of ventricular cardiomyocyte and pharyngeal muscle progenitors." PLoS Genetics 15.2 (2019): e1007962.

Dong, Chen, et al. "Derivation of trophoblast stem cells from naïve human pluripotent stem cells." elife 9 (2020): e52504.

Donnison, Martyn, et al. "Elf5 and Ets2 maintain the mouse extraembryonic ectoderm in a dosage dependent synergistic manner." Developmental biology 397.1 (2015): 77-88.

Efremova, Mirjana, et al. "CellPhoneDB: inferring cell—cell communication from combined expression of multi-subunit ligand-receptor complexes." Nature protocols 15.4 (2020): 1484-1506.

EMAP eMouse Atlas Project (http://www.emouseatlas.org). Human Genetics Unit, Medical Research Council, available at: "http://web.archive.org/web/20211129211233/http://www.emouseatlas.org/emap/ema/theiler_stages/StageDefinition/ts17definition.html" last accessed on Sep. 26, 2023 in 6 Pages.

Fierro-González, Juan Carlos, et al. "Cadherin-dependent filopodia control preimplantation embryo compaction." Nature cell biology 15.12 (2013): 1424-1433.

Foty, Ramsey A., and Malcolm S. Steinberg. "The differential adhesion hypothesis: a direct evaluation." Developmental biology 278.1 (2005): 255-263.

Fu, Jianping, Aryeh Warmflash, and Matthias P. Lutolf. "Stem-cell-based embryo models for fundamental research and translation." Nature materials 20.2 (2021): 132-144.

Gao et al., "Establishment of porcine and human expanded potential stem cells," Nature Cell Biology 2019, 21(6), 687-699.

Gao, Zhiguang, et al. "Ets1 is required for proper migration and differentiation of the cardiac neural crest." Development 137.9 (2010): 1543-1551.

Genbank, "FGF10, partial [Homo sapiens]," National Library of Medicine 2023, in 2 Pages.

Genbank, "FGF21 [Homo sapiens]," National Library of Medicine 2023, in 2 Pages.

Genbank, "fibroblast growth factor 2 isoform 34 kDa [Homo sapiens]," National Library of Medicine 2023, in 4 Pages.

Genbank, "fibroblast growth factor 8 isoform b [Homo sapiens]," National Library of Medicine 2023, in 2 Pages.

Genbank, "Keratinocyte growth factor [Homo sapiens]," National Library of Medicine 2023, in 1 Page.

Gene Ontology Consortium. "The Gene Ontology resource: enriching a GOld mine." Nucleic acids research vol. 49,D1 (2021): D325-D334.

Geneassembly, "Genome assembly GRCh38" Available at https://www.ncbi.nlm.nih.gov/datasets/genome/GCF_000001405.26/ last accessed on Sep. 27, 2023 in 5 Pages.

Geneassembly, "Genome assembly GRCm38" Available at https://www.ncbi.nlm.nih.gov/datasets/genome/GCF_000001635.20/ last accessed on Sep. 27, 2023 in 4 Pages.

Genebank, GDF11 "growth/differentiation factor-11, partial [Homo sapiens]" Available at: https://www.ncbi.nlm.nih.gov/protein/AAF21630, last accessed on Sep. 27, 2023 in 2 Pages.

Genebank, GDF8 "growth differentiation factor 8 [Homo sapiens]." Available at: https://www.ncbi.nlm.nih.gov/protein/EAX10880 last accessed on Sep. 27, 2023 in 2 Pages.

Germain, Pierre-Luc, et al. "Doublet identification in single-cell sequencing data using scDblFinder." F1000Research 10 (2021).

Gerri, Claudia, et al. "Initiation of a conserved trophectoderm program in human, cow and mouse embryos." Nature 587.7834 (2020): 443-447.

Github, "Human Model" available at https://github.com/bweatherbee/human_model/tree/main last accessed on Sep. 27, 2023 in 2 Pages.

Github, "EiTiX-embryoids" available at https://github.com/hernanRubinstein/EiTiX-embryoids last accessed on Oct. 27, 2023 in 3 Pages.

Gossen, Manfred, et al. "Transcriptional activation by tetracyclines in mammalian cells." Science 268.5218 (1995): 1766-1769.

Graf, Thomas, and Matthias Stadtfeld. "Heterogeneity of embryonic and adult stem cells." Cell stem cell 3.5 (2008): 480-483.

Graner, François, and James A. Glazier. "Simulation of biological cell sorting using a two-dimensional extended Potts model." Physical review letters 69.13 (1992): 2013.

Guo, Ge, et al. "Human naive epiblast cells possess unrestricted lineage potential." Cell stem cell 28.6 (2021): 1040-1056.

Halbleib, Jennifer M., and W. James Nelson. "Cadherins in development: cell adhesion, sorting, and tissue morphogenesis." Genes & development 20.23 (2006): 3199-3214.

Harris, Tony JC, and Ulrich Tepass. "Adherens junctions: from molecules to morphogenesis." Nature reviews Molecular cell biology 11.7 (2010): 502-514.

Harrison et al., "In vitro generation of mouse polarized embryo-like structures from embryonic and trophoblast stem cells," Nature Protocols 2018, 13(7), 1586-1602.

Heemskerk, Idse, and Sebastian J. Streichan. "Tissue cartography: compressing bio-image data by dimensional reduction." Nature methods 12.12 (2015): 1139-1142.

Hendrickson et al., "Conserved roles of mouse DUX and human DUX4 in activating cleavage-stage genes and MERVL/HERVL retrotransposons," Nature Genetics 2017, 49(6), 925-934.

Hollnagel, Angela, et al. "Id genes are direct targets of bone morphogenetic protein induction in embryonic stem cells." Journal of Biological Chemistry 274.28 (1999): 19838-19845.

Holz, Andreas, et al. "The transcription factors Nkx2. 2 and Nkx2. 9 play a novel role in floor plate development and commissural axon guidance." Development 137.24 (2010): 4249-4260.

Hu, Dong, and James C. Cross. "Development and function of trophoblast giant cells in the rodent placenta." International Journal of Developmental Biology 54.2-3 (2009): 341-354.

Hu, Ze-Lan, et al. "The role of the transcription factor Rbpj in the development of dorsal root ganglia." Neural Development 6 (2011): 1-14.

Huang, Da Wei, Brad T. Sherman, and Richard A. Lempicki. "Systematic and integrative analysis of large gene lists using David bioinformatics resources." Nature protocols 4.1 (2009): 44-57.

Io, Shingo, et al. "Capturing human trophoblast development with naive pluripotent stem cells in vitro." Cell stem cell 28.6 (2021): 1023-1039.

Jo, Kyoung, et al. "Efficient differentiation of human primordial germ cells through geometric control reveals a key role for Nodal signaling." Elife 11 (2022): e72811.

José-Edwards, Diana S., et al. "Brachyury, Foxa2 and the cis-Regulatory Origins of the Notochord." PLoS genetics 11.12 (2015): e1005730.

Kagawa, Harunobu, et al. "Human blastoids model blastocyst development and implantation." Nature 601.7894 (2022): 600-605.

Kahane, Nitza, and Chaya Kalcheim. "Neural tube development depends on notochord-derived sonic hedgehog released into the sclerotome." Development 147.10 (2020): dev183996.

Kaufman, M. H., H. H. Chang, and J. P. Shaw. "Craniofacial abnormalities in homozygous Small eye (Sey/Sey) embryos and newborn mice." Journal of anatomy 186.Pt 3 (1995): 607.

(56) References Cited

OTHER PUBLICATIONS

Keller, Patricia J., et al. "Mapping the cellular and molecular heterogeneity of normal and malignant breast tissues and cultured cell lines." Breast cancer research 12 (2010): 1-17.

Kemp et al., "Expression of all Wnt genes and their secreted antagonists during mouse blastocyst and postimplantation development," Developmental Dynamics 2005, 233(3), 1064-1075.

Keren-Shaul, Hadas, et al. "MARS-seq2. 0: an experimental and analytical pipeline for indexed sorting combined with single-cell RNA sequencing." Nature protocols 14.6 (2019): 1841-1862.

Kime et al., "Induced 2C expression and implantation-competent blastocyst-like cysts from primed pluripotent stem cells," Stem Cell Reports 2019, 13(3), 485-498.

Kiselev, Vladimir Yu, Andrew Yiu, and Martin Hemberg. "scmap: projection of single-cell RNA-seq data across data sets." Nature methods 15.5 (2018): 359-362.

Koot, Y. E. M., et al. "Molecular aspects of implantation failure." Biochimica et Biophysica Acta (BBA)-Molecular Basis of Disease 1822.12 (2012): 1943-1950.

Kovács, Mihaly, et al. "Mechanism of blebbistatin inhibition of myosin II." Journal of Biological Chemistry 279.34 (2004): 35557-35563.

Krendl, Christian, et al. "GATA2/3-TFAP2A/C transcription factor network couples human pluripotent stem cell differentiation to trophectoderm with repression of pluripotency." Proceedings of the National Academy of Sciences 114.45 (2017): E9579-E9588.

Krieg, Michael, et al. "Tensile forces govern germ-layer organization in zebrafish." Nature cell biology 10.4 (2008): 429-436.

Kwon, Gloria S et al. "The endoderm of the mouse embryo arises by dynamic widespread intercalation of embryonic and extraembryonic lineages." Developmental cell vol. 15,4 (2008): 509-20.

La Manno, Gioele, et al. "Molecular architecture of the developing mouse brain." Nature 596.7870 (2021): 92-96.

La Manno, Gioele, et al. "RNA velocity of single cells." Nature 560.7719 (2018): 494-498.

Latos, Paulina Anna, and Myriam Hemberger. "From the stem of the placental tree: trophoblast stem cells and their progeny." Development 143.20 (2016): 3650-3660.

Lau, Kasey YC, et al. "Mouse embryo model derived exclusively from embryonic stem cells undergoes neurulation and heart development." Cell Stem Cell 29.10 (2022): 1445-1458.

Li et al., "Generation of blastocyst-like structures from mouse embryonic and adult cell cultures," Cell 2019, 179(3), 687-702.

Li, Chen, et al. "Multi-omic single-cell velocity models epigenome-transcriptome interactions and improves cell fate prediction." Nature Biotechnology 41.3 (2023): 387-398.

Linneberg-Agerholm, Madeleine, et al. "Naïve human pluripotent stem cells respond to Wnt, Nodal and LIF signalling to produce expandable naïve extra-embryonic endoderm." Development 146. 24 (2019): dev180620.

Liu, Xiaodong, et al. "Modelling human blastocysts by reprogramming fibroblasts into iBlastoids." Nature 591.7851 (2021): 627-632.

Luckett, W. Patrick. "Origin and differentiation of the yolk sac and extraembryonic mesoderm in presomite human and rhesus monkey embryos." American Journal of Anatomy 152.1 (1978): 59-97.

Ma, Huaixiao, et al. "In vitro culture of cynomolgus monkey embryos beyond early gastrulation." Science 366.6467 (2019): eaax7890.

Mackinlay, Kirsty ML, et al. "An in vitro stem cell model of human epiblast and yolk sac interaction." Elife 10 (2021): e63930.

Macklon, Nick S., Joep PM Geraedts, and Ban CJM Fauser. "Conception to ongoing pregnancy: the 'black box' of early pregnancy loss." Human reproduction update 8.4 (2002): 333-343.

Maître, Jean-Léon, et al. "Adhesion functions in cell sorting by mechanically coupling the cortices of adhering cells." science 338.6104 (2012): 253-256.

Manderfield, Lauren J., et al. "Pax3 and hippo signaling coordinate melanocyte gene expression in neural crest." Cell reports 9.5 (2014): 1885-1895.

Martin, Beth K., et al. "An optimized protocol for single cell transcriptional profiling by combinatorial indexing." arXiv preprint arXiv:2110.15400 (2021).

Martyn, Iain, et al. "Self-organization of a human organizer by combined Wnt and Nodal signalling." Nature 558.7708 (2018): 132-135.

Massey et al., "Synergy with TGFβ ligands switches WNT pathway dynamics from transient to sustained during human pluripotent cell differentiation," Proceedings of the National Academy of Sciences 2019, 116(11), 4989-4998.

Melsted, Páll, et al. "Modular, efficient and constant-memory single-cell RNA-seq preprocessing." Nature biotechnology 39.7 (2021): 813-818.

Mi, Huaiyu, et al. "Panther version 14: more genomes, a new Panther GO-slim and improvements in enrichment analysis tools." Nucleic acids research 47.D1 (2019): D419-D426.

Mischler et al., "Two distinct trophectoderm lineage stem cells from human pluripotent stem cells," bioRxiv 2019, in 38 Pages.

Mittnenzweig, Markus, et al. "A single-embryo, single-cell time-resolved model for mouse gastrulation." Cell 184.11 (2021): 2825-2842.

Molè, Matteo A., Antonia Weberling, and Magdalena Zernicka-Goetz. "Comparative analysis of human and mouse development: From zygote to pre-gastrulation." Current topics in developmental biology 136 (2020): 113-138.

Molè, Matteo A., et al. "A single cell characterisation of human embryogenesis identifies pluripotency transitions and putative anterior hypoblast centre." Nature communications 12.1 (2021): 3679.

Molè, Matteo Amitaba, et al. "Integrin β1 coordinates survival and morphogenesis of the embryonic lineage upon implantation and pluripotency transition." Cell Reports 34.10 (2021).

Moris, Naomi, et al. "An in vitro model of early anteroposterior organization during human development." Nature 582.7812 (2020): 410-415.

Morris, Samantha A., et al. "Dynamics of anterior-posterior axis formation in the developing mouse embryo." Nature communications 3.1 (2012): 673.

Munger, Clara, et al. "Microgel culture and spatial identity mapping elucidate the signalling requirements for primate epiblast and amnion formation." Development 149.20 (2022): dev200263.

Muzumdar, Mandar Deepak, et al. "A global double-fluorescent Cre reporter mouse." genesis 45.9 (2007): 593-605.

Naiche, L. A., and Virginia E. Papaioannou. "Loss of Tbx4 blocks hindlimb development and affects vascularization and fusion of the allantois." (2003): 2681-2693.

Nakamura, Tomonori, et al. "A developmental coordinate of pluripotency among mice, monkeys and humans." Nature 537.7618 (2016): 57-62.

Nastri et al., "Low versus atmospheric oxygen tension for embryo culture in assisted reproduction: a systematic review and meta-analysis," Fertility and Sterility 2016, 106(1), 95-104.

National Library of Medicine Gene ID: 1001, "CDH3 cadherin 3 [ *Homo sapiens* (human) ]." Available at: www.ncbi.nlm.nih.gov/gene/?term=1001 accessed on Sep. 19, 2023 in 8 Pages.

National Library of Medicine Gene ID: 1004, "CDH6 cadherin 6 [ *Homo sapiens* (human) ]." Available at: www.ncbi.nlm.nih.gov/gene/?term=1004 accessed on Sep. 19, 2023 in 6 Pages.

National Library of Medicine Gene ID: 999, "CDH1 cadherin 1 [ *Homo sapiens* (human) ]." Available at: www.ncbi.nlm.nih.gov/gene/?term=999 accessed on Sep. 19, 2023 in 12 Pages.

Nishikawa, Makiya, and Leaf Huang. "Nonviral vectors in the new millennium: delivery barriers in gene transfer." Human gene therapy 12.8 (2001): 861-870.

Niwa, Hitoshi, and Lusubilo Mwalilino. "Ensemble of old and new techniques escorts ESCs to bona fide embryo-like structures." Cell Stem Cell 29.10 (2022): 1423-1425.

Niwa, Hitoshi, et al. "Interaction between Oct3/4 and Cdx2 determines trophectoderm differentiation." Cell 123.5 (2005): 917-929.

Niwayama, Ritsuya, et al. "A tug-of-war between cell shape and polarity controls division orientation to ensure robust patterning in the mouse blastocyst." Developmental cell 51.5 (2019): 564-574.

(56) References Cited

OTHER PUBLICATIONS

Nose, Akinao, Akira Nagafuchi, and Masatoshi Takeichi. "Expressed recombinant cadherins mediate cell sorting in model systems." Cell 54.7 (1988): 993-1001.
Okae, Hiroaki, et al. "Derivation of human trophoblast stem cells." Cell stem cell 22.1 (2018): 50-63.
O'rahilly R, Müller F. Developmental stages in human embryos: revised and new measurements. Cells Tissues Organs. 2010;192(2):73-84.
Palsson, Eirikur. "A 3-D model used to explore how cell adhesion and stiffness affect cell sorting and movement in multicellular systems." Journal of Theoretical Biology 254.1 (2008): 1-13.
Papaioannou, Virginia E., John Mkandawire, and John D. Biggers. "Development and phenotypic variability of genetically identical half mouse embryos." Development 106.4 (1989): 817-827.
Pera, "Human embryo research and the 14-day rule," Development 2017, 144(11), 1923-1925.
Petridou, Nicoletta I., et al. "Rigidity percolation uncovers a structural basis for embryonic tissue phase transitions." Cell 184.7 (2021): 1914-1928.
Petropoulos, Sophie, et al. "Single-cell RNA-seq reveals lineage and X chromosome dynamics in human preimplantation embryos." Cell 165.4 (2016): 1012-1026.
Pham, Thi Xuan Ai, et al. "Modeling human extraembryonic mesoderm cells using naive pluripotent stem cells." Cell stem cell 29.9 (2022): 1346-1365.
Pieters, Tim, and Roy, Frans Van. "Role of cell-cell adhesion complexes in embryonic stem cell biology." Journal of cell science 127.12 (2014): 2603-2613.
Priya, Rashmi, et al. "Tension heterogeneity directs form and fate to pattern the myocardial wall." Nature 588.7836 (2020): 130-134.
Qiu, Chengxiang, et al. "Systematic reconstruction of cellular trajectories across mouse embryogenesis." Nature genetics 54.3 (2022): 328-341.
Renaud, Gabriel, et al. "deML: robust demultiplexing of Illumina sequences using a likelihood-based approach." Bioinformatics 31.5 (2015): 770-772.
Richter et al., "Quantitative grading of a human blastocyst: optimal inner cell mass size and shape," Fertility and Sterility 2001, 76(6), 1157-1167.
Rinkenberger, Julie, and Zena Werb. "The labyrinthine placenta." Nature genetics 25.3 (2000): 248-250.
Rivron et al., "Blastocyst-like structures generated solely from stem cells," Nature 2018, 557(7703), 106-111.
Ross, Connor, and Thorsten E. Boroviak. "Origin and function of the yolk sac in primate embryogenesis." Nature communications 11.1 (2020): 3760.
Rossant & Tam, "Blastocyst lineage formation, early embryonic asymmetries and axis patterning in the mouse," Development 2009, 136(5), 701-713.
Rossant, Janet, and Patrick PL Tam. "Early human embryonic development: blastocyst formation to gastrulation." Developmental cell 57.2 (2022): 152-165.
Rossi, Giuliana, et al. "Capturing cardiogenesis in gastruloids." Cell stem cell 28.2 (2021): 230-240.
Rostovskaya, Maria et al. "Capacitation of human naïve pluripotent stem cells for multi-lineage differentiation." Development (Cambridge, England) vol. 146,7 dev172916. Apr. 3, 2019.
Ruane, Peter T., et al. "Trophectoderm differentiation to invasive syncytiotrophoblast is promoted by endometrial epithelial cells during human embryo implantation." Human Reproduction 37.4 (2022): 777-792.
Salbreux, Guillaume, Guillaume Charras, and Ewa Paluch. "Actin cortex mechanics and cellular morphogenesis." Trends in cell biology 22.10 (2012): 536-545.
Sansom, Stephen N., et al. "The level of the transcription factor Pax6 is essential for controlling the balance between neural stem cell self-renewal and neurogenesis." PLoS genetics 5.6 (2009): e1000511.

Sasaki, Kotaro, et al. "The germ cell fate of cynomolgus monkeys is specified in the nascent amnion." Developmental cell 39.2 (2016): 169-185.
Scheibner, Katharina, et al. "Epithelial cell plasticity drives endoderm formation during gastrulation." Nature cell biology 23.7 (2021): 692-703.
Schep, Alicia N et al. "chromVAR: inferring transcription-factor-associated accessibility from single-cell epigenomic data." Nature methods vol. 14,10 (2017): 975-978.
Schliwa, Manfred. "Action of cytochalasin D on cytoskeletal networks." The Journal of cell biology 92.1 (1982): 79-91.
Scotti, Martina, and Marie Kmita. "Recruitment of 5' Hoxa genes in the allantois is essential for proper extra-embryonic function in placental mammals." Development 139.4 (2012): 731-739.
Séguin, Cheryle A., et al. "Establishment of endoderm progenitors by SOX transcription factor expression in human embryonic stem cells." Cell stem cell 3.2 (2008): 182-195.
Shahbazi, Marta N., Eric D. Siggia, and Magdalena Zernicka-Goetz. "Self-organization of stem cells into embryos: a window on early mammalian development." Science 364.6444 (2019): 948-951.
Shahbazi, Marta N., et al. "Pluripotent state transitions coordinate morphogenesis in mouse and human embryos." Nature 552.7684 (2017): 239-243.
Shahbazi, Marta N., et al. "Self-organization of the human embryo in the absence of maternal tissues." Nature cell biology 18.6 (2016): 700-708.
Sherman, Brad T., et al. "David: a web server for functional enrichment analysis and functional annotation of gene lists (2021 update)." Nucleic acids research 50.W1 (2022): W216-W221.
Simmons, David G., and James C. Cross. "Determinants of trophoblast lineage and cell subtype specification in the mouse placenta." Developmental biology 284.1 (2005): 12-24.
Simunovic, Mijo, et al. "A 3D model of a human epiblast reveals BMP4-driven symmetry breaking." Nature cell biology 21.7 (2019): 900-910.
Simunovic, Mijo, et al. "In vitro attachment and symmetry breaking of a human embryo model assembled from primed embryonic stem cells." Cell stem cell 29.6 (2022): 962-972.
Sozen et al., "Self-organization of mouse stem cells into an extended potential blastoid," Developmental Cell 2019, 51(6), 698-712.
Sozen, Berna, et al. "Reconstructing aspects of human embryogenesis with pluripotent stem cells." Nature communications 12.1 (2021): 5550.
Sozen, Berna, et al. "Reconstructing human early embryogenesis in vitro with pluripotent stem cells." Biorxiv (2021): 2021-03.
Steinberg, Malcolm S. "Does differential adhesion govern self-assembly processes in histogenesis? Equilibrium configurations and the emergence of a hierarchy among populations of embryonic cells." Journal of Experimental Zoology 173.4 (1970): 395-433.
Steinberg, Malcolm S. "Reconstruction of tissues by dissociated cells: some morphogenetic tissue movements and the sorting out of embryonic cells may have a common explanation." Science 141. 3579 (1963): 401-408.
Stower, Matthew J., and Shankar Srinivas. "The head's tale: anterior-posterior axis formation in the mouse embryo." Current topics in developmental biology 128 (2018): 365-390.
Stuart, Tim, et al. "Single-cell chromatin state analysis with Signac." Nature methods 18.11 (2021): 1333-1341.
Takei, Yodai, et al. "Integrated spatial genomics reveals global architecture of single nuclei." Nature 590.7845 (2021): 344-350.
Tarazi, Shadi, et al. "Post-gastrulation synthetic embryos generated ex utero from mouse naive ESCs." Cell 185.18 (2022): 3290-3306.
Tarkowski, "Experiments on the development of isolated blastomeres of mouse eggs," Nature 1959, 184, 1286-1287.
Ten Berge, Derk, et al. "Wnt signaling mediates self-organization and axis formation in embryoid bodies." Cell stem cell 3.5 (2008): 508-518.
Tepass, Ulrich, et al. "Cadherins in embryonic and neural morphogenesis." Nature reviews Molecular cell biology 1.2 (2000): 91-100.
Thomas, Paul, and Beddington, Rosa. "Anterior primitive endoderm may be responsible for patterning the anterior neural plate in the mouse embryo." Current Biology 6.11 (1996): 1487-1496.

(56) References Cited

OTHER PUBLICATIONS

Toda, Satoshi, et al. "Programming self-organizing multicellular structures with synthetic cell-cell signaling." Science 361.6398 (2018): 156-162.

Townes, F. William, and Rafael A. Irizarry. "Quantile normalization of single-cell RNA-seq read counts without unique molecular identifiers." Genome biology 21.1 (2020): 1-17.

Tsai, Tony Y-C., et al. "An adhesion code ensures robust pattern formation during tissue morphogenesis." Science 370.6512 (2020): 113-116.

Tyser, Richard CV, et al. "Characterization of a common progenitor pool of the epicardium and myocardium." Science 371.6533 (2021): eabb2986.

Tyser, Richard CV, et al. "Single-cell transcriptomic characterization of a gastrulating human embryo." Nature 600.7888 (2021): 285-289.

UniProt "P12830 • CADH1_HUMAN" Available at: https://www. uniprot.org/uniprotkb/P12830 last accessed on Sep. 19, 2023 in 13 Pages.

UniProt "P22223 •CADH3_HUMAN" Available at: https://www. uniprot.org/uniprotkb/P22223 last accessed on Sep. 19, 2023 in 14 Pages.

UniProt "P55285 • CADH6_HUMAN" Available at: https://www. uniprot.org/uniprotkb/P55285 last accessed on Sep. 19, 2023 in 12 Pages.

Viotti, Manuel, Sonja Nowotschin, and Anna-Katerina Hadjantonakis. "SOX17 links gut endoderm morphogenesis and germ layer segregation." Nature cell biology 16.12 (2014): 1146-1156.

Viukov, Sergey, et al. "Human primed and naïve PSCs are both able to differentiate into trophoblast stem cells." Stem cell reports 17.11 (2022): 2484-2500.

Wamaitha, Sissy E., et al. "Gata6 potently initiates reprograming of pluripotent and differentiated cells to extraembryonic endoderm stem cells." Genes & development 29.12 (2015): 1239.

Wang, Xue, Xianjun Chen, and Yi Yang. "Spatiotemporal control of gene expression by a light-switchable transgene system." Nature methods 9.3 (2012): 266-269.

Wang, Xuepeng, and Qiang Wu. "The divergent pluripotent states in mouse and human cells." Genes 13.8 (2022): 1459.

Warmflash, Aryeh, et al. "A method to recapitulate early embryonic spatial patterning in human embryonic stem cells." Nature methods 11.8 (2014): 847-854.

Weatherbee, Bailey AT, et al. "Modeling human embryo development with embryonic and extra-embryonic stem cells." Developmental biology 474 (2021): 91-99.

Weatherbee, Bailey AT, et al. "Pluripotent stem cell-derived model of the post-implantation human embryo." Nature (Jun. 27, 2023): 1-10.

Weatherbee, Bailey AT, et al. "Transgene directed induction of a stem cell-derived human embryo model." bioRxiv (Jun. 15, 2023): 2023-06.

West, Rachel C., et al. "Dynamics of trophoblast differentiation in peri-implantation—stage human embryos." Proceedings of the National Academy of Sciences 116.45 (2019): 22635-22644.

Wickstroem, Sara A., and Carien M. Niessen. "Cell adhesion and mechanics as drivers of tissue organization and differentiation: local cues for large scale organization." Current opinion in cell biology 54 (2018): 89-97.

Xiang, Lifeng, et al. "A developmental landscape of 3D-cultured human pre-gastrulation embryos." Nature 577.7791 (2020): 537-542.

Yagi, Shinomi, and Nobuyoshi Shiojiri. "Identification of novel genetic markers for mouse yolk sac cells by using microarray analyses." Placenta 49 (2017): 68-71.

Yan, Liying, et al. "Single-cell RNA-Seq profiling of human preimplantation embryos and embryonic stem cells." Nature structural & molecular biology 20.9 (2013): 1131-1139.

Yanagida, Ayaka, et al. "Cell surface fluctuations regulate early embryonic lineage sorting." Cell 185.5 (2022): 777-793.

Yanagida, Ayaka, et al. "Naive stem cell blastocyst model captures human embryo lineage segregation." Cell stem cell 28.6 (2021): 1016-1022.

Yang et al., "Derivation of pluripotent stem cells with in vivo embryonic and extraembryonic potency," Cell 2017, 169(2), 243-257.

Yang et al., "Establishment of mouse expanded potential stem cells," Nature 2017, 550(7676), 393-397.

Yang, Ran, et al. "Amnion signals are essential for mesoderm formation in primates." Nature communications 12.1 (2021): 5126.

Young, Matthew D., et al. "Single-cell transcriptomes from human kidneys reveal the cellular identity of renal tumors." science 361. 6402 (2018): 594-599.

Yu, Leqian, et al. "Blastocyst-like structures generated from human pluripotent stem cells." Nature 591.7851 (2021): 620-626.

Zeevaert, Kira, et al. "Cell mechanics in embryoid bodies." Cells 9.10 (2020): 2270.

Zernicka-Goetz, M et al. "Following cell fate in the living mouse embryo." Development (Cambridge, England) vol. 124,6 (1997): 1133-7.

Zhang, Shaopeng, et al. "Implantation initiation of self-assembled embryo-like structures generated using three types of mouse blastocyst-derived stem cells." Nature communications 10.1 (2019): 496.

Zhang, Ying, et al. "Computer simulations of cell sorting due to differential adhesion." PloS one 6.10 (2011): e24999.

Zhao, Hui-Fen, et al. "A coumermycin/novobiocin-regulated gene expression system." Human gene therapy 14.17 (2003): 1619-1629.

Zheng, Yi, et al. "Controlled modelling of human epiblast and amnion development using stem cells." Nature 573.7774 (2019): 421-425.

Zheng, Yi, et al. "Single-cell analysis of embryoids reveals lineage diversification roadmaps of early human development." Cell Stem Cell 29.9 (2022): 1402-1419.

Zhou, Fan, et al. "Reconstituting the transcriptome and DNA methylome landscapes of human implantation." Nature 572.7771 (2019): 660-664.

Zhu et al., "Actomyosin polarisation through PLC-PKC triggers symmetry breaking of the mouse embryo," Nature Communications 2017, 8(1), in 16 Pages.

Zhu et al., "Mechanism of cell polarisation and first lineage segregation in the human embryo," bioRxiv 2020, in 26 Pages.

International Search Report and Written Opinion dated Apr. 17, 2023 in PCT Patent Application No. PCT/US2022/081424.

Harrison et al., "Assembly of embryonic and extraembryonic stem cells to mimic embryogenesis in vitro", Science 2017, 356(6334), in 23 pages.

Acampora et al., "OTD/OTX2 functional equivalence depends on 5' and 3' UTR-mediated control of Otx2 mRNA for nucleo-cytoplasmic export and epiblast-restricted translation," Development 2001, 128 (23), 4801-4813.

Addgene, "pSAM2_mCherry_Gata4," addgene.org 2023, in 4 pages. https://www.addgene.org/72690/.

Aguilera-Castrejon et al., "Ex utero mouse embryogenesis from pre-gastrulation to late organogenesis," Nature 2021, 593(7857), 119-124.

Amadei et al., "Embryo model completes gastrulation to neurulation and organogenesis," Nature 2022, 610(7930), 143-153.

Amadei et al., "Inducible stem-cell-derived embryos capture mouse morphogenetic events in vitro," Developmental Cell 2021, 56(3), 366-382.

Andrews, "FastQC: a quality control tool for high throughput sequence data," Github 2023, in 3 pages.

Ang et al., "Positive and negative signals from mesoderm regulate the expression of mouse Otx2 in ectoderm explants," Development 1994, 120(10), 2979-2989.

Beccari et al., "Multi-axial self-organization properties of mouse embryonic stem cells into gastruloids," Nature 2018, 562(7726), 272-276.

Bedzhov et al., "In vitro culture of mouse blastocysts beyond the implantation stages," Nature Protocols 2014, 9(12), 2732-2739.

Bergen et al., "Generalizing RNA velocity to transient cell states through dynamical modeling," Nature Biotechnology 2020, 38(12), 1408-1414.

(56) References Cited

OTHER PUBLICATIONS

Boulanger et al., "Patch-based nonlocal functional for denoising fluorescence microscopy image sequences," IEEE Transactions on Medical Imaging 2010, 29(2), 442-454.

Briggs et al., "The dynamics of gene expression in vertebrate embryogenesis at single-cell resolution," Science 2018, 360(6392), in 10 pages.

Briscoe et al., "Homeobox gene Nkx2. 2 and specification of neuronal identity by graded Sonic hedgehog signalling," Nature 1999, 398(6728), 622-627.

Burren et al., "Gene-environment interactions in the causation of neural tube defects: folate deficiency increases susceptibility conferred by loss of Pax3 function," Human Molecular Genetics 2008, 17(23), 3675-3685.

Compton, "Nucleic acid sequence-based amplification," Nature 1991, 350(6313), 91-92.

Copp et al., "Neural tube defects: recent advances, unsolved questions, and controversies," The Lancet Neurology 2013, 12(8), 799-810.

Copp et al., "The genetic basis of mammalian neurulation," Nature Reviews Genetics 2003, 4(10), 784-793.

Dicicco-Bloom et al., "The developmental neurobiology of autism spectrum disorder," Journal of Neuroscience 2006, 26(26), 6897-6906.

Egli et al., "Developmental reprogramming after chromosome transfer into mitotic mouse zygotes," Nature 2007, 447(7145), 679-685.

Ericson et al., "Pax6 controls progenitor cell identity and neuronal fate in response to graded Shh signaling," Cell 1997, 90(1), 169-180.

Girgin et al., "Bioengineered embryoids mimic post-implantation development in vitro," Nature Communications 2021, 12(1), in 15 pages.

Guatelli et al., "Isothermal, in vitro amplification of nucleic acids by a multienzyme reaction modeled after retroviral replication," Proceedings of the National Academy of Sciences 1990, 87(5), 1874-1878.

Hettige & Ernst, "FOXG1 dose in brain development," Frontiers in Pediatrics 2019, 7, in 12 pages.

Klein et al., "Droplet barcoding for single-cell transcriptomics applied to embryonic stem cells," Cell 2015, 161(5), 1187-1201.

Koch et al., "Antagonistic activities of Sox2 and brachyury control the fate choice of neuro-mesodermal progenitors," Developmental Cell 2017, 42(5), 514-526.

Korsunsky et al., "Fast, sensitive and accurate integration of single-cell data with Harmony," Nature Methods 2019, 16(12), 1289-1296.

Kwoh et al., "Transcription-based amplification system and detection of amplified human immunodeficiency virus type 1 with a bead-based sandwich hybridization format," Proceedings of the National Academy of Sciences 1989, 86(4), 1173-1177.

Lalit et al., "Lineage reprogramming of fibroblasts into proliferative induced cardiac progenitor cells by defined factors," Cell Stem Cell 2016, 18(3), 354-367.

Landegren et al., "A ligase-mediated gene detection technique," Science 1988, 241(4869), 1077-1080.

Lawson & Hage, "Clonal analysis of the origin of primordial germ cells in the mouse," Ciba Foundation Symposium 182-Germline Development: Germline Development: Ciba Foundation Symposium 182 2007, 84-91, Abstract Only.

Marshall et al., "Detection of HCV RNA by the asymmetric gap ligase chain reaction," Genome Research 1994, 4(2), 80-84.

Mesnard et al., "The anterior-posterior axis emerges respecting the morphology of the mouse embryo that changes and aligns with the uterus before gastrulation," Current Biology 2004, 14(3), 184-196.

Novitch et al., "Coordinate regulation of motor neuron subtype identity and pan-neuronal properties by the bHLH repressor Olig2," Neuron 2001, 31(5), 773-789.

Nowotschin et al., "The emergent landscape of the mouse gut endoderm at single-cell resolution," Nature 2019, 569(7756), 361-367.

Parekh et al., "zUMIs-A fast and flexible pipeline to process RNA sequencing data with UMIs," Gigascience 2018, in 9 pages.

Pevny et al., "A role for SOX1 in neural determination," Development 1998, 125(10), 1967-1978.

Pijuan-Sala et al., "A single-cell molecular map of mouse gastrulation and early organogenesis," Nature 2019, 566(7745), 490-495.

Pourquié, "3 Segmentation of the Paraxial Mesoderm and Vertebrate Somitogenesis," Current Topics in Developmental Biology 1999, 47, 81-105.

Rhee et al., "In vivo imaging and differential localization of lipid-modified GFP-variant fusions in embryonic stem cells and mice," Genesis 2006, 44(4), 202-218.

Ribes et al., "Distinct Sonic Hedgehog signaling dynamics specify floor plate and ventral neuronal progenitors in the vertebrate neural tube," Genes & Development 2010, 24(11), 1186-1200.

Saitou & Yamaji, "Primordial germ cells in mice," Cold Spring Harbor Perspectives in Biology 2012, 4(11), in 20 pages.

Saitou et al., "A molecular programme for the specification of germ cell fate in mice," Nature 2002, 418(6895), 293-300.

Sasaki & Hogan, "HNF-3β as a regulator of floor plate development," Cell 1994, 76(1), 103-115.

Schindelin et al., "Fiji: an open-source platform for biological-image analysis," Nature Methods 2012, 9(7), 676-682.

Serbedzija & Mcmahon, "Analysis of neural crest cell migration in Splotch mice using a neural crest-specific LacZ reporter," Developmental Biology 1997, 185(2), 139-147.

Southard-Smith et al., "Sox10 mutation disrupts neural crest development in Dom Hirschsprung mouse model," Nature Genetics 1998, 18(1), 60-64.

Sozen et al., "Self-assembly of embryonic and two extra-embryonic stem cell types into gastrulating embryo-like structures," Nature Cell Biology 2018, 20(8), 979-989.

Stuart et al., "Comprehensive integration of single-cell data," Cell 2019, 177(7), 1888-1902.

Tadeu & Valerie Horsley, "Notch signaling represses p63 expression in the developing surface ectoderm," Development 2013, 140(18), 3777-3786.

Tam & Snow, "Proliferation and migration of primordial germ cells during compensatory growth in mouse embryos," Journal of embryology and experimental morphology 1981, 64, 133-147.

Tanaka et al., "Circulation-independent differentiation pathway from extraembryonic mesoderm toward hematopoietic stem cells via hemogenic angioblasts," Cell Reports 2014, 8(1), 31-39.

Towbin et al., "Electrophoretic transfer of proteins from polyacrylamide gels to nitrocellulose sheets: procedure and some applications," Proceedings of the National Academy of Sciences 1979, 76(9), 4350-4354.

Turner et al., "Anteroposterior polarity and elongation in the absence of extra-embryonic tissues and of spatially localised signalling in gastruloids: mammalian embryonic organoids," Development 2017, 144(21), 3894-3906.

Tzouanacou et al., "Redefining the progression of lineage segregations during mammalian embryogenesis by clonal analysis," Developmental Cell 2009, 17(3), 365-376.

Van Den Brink et al., "Single-cell and spatial transcriptomics reveal somitogenesis in gastruloids," Nature 2020, 582(7812), 405-409.

Van Den Brink et al., "Symmetry breaking, germ layer specification and axial organisation in aggregates of mouse embryonic stem cells," Development 2014, 141(22), 4231-4242.

Veenvliet et al., "Mouse embryonic stem cells self-organize into trunk-like structures with neural tube and somites," Science 2020, 370(6522), in 8 pages.

Walker et al., "Strand displacement amplification (SDA) and transient-state fluorescence polarization detection of Mycobacterium tuberculosis DNA," Clinical Chemistry 1996, 42(1), 9-13.

Wang & Fenech, "A comparison of folic acid and 5-methyltetrahydrofolate for prevention of DNA damage and cell death in human lymphocytes in vitro," Mutagenesis 2003, 18(1), 81-86.

Wolf et al., "SCANPY: large-scale single-cell gene expression data analysis," Genome Biology 2018, 19 in 5 pages.

(56) References Cited

OTHER PUBLICATIONS

Wolock et al., "Scrublet: computational identification of cell doublets in single-cell transcriptomic data," Cell Systems 2019, 8(4), 281-291.

Wu & Wallace, "The ligation amplification reaction (LAR)—amplification of specific DNA sequences using sequential rounds of template-dependent ligation," Genomics 1989, 4(4), 560-569.

Xu et al., "Construction of a mammalian embryo model from stem cells organized by a morphogen signalling centre," Nature Communications 2021, 12(1), in 22 pages.

Zilionis et al., "Single-cell barcoding and sequencing using droplet microfluidics," Nature Protocols 2017, 12(1), 44-73.

Advisory Action dated Jul. 26, 2024 in U.S. Appl. No. 17/692,790.

Eiselleova, Livia, et al. "A complex role for FGF-2 in self-renewal, survival, and adhesion of human embryonic stem cells." Stem cells 27.8 (2009): 1847-1857.

Final office action dated Jun. 6, 2024 in U.S. Appl. No. 17/692,790.

Hui, Qi, et al. "FGF family: from drug development to clinical application." International journal of molecular sciences 19.7 (2018): 1875.

International Search Report and Written Opinion dated Dec. 26, 2023 in PCT Patent Application No. PCT/US2023/073377.

International Search Report and Written Opinion dated Mar. 7, 2024 in PCT Patent Application No. PCT/US2023/073364.

Irvine Scientific, "Irvine Scientific Introduces Continuous Single Culture-NX Low-lactate Culture Media for IVF" 2017 available at: https://fujifilmbiosciences.fujifilm.com/media/files/pr/10728ART_Press_release_CSCM-NX.pdf, 2 Pages.

Jinek, Martin, et al. "RNA-programmed genome editing in human cells." (2013).

Kosaka, Nobuyoshi, et al. "FGF-4 regulates neural progenitor cell proliferation and neuronal differentiation." The FASEB journal 20.9 (2006): 1484-1485.

Li, Qiuhui, et al. "Cancer stem cells and cell size: A causal link?." Seminars in cancer biology. vol. 35. Academic Press, 2015.

Millman, Jeffrey R., Jit Hin Tan, and Clark K. Colton. "The effects of low oxygen on self-renewal and differentiation of embryonic stem cells." Current opinion in organ transplantation 14.6 (2009): 694-700.

Non-final office action dated Jan. 31, 2025 in U.S. Appl. No. 17/692,790.

Non-final office action dated Jan. 4, 2024 in U.S. Appl. No. 17/692,790.

Notice of Allowance dated Jul. 16, 2025 in U.S. Appl. No. 17/692,790.

Schutte, Bert, et al. "Keratin 8/18 breakdown and reorganization during apoptosis." Experimental cell research 297.1 (2004): 11-26.

Select Science, "Continuous Single Culture-NX Complete by Irvine Scientific", 2020, available at: https://www.selectscience.net/product/continuous-single-culture-nx-complete#description, last accessed on Aug. 14, 2025, printed in 5 Pages.

Zachar, Vladimir, et al. "The effect of human embryonic stem cells (hESCs) long-term normoxic and hypoxic cultures on the maintenance of pluripotency." In Vitro Cellular & Developmental Biology-Animal 46.3 (2010): 276-283.

* cited by examiner

Natural embryos ETiX embryoids

- Early development
- Haematoendothelial progenitors
- Extraembryonic ectoderm
- Allantois
- Amniotic mesoderm
- Visceral endoderm
- Parietal endoderm
- Gut
- Surface ectoderm
- Neuroectoderm
- Neural crest
- Neuromesodermal progenitors
- Paraxial mesoderm
- Cardiac mesoderm
- Heart field
- Primitive erythroid cells
- Megakaryocytes
- White blood cells
- Endothelium

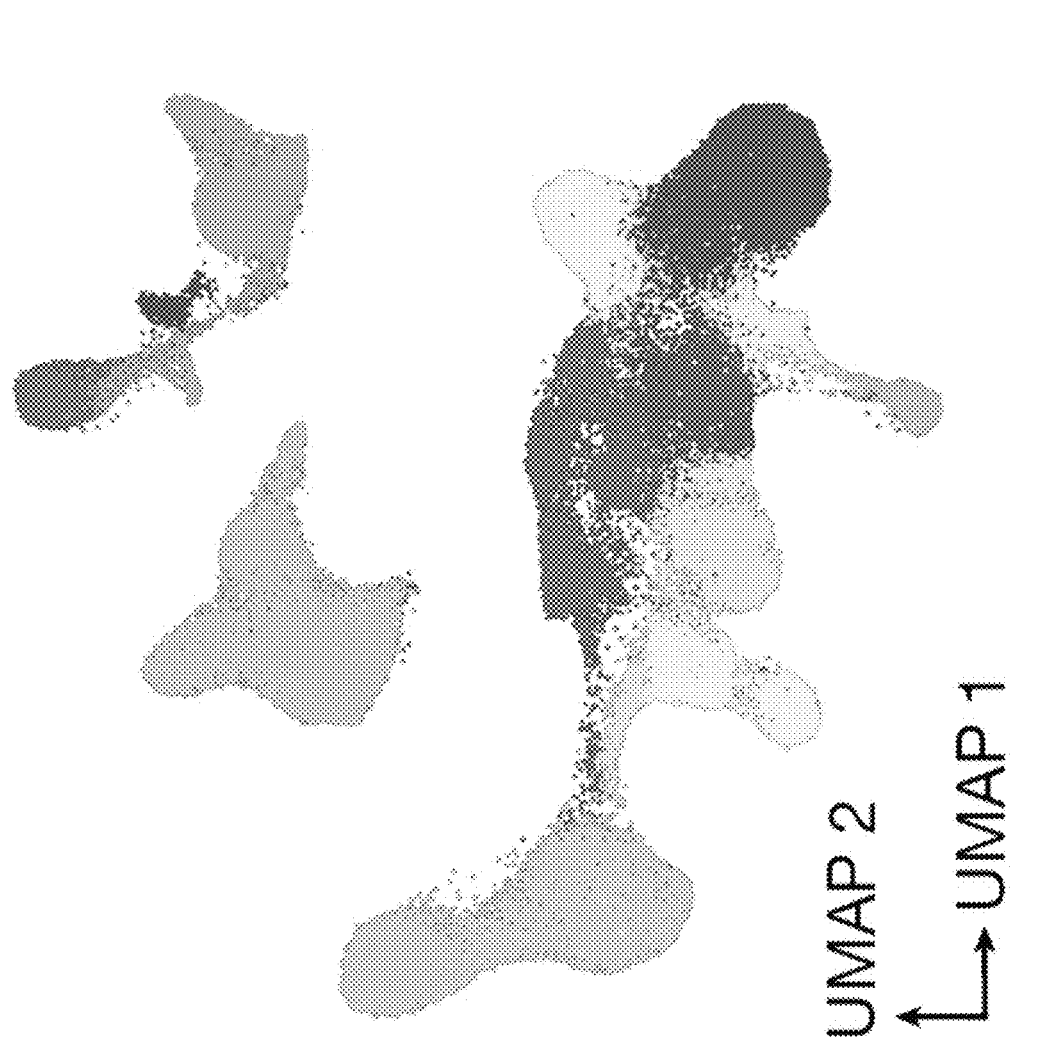

UMAP 2

UMAP 1

*FIG. 1F*

UMAP 2

↱ UMAP 1

▦ Roof plate
▦ Prosencephalon
▦ Mesencephalon and MHB
▦ Hindbrain and spinal cord
■ Floor plate
■ Early neurons ETiX embryoids          Natural embryos Day 6

E7.5

E8.0

Day 8

SIZE OF THE
SCALE BAR
NOT
PROVIDED

Natural embryos

*Tbx4*                          *Hoxa13*

ETiX embryoids

*Tbx4*                          *Hoxa13*

Differentiated yolk sac
Immature yolk sac
Early VE
Early VE 2
ETiX-only extraembryonic endoderm
Parietal endoderm

UMAP 2
UMAP 1

Chorio-allantoic
dissection and
sectioning of ETiX8

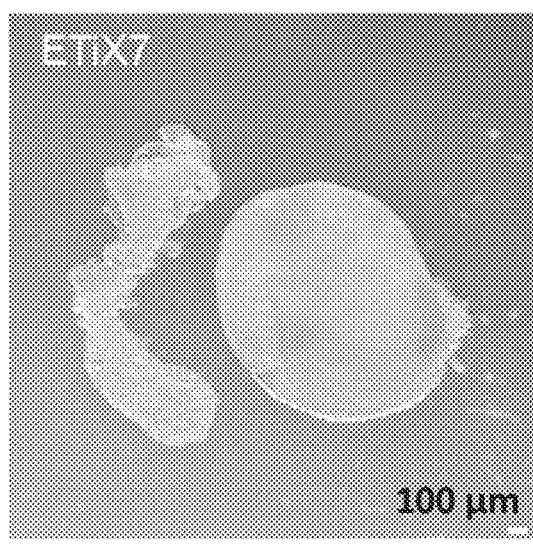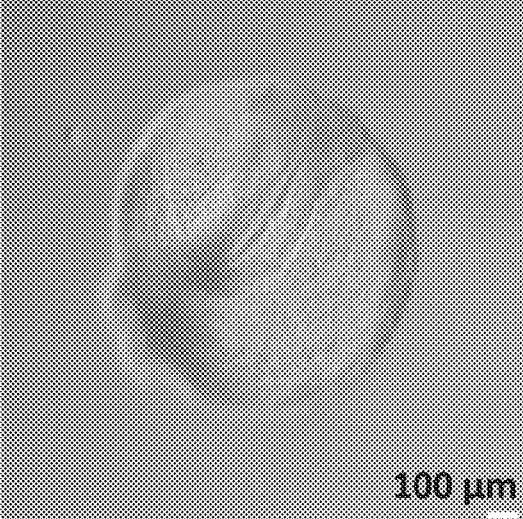

FIG. 7C

- Neuroectoderm
- Endothelium
- Epiblast
- Gut precursors
- Cardiac mesoderm
- Somites
- Surface ectoderm
- Cardiomyocytes
- Nascent mesoderm
- Allantois
- AVE
- PLPM
- Definitive endoderm
- Mesenchyme
- CLE/NMP
- ExE VE
- Notochord
- Erythroid progenitors
- Parietal endoderm
- ExE ectoderm
- Megakaryocytes
- VE
- Amnion
- Ectoplacental cone
- Junctional zone
- Primitive streak

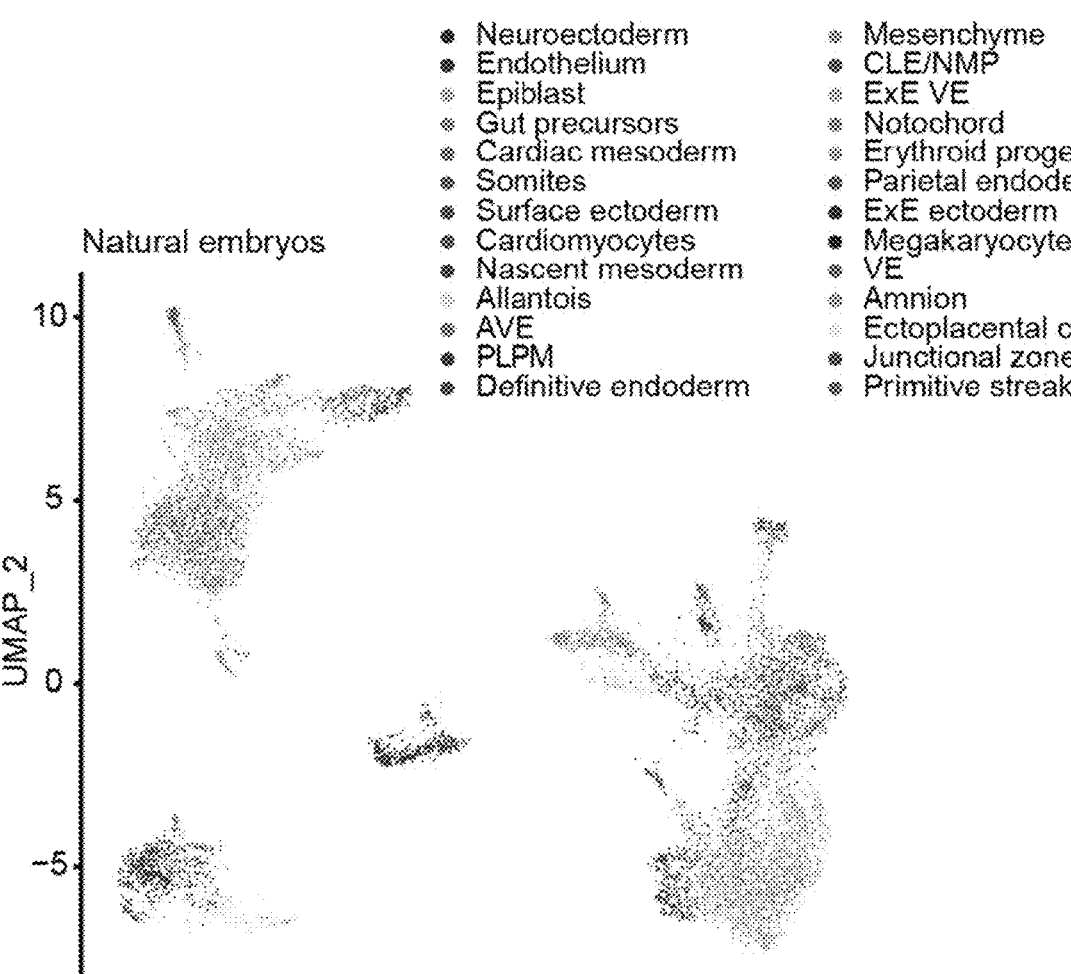

Natural embryos

FIG. 7D

ETiX-embryoids

Failed ETiX-embryoids

Natural Embryos

*FIG. 9I*

Mouse embryos (E6.5 ~ E8.5), Pijuan-Sala et al., 2019

ETiX-embryoids and natural embryos (this study)

Mouse embryos (E8.5), Qiu et al., 2022

Natural embryo

ETiX-embryoid

ETiX-embryoid

Natural embryo

Definitive endoderm

Epiblast

Gut precursors

Primitive streak

UMAP1

UMAP2

Cultured natural embryos

ETiX embryoids

Differentiated yolk sac
Immature yolk sac
Early VE
Early VE 2
ETiX-only extraembryonic endoderm
Parietal endoderm

UMAP 2
UMAP 1

1 Stella+ve
2 Stella/Sox2+ve
3 Stella/Nanog+ve
4 Stella/Nanog/
Sox2+ve
5 Total Stella+ve

SEQUENCE LISTING

```
Sequence total quantity: 9
SEQ ID NO: 1              moltype = DNA   length = 29
FEATURE                   Location/Qualifiers
source                    1..29
                          mol_type = other DNA
                          organism = synthetic construct
SEQUENCE: 1
ggggacaagt ttgtacaaaa aagcaggct                                      29

SEQ ID NO: 2              moltype = DNA   length = 29
FEATURE                   Location/Qualifiers
source                    1..29
                          mol_type = other DNA
                          organism = synthetic construct
SEQUENCE: 2
ggggaccact ttgtacaaga aagctgggt                                      29

SEQ ID NO: 3              moltype = RNA   length = 25
FEATURE                   Location/Qualifiers
source                    1..25
                          mol_type = other RNA
                          organism = synthetic construct
SEQUENCE: 3
caccgctccc cctccttcct gttgc                                          25

SEQ ID NO: 4              moltype = RNA   length = 25
FEATURE                   Location/Qualifiers
source                    1..25
                          mol_type = other RNA
                          organism = synthetic construct
SEQUENCE: 4
aaacgcaaca ggaaggaggg ggagc                                          25

SEQ ID NO: 5              moltype = RNA   length = 25
FEATURE                   Location/Qualifiers
source                    1..25
```

-continued

```
                     mol_type = other RNA
                     organism = synthetic construct
SEQUENCE: 5
caccgagatg cgacttcagc tgaag                                          25

SEQ ID NO: 6         moltype = RNA  length = 25
FEATURE              Location/Qualifiers
source               1..25
                     mol_type = other RNA
                     organism = synthetic construct
SEQUENCE: 6
aaaccttcag ctgaagtcgc atctc                                          25

SEQ ID NO: 7         moltype = DNA  length = 20
FEATURE              Location/Qualifiers
source               1..20
                     mol_type = other DNA
                     organism = synthetic construct
SEQUENCE: 7
aagagacctt gcgagagcac                                                20

SEQ ID NO: 8         moltype = DNA  length = 20
FEATURE              Location/Qualifiers
source               1..20
                     mol_type = other DNA
                     organism = synthetic construct
SEQUENCE: 8
gaactttccc accaggagca                                                20

SEQ ID NO: 9         moltype = DNA  length = 25
FEATURE              Location/Qualifiers
source               1..25
                     mol_type = other DNA
                     organism = synthetic construct
SEQUENCE: 9
tgcatatacg atacaaggct gttag                                          25
```

METHODS, CULTURE MEDIAS AND DEVICES FOR GENERATING EMBRYOS IN VITRO FROM STEM CELLS

RELATED APPLICATIONS

This application claims the benefit under 35 U.S.C. § 119(e) of U.S. Provisional Patent Application No. 63/289,587, filed Dec. 14, 2021, the content of this related application is incorporated herein by reference in its entirety for all purposes.

STATEMENT REGARDING FEDERALLY SPONSORED R&D

This invention was made with government support under Grant No. HD104575 awarded by the National Institutes of Health. The government has certain rights in the invention.

REFERENCE TO SEQUENCE LISTING

The present application is being filed along with a Sequence Listing in electronic format. The Sequence Listing is provided as a file entitled 30KJ-365851-WO_Sequence-_Listing, created Dec. 13, 2022, which is 9 kilobytes in size. The information in the electronic format of the Sequence Listing is incorporated herein by reference in its entirety.

BACKGROUND

Field

The present disclosure relates generally to the field of cell culture, in particular, culturing embryos and stem cells.

Description of the Related Art

In natural development, the zygote develops into the epiblast, which will form the organism; the extraembryonic visceral endoderm (VE), which contributes to the yolk sac; and the extraembryonic ectoderm (ExE), which contributes to the placenta. Stem cells corresponding to these three lineages offer the possibility to completely regenerate the mammalian organism from multiple components, instead of from a single totipotent zygote.

Embryonic stem (ES) cells, which are derived from the epiblast, show a remarkable ability to form embryo-like structures upon aggregation and, when embedded in Matrigel, can be induced to form trunk-like structures with somites, a neural tube and a gut. Although neural development can be promoted in such 'gastruloids' by inhibiting the initial burst of Wnt activity, they do not accurately replicate gastrulation movements, nor do they represent the complete anatomy of natural embryos. Other model embryoids generated from ES cells aggregated with an ectopic morphogen signaling center can develop the posterior midbrain, neural tube, cardiac tissue and gut tube only. Thus, these models do not recapitulate the entirety of development to neurulation.

There is a need for stem-cell-based embryonic models that can capture natural stages of mammalian development in vitro through and beyond gastrulation and neurulation.

SUMMARY

Disclosed herein includes a method of generating a synthetic embryo in vitro. The method, in some embodiments, comprises: (a) co-culturing a mammalian pluripotent stem cell and at least one extra-embryonic stem cell in a first culture media under a first static condition allowing the mammalian pluripotent stem cell and the extra-embryonic stem cell to self-assemble into a post-implantation embryo structure; (b) culturing the post-implantation embryo structure in a second culture media under a second static condition allowing the post-implantation embryo structure embryo structure to develop into a neurulating embryo structure; and (c) culturing the neurulating embryo structure for at least one day under a dynamic condition in a culture chamber allowing the neurulating embryo structure to develop into a synthetic embryo of at least early organogenesis stage.

The mammalian pluripotent stem cell can comprise a mammalian embryonic stem cell. In some embodiments, the at least one extra-embryonic stem cell comprises a trophoblast stem cell, an inducible extra-embryonic endoderm stem cell, or both. In some embodiments, the inducible extra-embryonic endoderm stem cell is capable of expressing a GATA transcription factor upon induction. The GATA transcription factor can be, for example, GATA4.

In some embodiments, the mammalian pluripotent stem cell and the extra-embryonic stem cell are cultured in the first culture media for up to 4 days.

In some embodiments, step (a) is from embryonic day E0-E5.5. In some embodiments, the post-implantation embryo structure is a post-implantation pre-gastrulation embryo structure. In some embodiments, the post-implantation pre-gastrulation embryo structure resembles an E5.5 natural embryo structure. In some embodiments, the mammalian pluripotent stem cell and the extra-embryonic stem cell are cultured in a substrate, for example a substrate comprising a dish, a U-plate, a flask or a microwell plate. In some embodiments, the mammalian pluripotent stem cell and the extra-embryonic stem cell are cultured in inverted pyramidal microwells. In some embodiments, each of the inverted-pyramidal microwells is about 400 μm or about 800 μm in size, optionally about 400 μm or about 800 μm diameter.

In some embodiments, step (a) comprises culturing the mammalian pluripotent stem cell and the extra-embryonic stem cell in a feeder cell (FC) media, optionally passaging the mammalian pluripotent stem cell and the extra-embryonic stem cell in the feeder cell media at least two times. In some embodiments, the mammalian pluripotent stem cell and the extra-embryonic stem cell are cultured in the FC media for about 2 days. In some embodiments, step (a) comprises culturing mammalian pluripotent stem cell and the extra-embryonic stem cell in an in vitro culture (IVC) media, optionally following culturing the mammalian pluripotent stem cell and the extra-embryonic stem cell in the FC media. In some embodiments, the mammalian pluripotent stem cell and the extra-embryonic stem cell are cultured in the IVC media for about 2 days. In some embodiments, the FC media and the VC media comprise a basal culture medium. The basal culture medium can, for example, comprise Dulbecco's Modified Eagle Media (DMEM), DMEM Nutrient Mixture 12 (DMEM/F12), a non-human serum or serum substitute thereof, a reducing agent, an antibiotic, L-glutamine or an analogue thereof, or any combination thereof.

In some embodiments, the non-human serum or serum substitute comprises fetal bovine serum, bovine serum albumin, KnockOut™ Serum Replacement, or any combination thereof. In some embodiments, the reducing agent comprises beta-mercaptoethanol (BME), N-acetyl-L-cysteine, dithiothreitol (DTT), or any combination thereof. In some embodiments, the antibiotic comprises Penicillin-streptomycin, Amphotericin B, Ampicillin, Erythromycin, Gentamycin, Kanamycin, Neomycin, Nystatin, Polymyxin B, Tetracycline, Thiabendazole, Tylosin, or any combination thereof. The FC media can comprise, for example, sodium pyruvate and/or one or more non-essential amino acids.

In some embodiments, the FC media comprises DMEM, fetal bovine serum, sodium pyruvate, GlutaMax, MEM non-essential amino acids, 2-mercaptoethanol, penicillin and/or streptomycin, or any combination thereof. In some embodiments, the FC media comprises DMEM, about 15% fetal bovine serum, about 1 mM sodium pyruvate, about 2 mM GlutaMax, about 1% MEM non-essential amino acids, about 0.1 mM 2-mercaptoethanol, about 1% penicillin and/or streptomycin, or any combination thereof. In some embodiments, the FC media further comprises an anticoagulant, optionally heparin, a fibroblast growth factor (FGF), optionally FGF2 and/or FGF4, or any combination thereof.

In some embodiments, the IVC media comprises: a) insulin, an insulin analogue, or an insulin receptor agonist; b) estrogen, an estrogen analogue, or an estrogen receptor agonist; and c) progesterone, a progesterone analogue, or a progesterone receptor agonist. The insulin receptor agonist can be selected from IGF-I, IGF-II, analogues thereof, and any combination thereof. The estrogen receptor agonist can be, for example, β-estradiol, estrone, estriol and estetrol, or any analogue thereof.

The IVC media can comprise transferrin, sodium selenium, ethanolamine, or any analogue thereof. In some embodiments, the IVC media does not comprise sodium pyruvate.

In some embodiments, the IVC media comprises DMEM/F12, fetal bovine serum, GlutaMax, ITS-X, β-estradiol, progesterone, N-acetyl-L-cysteine, penicillin and/or streptomycin, or any combination thereof. In some embodiments, the VC media comprises DMEM/F12, about 20% fetal bovine serum, about 2 mM GlutaMax, about 1×ITS-X, about 8 nM β-estradiol, about 200 ng/ml progesterone, about 25 μM N-acetyl-L-cysteine, about 1% penicillin and/or streptomycin, or any combination thereof.

In some embodiments, culturing the mammalian pluripotent stem cell and the extra-embryonic stem cell in the first culture media comprises increasing serum concentrations, optionally increasing the serum concentration from about 20% to about 30%. In some embodiments, step (a) comprises transferring the mammalian pluripotent stem cell and the extra-embryonic stem cell from one substrate to another substrate.

In some embodiments, the post-implantation embryo structure is cultured in the second culture media for up to 3 days. In some embodiments, step (b) is from embryonic day E5.5 to E8.0. In some embodiments, the neutralizing embryo structure resembles an E8.0 natural embryo structure. In some embodiments, the neutralizing embryo structure is cultured in a substrate, optionally, the substrate comprises a dish, a U-plate, a flask or a microwell plate. In some embodiments, the second culture media is a post-implantation culture media capable of supporting the development of embryo ex utero. In some embodiments, the second culture media comprises DMEM, non-human serum, human cord serum, L-glutamine or an analogue thereof, antibiotics, or any combination thereof. In some embodiments, the non-human serums comprises rat and/or bovine serum. In some embodiments, the second culture media comprises bicarbonate. In some embodiments, the second culture media comprises HEPES. In some embodiments, the non-human serum is rat serum. In some embodiments, the second culture media comprises DMEM, rat serum, human cord serum, GlutaMax, penicillin and/or streptomycin, HEPES, or any combination thereof. In some embodiments, the second culture media comprises about 25% DMEM, about 50% rat serum, and about 25% human cord serum.

In some embodiments, step (b) comprising supplying the second culture media with glucose, for example at least 3 mg/ml glucose. In some embodiments, the glucose is supplied for at least once, optionally the third day of the culturing. In some embodiments, step (b) comprises culturing the post-implantation embryo structure in a media comprising about 1 mg/ml glucose for two days and culturing the post-implantation embryo structure in a media comprising about 3 mg/ml glucose for one day.

In some embodiments, step (c) is from embryonic day E8.0 to at least E8.5. In some embodiments, the synthetic embryo resembles an E8.5 natural embryo structure. In some embodiments, the synthetic embryo resembles an E9.0 natural embryo structure. In some embodiments, the neutralizing embryo structure is cultured under the dynamic condition in the second culture media. In some embodiments, the second culture media in step (c) comprises at least 30% non-human serum.

In some embodiments, step (b) comprising supplying the second culture media with at least 3 mg/ml glucose, optionally at least 3.5 mg/ml glucose.

In some embodiments, the dynamic condition comprises suspension agitation, optionally rotation. In some embodiments, step (c) is performed in a rotating bottle. In some embodiments, each rotating bottle contains 2 synthetic embryoid in about 3 ml medium. In some embodiments, the dynamic condition comprises providing a plurality of gases to the culture chamber. In some embodiments, the dynamic condition comprises a gas pressure of about 0.5 to about 3 pounds per square inch (psi), optionally about 0.5 to 1 psi, optionally about 0.5 psi. In some embodiments, the dynamic condition comprises supplying oxygen at a constant concentration to the culture chamber. In some embodiments, the dynamic condition comprises supplying oxygen at an increasing concentration to the culture chamber. In some embodiments, the culture chamber has an atmosphere comprising an increasing oxygen concentration from about 5% to about 25%, optionally from about 5% to about 13%, optionally from about 13% to about 18%, optionally from about 18% to about 21%.

In some embodiments, the synthetic embryo has established brain regions, a neural tube, a beating heart, and/or a gut tube. In some embodiments, the synthetic embryo has developing somites and primordial germ cells.

In some embodiments, the method does not comprise any in vivo step.

In some embodiments, none of the mammalian pluripotent stem cell, the extra-embryonic stem cell, the post-implantation embryo structure and the neutralizing embryo structure is present in an in vivo environment in culturing steps (a), (b) and (c); and optionally wherein the in vivo environment comprises a tissue, an organ, an organism, or a combination thereof. In some embodiments, the synthetic embryo is a mouse embryo. In some embodiments, the synthetic embryo is a non-human mammalian embryo.

Provided herein include any synthetic embryo obtained by the methods disclosed herein.

Also provided herein includes an in vitro culture (IVC) media for generating a synthetic embryo in vitro according to the methods disclosed herein, comprising: a basal culture medium comprising at least 20% non-human serum; insulin, an insulin analogue, or an insulin receptor agonist; estrogen, an estrogen analogue, or an estrogen receptor agonist; and progesterone, a progesterone analogue, or a progesterone receptor agonist. The basal culture medium can comprise a reducing agent, an antibiotic, or a combination thereof. The non-human serum can comprise, e.g., fetal bovine serum, bovine serum albumin, or both.

Disclosed herein includes a method of investigating mechanisms involved in embryogenesis, comprising any of the methods for generating a synthetic embryo in vitro; a method of identifying a compound useful for treating a disease, comprising contacting a synthetic embryo obtainable by any of the in vitro methods disclosed herein with the compound; a method for diagnosing or treating a disease or disorder in a subject, comprising generating a synthetic embryo in according to any of the in vitro methods disclosed herein; and transplanting the synthetic embryo into the subject.

As disclosed herein, in some embodiments, the pluripotent stem cell and the at least one extraembryonic stem cells are obtained from the subject.

Also provided herein includes a method of elucidating the role of a gene in embryo development, comprising obtaining a pluripotent stem cell and/or an extra-embryonic stem cell where the gene has been modified or knocked out and culturing the pluripotent stem cell and the extra-embryonic stem cell using any of the in vitro methods disclosed herein.

BRIEF DESCRIPTION OF THE DRAWINGS

The patent or application file contains at least one drawing executed in color. Copies of this patent or patent application publication with drawing(s) will be provided by the Office upon request and payment of the necessary fee.

FIG. 1A-FIG. 1H depict non-limiting exemplary embodiments and data related to exemplary ETiX embryoids described herein which recapitulate developmental milestones of the natural mouse embryo up to 8.5 embryonic days (E8.5). FIG. 1A depicts schematic of ETiX embryoid formation. ETiX embryoids were formed by aggregating ES cells, TS cells and ES cells transiently expressing GATA4. By day 4 (ETiX4), they generated structures that resembled post-implantation stage natural E5.5 embryos. They subsequently developed to gastrulation (E6.5/ETiX day 5 (ETiX5)) and neurulation (E8.0/ETiX day 7 (ETiX7)) stages before initiating organogenesis (E8.5/ETiX day 8 (ETiX8)). FIG. 1B-FIG. 1C depict bright-field images of natural mouse embryos (FIG. 1B) and ETiX embryoids (FIG. 1C) at different time points highlighting morphological similarities (n=1,197 ETiX4, 237 ETiX5, 170 ETiX6, 100 ETiX7 and 40 ETiX8, from 17 independent experiments). Scale bars, 100 μm. FIG. 1D depicts uniform manifold approximation and projection (UMAP) analysis of scRNA-seq data at indicated time points for natural embryos on E6.5, E7.5 and E8.5 and ETiX embryoids on days 5, 6 and 8 (n=29 ETiX5, 10 ETiX6, 7 ETiX8, 12 E6.5, 14 E7.5 and 9 E8.5) analyzed by inDrops sequencing. FIG. 1E depicts single-cell inDrops RNA-seq UMAP annotated to show cell types identified in natural embryos and ETiX embryoids. AVE, anterior visceral endoderm; CLE, caudal lateral epiblast; NMP, neuro-mesodermal progenitors; PLPM, posterior lateral plate mesoderm. FIG. 1F depicts annotated and combined UMAP of natural embryos cultured ex utero and collected at indicated time points (E7.5, E8, E8.5, E8.75 and E9.5) and ETiX embryoids (day 6 and day 8) individually labeled and analyzed by tiny-sci-RNA-seq. n=8 natural embryos ranging from E7.5 to E9.5, n=3 ETiX6, 2 failed ETiX6, 5 ETiX8 and 4 failed ETiX8. FIG. 1G depicts cell-type composition of natural embryos at indicated time points (E7.5, E8, E8.5, E8.75 and E9.5) and ETiX embryoids (day 6 and day 8). FIG. 1H depicts the density plots highlighting the proportions of tissue types that emerge during natural and ETiX embryo development.

FIG. 2A-FIG. 2B depict the ventral view (main image) of day 7 ETiX embryoids after static culture (FIG. 2A) and E8.0 natural embryo (FIG. 2B) showing SOX1-positive neural folds and neural tubes extending from the anterior towards the Brachyury-positive posterior. Optical yz (bottom) and xz (right) sections show notochord lying below the neural tube (n=11 day 7 ETiX embryoids from 4 experiments, n=3 E8.0 embryos). Scale bars, 100 μm. FIG. 2C depicts a dot plot showing average levels and proportion of cells expressing indicated genes in selected tissues of natural embryos and ETiX embryoids (from inDrops scRNA-seq data). Epi, epiblast. FIG. 2D-FIG. 2E depict the lateral view of day 8 ETiX embryoid (FIG. 2D) and E8.5 natural embryo (FIG. 2E) showing FOXG1 in telencephalon and OTX2 in forebrain and midbrain (n=4 ETiX8 from 3 experiments; n=2 E8.5 embryos). Scale bars, 100 μm. FIG. 2F depicts the coronal view of neural tube sections showing dorso-ventral patterning in day 8 ETiX embryoids. Sections revealed pan-neural markers (SOX1 and SOX2), dorsal markers (PAX6 and PAX3), ventral markers (FOXA2, OLIG2 and NKX2-2) and neural crest markers (SOX10 and PAX3). Scale bars, 50 μm. n=3 ETiX8 from 3 experiments. FIG. 2G depicts the subclustered UMAP of neural progenitors highlighting neural subtypes from tiny-sci-RNA-seq. FIG. 2H depicts the individual UMAPs showing the contribution of each time point to global UMAP in FIG. 2G. FIG. 2I depicts the proportion of cell types in FIG. 2G in each individual day 8 ETiX embryoid sequenced by tiny-sci-RNA-seq. MHB, midbrain-hindbrain boundary. FIG. 2J depicts ETiX8 embryos following culture in the absence (left) or presence (right) of 5-Methyl-tetrahydrofolate (50 ng/ml) and stained to reveal Sox1, Bry and DNA (n=4 control ETiX, 3 treated ETiX from 2 independent experiments). Scale bar=100 μm.

FIG. 3A depicts the coronal sections of wild-type (WT) and Pax6-knockout (KO) ETiX embryoids stained to reveal dorsal and ventral neural tube markers. Scale bar, 50 μm.

FIG. 3B depicts the quantification of images represented in FIG. 3A, showing no significant difference in SOX1-positive cell number in the neural tube but an increased proportion of NKX2-2-positive cells following Pax6-knockout (3 control day 8 ETiX and 4 day 8 Pax6-KO ETiX from 3 experiments). Violin plots show median and quartiles. Two-sided Mann-Whitney U-test, *P<0.05. For SOX1-positive cells, P=0.5382; for NKX2-2 positive cells, P=0.0135. FIG. 3C depicts the Gene Ontology (GO) analysis of genes enriched in 2 Pax6-knockout ETiX embryoids at day 8 (tiny-sci-RNA-seq) compared with 5 ETiX day 8 controls. NS, not significant (P>0.05).

FIG. 4A-FIG. 4B depict the lateral view of day 8 ETiX embryoid (FIG. 4A) and natural E8.5 embryo (FIG. 4B) showing SOX2, Brachyury (BRY) and DNA (DAPI), highlighting NMPs in the tail bud region (n=5 ETiX8 from 4 experiments, n=3 embryos). Inset, schematic view. FIG. 4C-FIG. 4D depict the dorsal view of day 7 ETiX embryoid after stationary culture (FIG. 4C) and natural E8.0 embryo (FIG. 4D) showing SOX2, HOXB4 and DNA, highlighting somite formation flanking neural tube. Right, magnified views of outlined region containing somites (n=9 day 7 ETiX embryoids from 4 experiments, n=5 E8.0 embryos). Inset, schematic view. Scale bars FIG. 4A-FIG. 4D, 100 μm (main image), 50 μm (magnified view FIG. 4A-FIG. 4B and top magnified view of FIG. 4C), 20 μm (bottom magnified view of FIG. 4C and magnified views FIG. 4D). FIG. 4E depicts the quantification of somite pairs in natural E8.0 embryos and day 7 ETiX embryoids. Violin plots show median and quartiles. Two-sided Mann-Whitney U-test, P=0.3020. FIG. 4F depicts the somite area of E8.0 embryos and day 7 ETiX embryoids. Violin plots show median and quartiles. Two-sided Mann-Whitney U-test. P=0.2717. For FIG. 4E and FIG. 4F, n=9 day 7 ETiX embryoids from 4 experiments, n=5 E8.0 embryos. FIG. 4G-FIG. 4H depict a day 8 ETiX embryoid (FIG. 4G) (lateral view) and a natural E8.75 embryo (FIG. 4H) (lateral view) showing OTX2, MYH2 and GATA4, highlighting heart (n=8 ETiX8 from 3 experiments, n=2 natural embryos). Outlined areas are magnified on the right. Scale bars, 100 μm (main image), 20 μm (magnified view). FIG. 4I depicts the schematic of mouse heart at E8.5, indicating location of sections. FIG. 4J depicts the coronal sections of ETiX embryoid at day 8 showing GATA4, NKX2-5 and MYH2. Scale bar, 100 μm. n=3 ETiX8 from 3 independent experiments. FIG. 4K depicts a dot plot showing levels and proportion of cells expressing indicated genes in indicated tissues from natural embryos (NE) and ETiX embryoids by inDrops scRNA-seq. FIG. 4L depicts the velocity plots for epiblast and mesodermal derivatives for time series in the inDrops sequencing dataset.

FIG. 5A-FIG. 5B depict the sagittal sections of natural embryos at E8.5 (FIG. 5A) and day 8 ETiX embryoids (FIG. 5B) showing SOX2, SOX17 and GATA4. Scale bars, 100 μm. n=3 ETiX8 from 3 experiments, n=2 natural embryos. fg, foregut; hg, hindgut. FIG. 5C depicts a dot plot showing levels and proportion of cells expressing indicated genes in selected tissues of natural embryos and ETiX embryoids by inDrops scRNA-seq. FIG. 5D depicts the UMAP of tiny-sci-RNA-seq dataset showing VE, gut and early development cell types. FIG. 5E depicts a day 6 ETiX embryoid (top) and a natural E7.5 embryo (bottom) showing STELLA, NANOG and SOX2, highlighting the presence of committed PGCs (n=9 ETiX6 from 2 experiments, n=4 embryos). Outlined regions are magnified on the right. FIG. 5F depicts the quantification of PGCs during ETiX embryoid development (n=9 ETiX6, 4 E7.5, 2 ETiX7, 4 E8.0, 4 ETiX8 and 3 E8.5). PGCs were scored for STELLA, NANOG and SOX2 expression. Violin plots show median and quartiles. Two-sided Mann-Whitney U-test, P=0.3375 for ETiX6/E7.5 total STELLA-positive cells, P=0.3042 for ETiX6/E7.5 triple-positive cells, P=0.2277 for ETiX8/E8.5 total STELLA-positive cells, and P=0.2536 for ETiX8/E8.5 triple-positive cells. FIG. 5G-FIG. 5H depict an ETiX embryoid (FIG. 5G) and a natural E8.75 embryo (FIG. 5H) stained to reveal Sox17, Gata4 and Sox2, highlighting gut formation in relation to the neural tube (n=6 ETiX8 from 3 independent experiments, n=3 embryos). Boxes indicate magnified regions beneath each panel. Scale bar for FIG. 5G-FIG. 5H=100 μm. Scale bar for magnified square=50 μm. FIG. 5I depicts the ETiX8 embryoids sectioned coronally and stained to reveal Sox2, FoxA2 and DNA to highlight the formation of gut pocket in relation to the neural tube. Scale bar=100 μm. Scale bar for magnified square=20 μm.

FIG. 6A depicts the global UMAP of the tiny-sci dataset as shown in FIG. 1F. Selected cell clusters are highlighted. FIG. 6B depicts the gene expression of the amnion marker periostin (Postn) in natural embryos and ETiX embryoids from the tiny-sci-RNA-seq dataset. FIG. 6C depicts the gene expression of the allantois markers 7bx4 and Hoxa13 in natural embryos and ETiX embryoids from the tiny-sci-RNA-seq dataset. FIG. 6D depicts the subclustered and annotated UMAP of extraembryonic endoderm from the tiny-sci-RNA-seq dataset. FIG. 6E depicts the schematic of dissection of chorioallantoic attachment of ETiX embryoids. FIG. 6F depicts sagittal section of chorioallantoic attachment and yolk sac of day 8 ETiX embryoid showing RUNX1 and DNA (left). Arrows highlight blood islands. Outlined regions are magnified in the middle and right panels. n=3 ETiX8 from 3 experiments. Scale bars: 100 μm (left), 20 μm (middle and right). FIG. 6G depicts the subclustered and annotated UMAP of ExE and trophoblast cells from the tiny-sci-RNA-seq dataset. FIG. 6H depicts the contribution of individual time points to the subclustered UMAP of the ExE and trophoblast cells. FIG. 6I-FIG. 6J depict the expression of selected prolactin genes in the subclustered UMAP of ExE and trophoblast cells for natural embryos (FIG. 6I) and ETiX embryoids (FIG. 6J).

FIG. 7A-FIG. 7J depict non-limiting exemplary embodiments and data related to ETiX embryoids developing to comparable sizes and showing gene expression patterns similar to natural embryos with reproducible efficiency. FIG. 7A depicts the quantification of ETiX embryoid and natural embryo dimensions at comparable developmental time points (n=42 for ETiX4, 24 for ETiX5, 14 for ETiX6, 18 for ETiX7, 12 for ETiX8, 32 for E5.5, 18 for E6.5, 3 for E7.5, 8 for E8.0, 5 for E8.5, from 30 independent experiments). FIG. 7B depicts the quantification of ETiX embryoid formation efficiency from day 5 to day 8 (n=1197 ETiX4, 237 for ETiX5, 170 for ETiX6, 100 for ETiX7, 40 for ETiX8, from 17 independent experiments). Error bars represent the S.E.M. FIG. 7C depicts the brightfield images of ETiX embryoids recovered after static culture on day 7 prior to dissection to highlight the presence of yolk sac. Scale bar, 100 μm (n=100 for ETiX7, from 17 independent experiments) FIG. 7D-FIG. 7E depict the separated UMAPs of natural embryos (FIG. 7D) and ETiX embryoids (FIG. 7E) analyzed by inDrops scRNA-seq. FIG. 7F depicts the stacked column graph binning all sequenced cells in natural embryos and ETiX embryoids according to germ layer and embryonic and extraembryonic origin at indicated time points (inDrops scRNA-seq). FIG. 7G depicts the stacked column graph highlighting the proportions of tissue types that emerged during natural embryo and ETiX embryoid development (inDrops scRNA-seq). FIG. 7H depicts the Pearson correlation matrices showing global level of similarity across all identified tissues in natural embryos (rows) in comparison to ETiX embryoids (columns) (inDrops scRNA-seq). FIG. 7I depicts the pairwise visualizations of cell-type proportions between natural embryos and ETiX embryoids (inDrops scRNA-seq). FIG. 7J depicts the Pearson correlation matrix showing the global level of similarity across all comparisons of tissue types in natural and ETiX embryos.

FIG. 8A depicts the typical day 8 ETiX embryoids judged as developing successfully. FIG. 8B depicts the typical failed ETiX embryoids on day 8. FIG. 8C depicts the natural embryos cultured ex utero from E6.5 to E8.5. All structures were stained with DAPI. Morphological features: Hf, Headfolds; H, Heart; T, Tail: All, Allantois. (Some of these samples are also shown in the following panels: sample in panel v of FIG. 8A is also in FIG. 4G; sample in panel vi of FIG. 9A is also in FIG. 2D; sample in panel viii of FIG. 8A is also in FIG. 13G; sample in panel xi of FIG. 8A is also in FIG. 10 A; sample in panel xii of FIG. 8C is also in FIG. 11C; sample in panel xiii of FIG. 8C is also in FIG. 4B; sample in panel xvi of FIG. 8C is also in FIG. 4H; and sample in panel xvii of FIG. 8C is also in FIG. 2E).

FIG. 9A-FIG. 9J depict non-limiting exemplary embodiments and data related to the analysis of ETiX embryoids and natural embryos by tiny sci-RNA-seq. FIG. 9A-FIG. 9B depict the quality control for the first (FIG. 9A) and second (FIG. 9B) replicates of the tiny sci-RNA-seq. Cells with an abnormal percentage of reads mapping to an exon, and too high or too low UMI counts per cell were removed. FIG. 9C depicts the UMAP of the first and second replicates of the tiny sci-RNA-seq. The total number of cells in each dataset is indicated. FIG. 9D depicts the batch variation for the first and second replicates of tiny sci-RNA-seq. FIG. 9E-FIG. 9F depict the separated UMAPs of natural embryos (FIG. 9E) and ETiX embryoids (FIG. 9F) analyzed with tiny sci-RNA-seq. FIG. 9G depicts the contribution of each time point to the global UMAP of the tiny sci-RNA-seq. FIG. 9H depicts the individual UMAPs of standard ETiX embryoids analyzed on day 6 and day 8 with tiny sci-RNA-seq. FIG. 9I depicts the PCA analysis of all the natural embryo and standard ETiX-embryoid samples analyzed with tiny sci-RNA-seq. FIG. 9J depicts the correlation matrix following a nonnegative least-squares (NNLS) regression analysis showing the global level of similarity across all identified tissues in natural embryos (columns) in comparison to ETiX embryoids (rows) in the samples analyzed by tiny sci-RNA-seq.

FIG. 10A-FIG. 10C depict the integration of the tiny sci-RNA-seq dataset generated hereby with two published single-cell sequencing mouse datasets. In FIG. 10A: 1 Allantois, 2 Anterior Primitive Streak, 3 Blood progenitors 1, 4 Blood progenitors 2, 5 Cardiomyocytes, 6 Caudal epiblast, 7 Caudal Mesoderm, 8 Caudal neurectoderm, 9 Def. endoderm, 10 Endothelium, 11 Epiblast, 12 Erythroid1, 13 Erythroid2, 14 Erythroid3, 15 ExE ectoderm, 16 ExE endoderm, 17 ExE mesoderm, 18 Forebrain/Midbrain/Hindbrain, 19 Gut, 20 Haematoendothelial progenitors, 21 Intermediate mesoderm, 22 Mesenchyme, 23 Mixed mesoderm, 24 Nascent mesoderm, 25 Neural crest, 26 NMP, 27 Notochord, 28 Paraxial mesoderm, 29 Parietal endoderm, 30 PGC, 31 Pharyngeal mesoderm, 32 Primitive Streak, 33 Rostral neurectoderm, 34 Semitic mesoderm, 35 Spinal cord, 36 Surface ectoderm, 37 Visceral endoderm. In FIG.

10B: 1 Allantois, 2 Amniochorionic mesoderm A, 3 Amniochorionic mesoderm 8, 4 Anterior floor plate, 5 Blood progenitors, 6 Definitive endoderm, 7 Endothelium, 8 Extraembryonic mesoderm, 9 Extraembryonic visceral endoderm, 10 First heart field, 11 Forebrain/midbrain, 12 Fusing epithelium, 13 Gut, 14 Hematoendothelial progenitors, 15 Hindbrain, 16 Intermediate mesoderm, 17 Neural crest, 18 Neuromesodermal progenitors, 19 Notochord, 20 Paraxial mesoderm A, 21 Paraxial mesoderm B, 22 Placodal area, 23 Posterior floor plate, 24 Pre-epidermal keratinocytes, 25 Primitive erythroid cells, 26 PDCs, 27 Second heart field, 28 Somatic mesoderm, 29 Spinal cord, 30 Splanchnic mesoderm. In FIG. 10C: 1 Allantois, 2 Amniotic mesoderm, 3 Definitive endoderm, 4 Early development, 5 Endothelium, 6 Extraembryonic ectoderm, 7 Heart field, 8 Hematoendothelial progenitors, 9 Lateral plate mesoderm, 10 Megakaryocytes, 11 Neural crest, 12 Neuroectoderm, 13 Neuromesodermal progenitors, 14 Paraxial mesoderm, 15 Parietal endoderm, 16 Primitive erythroid cells, 17 Surface ectoderm, 18 Visceral endoderm, 19 White blood cells. FIG. 10D depicts the cell type proportions for each individual well-formed (standard) ETiX embryoid and each "failed" ETiX embryoid (classified through aberrant morphology) sequenced on day 6 and day 8 with tiny sci-RNA-seq (n=3 for standard ETiX6, 2 for failed ETiX6, 5 for standard ETiX8, 4 for failed ETiX8 from 2 independent experiments). FIG. 10E depicts the averaged cell type proportions for well-formed (standard) and "failed" ETiX embryoids sequenced on day 8 with tiny sci-RNA-seq. Cell type proportions from each individual sample were also plotted. In each boxplot, the center line shows the medians; the box limits indicate the 25th and 75th percentiles; the whiskers extend to the 5th and 95th percentiles; the replicates are represented by the dots. (n=5 for standard ETiX8, 4 for failed ETiX8 from 2 independent experiments). In FIG. 10E, 1, Endothelium; 2, White blood cells; 3, Megakaryocytes; 4, Primitive erythroid cells; 5, Heart field; 6, Cardiac mesoderm; 7. Paraxial mesoderm; 8, Neuromesodermal progenitors; 9, Neural crest; 10, Neuroectoderm; 11, Surface ectoderm; 12, Gut; 13, Parietal endoderm; 14, Visceral endoderm; 15, Amniotic mesoderm; 16, Allantois; 17, Extraembryonic ectoderm; 18, Hematoendothelial progenitors; 19, Early development.

FIG. 11A depicts a day 7 ETiX embryoid recovered after stationary culture stained to reveal SOX2, SOX1 and DNA highlighting the formation of the rostral neural folds (n=11 ETiX7 from 4 independent experiments, n=3 E8.0 natural embryos). FIG. 11B depicts the dorsal views of day 7 ETiX embryoid recovered after stationary culture (left) and natural E8.0 embryo (right) showing the formation of SOX1 positive neural folds and BRY-positive notochord and tail bud (n=11 ETiX7 from 4 independent experiments, n=3 embryos). Scale bar, 100 μm. FIG. 11C depicts the lateral view of day 8 ETiX embryoid and E8.5 natural embryo (FIG. 11C (Continued)) showing FOXG1 expression in the telencephalon and OTX2 restricted to the forebrain and midbrain (n=4 ETiX8 from 3 independent experiments, n=2 embryos). Scale bar for FIG. 11A to FIG. 11C, 100 μm. FIG. 11D depicts the quantification of brain areas in E8.5 natural embryos and day 8 ETiX-embryoids. OTX2 was used to delineate the measured areas. Each dot represents a sample (n=6 E8.5 embryos and n=17 ETiX8 from 7 independent experiments). Data are presented as violin plots with median and quartiles. Two-sided unpaired t-test, ns=p>0.05 (p=0.5223). FIG. 11E depicts the velocity plots for epiblast, neuroectoderm, and surface ectoderm for all time points analyzed in the inDrops sequencing dataset. FIG. 11F depicts the latent time analysis for epiblast, neuroectoderm, and surface ectoderm for all time points analyzed in the inDrops sequencing dataset. FIG. 11G depicts the quantification of the latent time analysis for epiblast, neuroectoderm, and surface ectoderm for all time points analyzed in the inDrops sequencing dataset.

FIG. 12A-FIG. 12J depict non-limiting exemplary embodiments and data related to the expression of selected markers for the annotation of neural tissue and localized expression of transcripts revealed by sequential single molecule FISH in natural embryos and ETiX embryoids. Expression of selected gene markers in annotated clusters is shown in FIG. 2G. FIG. 12A-F provide plots showing the expression of gene markers of cell populations representing the prosencephalon (FIG. 12A), mesencephalon and mid-brain-hindbrain boundary (FIG. 12B), hindbrain and spinal cord (FIG. 12C), floor plate/roof plate (FIG. 12D), early neurons (FIG. 12E) and neural crest (FIG. 12F) (tiny sci-RNA-seq). FIG. 12G depicts a schematic representation of sample sectioning for single-molecule fluorescence in situ hybridization (smFISH)smFISH and the expected expression pattern of selected genes. FIG. 12H-FIG. 12I depict smFISH panel of n=1 natural embryo cultured ex utero from E6.5 to E8.5 (FIG. 12H) and n=1 day 8 ETiX-embryoid (FIG. 12I) Scale bar=200 μm. FIG. 12J depicts the proportion of cell types annotated in FIG. 1F and in each individual day 8 ETiX embryoid and Pax6 knockout ETiX embryoid sequenced by tiny sci-RNA-seq.

FIG. 13A depicts the lateral view of the day 8 ETiX embryoid shown in FIG. 3A, highlighting the individual channels. Square regions are shown magnified on the right. Scale bars, 100 μm. FIG. 13B depicts the percentages of cells co-expressing BRY and SOX2 in natural embryos and ETiX embryoids. (n=3 E8.5 embryos and n=4 ETiX8). Data are presented as violin plots with median and quartiles. Each dot represents a sample. Two-sided Mann-Whitney U-test, ns=p>0.05 (p=0.5182). FIG. 13C depicts the dorsal view of the day 7 ETiX embryoid shown in FIG. 3C, highlighting the individual channels. YZ and XZ views are also shown (n=9 ETiX7 from 4 experiments, n=5 E8.0 embryos). FIG. 13D-FIG. 13E depicts the dorsal (FIG. 13D) and lateral (FIG. 13E) view of day 7 ETiX embryoid recovered after stationary culture stained to reveal SOX2, HOXB4 and DNA to highlight somite formation flanking the neural tube (n=9 ETiX7 from 4 independent experiments). YZ and XZ views are also shown. FIG. 13F depicts the orthogonal views of the day 8 ETiX-embryoid shown in FIG. 4G. FIG. 13G depicts the lateral view of day 8 ETiX embryoid stained to reveal OTX2, MYH2 and DNA to highlight heart formation (n=8 ETiX8 from 3 independent experiments). YZ and XZ views are also shown. Scale bar for FIG. 13A-FIG. 13D, 100 μm. Scale bar for magnified region, 50 μm. FIG. 13H depicts a day 8 ETiX embryoid (top) and an E8.5 natural embryo (below) sectioned coronally and stained to reveal GATA6 and MYH2 to highlight heart morphogenesis. Scale bar, 200 μm. FIG. 13I depicts the quantifications of the area of the heart in natural embryos and ETiX embryoids. The MYH2-positive region was utilized to measure the area of the heart or heart-like structure (n=3 E8.5 embryos, n=3 ETiX8). Data are presented as violin plots with median and quartiles. Each dot represents a section of the heart and heart-like region. Two-sided unpaired t-test **=p≤0.01 (exact p value=0.01). FIG. 13J depicts the dorsal view of a natural E8.0 embryo stained to reveal Sox2, HoxB4 and DNA to highlight somite formation flanking the neural tube (n=2 embryos). Scale bar, 100 μm.

FIG. 14A depicts the latent time for epiblast and mesodermal derivatives for time series in inDrops sequencing dataset. FIG. 14B depicts the quantification of the latent time analysis for epiblast and all the mesodermal derivatives for all time points analyzed in the inDrops sequencing dataset. FIG. 14C depicts the annotated UMAP of the tiny sci-RNA-seq dataset highlighting the paraxial mesoderm cluster. FIG. 14D depicts the expression of somite markers Meox1, Meox2 and Pax3 in natural embryos and ETiX embryoids (tiny sci-RNA-seq dataset). FIG. 14E depicts the expression of cardiac markers Hand1, Hand2, atrial differentiation marker Nr2f2, ventricular differentiation marker Irx4, first heart field markers Tbx5, Hcn4, Nkx2-5 and second heart field marker Isl1 in natural embryos and ETiX embryoids (tiny sci-RNA-seq dataset). FIG. 14F depicts the UMAP showing individual time points for natural embryos and ETiX embryoids in combined UMAP presented in FIG. 4M.

FIG. 15A-FIG. 15B depict the sagittal sections of natural embryos at E8.5 (FIG. 15A) and day 8 ETiX embryoids (FIG. 15B) stained to reveal GATA6. (n=3 ETiX8 from 3 independent experiments, n=2 embryos). FIG. 15C-FIG. 15D depict the sagittal sections of natural embryos at E8.5 (FIG. 15C) and day 8 ETiX embryoids (FIG. 15D) stained to reveal CDX2, NKX2.5 and FOXG1. (n=3 ETiX8 from 3 independent experiments, n=2 embryos). The magnified regions on the right. FIG. 15E-FIG. 15F depict the sagittal sections of natural embryos at E8.5 (FIG. 15E) and day 8 ETiX embryoids (FIG. 15F) stained to reveal SOX2, OTX2 and FOXA2. The magnified regions in FIG. 15E and FIG. 15F are shown on the right. Scale bar for FIG. 15A-FIG. 15F, 100 μm. (n=3 ETiX8 from 3 experiments, n=2 embryos).

FIG. 16A depicts the velocity plots of epiblast, definitive endoderm, gut precursors and primitive streak for all time points analyzed in the inDrops sequencing dataset. FIG. 16B depicts the latent time analysis of epiblast, definitive endoderm, gut precursors and primitive streak for all time points analyzed in the inDrops sequencing dataset. FIG. 16C depicts the quantification of latent time analysis of epiblast, definitive endoderm, gut precursors and primitive streak for all time points analyzed in the inDrops sequencing dataset. FIG. 16D-FIG. 16K depict the expression of selected marker genes of the embryonic (FIG. 16D-FIG. 16J) and extraembryonic (FIG. 16K) endoderm contribution to the gut (tiny sci-RNA-seq dataset). FIG. 16L depicts the UMAP showing time series of individual natural embryos and ETiX embryoids to combine UMAP in FIG. 5D.

FIG. 17A-FIG. 17C depict an ETiX embryoid (FIG. 17A and FIG. 17C) at day 7 of development after stationary culture and a natural embryo (FIG. 17B) at E8.0 of development stained to reveal STELLA, NANOG and SOX2 to highlight the presence of committed PGCs (n=2 ETiX7 from 2 independent experiments, n=4 embryos). Boxes are magnified below (FIG. 17A-FIG. 17B) and on the right (FIG. 17C). Scale bars for FIG. 17A-FIG. 17C, 100 μm for the main panel, 50 μm for magnified boxes. FIG. 17D depicts day 8 ETiX-embryoid stained to reveal STELLA, NANOG and SOX2, highlighting the presence of committed PGCs. Scale bar for FIG. 17D, 100 sm. (n=4 ETiX8 from 3 experiments).

FIG. 18A-FIG. 18O depict non-limiting exemplary embodiments and data related to the characterization of yolk sac, endothelium and extraembryonic ectoderm in ETiX embryoids. FIG. 18A-FIG. 18B depict the partially dissected natural embryos (FIG. 18A) cultured from E6.5 to E8.5 and day 8 ETiX embryoids (FIG. 18B) highlighting their development within extraembryonic membranes. Legend: HF: headfolds, H: heart, T: tailbud and All: allantois. Scale bars, 100 μm. FIG. 18L-FIG. 18O depict the expression of marker genes presented in (FIG. 18I-FIG. 18K) in the ETiX embryoids UMAP.

FIG. 19A depicts the quantification of PGC formation at different stages of ETiX embryoid development (n=9 for ETiX6, 2 for ETiX7, 4 for ETiX8). PGCs were scored for Stella expression and co-expression of Nanog and Sox2. Data are presented as violin plots with median and quartiles. FIG. 19B depicts the sagittal section of chorioallantoic attachment and yolk sac for an ETiX8 embryo stained for Keratin18, Gata4 and DNA to visualize chorion and yolk sac. Scale bar for FIG. 19B=100 μm. Scale bar for magnified square=20 μm.

DETAILED DESCRIPTION

Figure 1A:
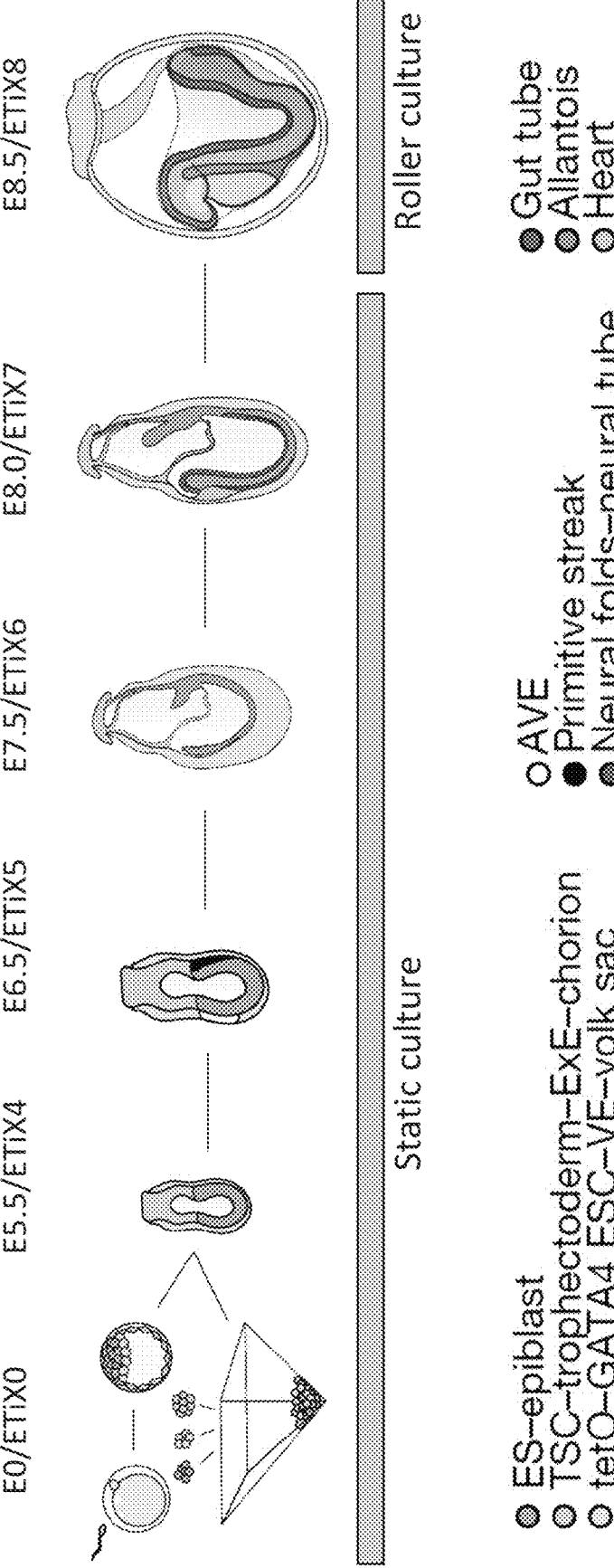

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, NY 1989). For purposes of the present disclosure, the following terms are defined below.

The term "about," as used herein when referring to a measurable value such as an amount of a compound, dose, time, temperature, and the like, is meant to encompass variations of 10%, 5%, 1%, 0.5%, or even 0.1% of a specified amount.

As used herein, the term "differentiation" can refer to the process by which an unspecialized ("uncommitted") or less specialized cell acquires the features of a specialized cell such as, for example, a neuronal cell. A differentiated cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. As used herein, the lineage of a cell defines the heredity of the cell, i.e., which cells it came from and to what cells it can give rise. The lineage of a cell places the cell within a hereditary scheme of development and differentiation. As used herein, a "lineage-specific marker" can refer to a characteristic specifically associated with the phenotype of cells of a lineage of interest and can be used to assess the differentiation of an uncommitted cell to the lineage of interest.

As used herein, "markers", "lineage markers" or, "lineage-specific markers" can refer to nucleic acid or polypeptide molecules that are differentially expressed in a cell of interest. Differential expression can mean an increased level for a positive marker and a decreased level for a negative marker as compared to an undifferentiated cell. The detectable level of the marker nucleic acid or polypeptide is sufficiently higher or lower in the cells of interest compared to other cells, such that the cell of interest can be identified and distinguished from other cells using any of a variety of methods known in the art. In some embodiments, a marker can be enriched. The term "enriched", as used herein, shall have its ordinary meaning, and can also refer to a statistically significant increase in levels of a gene product (e.g., mRNA and/or protein) in one condition as compared to another condition (e.g., in one cell layer as compared to another cell layer).

The term, "concentration" as used herein shall have its ordinary meaning, and can also refer to (a) mass concentration, molar concentration, volume concentration, mass fraction, molar fraction or volume fraction, or (b) a ratio of the mass or volume of one component in a mixture or solution to the mass or volume of another component in the mixture or solution (e.g., ng/ml). In some embodiments, the concentration can refer to fraction of activity units per volume (e.g., U/ml).

The term "analogue" as used herein refers to a compound which may be structurally related to the relevant molecule. The term "agonist" as used herein can refer to a compound which might not be structurally related to the relevant molecule. For example, an agonist may activate the relevant receptor by altering the conformation of the receptor. Nevertheless, in both cases the terms are used in this specification to refer to compounds or molecules which can mimic, reproduce or otherwise generally substitute for the specific biological activity of the relevant molecule.

As used herein the phrase "culture medium" refers to a liquid substance used to support the growth and development of stem cells and of an embryo. The culture medium used according to some embodiments of the invention can be a water-based medium which includes a combination of substances such as salts, nutrients, minerals, vitamins, amino acids, nucleic acids, and/or proteins such as cytokines, growth factors and hormones needed for cell growth and embryo development.

Disclosed herein includes an in vitro method of generating a synthetic embryo from stem cells. In some embodiments, the method comprises culturing a mammalian pluripotent stem cell and an extra-embryonic stem cell in a first culture media under a first static condition allowing the mammalian pluripotent stem cell and the extra-embryonic stem cell to self-assemble into a post-implantation embryo structure, culturing the post-implantation embryo structure in a second culture media under a second static condition allowing the post-implantation embryo structure to develop into a neurulating embryo structure, and culturing the neurulating embryo structure for at least one day under a dynamic condition in a culture chamber allowing the neurulating embryo structure to develop into a synthetic embryo of at least early organogenesis stage. Disclosed herein also includes a synthetic embryo structure obtained by the method disclosed herein.

Disclosed herein also includes an in vitro culture (IVC) media for generating a synthetic embryo in vitro according to the methods disclosed herein. The in vitro IVC media comprises a basal culture medium comprising at least 20% non-human serum, insulin, an insulin analogue, or an insulin receptor agonist, estrogen, an estrogen analogue, or an estrogen receptor agonist, and progesterone, a progesterone analogue, or a progesterone receptor agonist.

Disclosed herein also includes a method of investigating mechanisms involved in embryogenesis according to the in vitro methods disclosed herein.

Methods for Generating Synthetic Embryos In Vitro from Stem Cells

Embryonic stem (ES) cells can undergo many aspects of mammalian embryogenesis in vitro, but their developmental potential can be substantially extended by interactions with extraembryonic stem cells including trophoblast stem (TS) cells, extraembryonic endoderm stem (XEN) cells, and/or inducible XEN (iXEN) cells. Signals originating from extraembryonic tissues play an important role in patterning the epiblast and drive the establishment of the anterior-posterior axis.

Embryoids have been previously assembled by aggregating ES cells with TS cells derived from extraembryonic ectoderm (ExE) precursors and XEN cells derived from extraembryonic visceral endoderm (VE) precursors. Substituting XEN cells with ES cells that transiently express the VE master regulator GATA4 (iXEN cells) have shown to improve the efficiency and developmental potential of the resulting ETiX embryoids. ETiX embryoids specify an anterior organizer, the anterior visceral endoderm (AVE), which migrates to position the primitive streak to initiate gastrulation movements 10 that are essential for subsequent development.

Provided herein include methods and culture media for assembling synthetic embryos in vitro from mammalian pluripotent stem cells and extraembryonic stem cells, including for example ES cells, TS cells and iXEN cells. In some embodiments, the stem cell-derived synthetic embryos obtained using the methods and culture media disclosed herein can develop beyond gastrulation and neurulation to the equivalent of natural embryos 8.5 days post-fertilization or beyond. In some embodiments, the stem cell derived synthetic embryos establish all brain regions, a neural tube, a beating heart and a gut tube. The neural tube is flanked by developing somites and primordial germ cells (PGCs) form in the tail region. This complete embryo model develops within an extraembryonic yolk sac that forms blood islands. In some embodiments, the self-organization abilities of ES cells and extraembryonic stem cells to reconstitute mammalian development through and beyond gastrulation to neurulation and early organogenesis are demonstrated. Gastrulating and neurulating embryoids generated using the methods and culture media disclosed herein can offer a powerful, physiologically relevant model of post-implantation embryogenesis. These complete embryoids are also powerful in vitro models for dissecting the roles of diverse cell lineages and genes in development. Some of the methods and compositions disclosed herein are also disclosed in Amadei et al. "Embryo model completes gastrulation to neurulation and organogenesis." *Nature* 610, no. 7930 (2022): 143-153, the content of which is incorporated herein by reference in its entirety.

Disclosed herein includes an in vitro method of generating a synthetic embryo from stem cells. In some embodiments, the method comprises culturing a mammalian pluripotent stem cell and an extra-embryonic stem cell in a first culture media under a first static condition allowing the mammalian pluripotent stem cell and the extra-embryonic stem cell to self-assemble into a post-implantation embryo structure (e.g., post-implantation pre-gastrulation embryo structure). The method can further comprise culturing the post-implantation embryo structure in a second culture media under a second static condition allowing the post-implantation embryo structure to develop into a neurulating embryo structure. The method can further comprise culturing the neurulating embryo structure for at least one day under a dynamic condition in a culture chamber allowing the neurulating embryo structure to develop into a synthetic embryo of at least early organogenesis stage. Disclosed herein also includes a synthetic embryo structure obtained by the method disclosed herein.

In some embodiments, the methods disclosed herein do not comprise any in vivo step. In some embodiments, none of the mammalian pluripotent stem cell, the extra-embryonic stem cell, the post-implantation embryo structure and the neurulating embryo structure is present in an in vivo environment in any of the culturing steps disclosed herein. The in vivo environment can comprise a tissue, an organ, an organism, or a combination thereof.

Stem Cells and Mammalian Development

Disclosed herein are methods and compositions for, e.g., modelling mammalian early embryo development, by culturing mammalian pluripotent stem cells and at least one extra-embryonic stem cell (e.g., two types of extra-embryonic stem cells) in vitro. In some embodiments, the method comprises: (a) culturing a mammalian pluripotent stem cell and at least one extra-embryonic stem cell in a first culture media under a first static condition allowing the mammalian pluripotent stem cell and the extra-embryonic stem cell to self-assemble into a post-implantation structure, such as an early post-implantation structure (e.g., E5.5). In some embodiments, the mammalian pluripotent stem cell is an embryonic stem cell. In some embodiments, the mammalian pluripotent stem cell and the at least one extra-embryonic stem cell can self-assemble into a gastrulating embryo structure under the first static condition.

While mammalian embryogenesis has some common features across all species, it will be appreciated that different mammalian species develop in different ways and at different rates. In general, though, the fertilized egg undergoes a number of cleavage steps (passing through two cell, four cell and eight cell stages) before undergoing compaction to form a solid ball of cells called a morula, in which the cells continue to divide. Ultimately the internal cells of the morula give rise to the inner cell mass and the outer cells to the trophectoderm. The morula in turn develops into the blastocyst, which is surrounded by trophectoderm and contains a fluid-filled vesicle, with the inner cell mass at one end.

The term "embryo" as used herein refers to a mammalian organism from the single cell stage. The embryo described herein is generated from culturing in vitro from stem cells under appropriate conditions and resembles a natural embryo produced in vivo of a corresponding stage, such as having similar morphology, length, weight cell type compositions and expression of developmental marker genes.

A developmental stage of an embryo can be defined by the development of specific structures and can be used to define equivalent stages in development of other species. In some embodiments, a developmental stage of an embryo can be defined according to "Carnegie stages", which is a standardized system used to provide a unified developmental chronology of the vertebrate embryo. The earliest Carnegie stages are as follows in Table 1.

TABLE 1

| Carnegie stage | Days since ovulation (approx.) | Characteristic events/structures |
|---|---|---|
| | Carnegie Stages of Development | |
| 1 | 1 | fertilization; polar bodies |
| 2 | 2-3 | cleavage; morula; compaction |
| 3 | 4-5 | blastocyst and blastocoele; trophoblast and embryoblast |
| 4 | 6 | syncytiotrophoblast; cytotrophoblast; anchoring to endometrium |
| 5(a) | 7-8 | implantation; embryonic disc; bilaminar germ disc; primary yolk sac; |
| 5(b) | 9-10 | formation of trophoblast lacunae; complete penetration into endometrium; amniotic cavity; primary umbilical vesicle |
| 5(c) | 11-16 | pre-chordal plate; extra-embryonic mesoblast; secondary yolk sac |
| 6 | 17 | primitive streak, primitive node, primitive groove; secondary umbilical vesicle; primordial germ cells; body stalk; early gastrulation. |
| 7 | 19 | Gastrulation; neural plate; start of hematopoiesis. |
| 8 | 23 | Primitive pit |
| 9 | 25 | Neural groove; neural folds; septum transversum; placode; early heart. |

In some embodiments, the mammalian embryos generated herein are mouse embryos. Theiler has established numbered stages of murine development. The earliest stages, as applied to (C57BLxCBA)F1 mice, are described in the "emouse digital atlas" (www.emouseatlas.org) as follows in Table 2.

TABLE 2

| Theiler Stage | Dpc* (range) | Cell number | (C57BLxCBA)F1 mice |
|---|---|---|---|
| | Theiler Stages of Development | | |
| 1 | 0-0.9 (0-2.5) | | |
| 2 | 1 (1-2.5) | 2-4 | Dividing egg |
| 3 | 2 (1-3.5) | 4-16 (or 8-16) | Morula |
| 4 | 3 (2-4) | 16-40 (or 16-32) | Blastocyst, inner cell mass apparent |
| 5 | 4 (3-5.5) | | Blastocyst (zona-free) |
| 6 | 4.5 (4-5.5) | | Attachment of blastocyst; primary endoderm covers blastocoelic surface of inner cell mass |
| 7 | 5 (4.5-6) | | Implantation and formation of egg cylinder; Ectopiacental cone appears, enlarged epiblast, primary endoderm lines mural trophectoderm |
| 8 | 6 (5-6.5) | | Differentiation of egg cylinder. Implantation sites 2x3 mm. Ectopiacental cone region invaded by maternal blood, Reichert's membrane and proamniotic cavity form |
| 9a | 6.5 (6.25-7.25) | | Pre-streak(PS). advanced endometrial reaction, ecto lacental cone invaded by blood, extraembryonic ectoderm, embryonic axis visible |

TABLE 2-continued

Theiler Stages of Development

| Theiler Stage 1 | Dpc* (range) 0-0.9 (0-2.5) | Cell number | (C57BLxCBA)F1 mice |
|---|---|---|---|
| 9b | | | Early streak(ES), gastrulation starts, first evidence of mesoderm |
| 10a | 7 (6.5-7.75) | | Mid streak (MS), amniotic fold starts to form |
| 10b | | | Late streak, no bud (LSOB), exocoelom |
| 10c | | | Late streak, early bud (LSEB), allantoic bud first appears, node, amnion closing |
| 11a | 7.5 (7.25-8) | | Neural plate (NP), head process developing, amnion complete |
| 11b | | | Late neural plate (LNP), elongated allantoic bud |
| 11c | | | Early head fold (EHF) |
| 11d | | | Late head fold (LHF), foregut invagination |
| 12a | 8 (7.5-8.75) | | 1-4 somites, allantois extends, first branchial arch, heart starts to form, foregut pocket visible, preotic sulcus at 2-3 somite stage) |
| 12b | | | 5-7 somites, allantois contacts chorion at the end of TS12, Absent $2^{nd}$ arch, >7 somites |
| 13 | 8.5 (8-9.25) | | Turning of the embryo, $1^{st}$ branchial arch has maxillary and mandibular components, $2^{nd}$ arch present; Absent 3rd branchial arch |
| 14 | 9 (8.5-9.75) | | Formation & closure of ant. neuropore, otic pit indented but not closed, $3^{rd}$ branchial arch visible; Absent forelimb bud |
| 15 | 9.5 (9-10.5) | | Formation of post, neuropore, forelimb bud, forebrain vesicle subdivides; Absent hindlimb bud, Rathke's pouch |
| 16 | 10 (9.5-10.75) | | Posterior neuropore closes, Formation of hindlimb & tail buds, lens plate, Rathke's pouch; the indented nasal processes start to form; Absent thin & long tail |
| 17 | 10.5 (10-11.25) | | Deep lens indentation, adv. devel. of brain tube, tail elongates and thins, umbilical hernia starts to form; Absent nasal pits |
| 18 | 11 (10.5-11.25) | | Closure of lens vesicle, nasal pits, cervical somites no longer visible; Absent auditory hillocks, anterior footplate |
| 19 | 11.5 (11-12.25) | | Lens vesicle completely separated from the surface epithelium, Anterior, but no posterior, footplate. Auditory hillocks first visible; Absent retinal pigmentation and sign of fingers |
| 20 | 12 (11.5-13) | | Earliest sign of fingers, (splayedout), posterior footplate apparent, retina pigmentation apparent, tongue well-defined, brain vesicles clear; Absent 5 rows of whiskers, indented |
| 21 | 13 (12.5-14) | | Anterior footplate indented, elbow and wrist identifiable, 5 rows of whiskers, umbilical hernia now clearly apparent; Absent hair follicles, fingers separate distally |
| 22 | 14 (13.5-15) | | Fingers separate distally, only indentations between digits of the posterior footplate, long bones of limbs present, hair follicles in pectoral, pelvic and trunk regions; Absent open eyelids, hair follicles in cephalic region |
| 23 | 15 | | Fingers & Toes separate, hair follicles also in cephalic region but not at periphery of vibrissae, eyelids open; Absent nail primordia, fingers 2-5 parallel |
| 24 | 16 | | Reposition of umbilical hernia, eyelids closing, fingers 2-5 are parallel, nail primordia visible on Toes; Absent wrinkled skin, fingers & toes joined together |
| 25 | 17 | | Skin is wrinkled, eyelids are closed, umbilical hernia is gone; Absent ear extending over auditory meatus, long whiskers |
| 26 | 18 | | Long whiskers, eyes barely visible through closed eyelids, ear covers auditory meatus |
| 27 | 19 | | Newborn Mouse |

*"dpc" indicates days post conception, with the morning after the vaginal plug is found being designated 0.5 dpc or E0.5.

65

The developmental stage of a synthetic embryo generated herein can be defined according to its embryonic day. As used herein, the term "embryonic day (E)" in the context of a mammalian embryo (e.g., mouse embryo) refers to an embryo having developmental characteristic of an in vivo (in-uterine tube or in utero) mammalian embryo counterpart at the specified day following fertilization, wherein E0 is considered as the fertilized egg.

In some embodiments, the methods and compositions described herein enable culture up to or through to post-implantation stages corresponding to Theiler stage 7, 8, 9(a), 9(b), 10(a), 10(b), 10(c), 11(a), 11(b), 11(c), 11(d), 12(a), 12(b), 13, 14, 15, 16 and beyond, Carnegei stage (a), 5(b), 5(c), 6, 7, 8, 9 and beyond, and corresponding stages in other species. In some embodiments, the synthetic embryo generated herein can reach post-implantation stages of E4, E4.5, ES, E5.5, E6, E6.5, E7, E7.5, E8, E8.5, E9, E9.5 and beyond.

The methods and compositions herein described can be applied to embryos from any suitable mammalian species, such as: primates, including humans, great apes (e.g., gorillas, chimpanzees, orangutans), old world monkeys, new world monkeys; rodents (e.g., mice, rats, guinea, pigs, hamsters); cats; dogs; lagomorphs (e.g., rabbits); cows; sheep; goats; horses; pigs; and any other livestock, agricultural, laboratory or domestic mammals.

The methods and compositions herein described can be applied to an embryo from any non-human mammal, including but not limited to those described above. Thus, any of the culture media embodiments defined herein may be capable of supporting development of a nonhuman mammalian embryo on a substrate from a pre-implantation stage of development to a post-implantation stage of development.

The term "pre-implantation stage" can be used herein to refer to a stage of development earlier than the stage corresponding to Theiler stage 7, Carnegie stage 5(a), and corresponding stages in other species. As used herein, the term "post-implantation stage" can refer to a stage of development later than the stage corresponding to Theiler stage 7, Carnegie stage 5(a), and corresponding stages in other species. A "post-implantation stage" may be determined by detecting the up-regulation of one or more genes by the embryo. For example, such a stage may be determined by detecting one or more of the following changes: the epiblast up-regulates Fgf5; the primitive endoderm differentiates into visceral endoderm that up-regulates Cerl in a subpopulation of cells (the anterior visceral endoderm); the visceral endoderm up-regulates Eomes; and the trophectoderm up-regulate Hand1.

Stem cells (e.g., mammalian pluripotent stem cells and extra-embryonic stem cells) can be cultured using the media, kits and methods described herein. The term "stem cell" as used herein can refer to a cell capable of retaining a constant potential for differentiation even after cell division. Examples of stem cells include: embryonic (ES) stem cells with pluripotency derived from a fertilized egg or clone embryo; epiblast stem cells; trophoblast stem cells; extra-embryonic endoderm (XEN) stem cells; somatic stem cells and pluripotent stem cells that are present in tissues in a living organism e.g. hepatic stem cells, dermal stem cells, and reproductive stem cells that serve as the bases for respective tissues; pluripotent stem cells derived from reproductive stem cells; pluripotent stem cells obtained by nuclear reprogrammed somatic cells; totipotent stem cells and non-totipotent stem cells and the like. Also, partially committed stem cells e.g. progenitor cells may be cultured using the media and according to the methods described herein.

The methods and compositions described herein may be applied to stem cells from any suitable mammalian species, such as: primates, including humans, great apes (e.g., gorillas, chimpanzees, orangutans), old world monkeys, new world monkeys; rodents (e.g., mice, rats, guinea pigs, hamsters); cats; dogs; lagomorphs (e.g., rabbits); cows; sheep; goats; horses; pigs; and any other livestock, agricultural, laboratory or domestic mammals. The methods and compositions described herein may be applied to stem cells from any non-human mammal, including but not limited to those described above. In some embodiments, the non-human mammals are rodents.

The term "pluripotent stem cell" (PSC) as used herein refers to a stem cell permitting in vitro culture and having the potential for differentiating into all cells, but the placenta. The pluripotent stem cell has the potential to differentiate into any of the three germ layers: endoderm (which forms structures such as the gastrointestinal tract and the respiratory system), mesoderm (which forms structures such as the musculoskeletal system, the vascular system and the urogenital system), or ectoderm (which forms epidermal tissues and the nervous system).

A PSC may be obtained from a fertilized egg, clone embryo, reproductive stem cell, or stem cell in tissue. Also included are cells having differentiation pluripotency similar to that of embryonic stem cells, conferred artificially by transferring several different genes to a somatic cell (also referred to as induced pluripotent stem cells or iPS cells). Induced pluripotent stem cells may be derived from any suitable source (e.g. hair follicles, skin cells, fibroblasts, etc.). Pluripotent stem cells can be prepared by known methods in the art. Any of the stem cells as defined herein may be derived from diseased or non-diseased tissue. Stem cells can be from any suitable mammalian species, such as: primates, including humans, great apes (e.g. gorillas, chimpanzees, orangutans), old world monkeys, new world monkeys; rodents (e.g. mice, rats, guinea pigs, hamsters); cats; dogs; lagomorphs (including rabbits); cows; sheep; goats; horses; pigs; and any other livestock, agricultural, laboratory or domestic mammals. The presently disclosed methods may be applied to stem cells from any non-human mammal, including but not limited to those described above.

In some embodiments, the PSC cells disclosed herein are mammalian embryonic stem cells (ESCs). The term "embryonic stem cell" (ES cell) as used herein refers to a pluripotent stem cell derived from the inner cell mass of a blastocyst, which is an early-stage preimplantation embryo. It is envisaged that such cells may express genes involved in the naive pluripotency network (Oct4/Nanog, Sox2, Klf4 etc). Such cells may also have Oct4 proximal enhancer activity. They may contribute to all embryonic tissues in chimeras. The ES cells may be derived from mammalian embryos, obtained from iPS cells or obtained from appropriate cell lines. Non-limiting examples of said stem cells include embryonic stem cells of a mammal or the like established by culturing a pre-implantation early embryo, embryonic stem cells established by culturing an early embryo prepared by nuclear-transplanting the nucleus of a somatic cell, induced pluripotent stem cells (iPS cells) established by transferring several different transcriptional factors to a somatic cell, and pluripotent stem cells prepared by modifying a gene on a chromosome of embryonic stem cells or iPS cells using a gene engineering technique. More specifically, embryonic stem cells include embryonic stem cells established from an inner cell mass that constitutes an early embryo, embryonic stem cells established from a primordial germ cell, cells isolated from a cell population possessing the pluripotency of pre-implantation early embryos (for example, primordial ectoderm), and cells obtained by culturing these cells.

As would be understood by a person of skill in the art, ES cells may be obtained from stem cell banks such as the UK stem cell bank from which you can acquire human stem cell lines for research. The Jackson Laboratory, US (who provide Jax mice) also stores and derives mouse ES cells which are available for purchase. It is preferred that the ES cells are obtained or are obtainable by a method that does not involve the destruction of human or non-human animal embryos.

In some, embodiments, the at least one extra-embryonic stem cell comprises a trophoblast stem cell and an inducible extra-embryonic endoderm stem cell. The extra-embryonic stem cells in the methods described herein can be either genetically intact or genetically modified and capable of growth and self-renewal. In some embodiments, these cells may be derived from mouse embryos. These cells are preferably self-renewing stem cells which represent the extraembryonic stem cell compartment of the early embryo.

The term "trophoblast stem cell" as used herein refers to stem cells derived from the trophoblast lineage of the embryo. The trophoblast stem cells are preferably not extra-embryonic cells derived from the two cell types which are precursors of the human placenta: the cytotrophoblast and the syncitiotrophoblast. These cells can be derived at late pre-implantation stages E4.5 or early post-implantation stages (E5.5) but the resulting cell lines are equivalent to the stem cell compartment existing in the extra-embryonic ecto-derm of the post-implantation mouse egg cylinder. Tran-scription factors such as Elf5, Eomes, and Tfap2C mark this lineage. TS cells can also be considered as cells that are the precursors of the differentiated cells of the placenta. In the mouse, TS cells can be derived from outgrowths of either blastocyst polar trophectoderm or extraembryonic ectoderm, which originates from polar trophectoderm after implanta-tion.

The term "extra-embryonic endoderm stem cell" (XEN stem cell) as used herein refers to stem cells derived from the extraembryonic endoderm of an embryo (e.g., a mouse embryo). The extraembryonic endoderm is typically a derivative of the hypoblast cells that migrate into the blas-tocyst cavity (beginning on day 8 of human embryonic development), and line the cavity, giving rise to the primary and definitive yolk sacs. The extraembryonic endoderm fills the remaining cavity of the blastocyst. In some embodi-ments, the XEN stem cells used herein comprise an induc-ible XEN stem cell capable of expressing a GATA transcrip-tion factor upon induction (e.g., by doxycycline treatment). In some embodiments, the XEN cells also be induced from ESCs by overexpression of PrE-specific genes, GATA tran-scription factor (e.g., Gata4/6) or Sox17, or by treatment with growth factors. In some embodiments, the XEN stem cells used herein are inducible XEN stem cells capable of expressing GATA4 upon induction.

In some embodiments, the mammalian pluripotent stem cell and the extra-embryonic stem cell are cultured in the first culture media for up to 4 to 5 days (e.g., 4 or 5 days). In some embodiments, step (a) is from embryonic day E0-E5.5. The PSCs can be mammalian embryonic stem cells (ESCs). The mammalian ESCs can be mouse ESCs. The ESCs and/or extra-embryonic stem cell can be genetically modified.

Synthetic Embryos at Different Developmental Stages

Provided herein include methods, compositions, and cul-ture medias for modeling mammalian embryo development by culturing stem cells including pluripotent stem cells (e.g., embryonic stem cells) and extra-embryonic stem cells. The methods, compositions and culture media disclosed herein can generate synthetic embryos through various develop-mental stages.

In some embodiments, the synthetic embryos generated using the methods and compositions described herein can reach a post-implantation (e.g., a post-implantation, pre-gastrulation stage). In some embodiments, the synthetic embryos generated herein can reach an early gastrulation stage. In some embodiments, the synthetic embryos gener-ated herein can reach a late gastrulation stage. In some embodiments, the synthetic embryos generated herein can reach an early neurulation stage. In some embodiments, the synthetic embryos generated herein can reach a late neuru-lation stage. In some embodiments, the synthetic embryos generated herein can reach an early organogenesis stage or beyond.

The embryo structures generated using the methods and culture medias described herein can comprise post-implan-tation embryos, e.g., post-implantation pre-gastrulation embryo structure. As used herein, the term "post implanta-tion pre gastrulation" in the context of a mammalian embryo (e.g., a mouse embryo) refers to an embryo following the implanting blastocyst stage and prior to the early gastrula-tion stage and is characterized by an egg cylinder-shape prior to symmetry breaking. An embryo of a post implan-tation pre gastrulation stage can be defined as Theiler stages TS7-TS8 (see Table 2). In some embodiments, the post-implantation, pre-gastrulation stage refers to E4.5-6.5, optionally, E4.5-6, optionally E5-6.5, optionally E5-5.5. In some embodiments, the post-implantation, pre-gastrulation stage refers to E5.5.

In some embodiments, the post-implantation, pre-gastru-lation embryo structure is generated by co-culturing a mam-malian pluripotent stem cell and at least one extra-embry-onic stem cell in a culture media (e.g., FC and/or IVC culture media) under a static condition allowing the mammalian pluripotent stem cell and the extra-embryonic stem cell to self-assemble into a post-implantation, pre-gastrulation embryo structure. The co-culturing of the mammalian pluripotent stem cell and the at least one extra-embryonic stem cell can be up to 4 or 5 days. The co-culturing of the mammalian pluripotent stem cell and the at least one extra-embryonic stem cell can be from embryonic day E0-E5.5.

Embryonic stage of a synthetic embryo structure gener-ated using the methods and culture medias disclosed herein can be assessed by comparing to an in vivo natural embryo counterpart at the same developmental stage by multiple ways including, but not limited to, morphology, length, weight, cell type compositions and expression of develop-mental marker genes (e.g., Oct4, Nanog, Sox2, Klf4, Cdx2, Gata4, Gata6, Brachyury, Otx2, Fgf5 and others described in the Examples and known in the art) using specific antibodies or primers, or transcriptional profiling, single-cell RNA sequencing and other methods as further described in the Examples section. In some embodiments, the post-implan-tation pre-gastrulation embryo structure resembles an E5.5 natural embryo structure. In some embodiments, the post-implantation pre-gastrulation embryo structure and an E5.5 natural embryo structure have similar morphology, cell type compositions, and gene expression features. In some embodiments, the post-implantation pre-gastrulation embryo structure comprises cavitated epithelial embryonic stem (ES) cell and trophoblast stem (TS) cell compartments enveloped by a VE-like layer (see, for example, FIG. 1A, E5.5/ETiX4).

In some embodiments, the embryo structures generated using the methods and culture medias described herein comprise post-implantation embryos, e.g., early gastrulation embryo structure. As used herein, the term "gastrulation" in the context of an embryo refers to an embryo following the expanded blastocyst stage and prior to the somitogenesis stage and is characterized by the formation of the primitive streak and epithelial to mesenchymal transition forming three germinal layers. The gastrulation process is generally considered as the process through which the bilaminar embryonic disc is changed into a trilaminar disc as an intraembryonic mesoderm appears between the ectoderm and endoderm. As used herein, the term "early gastrulation" in the context of a mammalian embryo (e.g., mouse embryo) refers to an embryo following the post-implantation pre-gastrulation stage and prior to a late gastrulation stage and is characterized by egg cylinder shape with the primitive streak at the posterior side. An embryo of an early gastrulation stage can be defined as Theiler stages TS8-TS10 (see Table 2). In some embodiments, the early gastrulation stage refers to E5-7.75, optionally E5-6.5, optionally E6.25-7.25, optionally 6.5-7.75, optionally E6.5-E7.5. In some embodiments, the early gastrulation stage refers to E6.5-E7.

In some embodiments, an early gastrulation embryo structure has a proamniotic cavity (resulting from the merger of cavities in the ES cell and TS cell compartments, a fully migrated AVE (as the boundary of the ES cell and TS cell compartments) and gastrulating. The gastrulation can be revealed by the epithelial-to-mesenchymal transition and formation of a cell layer between the ES cells and VE-like layers (see, for example, FIG. 1A, E6.5/ETiX5).

In some embodiments, culturing of an embryo structure from a post-implantation pre-gastrulation stage to an early gastrulation stage is achieved by culturing the embryo structure in a culture media (e.g., an IVC media, a post-implantation culture media, or both) for a suitable time period. In some embodiments, culturing of an embryo structure from a post-implantation pre-gastrulation stage to an early gastrulation stage is effected for at least one day (e.g., one, two or three days). In some embodiments, the culturing is from E5.5 to E6.6.

In some embodiments, the gastrulating embryo structures generated using the methods and culture medias described herein resemble natural gastrulating embryos. In some embodiments, the synthetic gastrulating embryos and natural gastrulating embryos have similar morphology, cell type compositions, and gene expression features.

In some embodiments, culturing of a post-implantation pre-gastrulation embryo structure to its early gastrulation stage is continued allowing the post-implantation embryo structure to develop into a late gastrulation stage or to complete gastrulation. As used herein, the term "late gastrulation stage" in the context of a mammalian embryo (e.g., a mouse embryo) refers to an embryo following the early gastrulation stage and prior to the early somite stage and is characterized by an egg cylinder-shaped embryo with differentiated definitive endoderm, mesoderm and ectoderm layers. An embryo of a late gastrulation stage can be defined as Theiler stages TS10-TS11 (see Table 2). In some embodiments, a late gastrulation stage can correspond to E6.5-8, optionally E6.5-7.75, optionally E7.25-8, optionally E7-8.

In some embodiments, culturing of a post-implantation embryo structure is continued allowing the post-implantation embryo structure to develop through and beyond gastrulation to neurulation. Neurulation is typically considered as an embryo developmental process which begins when the notochord induces the formation of the central nervous system by signaling the ectoderm germ layer above it to form the thick and flat neural plate. The neural plate folds in upon itself to form the neural tube that will later differentiate into the brain and the spinal cord of the central nervous system. A neurulating embryo generated herein can be an embryo resembling any of a series of morphological phases during the neurulation process. A neurulating embryo generated herein can be at the early neurulation stage, in the middle of the neurulation stage, or at the late neurulation stage.

In some embodiments, the neurulating embryo structure is generated by culturing a post-implantation embryo structure (e.g., a post-implantation pre-gastrulation embryo structure) in a culture media (e.g., a post-implantation culture media) under a condition (e.g., a static condition) allowing the post-implantation embryo structure to develop into a neurulating embryo structure. In some embodiments, culturing of the post-implantation embryo structure can be up to 3 days. In some embodiments, culturing of the post-implantation embryo structure can be from E5.5 to E8.0.

In some embodiments, the neurulating embryo structures generated using the methods and culture medias described herein resemble natural neurulating embryos. In some embodiments, the synthetic neurulating embryos and natural neurulating embryos have similar morphology, cell type compositions, and gene expression features.

In some embodiments, the neurulating embryo structure resembles an E7-9 natural embryo structure, optionally an E7.5-8.5 natural embryo structure, optionally an E7.5-8 natural embryo structure. In some embodiments, neurulating embryo structures generated herein display an anterior-posterior axis with bifurcating neural folds extending into a neural tube and culminating in a tail bud, a morphology that resembles the early headfold stage of an E8.0 natural embryo. Posterior to this, the tail bud joins with allantois tissue which connects to a developing chorion (see e.g., FIG. 1C). In some embodiments, the embryoid, allantois and chorion are contained in a fluid-filled sac, which is equivalent to the yolk sac. In some embodiments, the neurulating embryo structure generated herein and a corresponding natural embryo counterpart display a largely conserved distribution of cells between the different germ layers of the epiblast (ectoderm, mesoderm and endoderm) and between embryonic and extraembryonic lineages.

In some embodiments, the neurulating embryo structure generated herein can express neuroectodermal and surface ectoderm markers including, but not limited to, Sox1, Sox2, Pax6, Pax3, Foxa2, Chordin, Shh, OTX2, FOXG1, PAX6, OLIG2, NKX2-2, SOX10, Brachyury, and others identifiable by a skilled person. The neurulating embryo can comprise a portion of SOX1-positive neural tube tissue culminated in two neural folds whereas the SOX1-negative, Brachyury-positive posterior exhibited a tail bud-like morphology. The neurulating embryo can have a Brachyury-positive notochord running below the neural tube.

In some embodiments, the neurulating embryo structure generated herein comprises cells expressing markers of the hindbrain and spinal cord, prosencephalon, mesencephalon and midbrain-hindbrain boundary, including for example Ets1, Sox10, Fezf1, Lhx2, Sx3, En1 and Dmbx1.

In some embodiments, the neurulating embryo structure can further develop into an embryo of somite stage or at a somitogenesis (e.g., from a late gastrulation and/or a neurulating stage to an early somite stage). As used herein, the term "somitogenesis" in the context of a mammalian embryo (e.g., mouse embryo) refers to an embryo following late gastrulation stage and prior to the early organogenesis stage and is characterized by the appearance of the first one to five somites distinguishable by bright field microscopy. An embryo of an early somite stage can be defined as Theiler stages TS12-TS13 (see Table 2). In some embodiments, early somitogenesis refers to E7.5-9.25, optionally E7.5-

8.75, optionally E8-9.25, optionally E8-9. In some embodiments, early somite stage refers to E8.5.

In some embodiments, the synthetic embryo structure described herein comprise cells expressing markers such as NKX2-5, GATA4, and/or MYH2, and/or having gene expression signatures leading to somite formation. The neurulating embryo structure can express cardiomyocyte markers such as troponin genes and myosin genes.

In some embodiments, the method can comprise culturing a neurulating embryo structure for at least one day (e.g., one, two, three, four or more days) under a dynamic condition in a culture chamber allowing the neurulating embryo structure to develop into a synthetic embryo of an organogenesis stage. In some embodiments, the method comprises culturing an embryo (e.g., mouse embryo) at a somitogenesis to organogenesis stage in a dynamic condition under conditions that allow the embryo to develop into organogenesis stage and beyond. In some embodiments, the organogenesis stage is an early organogenesis stage. The term "early organogenesis" in the context of a mammalian embryo (e.g., mouse embryo) refers to an embryo following the somitogenesis stage and prior to the appearance of the heart beat stage and is characterized by formation of the neural tube and mesoderm migration. In some embodiments, the early organogenesis stage refers to E8-9, optionally E8-8.5, optionally E8.5 of a natural embryo. A synthetic embryo at the early organogenesis stage can demonstrate development of definitive endoderm, which gives rise to the gut and associated organs. The presence of foregut and hindgut pockets can be observed in a synthetic embryo at the early organogenesis stage. In some embodiments, the embryoid development described herein can proceed further beyond the early organogenesis stage in culture.

In some embodiments, the synthetic embryo has developing somites and primordial germ cells. The synthetic embryo generated herein can have established brain regions, a neural tube, a beating heart, and/or a gut tube. The synthetic embryo generated herein can display one or more of the following features: headfolds with defined forebrain and midbrain regions, a beating heart-like structure, a trunk comprising a neural tube and somites, a tail bud containing neuromesodermal progenitors, a gut tube, and/or primordial germ cells.

Culturing an embryo cell in vitro from stem cells (e.g., a mammalian pluripotent stem cell and at least one extra-embryonic stem cell) can be effected until reaching early organogenesis or any developmental stage therein-between. In some embodiments, culturing a synthetic embryo in vitro can be continued allowing the synthetic embryo at the early organogenesis to develop onwards.

In some embodiments, the synthetic embryos generated using the methods and culture conditions described herein are mammalian embryos. In some embodiments, the mammalian embryos are non-human embryos, such as mouse embryos or rabbit embryos. In some embodiments, the mammalian embryos are human embryos.

Culturing conditions mentioned above for generating synthetic embryos at different developmental stages, including media, type, pressure, oxygen concentrations and the like, are described in the sections below as well as in specific embodiments of mouse embryos in the Examples section.

Embryonic stages of the synthetic embryos described herein can be assessed compared to an in vivo or natural embryo counterpart at the same developmental stage by multiple ways including, but not limited to, morphology, length, weight, weight, expression of developmental marker genes using specific antibodies or primers, transcriptional profiling and the like, as further described hereinbelow and in the Examples section.

Morphology assessment of embryonic development can be performed by previously established morphological features such as described in Carnegie stages of development (see, for example, Table 1; Developmental stages in human embryos. R. O'Rahilly and F. Müller (eds), Carnegie Institution of Washington, Washington, DC, 1987), in Theiler stages of development (see, for example, Table 2; www.e-mouseatlas.org) or according to embryonic days.

In some embodiments, one or more developmental markers as described herein can be used to assess the developmental stage of a synthetic embryo structure. Numerous methods exist in the art for detecting the presence, absence, or amount of a marker gene product (e.g., mRNA and/or protein), as well as its localization in an embryo structure or subcellular localization (e.g., nucleus and/or cytoplasm). Marker expression may be assessed by any of a wide variety of well-known methods for detecting expression of a transcribed molecule or a protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification and sequencing methods.

In some embodiments, activity of a particular gene is characterized by a measure of gene transcript (e.g., mRNA), by a measure of the quantity of translated protein, or by a measure of gene product activity. Marker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In another embodiment, detecting or determining expression levels of a marker and functionally similar homologs thereof, including a fragment or genetic alteration thereof (e.g., in regulatory or promoter regions thereof) comprises detecting or determining RNA levels for the marker of interest. In some embodiments, one or more cells from the synthetic embryo structure can be obtained and RNA is isolated from the cells. In some embodiments, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated. It is also be possible to obtain cells from, e.g., the synthetic embryo cells and culture the cells in vitro, such as to obtain a larger population of cells from which RNA can be extracted. Methods for establishing cultures of non-transformed cells, i.e., primary cell cultures, are known in the art. In some embodiments, cells can be dissociated (e.g., by enzymatic or mechanical means), and isolated by methods known in the art (e.g., Fluorescence-Activated Cell Sorting, Microfluidics, etc.)

When isolating RNA from, e.g., synthetic embryo structures at various developmental stages and/or cells comprising said synthetic embryo structures, it may be important to prevent any further changes in gene expression after the tissue or cells has been removed from the subject. Changes in expression levels are known to change rapidly following perturbations, e.g., heat shock or activation with lipopoly-saccharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from cells by a variety of methods, e.g., the guanidium thiocyanate lysis followed by CsCl centrifugation. Methods for obtaining RNA from single-cells are also known in the art. The RNA sample can then be enriched in particular species. In some embodiments, poly (A)+ RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand Island, N.Y.). In some embodiments, the RNA population is enriched in marker sequences. Enrichment can be undertaken, e.g., by primer-specific cDNA synthesis, or multiple rounds of linear amplification based on cDNA synthesis and template-directed in vitro transcription.

The population of RNA, enriched or not in particular species or sequences, can further be amplified. As defined herein, an "amplification process" increases the number of copies of a polynucleotide (e.g., RNA). For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope of the disclosed methods to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). Real time PCR may also be used. Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., Science 241, 1077 (1988)); self-sustained sequence replication (SSR) (see, e.g., Guatelli et al., Proc. Nat. Acad. Sci. USA, 87, 1874 (1990)); and transcription amplification (see, e.g., Kwoh et al., Proc. Natl. Acad. Sci. USA 86, 1173 (1989)). Many techniques are known in the state of the art for determining absolute and relative levels of gene expression, commonly used techniques suitable for use in the disclosed methods include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used. In some embodiments, the probe is labeled with a fluorescence moiety.

Alternatively, mRNA expression can be detected on a DNA array, chip or a microarray. Labeled nucleic acids of a test sample obtained from a subject may be hybridized to a solid surface comprising marker DNA. Positive hybridization signal is obtained with the sample containing marker transcripts. Methods of preparing DNA arrays and their use are well known in the art (see, e.g., U.S. Pat. Nos. 66,186, 796; 6,379,897; 6,664,377; 6,451,536; 548,257; U.S. 20030157485). Serial Analysis of Gene Expression (SAGE) can also be performed (See for example U.S. Patent Application 20030215858). In some embodiments, next generation sequencing (e.g., RNA-seq) can be used to analyze total mRNA expression from one (e.g., single-cell RNA-seq) or more cells. A nucleic acid target molecule labeled with a barcode (for example, an origin-specific barcode) can be sequenced with the barcode to produce a single read and/or contig containing the sequence, or portions thereof, of both the target molecule and the barcode. Exemplary next generation sequencing technologies include, for example, Illumina sequencing, Ion Torrent sequencing, 454 sequencing, SOLiD sequencing, and nanopore sequencing amongst others. Methods for constructing sequencing libraries are known in the art.

The single cell sequencing can be high-throughput single cell RNA sequencing. In certain embodiments, the single cell sequencing is a low cost high-throughput single cell RNA sequencing. Not being bound by any particular theory, the single cell RNA sequencing is capable of efficiently and cost effectively sequencing thousands to tens of thousands of single cells. In certain embodiments, single cell RNA sequencing comprises pairing single cells in droplets with oligonucleotides for reverse transcription, wherein the oligonucleotides are configured to provide cell-of-origin specific barcodes uniquely identifying transcripts from each cell and a unique molecular identifier (UMI) uniquely identifying each transcript. In certain embodiments, single cell RNA sequencing comprises pairing single cells in droplets with single microparticle beads coated with oligonucleotides for reverse transcription, wherein the oligonucleotides contain a bead-specific barcode uniquely identifying each bead and a unique molecular identifier (UMI) uniquely identifying each primer. In some aspects of the disclosure, unbiased classifying of cells in a biological sample comprises sequencing the transcriptomes of thousands of cells, preferably tens of thousands of cells (e.g., greater than 1000 cells, or greater than 10,000 cells).

The activity or level of a lineage marker protein can be detected and/or quantified by detecting or quantifying the expressed polypeptide. The polypeptide can be detected and quantified by any of a number of means well known to those of skill in the art. Any method known in the art for detecting polypeptides can be used. Such methods include, but are not limited to, immunodiffusion, immunoelectrophoresis, radio-immunoassay (RIA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like.

Described below are non-limiting examples of techniques that may be used to detect marker protein according to a practitioner's preference based upon the present disclosure. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Anti-marker protein antibodies (unlabeled) are then brought into contact with the support and assayed by a secondary immunological reagent, such as labeled protein A or anti-immunoglobulin (suitable labels including $^{125}$I, horseradish peroxidase, alkaline phosphatase, fluorophore). Chromatographic detection may also be used.

Immunohistochemistry may be used to detect expression of marker protein. A suitable antibody is brought into contact with, for example, a thin layer of cells, washed, and then contacted with a second, labeled antibody. Labeling may be by fluorescent markers, enzymes, such as peroxidase, avidin, or radiolabelling. The assay is scored visually, using microscopy. Anti-marker protein antibodies, such as intrabodies, can also be used for imaging purposes, for example, to detect the presence of marker protein in cells or, e.g., an embryo. Suitable labels include radioisotopes, iodine ($^{125}$I, $^{121}$I), carbon ($^{14}$C), sulphur ($^{35}$S), tritium ($^{3}$H), indium ($^{112}$In), and technetium ($^{99}$mTc), fluorescent labels, such as fluorescein and rhodamine, and biotin. Antibodies that may be used to detect marker protein include any antibody, whether natural or synthetic, full length or a fragment thereof, monoclonal or polyclonal, that binds sufficiently strongly and specifically to the marker protein to be detected. An antibody may have a $K_d$ of at most about $10^{-6}$M, $10^{-7}$M, $10^{-8}$M, $10^{-9}$M, $10^{-10}$M, $10^{-11}$M, $10^{-12}$M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to the marker protein relative to other proteins, such as related proteins.

Antibodies are commercially available or may be prepared according to methods known in the art. Antibodies and derivatives thereof that may be used encompass polyclonal or monoclonal antibodies, chimeric, human, humanized, primatized (CDR-grafted), veneered or single-chain antibodies as well as functional fragments, i.e., marker protein binding fragments, of antibodies. For example, antibody fragments capable of binding to a marker protein or portions thereof, including, but not limited to, Fv, Fab, Fab' and F(ab') 2 fragments can be used. Such fragments can be produced by enzymatic cleavage or by recombinant techniques. For example, papain or pepsin cleavage can generate Fab or F(ab') 2 fragments, respectively. Other proteases with the requisite substrate specificity can also be used to generate Fab or F(ab') 2 fragments. Antibodies can also be produced in a variety of truncated forms using antibody genes in which one or more stop codons have been introduced upstream of the natural stop site. For example, a chimeric gene encoding a F(ab') 2 heavy chain portion can be designed to include DNA sequences encoding the CH₁ domain and hinge region of the heavy chain. In some embodiments, agents that specifically bind to a marker protein other than antibodies are used, such as peptides. Peptides that specifically bind to a marker protein can be identified by any means known in the art. For example, specific peptide binders of a marker protein can be screened for using peptide phage display libraries.

Substrates for Culturing Synthetic Embryos

In some embodiments, the mammalian pluripotent stem cell and the extra-embryonic stem cell, the post-implantation embryo, the gastrulating embryo, the neurulating embryo and/or other synthetic embryos described herein are cultured in a substrate. In some embodiments, the method comprises transferring the embryo from one substrate to another substrate. The substrates used in the methods disclosed herein can be the same or different. For example, the mammalian pluripotent stem cell and the extra-embryonic stem cell can be cultured in a first substrate to form a post-implantation pre-gastrulation embryo structure. The post-implantation pre-gastrulation embryo can be transferred to a second substrate to develop into a neurulating embryo. The neurulating embryo can be transferred to a third substrate to develop into a synthetic embryo of another developmental stage. The first substrate, second substrate and third substrate can be a same type or different types. In some embodiments, the first substrate, second substrate and third substrate are of different types. For example, the first substrate and the second substrate can be a microwell plate comprising inverted pyramidal microwells and the third substrate can be a rotating bottle culture unit such as a rotating incubator.

The substrate as used herein can comprise a dish, a U-plate, a flask, or a microwell plate. The microwell plate can comprise inverted pyramidal microwells. The size (e.g., depth and/or diameter) of each of the inverted microwells can vary. Each of the inverted-pyramidal microwells can be about 400 μm or about 800 μm in size. Each of the inverted-pyramidal microwells can be about 400 μm or about 800 μm in diameter. In some embodiments, each of the inverted pyramidal microwells can be about 100, 200, 300, 400, 500, 600, 700, 800, 900 μm, 1 mM in size and/or diameter, or a number or a range between any two of these values. Each microwell (e.g., receptacle) may have a depth of about 250 μm to about 400 μm, e.g. about 300 μm to about 350 sm. Additionally or alternatively, said plurality of receptacles may have a mean depth of about 250 μm to about 400 μm, e.g. about 300 μm to about 350 μm. Especially when the receptacles are wells, they may be ordered on the substrate in an array, i.e. in a grid pattern having regular spacing in substantially orthogonal directions. Whatever the topography of the substrate, the substrate may carry one or more embryos. Where the substrate comprises one or more receptacles, each said receptacle may independently contain one or more embryos, e.g. 2, 3, 4 or 5 embryos, or more. In some embodiments, each embryo structure is located in a different respective well. In alternative embodiments, each receptacle comprises a plurality embryos, e.g. 2, 3, 4 or 5 embryos, or more.

The methods disclosed herein can be applied in culture volumes of any appropriate size. For example, the culture volume per embryo may be about 50 μl to about 10 ml, optionally about 100 μl to about 5 ml, optionally about 250 μl to about 5 ml, optionally about 1 ml to about 5 ml. The culture volume per embryo may be about 100, 150, 200, 250, 300, 350, 400, 450, 500, 550, 600, 650, 700, 750, 800, 850, 900, 950, 1000, 1500, 2000 μl, or more.

Conditions for Culturing Synthetic Embryos

The stem cells and/or embryos can be cultured in a static condition or a dynamic condition. In some embodiments, the stem cells and/or embryos herein described are cultured in a static condition. As used herein, the term "static condition" refers to a cell culture condition that is carried out without agitation of the culture. For example, the mammalian pluripotent stem cell and the extra-embryonic stem cell can be cultured under a first static condition in a static incubator to form a post-implantation embryo (e.g., a post-implantation pre-gastrulation embryo) for a certain time period (e.g., 1, 2, 3, 4 or more days). The post-implantation embryo can be cultured under a second static condition in a static incubator to develop into a neurulating embryo for a certain time period (e.g., 1, 2, 3 or more days). The first static condition and the second static condition can be the same or different. For example, different culture medias may be used for the two (or more) static conditions. The stem cells and embryos can be cultured under static conditions for 1, 2, 3, 4, 5, 6, 7 or more days. In some embodiments, the stem cells and/or embryos are cultured under a static condition for up to 7 days. In some embodiments, the stem cells and/or embryos are cultured under a static condition from E0 to E8.0.

In some embodiments, the methods comprise culturing in a static condition followed by a dynamic condition. Accordingly, the methods disclosed herein comprises culturing the embryos (e.g., neurulating embryos) under a dynamic condition in a culture chamber. As used herein, the term "dynamic condition" refers to a cell culture condition that is carried out with agitation (e.g., suspension agitation), including but not limited to rotating, rolling, shaking, inverting, of the culture. Non-limiting examples of dynamic cultures or dynamic culture conditions include a roller culture (a culture on a rolling device), a shaker culture (a culture on a shaker, e.g. orbital shaker), or other dynamic cultures identifiable to a person skilled in the art.

In some embodiments, the dynamic condition comprises providing a plurality of gases to the culture chamber. The plurality of gases can comprise $O_2$, $N_2$, $CO_2$, $H_2$, $H_2O$, or a combination thereof. In some embodiments, a mixture of gases is provided into a rotating culture chamber containing one or more embryos. In some embodiments, the dynamic condition comprises a gas pressure of about 0.5 to about 3 pounds per square inch (psi) in the culture chamber. In some embodiments, the gas pressure in the culture chamber is less than the sea level atmospheric pressure. For example, the gas pressure in the culture chamber is about 0.5 to less than 1 psi. In some embodiments, the gas mixture is delivered to the culture chamber at about 0.5 psi.

In some embodiments, the dynamic condition comprises supplying oxygen at a constant concentration to the culture chamber. In some embodiments, the oxygen is supplied to the culture chamber at an increasing concentration. The oxygen concentrations can be increased throughout the culturing starting from 5% up to 6%, 7%, 8%, 9%, 10%, 11%, 12%, 13%, 14%, 15%, 16%, 17%, 18%, 19%, 20%, 21%, 22%, 23%, 24%, 25% or higher at any suitable time interval (e.g., daily intervals). In some embodiments, the oxygen concentration is incrementally increased from about 5% to about 13% to about 18% to about 21% at daily intervals. In some embodiments, the culture chamber can have an atmosphere comprising an increasing oxygen concentration from about 5% to about 25% oxygen level, optionally from about 5% to about 13%, optionally from 13% to about 18%, optionally from about 18% to about 21%. In some embodiments, the increasing is effected by 1.5-2.5 fold or 1.5-2 fold in every step of the increasing. In some embodiments, the oxygen level in the culture chamber is less than 30%. In some embodiments, the dynamic condition used in culturing the neurulating embryos does not comprise decreasing the oxygen concentration throughout the culturing. In some embodiments, the increasing of oxygen concentration is effected every 0.5-2 days, every 0.5-1.5, every 1-2, or every 1-1.5 days of the culturing. In some embodiments, the increasing is effected every 20-28 hours of the culturing. In some embodiments, the increasing is effected at daily intervals.

The neurulating embryo can be cultured under a dynamic condition described herein for at least one day (e.g., 1, 2, 3, 4 or more days). In some embodiments, the neurulating embryos are cultured under a dynamic condition from E8.0 to at least E8.5 (e.g., E8.5, E9, or higher). In some embodiments, the neurulating embryo can be cultured under a dynamic condition in a culture chamber for at least one day to develop into a synthetic embryo of at least early organogenesis stage.

Culture Medias for Culturing Synthetic Embryos

In some embodiments, the method comprises co-culturing the mammalian pluripotent stem cell and the extra-embryonic stem cell in a feeder cell (FC) media, optionally passaging the mammalian pluripotent stem cell and the extra-embryonic stem cell in the feeder cell media at least two times (e.g., 2, 3, 4 or more times). The mammalian pluripotent stem cell and the extra-embryonic stem cell can be cultured in the FC media for 1, 2, 3, or 4 days. In some embodiments, the mammalian pluripotent stem cell and the extra-embryonic stem cell are cultured in the FC media for about 2 days.

In some embodiments, the method comprises co-culturing mammalian pluripotent stem cell and the extra-embryonic stem cell in an in vitro culture (IVC) media, optionally following culturing the mammalian pluripotent stem cell and the extra-embryonic stem cell in the FC media. The mammalian pluripotent stem cell and the extra-embryonic stem cell can be cultured in the IVC media for 1, 2, 3, or 4 days. In some embodiments, the mammalian pluripotent stem cell and the extra-embryonic stem cell are cultured in the IVC media for about 2 days, optionally following culturing in the FC media for about 2 days.

In some embodiments, the method comprises partially replacing a quantity of a FC media (e.g., at least half of the media) with a refresh FC media or an IVC media. The replacement can occur every 20-28 hours of the culturing (e.g., every 24 hours). In some embodiments, the method comprises partially replacing a quantity of an IVC media (e.g., at least half of the media) with a refresh IVC media.

In some embodiments, the method comprises culturing the post-implantation embryo structure in a second culture media under a second static condition allowing the post-implantation embryo structure embryo structure to develop into a neurulating embryo structure. The second culture media is a post-implantation culture media capable of supporting the development of an embryo ex utero. The post-implantation embryo structure can be cultured in the post-implantation culture media for up to 3 or more days (e.g., 1, 2, 3 or more days). The volume of the culture media can be increased every 20-28 hours (e.g., every 24 hours) by feeding the embryos with an amount of fresh culture media (e.g., 200-500 µl per embryo). In some embodiments, the method comprises culturing the neurulating embryo structure under a dynamic condition in the same post-implantation culture media. In some embodiments, the post-implantation culture media contains human cord serum. In some embodiments, the post-implantation culture media contains bicarbonate or HEPES.

The culture media disclosed herein can comprise a basal culture medium. The basal medium may comprise water, salts, amino acids, a carbon source, vitamins, lipids and a buffer. Suitable carbon sources may be assessed by one of skill in the art from compounds such as glucose, sucrose, sorbitol, galactose, mannose, fructose, mannitol, maltodextrin, trehalose dihydrate, and cyclodextrin. The basal culture medium can comprise Dulbecco's Modified Eagle Medium (DMEM), DMEM Nutrient Mixture 12 (DMEM/F12), a non-human serum or serum substitute thereof, an antibiotic, L-glutamine or an analogue thereof (e.g., GlutaMAX™), or any combination thereof.

The non-human serum or serum substitute can comprise fetal bovine serum, bovine serum albumin, rat serum, KnockOut™ Serum Replacement, or any combination thereof. The antibiotic can comprise Penicillin-streptomycin, Amphotericin B, Ampicillin, Erythromycin, Gentamycin, Kanamycin, Neomycin, Nystatin, Polymyxin B, Tetracycline, Thiabendazole, Tylosin, or any combination thereof. In some embodiments, the culture media (e.g., FC media and IVC media) comprises a reducing agent. The reducing agent can comprise beta-mercaptoethanol (BME), N-acetyl-L-cysteine, dithiothreitol (DTT), or any combination thereof.

The concentration or amount of one or more of the components in a solution or media can vary. The amount of, e.g., the non-human serum or serum substitute thereof, antibiotic, reducing agent, and/or L-glutamine (e.g., GlutaMax™) can vary, and, in some embodiments, can be adjusted as needed by one of skill in the art. In some embodiments, the amount of non-human serum or serum substitute thereof can comprise about 0.01% to about 40$^1$% (e.g., about 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, or a number or a range between any two of these values) volume per volume (% v/v), weight per volume (% w/v) or weight per weight (% w/w) of the medium. In some embodiments, the amount of antibiotic can comprise about 0.01% to about 10% (e.g., about 0.01%, 0.1%, 1%, 2%, 3%, 4%, 5%, 6%, 7%, 8%, 9%, 10% or a number or a range between any two of these values) volume per volume (% v/v), weight per volume (% w/v) or weight per weight (% w/w) of the medium. The amount of e.g., the reducing agent can vary. For example, in some embodiments, the concentration of the reducing agent in the composition can be about 0.1 μM to about 1 mM (e.g., about 0.1, 0.2, 0.3, 0.4, 0.5, 0.6, 0.7, 0.8, 0.9, 1, 10, 100, 200, 300, 400, 500, 600, 700, 800, 900 μM, 1 mM, or a number or a range between any two of these values). The amount of L-glutamine (e.g., Gluta-MAX™) can vary. For example, in some embodiments, the concentration of L-glutamine in the culture media can be about 0.1 mM to about 40 mM, about 0.2 mM to about 20 mM, about 0.5 mM to about 10 mM, about 1 mM to about 5 mM or about 1.5 mM to about 2.5 mM e.g., about 2 mM. Where percentages are provided for agents, ingredients and compounds, they can be % w/w, % w/v or % v/v with respect to the formulation as a whole, unless otherwise indicated.

Each component of the culture medium described herein may be present in an amount such that the culture medium is suitable for supporting the self-assembly of stem cells into a post-implantation embryo structure and/or further development of the post-implantation embryo structure. In some embodiments, the post-implantation embryo structure is a gastrulating embryo structure. In some embodiments, the post-implantation embryo structure is at a pre-gastrulation stage.

In the in vitro culture medium embodiments defined herein, the culture medium may be free, substantially free or essentially free of one or more of an epidermal growth factor (EGF) receptor agonist or an analogue thereof, such as EGF or an EGF substitute; a fibroblast growth factor family (FGF) receptor agonist or an analogue thereof, such as FGF or an FGF substitute; a Leukemia Inhibitory Factor (LIF) receptor agonist or an analogue thereof, such as LIF or a LIF substitute; a Bone Morphogenic Protein (BMP) receptor agonist or an analogue thereof, such as a BMP, or a BMP substitute; a WNT receptor agonist or an analogue thereof, such as WNT or a WNT substitute. The culture medium further may be free, substantially free or essentially free of a TGFβ receptor agonist or an analogue thereof. Unless otherwise indicated, the culture medium further may be free, substantially free or essentially free of nodal, activin, stem cell factor or members of the hedgehog family of proteins.

The stem cells described herein, e.g., the mammalian pluripotent stem cell and the at least one extra-embryonic stem cell, can be individually cultured prior to the co-culturing described herein in a suitable culture media described, for example, in U.S. Publication No. 2022/0308041, the content of which is incorporated herein by reference in its entirety.

The culture medium described herein may contain other components, or analogues thereof. As used herein, the term "analogue" can refer to a biologically active analogue of any of the components of the culture medium. Such an analogue may be natural or synthetic.

The specific biologically active ligands and compounds used in the media defined herein, such as insulin, progesterone, etc. are used for illustrative purposes. However, one of skill in the art will readily recognize that analogues of such ligands and compounds may equally be used as alternatives, provided that they retain the relevant biological activity. One of skill in the art will be able to identify, in a routine manner, other biologically active compounds that are suitable for use as substitutes. For instance, these may be naturally occurring compounds or compounds which can be made by synthetic or semi-synthetic methods.

In some embodiments, a FC media can further comprise an effective amount of sodium pyruvate, such as, for example, at a concentration of about 0.05 mM to about 20 mM (e.g., about 0.05, 0.1, 0.2, 0.3, 0.4, 0.5, 1, 1.5, 2, 2.5, 3, 3.5, 4, 4.5, 5, 6, 7, 8, 9, 10, 11, 12, 13, 14, 15, 16, 17, 18, 19, 20 mM or a number or a range between any two of these values). In some embodiments, the FC media comprises about 1 mM sodium pyruvate.

The FC media can also comprise an effective amount of an amino acid selected from the group comprising L-glycine, L-alanine, L-asparagine, L-aspartic acid, L-glutamic acid, L-proline and L-serine. The non-essential amino acids can have an effective amount of, for example, about 0.1% to about 2% (e.g., about 0.1%, 0.2%, 0.3%, 0.4%, 0.5%, 1%, 1.1%, 1.2%, 1.3%, 1.4%, 1.5%, 1.6%, 1.7%, 1.8%, 1.9%, 2%, or a number or a range between any two of these values) volume per volume (% v/v), weight per volume (% w/v) or weight per weight (% w/w) of the medium. In some embodiments, the FC media comprises about 1% non-essential amino acids. Non-essential amino acids may be included in the culture medium, for example, comprising glycine (about 1 mg/ml to about 25 mg/ml or about 5 mg/ml to about 10 mg/ml e.g., about 7.5 mg/ml), L-alanine (about 1 mg/ml to about 25 mg/ml or about 5 mg/ml to about 10 mg/ml e.g., about 9 mg/ml), L-asparagine (about 5 mg/ml to about 30 mg/ml or about 10 mg/ml to about 15 mg/ml e.g., about 13.2 mg/ml), L-aspartic acid (about 5 mg/ml to about 30 mg/ml or about 10 mg/ml to about 15 mg/ml e.g., about 13 mg/ml), L-glutamic acid (about 5 mg/ml to about 50 mg/ml or about 10 mg/ml to about 20 mg/ml e.g., about 15 mg/ml), L-proline (about 5 mg/ml to about 30 mg/ml or about 10 mg/ml to about 15 mg/ml e.g., about 11 mg/ml) and/or L-serine (about 5 mg/ml to about 30 mg/ml or about 10 mg/ml to about 15 mg/ml e.g., about 11 mg/ml). In some embodiments, culture medium may comprise L-glycine at a concentration of about 7.5 mg/ml, L-alanine at a concentration of about 9 mg/ml, L-asparagine at a concentration of about 13 mg/ml, L-aspartic acid at a concentration of about 13 mg/ml, L-glutamic acid at a concentration of about 14.5 mg/ml, L-proline at a concentration of about 11.5 mg/ml and L-serine at a concentration of about 10.5 mg/ml.

The non-human serum in the FC media can vary. In some embodiments, the FC media can comprise a non-human serum (e.g., fetal bovine serum) at about 5% to about 40% (e.g., 5%, 10%, 11%, 12%, 13%, 14%, 15%, 16%, 17%, 18%, 19%, 20%, 21%, 22%, 23%, 24%, 25%, 26%, 27%, 28%, 30%, 31%, 32%, 33%, 34%, 35%, 36%, 37%, 38%, 39%, 40%, or a number or a range between any two of these values) volume per volume (% v/v), weight per volume (% w/v) or weight per weight (% w/w) of the medium. In some embodiments, the FC media comprises about 15% to about 20% non-human serum (e.g., fetal bovine serum). In some embodiments, the FC media comprises about 15% fetal bovine serum. In some embodiments, the FC media comprises about 20% fetal bovine serum.

The FC media can comprise an effective amount of L-glutamine or an analogue thereof. L-glutamine may be included in the culture medium at a concentration of about 0.1 mM to about 40 mM, about 0.2 mM to about 20 mM, about 0.5 mM to about 10 mM, about 1 mM to about 5 mM or about 1.5 mM to about 2.5 mM e.g., about 2 mM. In some embodiments, L-glutamine is included in the FC medium at a concentration of about 2 mM.

The FC media can comprise an effective amount of a reducing agent. In some embodiments, the concentration of the reducing agent in the FC media can be about 0.1 μM to about 1 mM (e.g., about 0.1, 0.2, 0.3, 0.4, 0.5, 0.6, 0.7, 0.8, 0.9, 1, 10, 100, 200, 300, 400, 500, 600, 700, 800, 900 μM, 1 mM, or a number or a range between any two of these values). In some embodiments, the reducing agent is included in the FC media at a concentration of about 0.1 mM. In some embodiments, the FC media comprises P-mercaptoethanol (BME) at a concentration of about 0.1 mM.

In some embodiment, the FC media comprises an effective amount of an inhibitor of rho-associated protein kinase (ROCK) (also referred to herein as ROCK inhibitor). Exemplary ROCK inhibitors include, but are not limited to N-[(1S)-2-Hydroxy-1-phenylethyl]-N'-[4-(4-pyridinyl)phenyl]-urea (AS1892802), fasudil hydrochloride (also known as HA 1077), -[3-[[2-(4-Amino-1,2,5-oxadiazol-3-yl)-I-ethyl-1H-imidazo[4,5-c]pyridin-6-yl]oxy]phenyl]-4-[2-(4-morpholinyl)ethoxy]benzamide (GSK269962), 4-[4-(Trifluoromethyl)phenyl]-N-(6-Fluoro-1H-indazol-5-yl)-2-methyl-6-oxo-1,4,5,6-tetrahydro-3-pyridinecarboxamide (GSK 429286), (S)-(+)-2-Methyl-1-[(4-methyl-5-isoquinolinyl)sulfonyl]-hexahydro-1H-1,4-diazepine dihydrochloride (H 1152 dihydrochloride), (S)-(+)-4-Glycyl-2-methyl-1-[(4-methyl-5-isoquinolinyl)sulfonyl]-hexahydro-1H-1,4-diazepine dihydrochloride (glycyl-H 1152 dihydrochloride), N-[(3-Hydroxyphenyl)methyl]-N'-[4-(4-pyridinyl)-2-thiazolyl]urea dihydrochloride (RKI 1447 dihydrochloride), (3S)-1-[[2-(4-Amino-1,2,5-oxadiazol-3-yl)-1-ethyl-1H-imidazo[4,5-c]pyridin-7-yl]carbonyl]-3-pyrrolidinamine dihydrochloride (SB772077B dihydrochloride), N-[2-[2-(Dimethylamino)ethoxy]-4-(1H-pyrazol-4-yl)phenyl-2,3-dihydro-1,4-benzodioxin-2-carboxamide dihydrochloride (SR 3677 dihydrochloride), and trans-4-[(R)-1-Aminoethyl]-N-4-pyridinylcyclohexanecarboxamide dihydrochloride (Y-27632 dihydrochloride), N-Benzyl-[2-(pyrimidin-4-yl)amino]thiazole-4-carboxamide (Thiazovivin), Rock Inhibitor, a isoquinolinesulfonamide compound (Rho Kinase Inhibitor), N-(4-Pyridyl)-N'-(2,4,6-trichlorophenyl) urea (Rho Kinase Inhibitor II), 3-(4-Pyridyl)-1H-indole (Rho Kinase Inhibitor M, Rockout), and 4-pyrazoleboronic acid pinacol ester; a Rock antibody commercially available from Santa Cruz Biotechnology selected from the group consisting of Rock-1 (B 1), Rock-1 (C-19), Rock-1 (H-11), Rock-1 (G-6), Rock-1 (H-85), Rock-1 (K-18), Rock-2 (C-20), Rock-2 (D-2), Rock-2 (D-11), Rock-2 (N-19), Rock-2 (H-85), Rock-2 (30-J); a ROCK CRISPR/Cas9 knockout plasmid selected from the group consisting of Rock-1 CRISPR/Cas9 KO plasmid (h), Rock-2 CRISPR/Cas9 KO plasmid (h), Rock-1 CRISPR/Cas9 KO plasmid (m), Rock-2 CRISPR/Cas9 KO plasmid (m); a ROCK siRNA, shRNA plasmid and/or shRNA lentiviral particle gene silencer selected from the group consisting of Rock-1 siRNA (h): sc-29473, Rock-1 siRNA (m): sc-36432, Rock-1 siRNA (r): sc-72179, Rock-2 siRNA (h): sc-29474, Rock-2 siRNA (m): sc-36433, Rock-2 siRNA (r): sc-108088. In some embodiments, the ROCK inhibitor comprises Y-27632.

The FC media can comprise an effective amount of ROCK inhibitor, such as, for example, at a concentration of about 0.1 nM to about 100 nM (e.g., about 0.1, 0.2, 0.3, 0.4, 0.5, 1, 1.5, 2, 2.5, 3, 3.5, 4, 4.5, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 mM or a number or a range between any two of these values). In some embodiments, the FC media comprises a ROCK inhibitor at a concentration of about 7.5 nM. In some embodiments, the FC media comprises about 1 nM to about 100 nM Y-27632 (e.g., about 1, 1.5, 2, 2.5, 3, 3.5, 4, 4.5, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 nM or a number or a range between any two of these values). In some embodiments, the FC media comprises about 7.5 nM Y-27632. In some embodiments, the FC media does not comprise a ROCK inhibitor.

In some embodiments, the FC media comprises DMEM, fetal bovine serum, sodium pyruvate, GlutaMax™, MEM non-essential amino acids, 2-mercaptoethanol, penicillin and/or streptomycin, or any combination thereof. In some embodiments, the FC media comprises DMEM, about 15% fetal bovine serum, about 1 mM sodium pyruvate, about 2 mM GlutaMax, about 1% MEM non-essential amino acids, about 0.1 mM 2-mercaptoethanol, about 1% penicillin and/or streptomycin, or any combination thereof. In some embodiments, the FC medium comprises Dulbecco's modified essential medium (Gibco 41966052), about 15% fetal bovine serum (Cambridge Stem Cell Institute), about 1 mM sodium pyruvate (Gibco 11360039), about 2 mM GlutaMAX (Gibco 35050038), about 1% MEM non-essential amino acids (Gibco 11140035), about 0.1 mM 2-mercaptoethanol (Gibco 31350010) and about 1% penicillin/streptomycin (Gibco 15140122). The FC media can further comprise one or more anticoagulants, for example heparin and a fibroblast growth factor (FGF) (e.g., FGF2 and/or FGF4), or any combination thereof.

IVC Media

The IVC media contains a basal medium described herein. The basal medium can comprise water, salts, amino acids, a carbon source, vitamins, lipids and a buffer. Suitable carbon sources may be assessed by one of skill in the art from compounds such as glucose, sucrose, sorbitol, galactose, mannose, fructose, mannitol, maltodextrin, trehalose dihydrate, and cyclodextrin. Basal media are commercially available, for example, under the trade names Advanced DMEM/F12 (Gibco, 12634-010) and CMRL-1066 (Invitrogen or Sigma). The basal culture medium can comprise Dulbecco's Modified Eagle Medium (DMEM), DMEM Nutrient Mixture 12 (DMEM/F12), Roswell Park Memorial Institute (RPMI) medium 1640, Neurobasal®, Neurobasal® A, Connaught Medical Research Laboratory 1066 (CMRL-1066), or any combination thereof.

An IVC media can further comprise (a) insulin, an insulin analogue, or an insulin receptor agonist; (b) estrogen, an estrogen analogue, or an estrogen receptor agonist; and (c) progesterone, a progesterone analogue, or a progesterone receptor agonist.

The amount of the insulin, estrogen, progesterone, or analogues or receptor agonists thereof present in the IVC media can vary. For example, in some embodiments, the IVC media can comprise about 1 ng/ml to about 100 mg/ml (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900 ng/ml, 1 µg/ml, 10, 20, 30, 40, 50, 60, 70, 80, 90, 100 µg/ml, 1 mg/ml, 10, 20, 30, 40, 50, 60, 70, 80, 90, 100 mg/ml or a number or a range between any two of these values) of one or more hormones (e.g., progesterone) and/or one or more growth factors (e.g., insulin or an insulin-like growth factor). In some embodiments, the IVC media can comprise about 0.5 nM to about 1 mM (e.g., about 0.5, 1, 1.5, 2, 2.5, 3, 3.5, 4, 4.5 5 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900 nM, 0.5 mM, 1 mM, or a number or a range between any two of these values) of a hormone (e.g., estrogen) and/or insulin or an insulin-like growth factor.

In some embodiments, the insulin receptor agonist is selected from the group comprising IGF-I, IGF-II, analogues thereof, or any combination thereof. The estrogen receptor agonist can be selected from the group comprising A-estradiol, estrone, estriol and estetrol, or any analogue thereof. The IVC media can comprise transferrin, sodium selenium, ethanolamine, or any analogue thereof. The IVE media can comprise Insulin-Transferrin-Selenium-Ethanolamine (ITS-X). In some embodiments, the IVC media further comprises an agonist of the activin type 1 or type 2 receptors. The IVC media can comprise a reducing agent. In some embodiments, the reducing agent can comprise N-acetyl-L-cysteine, dithiothreitol (DTT), β-mercaptoethanol (BME), or any combination thereof.

The IVC media can comprise a non-human serum, the concentration of which can vary in different embodiments. In some embodiments, the IVC media can comprise a non-human serum (e.g., fetal bovine serum) at about 5% to about 40% (e.g., 5%, 10%, 11%, 12%, 13%, 14%, 15%, 16%, 17%, 18%, 19%, 20%, 21%, 22%, 23%, 24%, 25%, 26%, 27%, 28%, 30%, 31%, 32%, 33%, 34%, 35%, 36%, 37%, 38%, 39%, 40%, or a number or a range between any two of these values) volume per volume (% v/v), weight per volume (% w/v) or weight per weight (% w/w) of the medium. In some embodiments, the IVC media comprises about 20% to about 30% non-human serum (e.g., fetal bovine serum). In some embodiments, the IVC media comprises about 20% fetal bovine serum. In some embodiments, the IVC media comprises about 30% fetal bovine serum. In some embodiments, culturing the mammalian pluripotent stem cell and the extra-embryonic stem cell in the IVC media comprises increasing serum concentrations, optionally increasing the serum concentration from about 20% to about 30%.

The IVC media can comprise L-glutamine. L-glutamine may be included in the culture medium at a concentration of about 0.1 mM to about 40 mM, about 0.2 mM to about 20 mM, about 0.5 mM to about 10 mM, about 1 mM to about 5 mM or about 1.5 mM to about 2.5 mM e.g., about 2 mM. In some embodiments, L-glutamine is included in the culture medium at a concentration of about 2 mM.

The IVC media can comprise an effective amount of a reducing agent. In some embodiments, the concentration of the reducing agent in the IVC media can be about 0.1 µM to about 1 mM (e.g., about 0.1, 0.2, 0.3, 0.4, 0.5, 0.6, 0.7, 0.8, 0.9, 1, 10, 100, 200, 300, 400, 500, 600, 700, 800, 900 µM, 1 mM, or a number or a range between any two of these values). In some embodiments, the reducing agent is included in the IVC media at a concentration of about 25 µM. In some embodiments, the IVC media comprises N-acetyl-L-cysteine at a concentration of about 25 µM.

Penicillin may be included in the culture medium at a concentration of about 1 unit/ml to about 500 units/ml, about 2 units/ml to about 250 units/ml, about 5 units/ml to about 100 units/ml, about 10 units/ml to about 50 units/ml, or about 20 units/ml to about 30 units/ml e.g., about 25 units/ml. Streptomycin may be included in the culture medium at a concentration of about 1 µg/ml to about 500 µg/ml, about 2 µg/ml to about 250 µg/ml, about 5 µg/ml to about 100 µg/ml, about 10 µg/ml to about 50 µg/ml, 25 or about 20 µg/ml to about 30 µg/ml e.g., about 25 µg/ml. The culture medium can comprise penicillin at a concentration of about 25 units/ml and/or streptomycin at a concentration of about 25 µg/ml.

The culture medium can comprise a basal medium, as described herein, (e.g., Advanced DMEM/F12) supplemented with, an insulin receptor agonist, e.g., Insulin (e.g., about 2 mg/ml to about 25 mg/ml), Transferrin (e.g., about 1 mg/ml to about 10 mg/ml), Selenium e.g., sodium selenite (e.g., about 0.001 mg/ml to about 0.01 mg/ml), Ethanolamine (e.g., about 0.5 mg/ml to about 10 mg/ml), an estrogen receptor agonist e.g., estradiol (e.g., about 5 nM to about 10 nM), a progesterone receptor agonist e.g., Progesterone (e.g., about 50 ng/ml to about 500 ng/ml) and a reducing agent e.g., N-acetyl-L-cysteine (e.g., about 17.5 µM to about 40 µM). In some embodiments, the IVC media is free or substantially free of sodium pyruvate.

In some embodiments, the IVC media comprises DMEM/ F12, fetal bovine serum, GlutaMax, ITS-X, β-estradiol, progesterone, N-acetyl-L-cysteine, penicillin and/or streptomycin, or any combination thereof. In some embodiments, the IVC media comprises DMEM/F12, about 20% fetal bovine serum, about 2 mM GlutaMax, about 1×ITS-X, about 8 nM β-estradiol, about 200 ng/ml progesterone, about 25 μM N-acetyl-L-cysteine, about 1% penicillin and/or streptomycin, or any combination thereof.

Post-Implantation Media

In some embodiments, the post-implantation embryo is cultured in a post-implantation media capable of supporting the development of embryos ex utero. The method described herein comprises culturing the post-implantation embryo structure in a post-implantation media under a static condition allowing the post-implantation embryo structure embryo structure to develop into a neurulating embryo structure. The method can also comprise culturing the neurulating embryo structure for at least one day in a post-implantation media under a dynamic condition in a culture chamber allowing the neurulating embryo structure to develop into a synthetic embryo of at least early organogenesis stage.

In some embodiments, the post-implantation embryo comprises a basal medium described herein. The basal medium can comprise Dulbecco's Modified Eagle Medium (DMEM) or DMEM Nutrient Mixture 12 (DMEM/F12), non-human serum (e.g., rat and/or bovine serum), human cord serum, L-glutamine or an analogue thereof (e.g., GlutaMAX™), antibiotics, or any combination thereof.

The DMEM or DMEM/F12 can be present in the media at about 5% to about 40% (e.g., 5%, 10%, 11%, 12%, 13%, 14%, 15%, 16%, 17%, 18%, 19%, 20%, 21%, 22%, 23%, 24%, 25%, 26%, 27%, 28%, 30%, 31%, 32%, 33%, 34%, 35%, 36%, 37%, 38%, 39%, 40%, or a number or a range between any two of these values) volume per volume (% v/v), weight per volume (% w/v) or weight per weight (% w/w) of the medium. In some embodiments, the DMEM or DMEM/F12 is present in the media at about 25%. In some embodiments, the post-implantation media comprises DMEM at about 25%.

The post-implantation media comprises an effective amount of non-human serum at about 5% to about 60% (e.g., 5%, 10%, 11%, 12%, 13%, 14%, 15%, 16%, 17%, 18%, 19%, 20%, 21%, 22%, 23%, 24%, 25%, 26%, 27%, 28%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, or a number or a range between any two of these values) volume per volume (% v/v), weight per volume (% w/v) or weight per weight (% w/w) of the medium. In some embodiments, the post-implantation media comprises about 50% non-human serum. In some embodiments, the post-implantation media comprises about 50% rat serum.

The human cord serum in the post-implantation media can vary. In some embodiments, the post-implantation media comprises an effective amount of human cord serum at about 5% to about 40% (e.g., 5%, 10%, 11%, 12%, 13%, 14%, 15%, 16%, 17%, 18%, 19%, 20%, 21%, 22%, 23%, 24%, 25%, 26%, 27%, 28%, 30%, 31%, 32%, 33%, 34%, 35%, 36%, 37%, 38%, 39%, 40%, or a number or a range between any two of these values) volume per volume (% v/v), weight per volume (% w/v) or weight per weight (% w/w) of the medium. In some embodiments, the post-implantation media comprises about 25% human cord serum.

In some embodiments, the post-implantation media comprises about 25% DMEM, about 50% rat serum, and about 25% human cord serum.

In some embodiments, the post-implantation media further comprises an effective amount of bicarbonate. The bicarbonate can be present in the post-implantation media at a concentration from about 0.1 mM to about 30 mM, optionally from 1 mM to about 20 mM.

In some embodiments, the post-implantation media comprises an effective amount of HEPES. The HEPES can be present in the post-implantation media at a concentration from about 0.1 mM to about 30 mM, optionally from 1 mM to about 20 mM.

The post-implantation media can comprise an effective amount of L-glutamine or an analogue thereof (e.g., GlutaMAX™). L-glutamine may be included in the culture medium at a concentration of about 0.1 mM to about 40 mM, about 0.2 mM to about 20 mM, about 0.5 mM to about 10 mM, about 1 mM to about 5 mM or about 1.5 mM to about 2.5 mM e.g., about 2 mM.

The antibiotics can be include in the post-implantation media at a concentration of about 1 unit/ml to about 500 units/ml. For example, penicillin may be included in the culture medium at a concentration of about 1 unit/ml to about 500 units/ml, about 2 units/ml to about 250 units/ml, about 5 units/ml to about 100 units/ml, about 10 units/ml to about 50 units/ml, or about 20 units/ml to about 30 units/ml e.g., about 25 units/mi. Streptomycin may be included in the culture medium at a concentration of about 1 μg/ml to about 500 μg/ml, about 2 μg/ml to about 250 μg/ml, about 5 μg/ml to about 100 μg/ml, about 10 μg/ml to about 50 μg/ml, 25 or about 20 μg/ml to about 30 μg/ml e.g., about 25 μg/ml. The post-implantation media can comprise penicillin at a concentration of about 100 units/ml and/or streptomycin at a concentration of about 100 μg/ml.

The post-implantation media can for example comprise DMEM, rat serum, human cord serum, GlutaMax, penicillin and/or streptomycin, HEPES, or any combination thereof. In some embodiments, the post-implantation media comprises about 25% DMEM, about 50% rat serum, and about 25% human cord serum. The post-implantation media is further supplied with 1× Glutamax (GIBCO, 35050061), 100 units/ml penicillin and 100 μg/ml streptomycin and 11 mM HEPES (GIBCO 15630056).

In some embodiments, culturing the post-implantation embryo comprises supplying the post-implantation media with glucose. The glucose can be provided in the post-implantation media or in the basal cultural medium in increasing concentrations throughput the culturing. The glucose concentration can be increased from at least about 3 mg/ml up to about 4-5 mg/ml. In some embodiments, the glucose is supplied to the post-implantation media from about 3 mg/ml up to about 3.5 mg/ml. The glucose can be supplied for at least once (e.g., one, two, three or more times) at a concentration of at least 3 mg/ml (e.g., 3, 3.5, 4, 4.5, 5, or higher). The post-implantation media can be supplied with a glucose of at least 3 mg/ml at about day three of culturing in the post-implantation media. In some embodiments, the media comprises at least about 3 mg/ml glucose when the embryo reaches the neurulating stage and onwards, followed by at least about 3.5 mg/ml glucose the following day.

In some embodiments, the glucose is provided in the post-implantation media in increasing concentrations throughout the culturing. In some embodiments, the glucose is provided in the post-implantation media in a constant concentration followed by increasing concentrations. In some embodiments, the glucose is provided in the post-implantation media in a constant concentration throughout a static condition followed by increasing concentrations throughout a dynamic condition. In some embodiments, the glucose can be provided in the post-implantation media at a constant concentration under a static condition followed by increasing concentrations in the same or different static concentration. For example, culturing the post-implantation embryo can comprise culturing, under a static condition, the post-implantation embryo structure in a media comprising about 1 mg/ml glucose for about two days and culturing the post-implantation embryo structure in a media comprising about 3 mg/ml glucose for about one day.

In some embodiments, the glucose is provided at increasing concentrations when transferring the embryos from a static condition to a dynamic condition. For example, the method can comprise culturing the post-implantation embryo structure in a media comprising about 3 mg/ml glucose for about one day under a static condition (e.g., when the embryo reaches a neurulating stage), followed by culturing in a media comprising about 3.5 mg/ml glucose for at least one day under a dynamic condition. In some embodiments, the glucose is provide in the media in increasing concentrations throughout the dynamic condition.

Also disclosed herein includes embryo culturing systems (e.g., embryo culturing devices) suitable for generating a synthetic embryo in vitro using any of the methods disclosed herein.

Applications

Provided herein also includes a synthetic embryo obtainable by the in vitro method described herein for use in a method of diagnosing, preventing or treating a disease in a patient in need thereof. For example, embryo cells obtainable from the present invention may be used in stem cell therapies, such as treatments for cancers, replacement tissue, reconstructive surgery, tissue repair, wound healing, bone marrow transplantation, stroke, baldness, blindness, deafness, diabetes, heart disease, bowel disease, arthritis, skeletal injury, teeth replacement, neuronal disease and any other condition where replacement cells or tissues may be advantageous. The cells may also be utilized for screening therapeutic compounds for efficacy and safety, as would be understood by a person of skill in the art.

In some embodiments, the synthetic embryo structure for use in a method of diagnosing, preventing or treating a disease in a patient in need thereof as described herein may be used for transplantation into the patient. It is envisaged that in certain embodiments, the pluripotent stem cell used to obtain the embryo may have been obtained from the patient originally, thus reducing the likelihood of rejection by the patient's immune system. Thus, a pluripotent stem cell, for example an embryonic stem cell, and extraembryonic stem cell obtained from a patient may be cultured using the methods described herein to provide material for transplantation back into that patient to prevent or treat a condition. For example, the embryo may be used to grow replacement organs or tissues for the patient to regain function of such organs or tissues in the patient following loss of function through degeneration, ageing and/or disease.

Disclosed herein also includes a method of providing a transgenic non-human animal, comprising gestating an embryo derived from a cell cultured using an in vitro method described herein. Such transgenic non-human animals may be useful in drug screening or in the study of disease. For example, model animals may be produced to study specific conditions. It is envisaged that the methods provided herein could be used to more efficiently develop transgenic and chimeric embryos (which currently relies for example, on the labor-intensive process of harvesting blastocysts and manually replacing the inner cell mass).

Disclosed herein include methods for investigating the effect of a test agent on embryonic development. In some embodiments, the method comprises: a) generating a synthetic embryo using the method described herein; b) contacting the synthetic embryo with a test agent; and c) determining the effect of the test agent on the synthetic embryo. In some embodiments, the determining comprises comparing a phenotype or a genotype of the synthetic embryo in the presence of the test agent with the phenotype or genotype of the synthetic embryo in the absence of the test agent. The method can comprise contacting the mammalian pluripotent stem cell and at least one extraembryonic stem cell with the test agent during or following step (a) and prior to step (b), during or following step (b) and prior to step (c), or during or following step (c).

The method can comprise determining the subsequent effect on formation of a synthetic embryo at various developmental stages. The determining can be performed using any method known in the art. For example, the method can comprise recording one or more images of the embryo structure.

Disclosed herein include methods for investigating mechanisms involved in embryogenesis. In some embodiments, the method comprises any of the in vitro methods for generating a synthetic embryo structure at various developmental stages described herein. Investigating mechanism involved in embryogenesis can comprise any method known in the art. For example, said investigating can comprise investigating the effect of a test agent on embryonic development as described above. In some embodiments, investigating mechanisms involved in embryogenesis can comprise determining the effect of genetic perturbation(s) in the embryo structure.

The method may comprise recording a plurality of images of the synthetic embryo structure. The plurality of images may be recorded over a pre-determined period of time, thus illustrating the development of the embryonic structure over time. The imaging apparatus may comprise microscopy apparatus, suitable recording apparatus, and optionally image processing apparatus.

Typically, fluorescent markers, such as fluorescent dyes or fluorescent marker proteins, are used in the imaging of embryonic development. Such markers may be added to the culture system. For example, fluorescent dyes may be added to visualize particular molecules or cellular structures. For example, DAPI may be used to stain DNA or MitoTracker (Invitrogen) may be used to stain the mitochondria. Additionally or alternatively, the embryo structure may produce such fluorescent markers endogenously, e.g., it may contain one or more cells which express a fluorescent marker protein. Such cells may have been genetically modified in order to confer the ability to express such a marker protein. Thus, fluorescence imaging apparatus may be particularly suitable for the methods described. The imaging apparatus may thus comprise a fluorescence microscope, such as a confocal microscope, that can include but is not limited to wide field, scanning and spinning disc confocal, and light sheet microscope.

Confocal microscopes image a single point of a specimen at any given time but allow generation of two dimensional or three dimensional images by scanning different points in a specimen in a regular raster to provide image data which can be assembled into a two or three dimensional image. For example, scanning a specimen in a single plane enables generation of a two dimensional image of a slice through the specimen. A plurality or "stack" of such two dimensional images can be combined to yield a three dimensional image. Spinning disc confocal microscopy provides added advantages over confocal laser scanning microscopy. Additionally, light sheet microscopy can also provide good imaging of embryonic development.

Disclosed herein also includes a method of elucidating the role of a gene in embryo development, the method comprising obtaining a pluripotent stem cell and/or an extra-embryonic stem cell where the gene has been modified or knocked out and culturing the pluripotent stem cell and the extra-embryonic stem cell using the in vitro method described herein. Thus, the methods may aid in the development of treatments for conditions relating to embryo development, such as fertility treatment.

Disclosed herein also includes a method of imaging an embryo during development comprising culturing a mammalian pluripotent stem and an extra-embryonic stem cell or a mammalian synthetic embryo structure using the methods described herein, and recording an image of said embryo using an imaging apparatus. The image may be a two dimensional or three dimensional image. A plurality of images may be recorded of the same embryo. An imaging apparatus can comprise microscopy apparatus and suitable recording apparatus. An imaging apparatus may further comprise image processing apparatus. Additionally, an imaging apparatus may further comprise a fluorescent microscope. Additionally, or alternatively, an imaging apparatus may further comprise a confocal microscope.

EXAMPLES

Some aspects of the embodiments discussed above are disclosed in further detail in the following examples, which are not in any way intended to limit the scope of the present disclosure.

Example 1

Materials and Methods

This example provides general experimental materials and methods used for Examples 2-7 described below:

Cell Lines and Culture Conditions

All cell lines used hereby were mouse cell lines and include the following. CAG-GFP/tetO-mCherry mouse ES cells (constitutive GFP expression in the membrane; transient mCherry expression upon Dox treatment). The parent CAG-GFP/tetO-mCherry ES cell line was derived from an existing mouse line with constitutive CAG-GFP expression and Dox-induced transient mCherry expression. This line was generated by breeding CAG-GFP reporter mice and tetO-mCherry Histone mice. An independent Dox-inducible Gata4-expressing cassette was hereby introduced into the CAG-GFP/tetO-mCherry ES cell line by piggyBac-based transposition. Thus, mCherry and Gata4 were regulated by two, independent Dox-responsive promoters. CAG-GFP/tetO-mCherry/tetO-Gata4 ES cells were generated in-house. Cerl-GFP ES cells (GFP expression under the control of the Cerl-promoter) were derived from a published Cerl-GFP mouse line. Cerl-GFP/tetO-Gata4 ES cells were generated in-house. Wild-type CD1 TS cells were generated in-house. Wild-type CD1 ES cells were a gift. CD1/tetO-Gata4 ES cells were generated in-house. Sox2-Venus/Brachyury-mCherry/Oct4-ECFP ES cells, Blimp1-GFP ES cells and BVSC ES cells were gifts.

For the experiments described herein, ETiX embryoids were successfully generated with the following ES cell lines: wild-type CD1 ES cells; Sox2-Venus/Brachyury-mCherry/

Oct4-ECFP ES cells; CAG-GFP/tetO-mCherry ES cells; Blimp1-GFP ES cells; and BVSC ES cells.

In addition to the lines indicated above, five more that could progress to day 5 and 6 but not beyond were also tried. These lines were: Lfng reporter (LuVeLu) ES cells; Msgn1-Venus ES cells; Hes7-Achilles ES cells; Sox1-GFP ES cells; mTmG ES cells (generated in-house). No results described hereby were generated with these five unsuccessful lines.

The majority of the structures presented hereby were generated using wild-type CD1 ES cells, wild-type CD1 TS cells and CD1/tetO-Gata4 ES cells. The sex of the cell lines was not known because the cells were not genotyped to determine it. All cell lines were routinely tested every two weeks to ensure that they were not contaminated with *mycoplasma*. Mouse ES cells and TS cells were cultured as detailed in "Inducible Stem-Cell-Derived Embryos Capture Mouse Morphogenetic Events In Vitro", Amadei et al., 2021, Developmental Cell 56, 366-382 (//doi.org/10.1016/j.devcel.2020.12.004) (Amadei 2021), the content of which is incorporated herein by reference in its entirety. Establishment of CD1 tetO-Gata4 Dox-inducible cell lines was performed as described elsewhere. Cell lines were not authenticated.

Culturing Mouse ES Cells and TS Cells

Mouse ES cells and TS cells were cultured as detailed in Amadei 2021. Briefly, mouse ES cells were cultured on gelatinized plates at 37° C., 5% $CO_2$, 21% $O_2$ in N2B27, which comprised of 50% Neurobasal-A (Gibco 10888022), 50% DMEM/F-12 (Gibco 21331020), 0.5% N-2 (in-house), 1% B-27 (Gibco 10889038), 2 mM GlutaMAX (Gibco 35050038), 0.1 mM 2-mercaptoethanol (Gibco 31350010) and 1% penicillin/streptomycin (Gibco 15140122). N2B27 was supplemented with 3 μM CHIR99021 (Cambridge Stem Cell Institute), 1 μM PD0325901 (Cambridge Stem Cell Institute) and 10 ng/ml leukemia inhibitory factor (Cambridge Stem Cell Institute). Mouse TS cells were cultured at 37° C. and 5% $CO_2$, in RPMI 1640 (Sigma) with 20% fetal bovine serum (FBS), 2 mM 1-glutamine, 0.1 mM 2-ME, 1 mM sodium pyruvate, and 1% penicillin-streptomycin (TS cell media), supplemented with 25 ng/ml FGF4 (R&D Systems 7486-F4-025) and 1 μg/ml heparin (Sigma-Aldrich H3149-25KU) (TSC/F4H) on mitotically inactivated mouse embryonic fibroblasts (MEFs, Insight Biotechnology, ASF-1201). MEFs were cultured in feeder cell (FC) medium, which contained Dulbecco's modified essential medium (Gibco 41966052), 15% FBS (Cambridge Stem Cell Institute), 1 mM sodium pyruvate (Gibco 11360039), 2 mM GlutaMAX (Gibco 35050038), 1% MEM non-essential amino acids (Gibco 11140035), 0.1 mM 2-mercaptoethanol (Gibco 31350010) and 1% penicillin/streptomycin (Gibco 15140122). Passaging of ES cells and TS cells was performed when they were at 70% confluency as follows: cells were washed once in 1×PBS (Life Technologies 10010056) and trypsinized (Trypsin-EDTA 0.05% Life Technologies 25300054) for 3 min at 37° C. The reaction was stopped by adding 2 ml of FC or TS cell media respectively. Cells were dissociated by pipetting gently 4-5 times and centrifuged for 4 min at 200×g. TS cells were then resuspended in TS cell/F4H culture media and plated onto MEF-coated plates in 1:20 or 1:10 dilution. ES cells were washed once with 1 ml of 1×PBS, centrifuged again, resuspended in N2B27 2iLIF and plated in 1:10 or 1:20 dilution onto gelatin-coated plates.

CRISPR-Cas9 Pax6 Knockout

Pax6 was targeted in the region 104 bp immediately prior to the homeobox sequence on exon 6. Guide RNA (gRNA) oligonucleotides were designed using an online CRISPR design tool. Those least likely to have off-targets based on the prediction of the software were selected. gRNAs were annealed with their respective reverse oligonucleotides, cloned into PX459 and transformed into DH5ca cells as previously described. Minipreps were sent for Sanger sequencing with sequencing primer: 5'-TGCATATACGA-TACAAGGCTGTTAG-3' (SEQ ID NO: 9). Wild-type ES cells (CD1 background) were transfected using Lipofectamine 3000 according to the manufacturers' instructions. In brief, a density of 25,000 cells per well was plated in a 24-well plate the day prior to transfection. The following day, pairs of gRNAs in PX459 were transfected into the cells (500 ng per plasmid). A PIP Fucci construct without an antibiotic resistance cassette in a separate well was used as a control for the transfection. A negative control (no DNA) was also performed in parallel. Following 2 days of selection with 1 μg/ml antibiotics, the cells were washed in fresh medium and allowed to recover from the antibiotic. Individual clones were isolated and cultured in 96-well plates until colonies became visible. Of 46 wells, 18 were growing a single colony. Each of these was passaged and split into 3 new wells, each in a different 96-well plate. Two of these plates were trypsinized and frozen using FC medium+10% DMSO+25% FBS. Colonies in the remaining plates were grown until confluency. Genomic DNA from each single clone was extracted and genotyped using Platinum Taq DNA Polymerase (Invitrogen, 13001012) and the following primers: FW: 5'-AAGAGACCTTGCGAGAGCAC-3' (SEQ ID NO: 7). RV: 5'-GAACTTTCCCACCAGGAGCA-3' (SEQ ID NO: 8). A standard 25-μl reaction was set up with 12.5 μl Platinum Taq PCR Master Mix, 2 μl template DNA, 0.5 μl of 10 μM stock from each primer and 9.5 μl H₂O. The PCR cycling conditions were as follows: Initial denaturation was performed at 94° C. for 2 min, followed by 35 cycles of: denaturation at 94° C. for 30 s, annealing at 56° C. for 30 s and extension at 72° C. for 40 s. The PCR product was then examined using gel electrophoresis. Promising clones that ran at sizes lower than the wild-type (lower than 715 bp) were sent for Sanger sequencing. Deletion was confirmed by immunofluorescence following a neural differentiation protocol.

Formation of ETiX Embryoids

Formation of ETiX embryoids was performed as previously described in Amadei 2021. In brief, to prepare the AggreWell plate (STEMCELL Technologies 34415), 500 μl of anti-adherence rinsing solution (STEMCELL Technologies 07010) was added to each well. The plate was then centrifuged at 2,000×g for 5 min and was incubated for 20 min at room temperature. Rinsing solution was then aspirated from the well. 1 ml of PBS was added to wash each well. 500 μl of FC medium was added to each well after aspirating the PBS.

To generate ETiX embryos, doxycycline (1 μg/ml) (Sigma-Aldrich D9891-5G) was added to CAG-GFP tetO-Gata4 ES cells for 6 hours. TSCs were trypsinized and were added to a gelatinized plate to deplete the MEFs for 20 min at 37° C. CAG-GFP WT ES cells and CAG-GFP tetO-Gata4 ES cells were subsequently trypsinized. ES cells were washed once with 1×PBS, and trypsinized with 0.05% trypsin-EDTA (ThermoFisher Scientific) for 3 min at 37° C. The reaction was stopped by adding 2 ml of FC medium. Cells were dissociated gently by pipetting for 4-5 times and centrifuged at 200×g for 4 min. The cell pellets were washed once with 1×PBS, centrifuged again and resuspended in 1-2 ml of FC medium. Cell suspensions with 19,200 TS cells, 6,000 CAG-GFP WT ES cells and 6,000 CAG-GFP tetO-Gata4 ES cells were mixed and pelleted by centrifugation.

The cell pellets were resuspended in 1 ml of FC medium with 7.5 nM ROCK inhibitor (Y27632, STEMCELL Technologies 72304). After adding the cell mixture dropwise to the AggreWell, the plate was centrifuged at 100×g for 3 min to have the cells plated in the AggreWell (day 0).

On the next day (day 1), medium change was performed twice by removing 1 ml of medium from each well and adding 1 ml of fresh FC medium without ROCK inhibitor. On day 2, medium change was performed once to replace 1 ml of medium with 1 ml of fresh FC medium. On day 3, 1 ml of medium was removed from each well and 1.5 ml of In Vitro Culture Medium 1 (IVC1) (with FBS at 20% v/v) was added, after equilibrating for 20 min in the incubator. IVC1 is made of advanced DMEM/F12 (Gibco, 21331-020) supplemented with 20% (v/v) FBS, 2 mM GlutaMax, 1% v/v penicillin-streptomycin, 1×ITS-X (Thermo Fisher Scientific, 51500-056), 8 nM p-estradiol, 200 ng/ml progesterone and 25 μM N-acetyl-L-cysteine. On day 4, ETiX embryoids in the AggreWell were transferred to Cellstar 6-well multi-well plate for suspension culture (Greiner Bio-One 657185) with 5 ml of IVC1 (with FBS at 30% v/v) per well.

Ex utero culture of mouse embryos was as previously described. DRH medium comprised 25% DMEM, 50% rat serum and 25% human cord serum, and permitted development to the somite stage in stationary culture and beyond, following transfer to the Precision rotating bottle culture apparatus (BTC Engineering). Glutamine and antibiotics (100 units/ml penicillin and 100 μg/ml streptomycin) were added to bicarbonate-buffered DMEM without glutamine (Gibco 11054). As depletion of glucose has been described to be a major cause of malformations and growth retardation, the low glucose DMEM (1 mg/ml) was supplemented with 3 mg/ml glucose. As phenol red is fluorescent, embryos were routinely cultured in medium lacking phenol red. The medium had the same proportions of DMEM (Gibco 11880), rat serum and human cord serum as DRH, but was buffered with HEPES rather than bicarbonate (and was renamed ex utero culture medium (EUCM)). EUCM comprises 25% DMEM (GIBCO 11880) supplemented with 1× Glutamax (GIBCO, 35050061), 100 units/ml penicillin and 100 μg/ml streptomycin and 11 mM HEPES (GIBCO 15630056), plus 50% rat serum and 25% human chord serum. Rat whole embryo culture serum was from Charles River. Human cord serum was provided by the Cambridge Blood and Stem Cell Biobank, which was supported by the Cambridge NIHR Biomedical Research Centre, Wellcome Trust-MRC Stem Cell Institute and the Cambridge Experimental Cancer Medicine Centre, UK. Human and rat serums were heat-inactivated for 35 min (from frozen) at 56° C. and sterilized by filtration.

Routinely, on day 5, IVC1 was replaced with DRH or EUCM containing 1× Glutamax (GIBCO, 35050061), 100 units/ml penicillin and 100 μg/ml streptomycin and 11 mM HEPES (GIBCO 15630056). Each ETiX embryoid was transferred to a single well of 24-well, non-adherent dish (Greiner 662102) with 250 μl DRH or EUCM. On day 6, each ETiX embryoid was fed with an additional 250 μl of DRH or EUCM. A supplement of 3.0 mg/ml D-glucose (Sigma G8644) was added to low glucose medium on day 7 when the samples were moved to the rotating bottle culture chamber apparatus. Each rotating bottle contained 2 ml medium and 3 ETiX embryoids. On day 8 the medium was further supplemented with 3.5 mg/ml D-glucose. In each rotating bottle, 2 ETiX embryoids were cultured with 3 ml medium.

A device to regulate gas pressure and gas mixing on the roller bottles was previously described. The device was modified to enable pressure generation but not gas mixing. Therefore, only the pressure-generating component of this device was used to enable the development of embryoids to day 8. A device was built herein to deliver defined gas mixtures at 0.5 psi rather than 6.5 psi as previously described. This device was used to successfully culture embryoids and natural embryos for sequential smFISH. Delivery of gas mixtures at this lower pressure was effective in promoting development either when 21% oxygen was continuously supplied during culture or when the oxygen concentration was incrementally increased from 5% to 13% to 18% to 21% at daily intervals. DRH medium necessitated use of 5% C02.

Mouse Model and Embryo Recovery

Mice (six-week-old CD-1 males from Charles River and transgenic females bred in house) used in the experiments were kept in the animal house, following national and international guidelines. All experiments performed were under the regulation of the Animals (Scientific Procedures) Act 1986 Amendment Regulations 2012 and were reviewed by the University of Cambridge Animal Welfare and Ethical Review Body (AWERB). Experiments were also approved by the Home Office. Mice were maintained in the animal facility at 12:12 light cycle and provided with food and water and libitum.

Natural mating was performed with six-week-old transgenic females and CD-1 males. Mouse embryos were recovered at embryonic days E5.5, E6.5 and E7.5 by dissecting them from the deciduae in M2 medium (Sigma M7167). Embryos at E6.5 were cultured in EUCM in stationary conditions until E8.5 as previously reported in the same way as the ETiX embryoids. At E8.5, embryos were moved to a rotating bottle in DRH or EUCM supplemented with 3.0 mg/ml of D-glucose. Each bottle contained 2 ml of DRH or EUCM medium and 3 embryos. Both male and female embryos were used. Embryos were randomly allocated. Researchers were not blinded for embryo allocation.

Plasmids and Transfection

Gata4 cDNA was PCR-amplified from pSAM2-mCherry-Gata4 using the Gata4/AttB primers (see Table 3). The primers were designed as outlined in the Gateway cloning manual. Because the plasmid already contained AttB sites, there was no need to incorporate parts of the Gata4 open reading frame in the primer design. pSAM2-mCherry-Gata4 was obtained as a gift (Addgene plasmid #72690; //n2t.net/ addgene:72690; RRID:Addgene_72690). It was subsequently cloned into PB-tetO-hygromycin by Gateway technology (Thermo Fisher Scientific), according to the manufacturer's instructions. Clones were verified by sequencing. Transformations were performed using 5a-competent *E. coli* (New England Biolabs C29871). To generate ES cells with Doxycycline inducible Gata4, PB-tetO-hygro-Gata4, pBAse and rtTA-zcocyin (0.25 µg/each/reaction) were transfected into 12,000 CAG-GFP ES cells using Lipofectamine 3000 Transfection Reagent (Invitrogen L3000001), followed by antibiotics selection for 7 days with hygromycin (1:250; Gibco 10687010) and zeocyin (1:1000; InvivoGen ant-zn-1). The PB-tetO-hygro, pBAse and rtTA-zeocyin were obtained as a gift from the Stem Cell Institute (Cambridge, UK).

TABLE 3

OLIGONUCLEOTIDE TABLE

| NAME | SEQ ID NO: |
|---|---|
| PCR primer: Gata4-AttB Forward GGGGACAAGTTTGTACAAAAAAGCAGGCT | 1 |
| PCR primer: Gata4-AttB Reverse: GGGGACCACTTTGTACAAGAAAGCTGGGT | 2 |
| Pax6 KO gRNA: gRNA1: 5'-CACCGCTCCCCCTCCTTCCTGTTGC-3' | 3 |
| Pax6 KO gRNA: RV: 5'- AAACGCAACAGGAAGGAGGGGGAGC-3' | 4 |
| Pax6 KO gRNA2: 5'-CACCGAGATGCGACTTCAGCTGAAG-3' | 5 |
| Pax6 KO gRNA2: RV: 5'- AAACCTTCAGCTGAAGTCGCATCTC-3' | 6 |
| Pax6 PCR primer: Forward: 5'-AAGAGACCTTGCGAGAGCAC-3' | 7 |
| Pax6 PCR primer: Reverse: 5'-GAACTTTCCCACCAGGAGCA-3' | 8 |

Immunofluorescence

ETiX embryoids and natural embryos were processed for immunofluorescence as previously reported in Amadei 2021. Briefly, ETiX embryos and natural mouse embryos were fixed with 4% paraformaldehyde at room temperature for 20 min and washed with PBST (PBS with 0.1% Tween 20) for three times. They were then permeabilized in permeabilization buffer (0.1 M glycine and 0.3% Triton X-100 in PBST). For embryos up to E7.5 and ETiX embryos up to day 6, permeabilization was performed for 30 min at room temperature, followed by three washes with PBST of five min each. Natural embryos older than E7.5 and ETiX embryoids older than day 6 were permeabilized for 35 min. Samples were incubated with primary antibodies diluted in blocking buffer (10% FBS and 0.1% Tween 20 in PBS) at 4° C. overnight. After washing with PBST for three times, they were incubated with secondary antibodies and DAPI at 4° C. overnight or for 2 hours at room temperature followed by another three washes with PBST before imaging.

Cryosectioning and Slide Immunofluorescence

Natural embryo and ETiX embryoid samples after fixation were cryoprotected in 30% sucrose/PBS (w/v) overnight at 4° C. Samples were then transferred to a cryomold filled with optimal cutting temperature (OCT) compound (Agar Scientific) and frozen on a metal block cooled on dry ice. The samples were cut at a thickness of 12 µm on a cryostat, collected on lysine-coated slides and stored at −80° C. until ready for immunofluorescence. Slides were washed in PBS to remove OCT compound for 5-10 min and then briefly allowed to air dry for 5-10 min. Samples were permeabilized for 10 min at room temperature with permeabilization buffer (0.1 M glycine and 0.3% Triton X-100 in PBST) and then blocked for 1 h at room temperature with blocking buffer (10% FBS and 0.1% Tween 20 in PBS). After permeabilization and blocking, samples were processed as described above. Slides were mounted with Vectashield, sealed with nail polish, and allowed to air dry overnight in the dark prior to imaging.

inDrops scRNA-Seq Sample Preparation and Dissociation

After recovery, natural embryos and ETiX embryoids were dissociated for single-cell sequencing as previously described in Amadei 2021. In brief, natural embryos and ETiX embryos were cut to pieces, transferred to a Falcon tube, centrifuged, washed in PBS and incubated in Tryple Express (Gibco™ 12604013) for 15 min, with vigorous pipetting for 20 times every 5 min to dissociate to single cells. If there were clumps left, the incubation was extended for an additional 5 min and the samples were pipetted further. Samples were filtered with a 40 μm filter to remove large clumps, centrifuged at 200×g for 5 min and resuspended in PBST (PBS with 0.02% Tween20). The suspension was quantified with Trypan Blue (Sigma T8154) in a 1:1 ratio to determine the proportion of live and dead cells and then processed for encapsulation (see below). Samples analyzed: n=29 for ETiX5, 10 for ETiX6, 7 for ETiX8, 12 for E6.5, 14 for E7.5 and 9 for E8.5.

inDrops scRNA-Seq Library Preparation and Sequencing

Libraries were prepared according to the inDrops v3 workflow with v3 barcoding scheme. In brief, polyacrylamide beads were generated and barcoded to obtain a diversity of 147,456 barcodes. Single-cell suspensions were diluted to a concentration of 100,000 cells per ml and co-encapsulated with the barcoded beads and reverse transcriptase and lysis mix. Fractions of ~1,000 cells were collected in 1.5 ml Eppendorf tubes pre-filled with 200 μl mineral oil, subjected to UV photocleavage And incubated at 50° C. for 2 h and 70° C. for 20 min. The droplets were then de-emulsified and further amplified using second-strand synthesis and in vitro transcription. The libraries were then fragmented and reverse transcribed. The final libraries were amplified using a unique 8-bp index and limited-cycle PCR and quantified using a Qubit High Sensitivity kit (Invitrogen) and Bioanalyzer High Sensitivity DNA kit (Agilent). Libraries were pooled at equimolar ratios and purified using a 1.5× volumetric ratio of AmpureXP beads. The libraries were sequenced on a Nextseq 75 cycle 400M read High Output kit with 5% PhiX spike-in as an internal control. The read cycle distribution was the following: read 1, 61 cycles; index 1, 8 cycles; index 2, 8 cycles; read 2, 14 cycles.

scRNA-Seq Bioinformatic Analysis

The BCL files were converted to Fastq files using Illumina's bcl2fastq software. The sequenced libraries were quality-inspected using the FastQC tool v0.11.9 (www.bioinformatics.babraham.ac.uk/projects/fastqc/) and de-multiplexed using the Pheniqs tool from biosails v2.1.0. The fastq files were further filtered, mapped to a mouse GRCm38.99 reference genome with GRCm38.99 gtf annotation and deduplicated using the zUMIs pipeline v2.9.7. The count matrices with exonic and intronic counts were then used as input for downstream analysis using Seurat version 3. Cells were filtered based on the number of genes detected (between 700 and 4,000), unique molecular identifiers (UMIs) detected (lower than 7,500), percentage of UMI counts mapping to mitochondrial genes (between 1 and 15%) and doublet scores computed using Scrublet v0.1 (lower than 0.3), which yielded a total of 26,748 cells overall. The natural and synthetic embryo datasets were integrated in Seurat. Shared embeddings were corrected for batch effect (both systems and time points collected) using Harmony v4.3.12. Louvain clustering was performed on the shared embeddings. Markers, computed using the FindAllMarkers function of Seurat, were used to annotate cell types. Pearson correlation coefficients between cell types for each system, single-cell velocity profiles and latent times were computed using the Scanpy v1.0 and scVelo v0.2.4 tools. Plots were generated using Scanpy (in Python for dot plots and velocity) and Seurat (in R for UMAP plots), as well as ggplot2 for the remainder of the plots (in R for bar plots and proportion scatter plots).

Generating Single-Cell Sequencing Data Using Tiny-Sci-RNA-Seq

A simplified version of sci-RNA-seq3 was performed, which is further optimized for 'tiny' samples. In brief, to each tube, 100 μl of a hypotonic, PBS-based lysis buffer was added with DEPC as an RNase inhibitor. The resulting nuclei were then fixed with four volumes of a mix of methanol and dithiobis (succinimidyl propionate) (DSP). After rehydrating and washing the nuclei carefully in a sucrose/PBS/triton/MgCl$_2$ buffer (SPBSTM), the nuclei were distributed to two 96-well plates for reverse transcription, allocating 8 wells per embryo. After reverse transcription, nuclei were pooled, washed in SPBSTM and redistributed to a fresh plate for ligation of the second index primer with T4 DNA ligase. Nuclei were then again pooled, washed, and redistributed to three final plates for second-strand synthesis, extraction, tagmentation, and PCR amplification to add the third index plus a plate index. Products were pooled by PCR plate, size-selected and sequenced on two Illumina NextSeq runs (NextSeq-1 and NextSeq-2). Samples analyzed: n=8 natural embryos ranging from E7.5 to E9.5, n=3 for ETiX6, n=2 for failed ETiX6, 5 for ETiX8, 4 failed ETiX8 and 2 Pax6-knockout ETiX8.

Processing of Sequencing Reads Oftiny-Sci-RNA-Seq Data

For each NextSeq run of newly generated tiny-sci-RNA-seq data, read alignment and gene count matrix generation were performed using the pipeline developed for sci-RNA-seq3 with minor modifications: base calls were converted to fastq format using Illumina's bcl2fastq v2.20 and de-multiplexed based on PCR i5 and i7 barcodes using maximum likelihood demultiplexing package deML with default settings. Downstream sequence processing and single-cell digital expression matrix generation were similar to sci-RNA-seq except that the reverse transcription (RT) index was combined with hairpin adaptor index. Thus, the mapped reads were split into constituent cellular indices by demultiplexing reads using both the RT index and ligation index (Levenshtein edit distance (ED)<2, including insertions and deletions). In brief, de-multiplexed reads were filtered based on RT index and ligation index (ED<2, including insertions and deletions) and adaptor-clipped using trim_galore v0.6.5 with default settings. Trimmed reads were mapped to the mouse reference genome (mm10) for mouse embryo nuclei, using STAR v2.6.1d with default settings and gene annotations (Gencode VM12 for mouse). Uniquely mapped reads were extracted. Duplicates were removed using the UMI sequence (ED<2, including insertions and deletions), RT index, hairpin ligation adaptor index and read 2 end-coordinate (that is, reads with UMI sequence less than 2 edit distance. RT index, ligation adaptor index and tagmentation site were considered duplicates). Finally, mapped reads were split into constituent cellular indices by further demultiplexing reads using the RT index and ligation hairpin (ED<2, including insertions and deletions). To generate digital expression matrices, the number of strand-specific UMIs for each cell mapping to the exonic and intronic regions of each gene was calculated with Python v2.7.13 HTseq package. For multi-mapped reads, reads were assigned to the closest gene, except in cases where another intersected gene fell within 100 bp of the end of the closest gene, in which case the read was discarded. For most analysis, both expected-strand intronic and exonic UMIs in per gene single-cell expression matrices were included. After the single-cell gene count matrix was generated, doublets cells and potential low quality cells (by investigating the numbers of UMIs and the proportion of reads mapping to the exonic regions per cell) were filtered out, leaving 285,640 cells (n=130,611 cells for NextSeq-1, and n=155,029 cells for NextSeq-2; FIG. 9A-FIG. 9D). The following common, freely available data analysis software was used in this project: scrublet version 0.1, Scanpy version 1.6.0, Monocle versions 2, 3 and 3-alpha, Seurat version 3 and ggplot2 version 3.3.5.

Subclustering

Conventional scRNA-seq data processing was performed using Seurat v3: (1) normalizing the UMI counts by the total count per cell followed by log transformation; (2) selecting the 2,500 most highly variable genes and scaling the expression of each to zero mean and unit variance; (3) applying principal component analysis and then using the top 30 principal components to create a k-nearest neighbors graph, followed by Louvain clustering (resolution=1); (4) performing UMAP visualization in 2D space (dims (which dimensions to use as input features)=1:30, min_dist=0.3). Neighboring clusters were manually merged if there were a limited number of differential expressed genes between them. For subclustering, a subset of cells of interest (for example, cardiac mesoderm) was taken to identify more detailed cell populations following the above approach.

Identification of Correlated Cell Types Between ETiX Embryoids and Natural Embryos Using NNLS Regression Transcriptional profiles for cells within each cell type were first aggregated for either ETiX embryoids or natural embryos in the newly generated tiny-sci-RNA-seq data. NNLS regression was applied to predict gene expression in target cell type $(T_a)$ in dataset A based on the gene expression of all cell types $(M_b)$ in dataset B: $T_a=\beta_{0a}+\beta_{1a}M_b$ (where $\beta_{0a}$ is the intercept of the regression and $\beta_{1a}$ is the $\beta$-coefficient of the regression), based on the union of the 3,000 most highly expressed genes and 3,000 most highly specific genes in the target cell type. The roles of datasets A and B was then switched. Thus, the gene expression of target cell type $(T_b)$ was predicted in dataset B from the gene expression of all cell types $(M_a)$ in dataset A: $T_b=\beta_{0b}+\beta_{1b}M_a$. Finally, for each cell type a in dataset A and each cell type b in dataset B, the two correlation coefficients were combined: $\beta=2(\beta_{ab}+0.01)(\beta_{ba}+0.01)$ to obtain a statistic, for which high values reflected reciprocal and specific predictivity.

Inclusion Criteria of ETiX Embryoids

All ETiX embryoids were collected from AggreWell for analysis at 4 days of development and analyzed under a stereomicroscope. ETiX embryoids with cylindrical morphology and two clearly defined cellular compartments (an ES cell compartment and TS cell compartment) surrounded by an outer cell layer, the VE-like layer, were selected. The ES cell compartment was expected to be epithelialized with a lumen. The TS cell compartment was more variable in appearance. Therefore, even though one would also want an epithelial-looking TS cell compartment similar to the ExE of natural embryos, a wider range of appearances for the TS cell compartment was selected. Since the majority of ETiX embryoids were generated by using wild-type, unlabelled stem cell lines, the selection was based on morphology alone. ETiX embryoids with the correct body plan of ES cell and TS cell compartments surrounded by a VE-like layer were then transferred to an equilibrated medium to continue their culture. During selection on day 5, however, additional criteria were included: (1) the lumens of the ES cell and TS cell compartments were expected to be merged; (2) ideally, the beginning of gastrulation on one side of the ETiX embryoids can be observed; (3) the AVE was expected to have migrated to the ES cell-TS cell boundary and be opposite to the forming streak; (4) ETiX embryoids with the AVE stuck at the tip of the structure or not at the boundary were excluded; and 5) when using the Triple reporter cells, one side showing higher Sox2-Venus expression was ensured. On day 4, 10%-15% of the structures formed in the pyramidal microwells were collected. From day 4 to day 5, 20% of the structures collected on day 4 were cultured.

Image Acquisition, Processing and Analysis

Images were acquired using Leica SP5 and SP8 confocal microscopes (Leica Microsystems) with 40× oil objective and 25× water objective, respectively. A 405-nm diode laser (DAPI), a 488-nm argon laser (Alexa Fluor 488), a 543-nm HeNe laser (Alexa Fluor 568) and a 633-nm HeNe laser (Alexa Fluor 647) were used to excite the fluorophores. Images were taken with a z-step of 1.2-5 µm. FIJI and NDSAFIR 3.0, the Smart Denoise (Gurdon Institute) were used to process and analyze the images. Area measurements used to generate the quantifications were also collected using Fiji. Figures were assembled with Adobe Illustrator v26.0.1.

The images provided were representative of multiple experiments analyzed. As with natural embryos, the features of the ETiX embryoids described can be observed under a regular stereomicroscope—for example, the beating heart-like structure was clearly visible in 87% of the structures obtained. The headfolds and somites were also readily observable and recognizable. Observation of such morphology in bright-field microscopy was predictive of staining reproducibility. Furthermore, analysis by single-cell sequencing of individual ETiX embryoids showed great reproducibility among these structures. Quantifications suggested that, albeit greater size variability was observed across ETiX embryoids, the organs and regions analyzed were of comparable size to those of natural embryos. Finally, it is also likely that some of the variability observed in ETiX embryoids was caused by ex utero culture itself, since it caused variability in the development of natural embryos as well.

Sequential smFISH—Primary Probe Design

Gene-specific primary probe sets were designed as previously described with some modifications. In brief, probe sets of 35-nt binding sites were crafted for each gene using exonic sequences from the consensus regions for all spliced isoforms. For genes that did not yield enough targets (>40), the intronic and 5' untranslated region sequences were also used. The masked genome and annotation databases from University of California Santa Cruz (UCSC) were used to obtain the gene sequences and extract 35-bp sequences with 45-75% GC content and without a region of repeating 5-nt bases of the same kind. Each probe sequence was then run against a BLAST database constructed from GENCODE-reversed introns and mRNA sequences. All probes with BLAST hits on any sequence other than the target gene with at least a 15-nt match were considered off-target hits and dropped from the probe set. All probe sets for each gene were then trimmed to a maximum of 40 probes, removing all probes lying furthest from the targeted 55% GC content.

Sequential smFISH—Readout Probe Design.

Readout probes were used as previously designed. In brief, a set of 20-nt probe sequences was generated randomly by combinations of A, T, G and C nucleotides. Sequences of 45-60% GC were selected and run against a BLAST database to eliminate any sequences that matched with any contiguous homology sequences longer than 14 nt to the mouse transcriptome. The reverse complements of these readout sequences were included in the primary probes with AA or TAAT linkers in a manner as follows: [readout]-AA-[readout]-AA-[readout]-TAAT-[probe binding sequence]-TAAT-[readout]-AA-[readout]-AA-[readout]. Thus, each probe was 141 nt long.

Sequential smFISH—Primary Probe and Readout Probe Construction.

Primary probes were ordered as IDT oligonucleotide pools with 50 µmol per probe concentration and 5'-phosphate modification. Readout probes were ordered from IDT as 250 nmol DNA oligonucleotides with HPLC purification and 5'-fluorophore modifications (5' Alexa Fluor 647N, 5' Alexa Fluor 488N or 5' Alexa Fluor 546N).

Sequential smFIsH—Coverslip Functionalization.

Coverslips were functionalized by 1 M HCl treatment at room temperature for 1 h, rinsing with water once, 1 M NaOH treatment at room temperature for 1 h, and then immersion in 1% bind-silane (GE-Healthcare, 17-1330-01) prepared in pH 3.5 10% (v/v) acidic ethanol solution for 30 min. The coverslips were then thoroughly rinsed in 100% ethanol 3 times and placed on glass slides for heat-curing in an oven at >90° C. for 30 min. The coverslips were allowed to cool down. The area of the coverslip intended for final tissue section placement was covered with 100 µg/µl of poly-D-lysine (Gibco, A3890401) for >1 h. The coverslips were then thoroughly rinsed with water three times and then allowed to dry in a tissue culture hood with UV-sanitation. For long-term storage, the coverslips were kept dry at 4° C. for <2 weeks before use.

Sequential smFISH—Sequential smFISH Experiment on ETiX Embryoids.

ETiX embryoids and natural embryos were fixed with 4% paraformaldehyde at 4° C. overnight. They were then washed with PBST (PBS with 0.1% Tween 20) twice at 4° C. and dehydrated into methanol gradually with a series of graded methanol/PBST washes for 10 min each at 4° C. Samples were stored at −20° C. overnight before they were rehydrated in a series of graded methanol/PBST washes and washed twice in PBST at 4° C. for 10 min. Embryo samples were then immersed in 30% sucrose/PBS (w/v) overnight at 4° C. or until the sample sank to the bottom of the tube. Samples were transferred to a cryomold, carefully positioned in OCT compound solution (Agar Scientific), and frozen in dry ice ethanol. Samples were stored at −80° C. before sectioning.

The tissue blocks were cut at 20-µm thickness using a micron cryostat and placed onto the functionalized coverslips. After drying out for >15 min, the coverslips were placed at −80° C. for long-term storage. After at least one day of storage at −20° C., the tissue sections were permeabilized in 70% ethanol at 4° C. for >1 h, and then dried and cleared with 1 ml of 8% SDS (Invitrogen, AM9822) in 1×PBS at room temperature for 30 min. After rinsing with PBS two times and nuclease-free water one time, a custom-made flow cell (fluidic volume about 30 µl), which were made from glass slide (25×75 mm) with 1 mm thickness and 1 mm diameter holes and a PET film coated on both sides with an acrylic adhesive with total thickness of 0.25 mm (Grace Bio-Labs, RD481902) was attached to the coverslips. Using the 1 mm diameter holes, the tissue samples were incubated in 30% hybridization buffer (Molecular Instruments) containing 3.3 nM of each probe overnight at 37° C. The holes of the flow cells were covered using a sticker (Grace Bio-Labs, GBL629200) to prevent evaporation during incubation. The samples were then washed with 30% wash buffer (Molecular Instruments) for 4 times over 1 h, and then rinsed with 4× saline-sodium citrate buffer (SSC) (Thermo Fisher, 15557036) 5 times.

Sequential smFISH—Sequential smFISH on Control Embryos.

All steps for ETiX embryoid smFISH experiment were followed with the additional clearing steps to improve signal-to-noise ratio in the resulting images. In addition to the gene marker probes, a poly-30-T LNA oligonucleotide with 5'-acrydite modification (IDT) was hybridized at 2 µM. After 30% wash buffer washes, a sticker containing a circle cutout of 3 mm diameter and 100 µm thickness was applied to the sample. A gel solution containing 4% acrylamide and 0.2% bis-acrylamide (Bio-Rad, 1610154) with 0.25% VA-044 (Fujifilm, LB-VA044-50GS) was assembled on ice and treated with nitrogen for >5 min. Twenty microliters of the solution was dropped onto the sample (contained inside the circle cutout within the sticker) and a 22×22 mm coverslip was applied on top of the sample. The sample was then placed into a humidified airtight chamber and all the oxygen was removed by flowing in nitrogen for >10 min. To allow infiltration of the sample with the hydrogel, the sample was incubated at 4° C. overnight, and then placed at 37° C. for 3.5 h to allow the hydrogel to solidify. The small glass coverslip and sticker were then removed. The samples were treated with 1:100 Proteinase K (NEB, P8107S), 50 mM pH 8.0 Tris-HCl (Thermo Fisher, 15568025), 1 mM EDTA (Thermo Fisher, 15575020), 0.5% Triton X-100 (Sigma, 93443), 500 mM NaCl (Sigma, S5150), and 1% SDS (Invitrogen, AM9822) for 2.5 h at 37° C. in a humidified chamber. The sample was then washed with 2×SSC for 15 min, and treated with Label-X as previously described (0.1 µg/µl of Acryoyl-X SE (Thermo Fisher A20770) and 0.1 µg/µl of Label-IT Reagent (Mirus, MIR3900)) for 45 min at 37° C. The sample was washed with 2×SSC, and then re-embedded in a hydrogel as done above for further stabilization for long-term imaging.

Sequential smFISH—Microscope Setup.

All imaging experiments were performed with the imaging platform and fluidics delivery system like those previously described. The microscope (Ti Eclipse) was equipped with a confocal scanner unit (Yokogawa CSU-W1), a sCMOS camera (Andor Zyla 4.2), a 60× oil objective (Nikon Plan/Apo, NA 1.4, WD 0.13), a motorized stage (ASI MS-2000), and a 7-wavelength Nikon LUNF XL laser launch. The following filters were used: 435/26 bp (Chroma) for 405 nm, 525/36 bp (Chroma) for 488 nm, 588-700 bp (Chroma 59007 dual band pass) for 561 nm, and 705/72 bp (Chroma) for 647 nm. A custom-made automated sampler was used to move designated readout probes in hybridization buffer (10 nM per readout probe in 2×SSC, 10% ethylene carbonate (Sigma, E26258), 10% dextran sulfate (Sigma, D4911), and 0.1 µg/mL DAPI (Thermo Fisher, D1306)) from a 2.0 ml 96-well plate through a multichannel fluidic valve (IDEX Health and Science, EZ1213-820-4) to the custom-made flow cell using a syringe pump (Hamilton Company, 63133-01). Other buffers, like 2×SSC, 10% wash buffer (2×SSC, 10% formamide (Thermo Fisher, AM9342), 0.1% Triton X-100 in nuclease-free water), 55% wash buffer (2×SSC, 55% formamide, 0.1% Triton X-100 in nuclease-free water), and anti-bleaching buffer (3 mM Trolox (Sigma, 238813), 1% w/v D-glucose (Sigma, G7528), 1:100 diluted catalase (Sigma, C3155), 1.0 mg/ml glucose oxidase (Sigma, G2133), and 50 mM pH 8.0 Tris-HCl) were also moved through the multichannel fluidic valve to the custom-made flow cell using the syringe pump. The integration of imaging and the automated fluidics delivery system was controlled by custom-written scripts in μManager and Python using Jupyter notebooks.

Sequential smFISH—Imaging.

The sequential hybridization and imaging routines were performed similarly to those previously described with some modifications. The sample with the custom-made flow cell was first connected to the automated fluidics system on the motorized stage on the microscope. The region of interest (8×8 tile scan with 25% overlap for ETiX embryoid, 8×9 tile scan with 20% overlap for control embryo) was identified and used for sequential rounds of hybridization and imaging as follows. The hybridization buffer with readouts and DAPI was flowed onto the sample and allowed to incubate for 60 min, then washed with 10% wash buffer for 1 min, and washed with 2×SSC three times before applying anti-bleaching buffer for image acquisition. Z-stacks with sections of optical thickness of 0.65 μm were acquired for each tile, using 500-2,000 ms exposure times for all lasers used. After image acquisition, the readout probes were washed off the sample with 3 washes of 55% wash buffer, with 5-min incubation periods between each wash, followed by one wash with 2×SSC. This process was then repeated for all rounds of gene markers. For the last round of smFISH imaging, the sample was stripped of readout probes and incubated with 0.1 sg/ml DAPI in 2×SSC for 30 min prior to imaging in all channels.

Each readout probe hybridization and stripping routine took approximately 1.5 h. Imaging time per tile took around 8 min each. Thus, the entire tile scan took around 8.5 h. Therefore, it took approximately 5 days to complete the 11 rounds of hybridization and imaging routine for each experiment.

Sequential smFISH—Image Analysis.

To increase signal-to-noise ratio in the ETiX embryoid images, the last round of imaging (DAPI only, without readout probes) was used to subtract away the sample background signal. This was not done for the control embryo FISH images because the background in that experiment was minimal due to the additional hydrogel clearing steps. Thus, for the ETiX embryoid images, each tile of the background round was registered using the phase_cross_correlation function (without normalization) from the skimage package in Python to the corresponding tile of each smFISH round using the DAPI channel as a reference to generate a shift vector. The shift vector was then applied to the rest of the channels (488 nm, 561 nm and 647 nm) for the background round and the registered sample background was subtracted against the corresponding channel for each tile of each smFISH ETiX embryoid round.

For both the ETiX embryoid and control embryo FISH images, the background signal was further reduced for each tile by using the ImageJ rolling ball background subtraction algorithm with a radius of 50 pixels. Each DAPI tile was then max-projected and the tiles of each round were then stitched together using the ImageJ Grid/Collection stitching algorithm with regression threshold as 0.01, without overlapping computation, and standard settings otherwise. To stitch the other channels in the same manner as the DAPI channel, the rest of the channels were then max-projected. The tiles for each round were stitched together using the settings acquired from the tile configuration file generated from the DAPI tile stitching.

An Ilastik classifier was then trained and used to classify the signal for each channel (405 nm, 488 nm, 561 nm and 647 nm) of each FISH round into foreground and background. The DAPI foreground mask was dilated using a disk structuring element with 10-pixel radius and used to mask out any erroneous foreground signal from the 488 nm, 561 nm and 647 nm channels that laid far outside of nuclei-positive imaging regions. The foreground for each of the 488 nm, 561 nm and 647 nm channels was distance transformed and used to find local minima, which were used to perform a watershed to obtain a final label image, in which each label represented one detected, unique transcript. To visualize gene expression across different imaging rounds, the stitched DAPI images were then registered across different rounds to obtain a shift vector for each round. This shift vector was then applied to the label positions corresponding to their respective round. For figure visualization, the center of each label was then plotted as a disk with 7-pixel radius.

Gene Ontology Analysis

Gene Ontology (GO) for the extraembryonic endoderm was performed using the online platform DAVID. Differentially expressed genes from pairwise comparisons were selected by choosing genes with an adjusted p-value <0.05 and enriched in one sample or the other of the pairwise comparison. The list was then uploaded in the DAVID user interface and analyzed with the Gene Functional Annotation Clustering tool and the Gene Functional Annotation Table. The first 20 clusters with the highest Enrichment Score (−log P-value) were graphed. GO analysis was performed to explore the functional roles of differentially expressed mRNAs in terms of 'biological processes' between natural embryos and ETiX embryoids, and between wild-type and Pax6-knockout ETiX embryoids using the GO Enrichment Analysis online tool (GO Ontology database). Differentially expressed genes for the pairwise comparison were selected as described above. GO terms were inputted into excel for graphing purposes.

Statistical Analysis

Data were tested for normality using the Shapiro-Wilk test. Normally distributed data was analyzed with unpaired t-test as indicated in the figure legends. Data that was not normally distributed was analyzed with a Mann-Whitney U-test. All tests were performed in Prism GraphPad software v9.2. Number of samples for the statistical test is indicated in the BRIEF DESCRIPTION OF THE DRAWINGS section above. All tests were performed as two-tailed. For each test, different samples were used with the exception of FIG. 4F, in which multiple somites per sample were measured to determine the area and with the exception of FIG. 13I, in which multiple sections of a heart sample were measured for area measurements. All replicates were biological, not technical. Sample size was not predetermined. Sample allocation was randomized. Researchers were not blinded to the type of samples that they were working with.

Example 2

Embryoid Development Through Neurulation

This Example reports that ETiX embryoids cultured ex utero can develop through neurulation with high efficiency. As evidenced by the morphology and gene expression and cell type analysis, ETiX8 embryoids resembled those of natural embryos on E8.5, which is known to develop through neurulation.

To examine anterior brain development in ETiX embryoids, ES cells, TS cells and iXEN cells were seeded and allowed to self-assemble. On day 4, the ETiX embryoids with correct post-implantation morphology were transferred to suspension culture (FIG. 1A). Typically, 2-4 wells of an AggreWell plate were set up to obtain between 100 and 150 embryo-like structures on day 4, in which cavitated epithelial ES cell and TS cell compartments were enveloped by a VE-like layer. These well-organized structures constituted 10-15% of all the structures recovered from any given well. This variability reflected the random collisions between the three types of stem cells in a microwell and the variation in expression of distinct cadherins between these cell types. On day 5, ETiX embryoids that had a proamniotic cavity (resulting from the merger of cavities in the ES cell and TS cell compartments), a fully migrated AVE (at the boundary of the ES cell and TS cell compartments), and were gastrulating (as revealed by the epithelial-to-mesenchymal transition and formation of a cell layer between the ES cells and VE-like layers) were further cultured under conditions that can support the development of embryos ex utero beyond embryonic day (E) 7.5. This included supplementing the medium with glucose on day 7 and transferring gastrulating embryoids to rotating culture bottles for one additional day (from day 7 to day 8) (FIG. 1A and Methods).

Figures 1B, 1C:
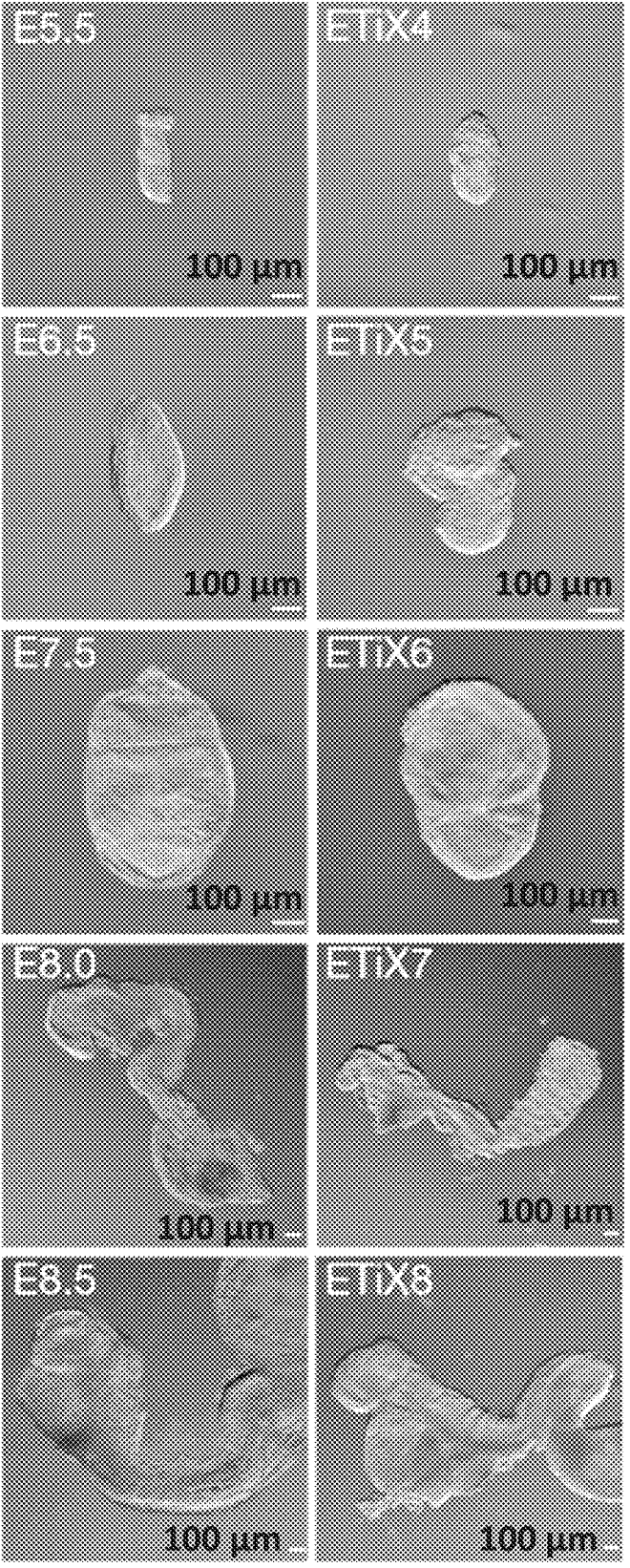
Figures 7A, 7B:
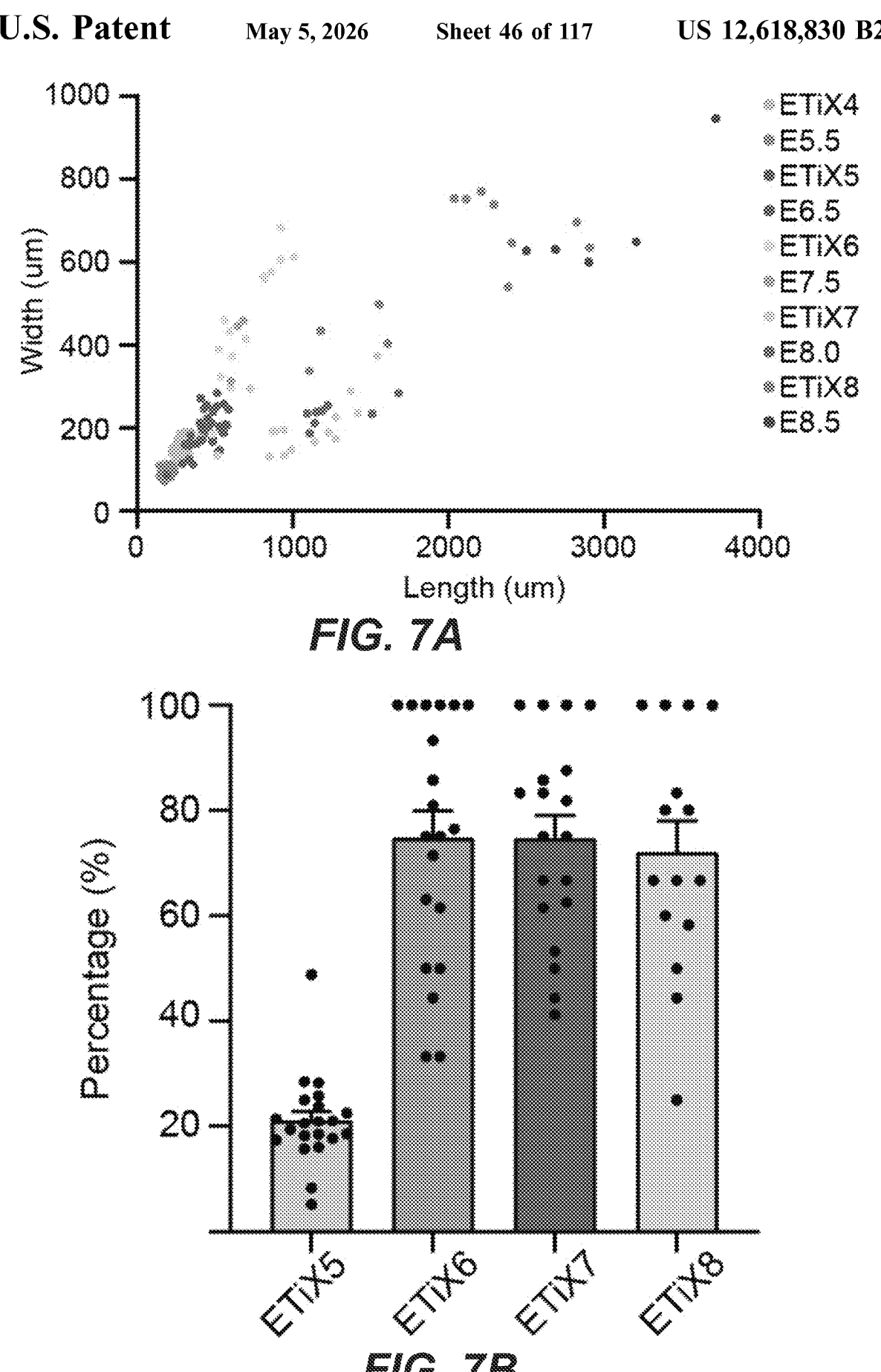

Gastrulating ETiX embryoids strongly resembled natural gastrulating embryos (FIG. 1B-FIG. 1C), although ETiX embryoids displayed greater size variability (FIG. 7A). The efficiency of ETiX embryoid development from day 4 to day 5 was on average 21%. Of the structures selected on day 5 for further culture, the efficiency of transitioning from day 5 to day 6, from day 6 to day 7 and from day 7 to day 8 was over 70% at each transition (FIG. 7B). Notably, on day 7, neurulating ETiX embryoids cultured in stationary conditions displayed an anterior-posterior axis with bifurcating neural folds extending into a neural tube and culminating in a tail bud, a morphology that resembles the early headfold stage of an E8.0 natural embryo. Posterior to this, the tail bud joined with allantois tissue, which connected to the developing chorion (FIG. 1C). The embryoid, allantois and chorion were contained in a fluid-filled sac, which was equivalent to the yolk sac (FIG. 7C). Thus, these conditions enabled ETiX embryoids to develop through and beyond gastrulation to neurulation.

Figure 1D:
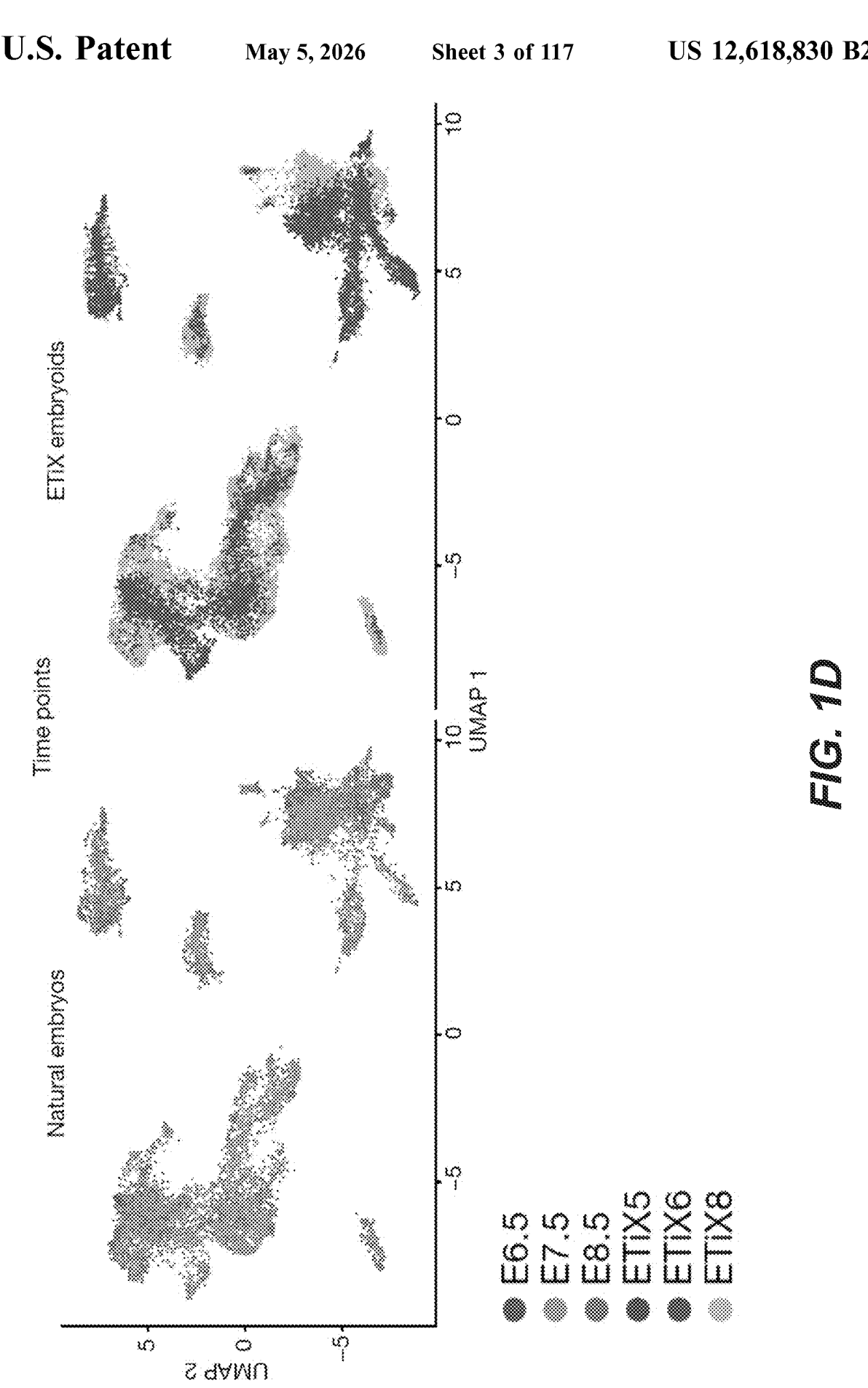
Figure 7E:
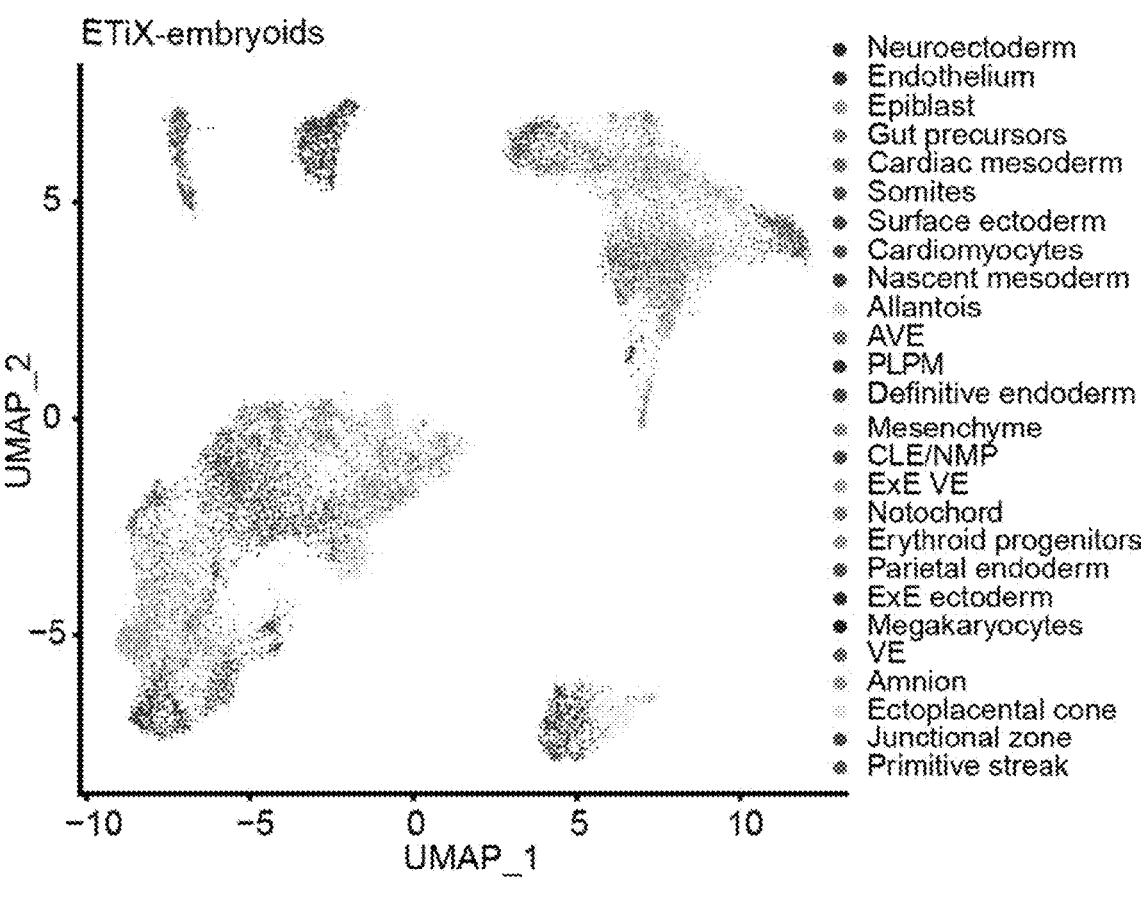

To monitor development by examining changes in gene expression at single-cell resolution, ETiX embryoids were isolated on day 5, day 6 and day 8, and natural embryos dissected on E6.5, E7.5 and E8.5 (n=29 for ETiX5, 10 for ETiX6, 7 for ETiX8, 12 for E6.5, 14 for E7.5 and 9 for E8.5). The ETiX embryoids and natural embryos were dissociated into single cells and sequenced with single-cell RNA sequencing (scRNA-seq) using the inDrops method (see Example 1). UMAP analysis revealed a similar contribution of cells to the developing lineages in natural embryos and ETiX embryoids (FIG. 1D). To determine cell types, the cell populations were subclustered using Seurat and subsequently annotated on the basis of published datasets (FIG. 1E). 26 cell types were identified on the basis of gene expression patterns, all of which were clearly presented in both natural embryos and ETiX embryoid datasets. Individual clustering of natural embryos versus ETiX embryoids showed similar local cluster topography in the UMAP (FIG. 7D-FIG. 7E). Only one cluster in natural embryos was not presented in ETiX embryoids. This missing cluster corresponded to the junctional zone of the placental cluster of the natural embryo. During development, this cell population gave rise to trophoblast giant cells and spongiotrophoblast. Some other cell types, notably PGCs and neural crest cells, were not detectable by scRNA-seq in either natural embryos or ETiX embryoids, but were observed by immunofluorescence.

Figure 1E:
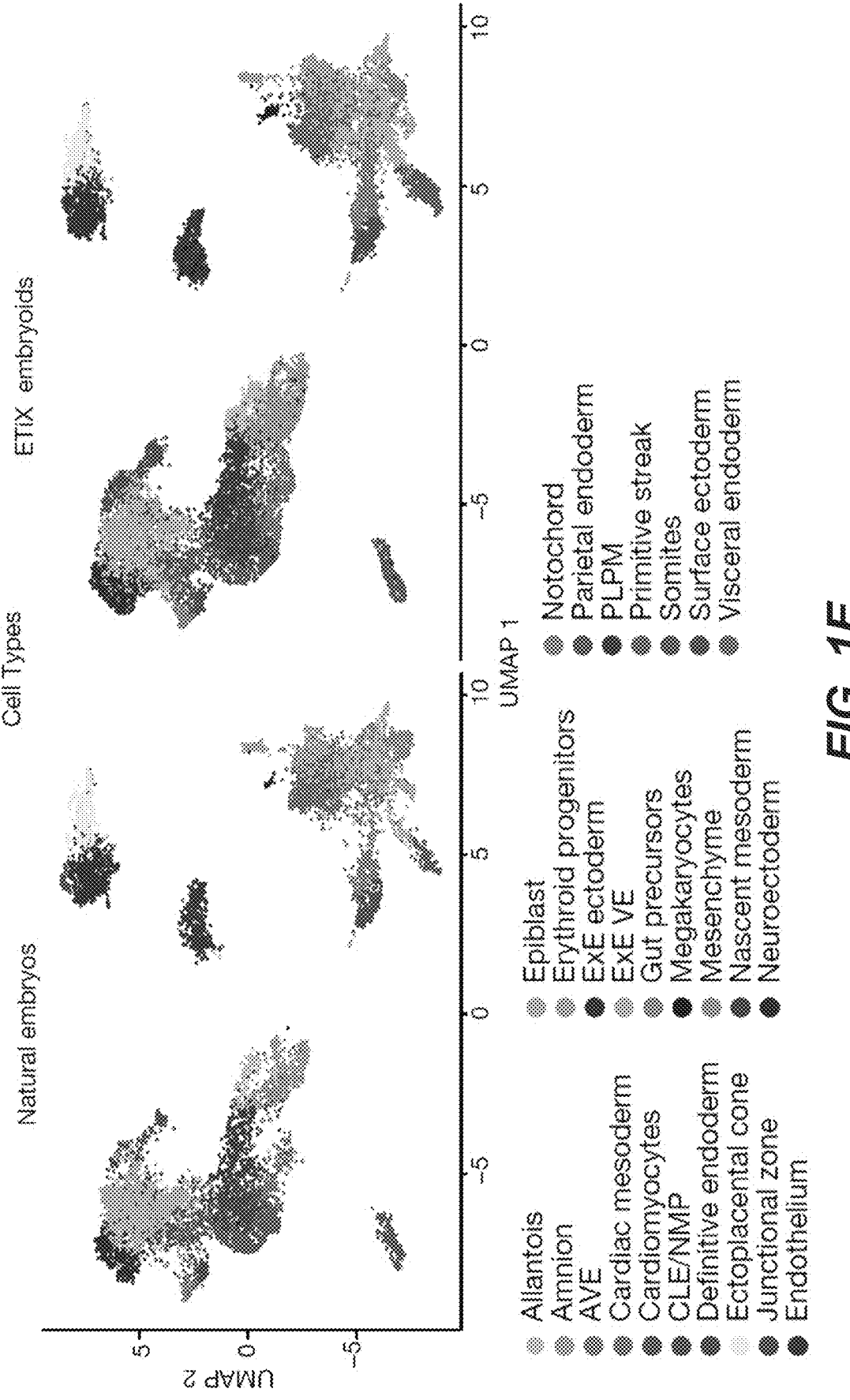
Figure 1G:
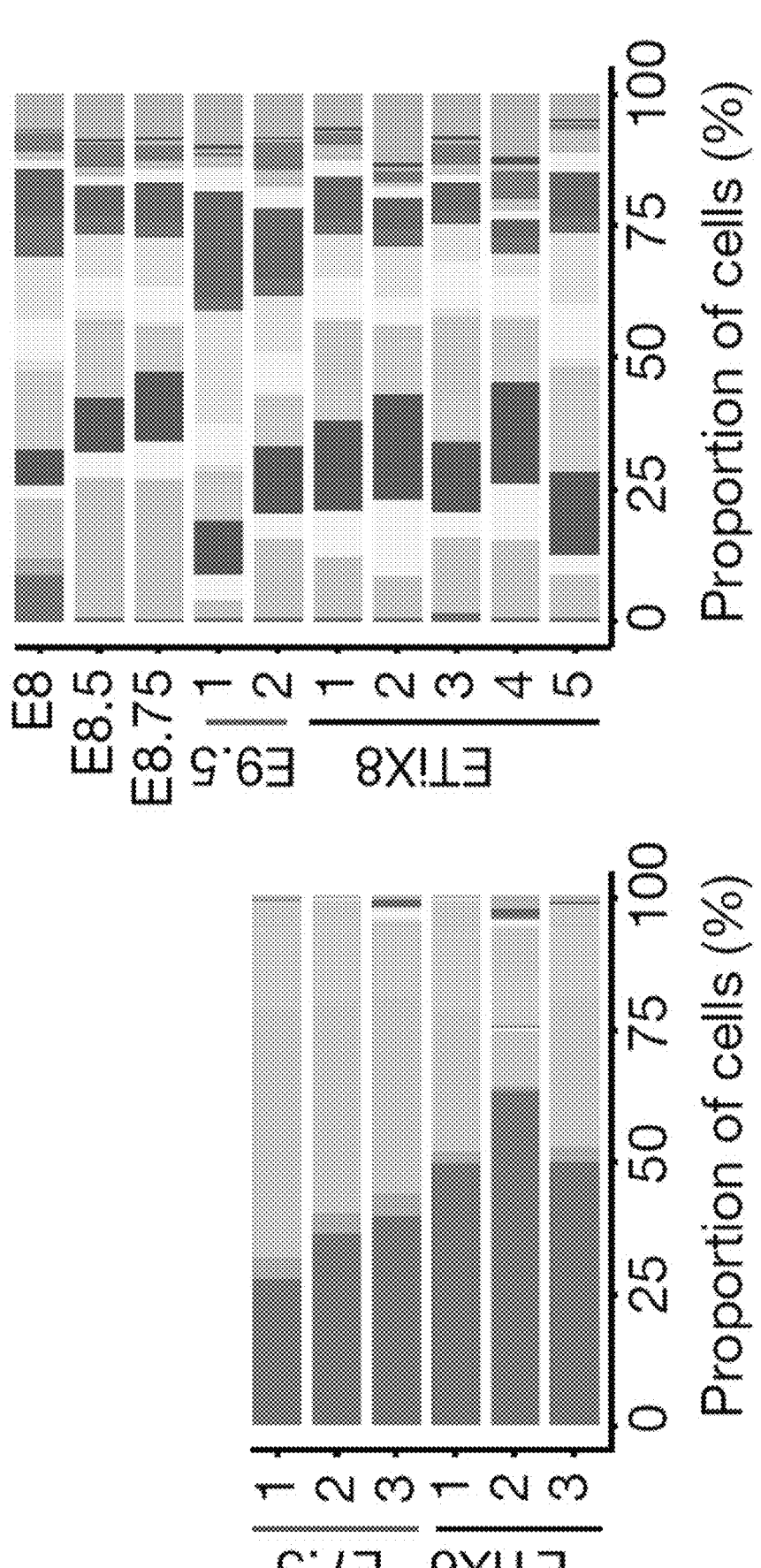
Figure 1H:
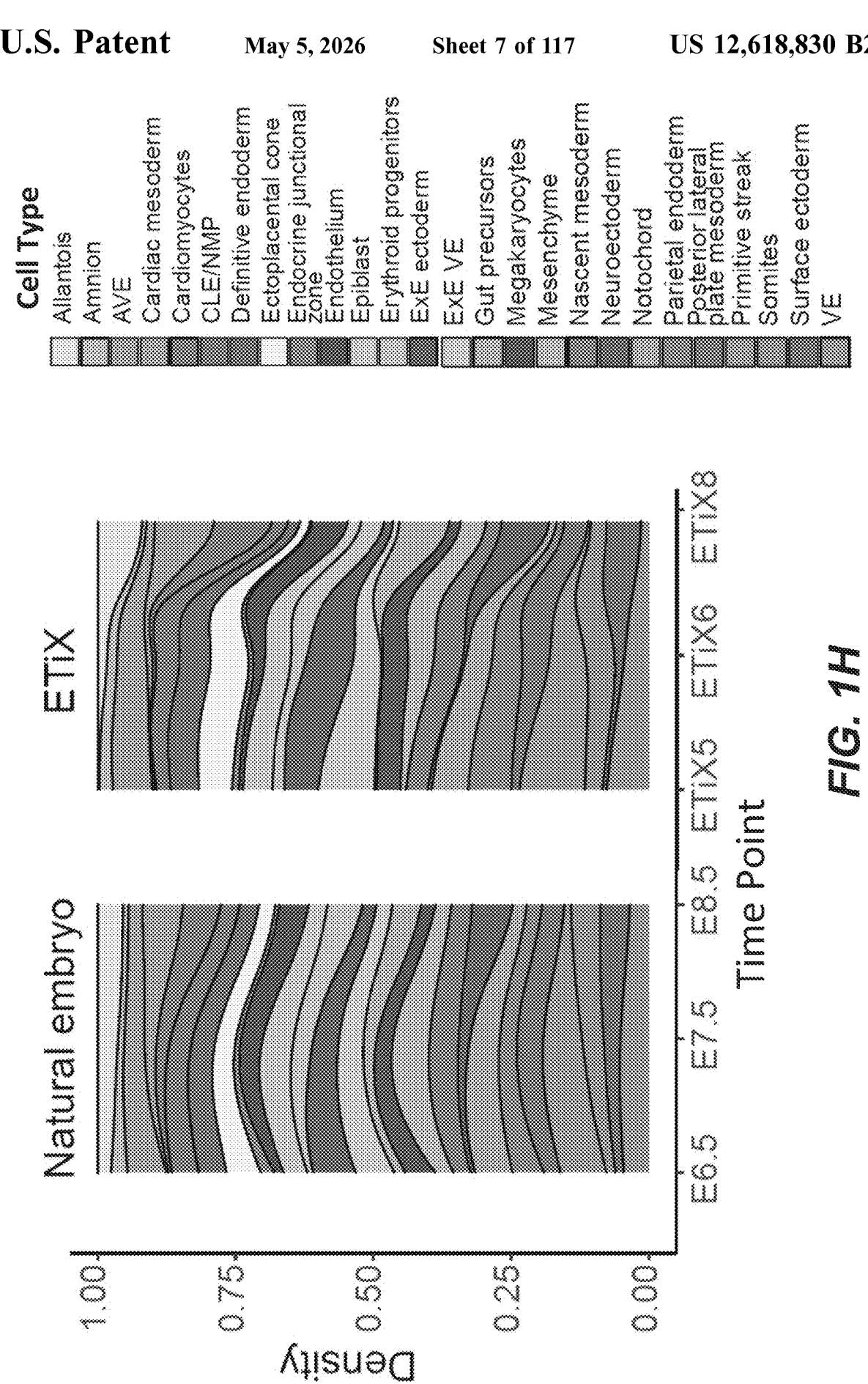
Figure 7F:
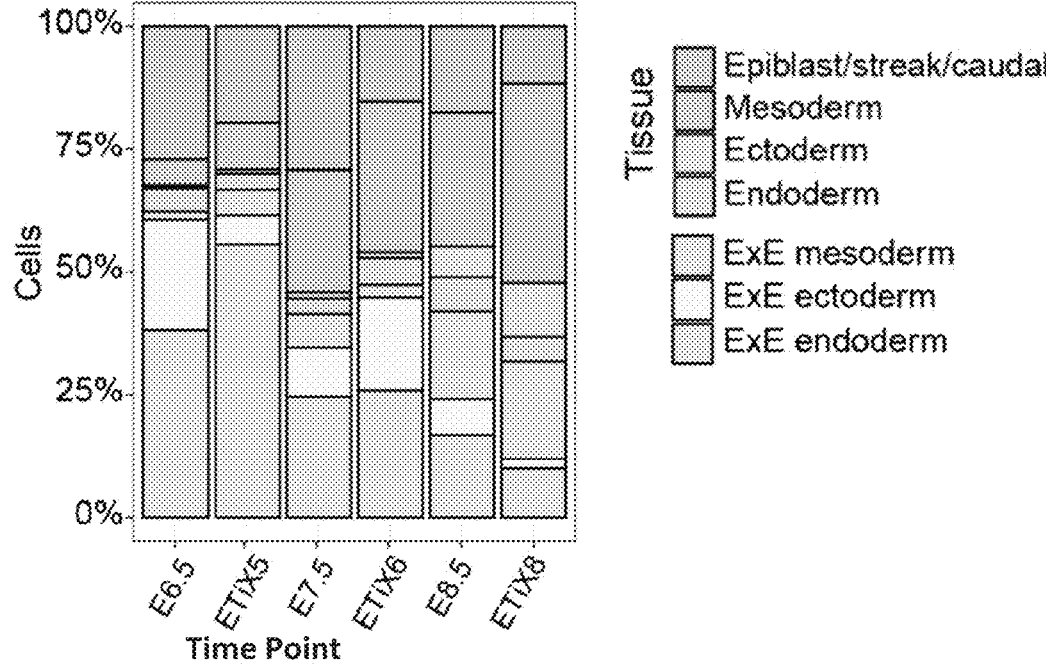
Figure 7G:
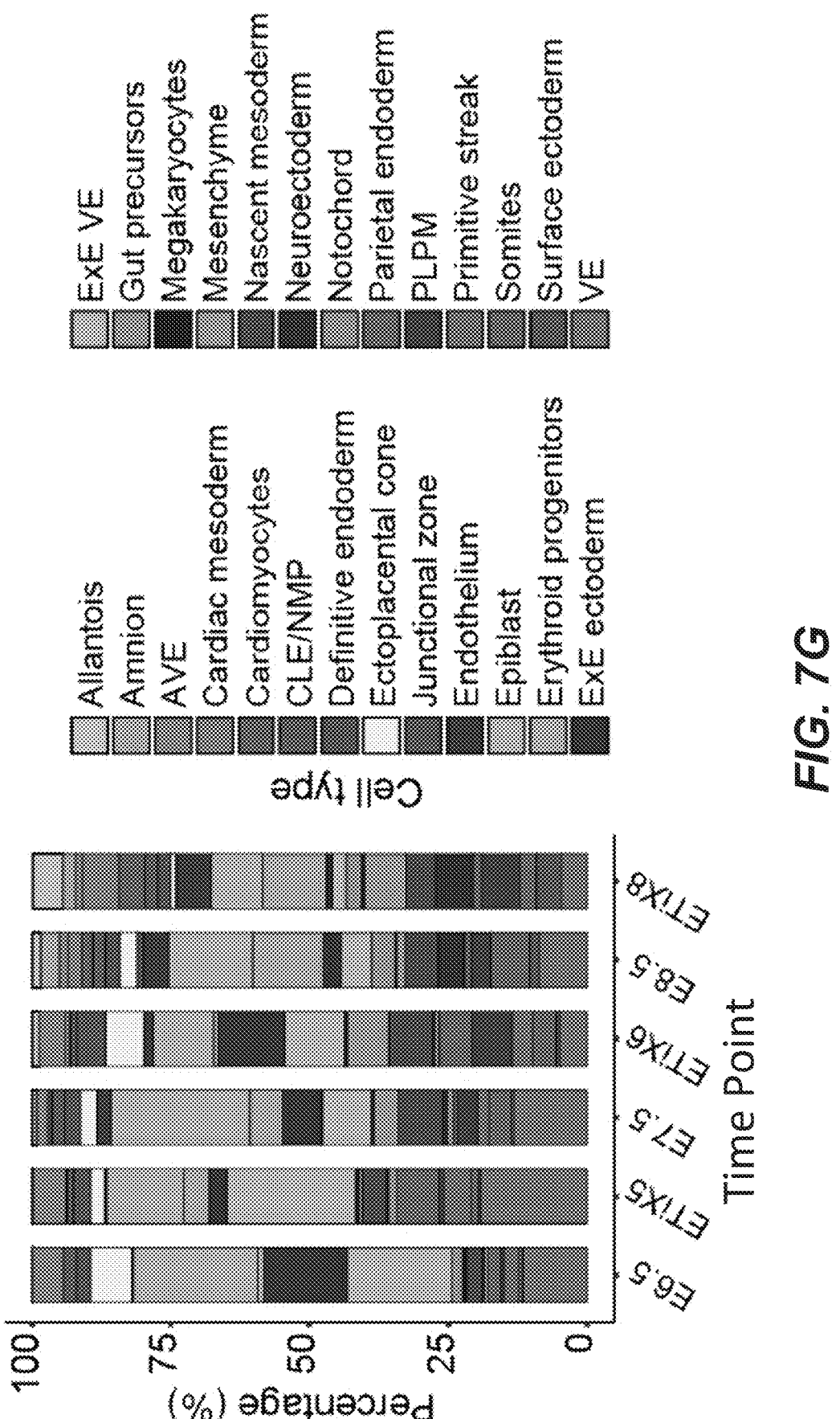
Figure 7H:
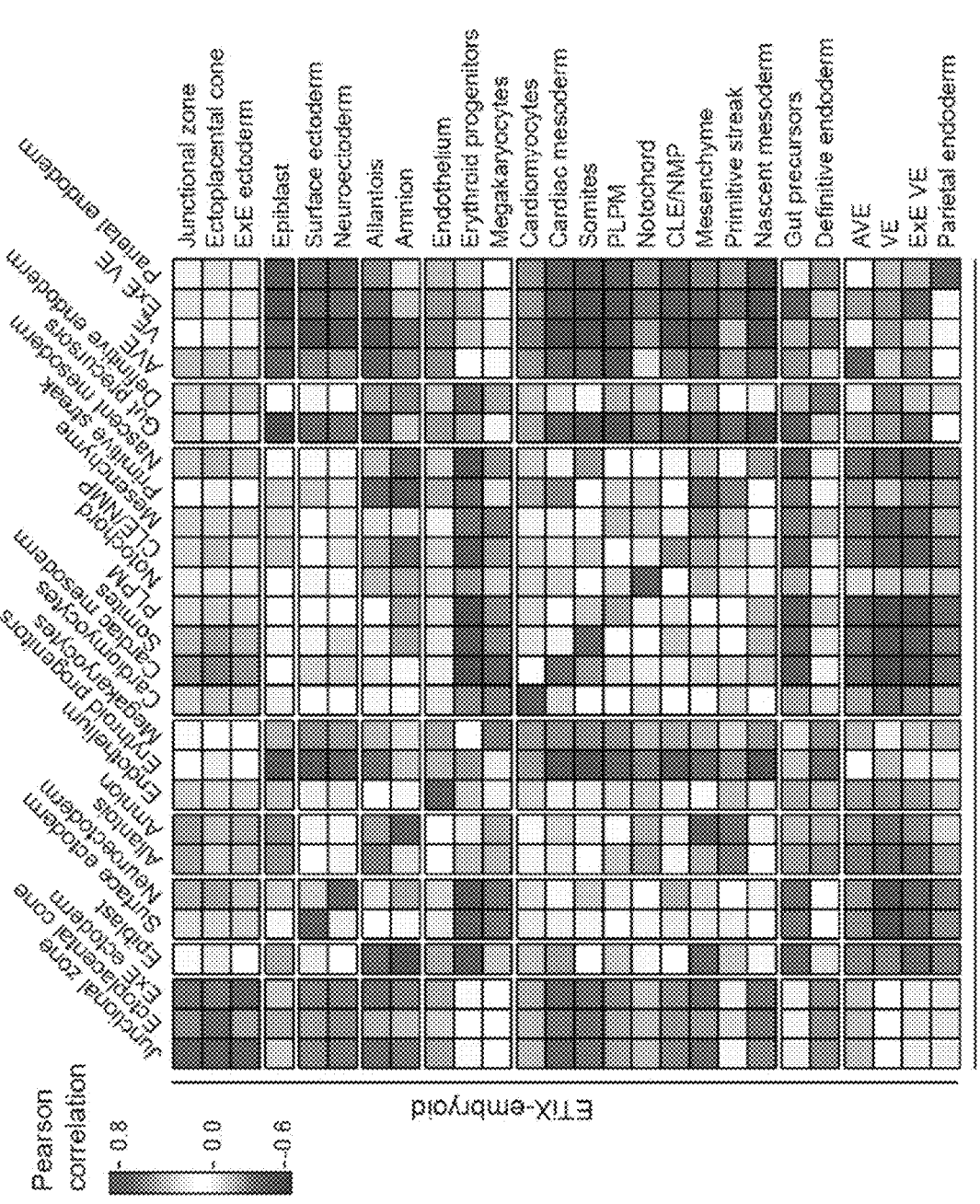
Figure 7I:
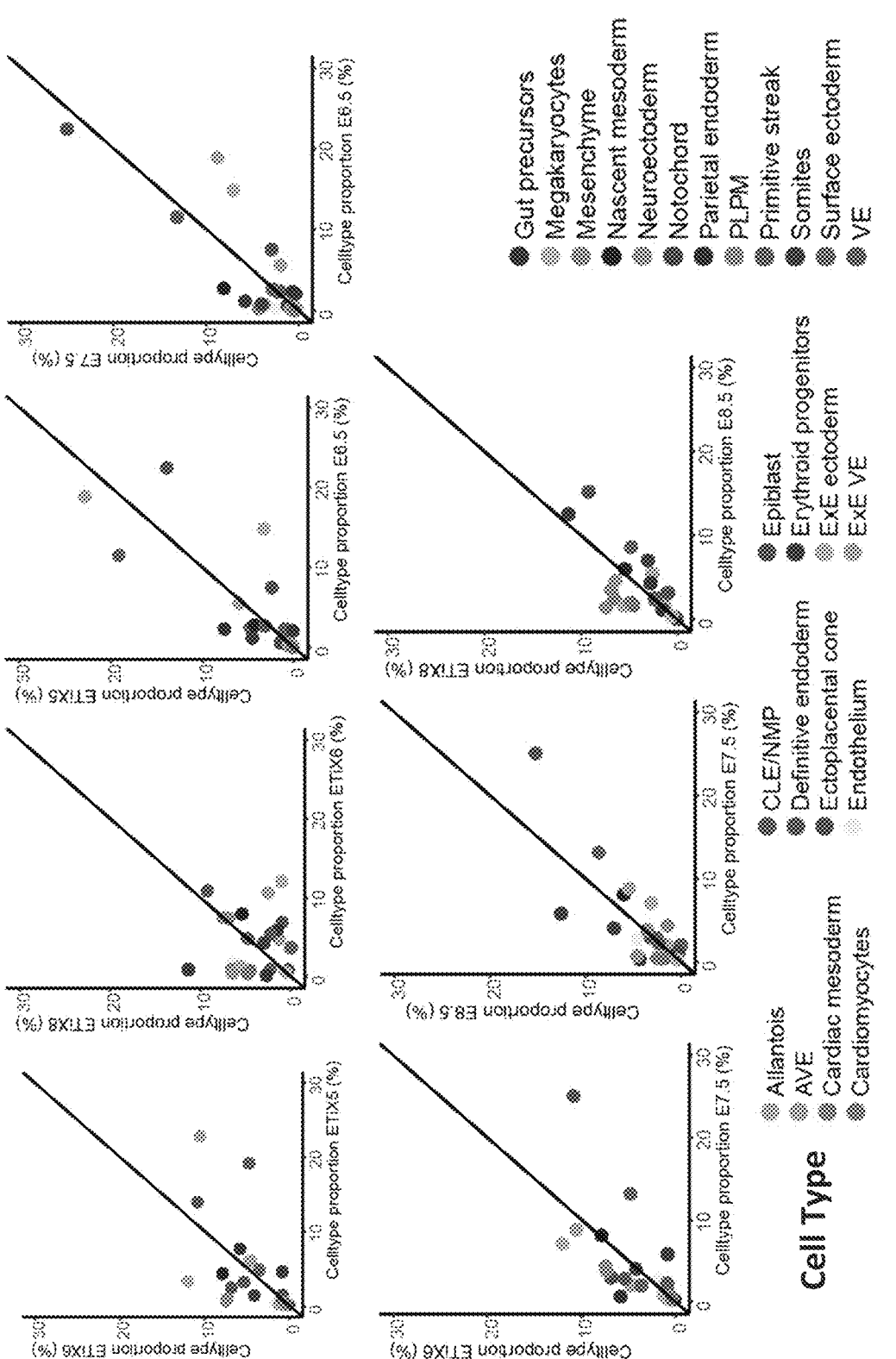
Figure 7J:
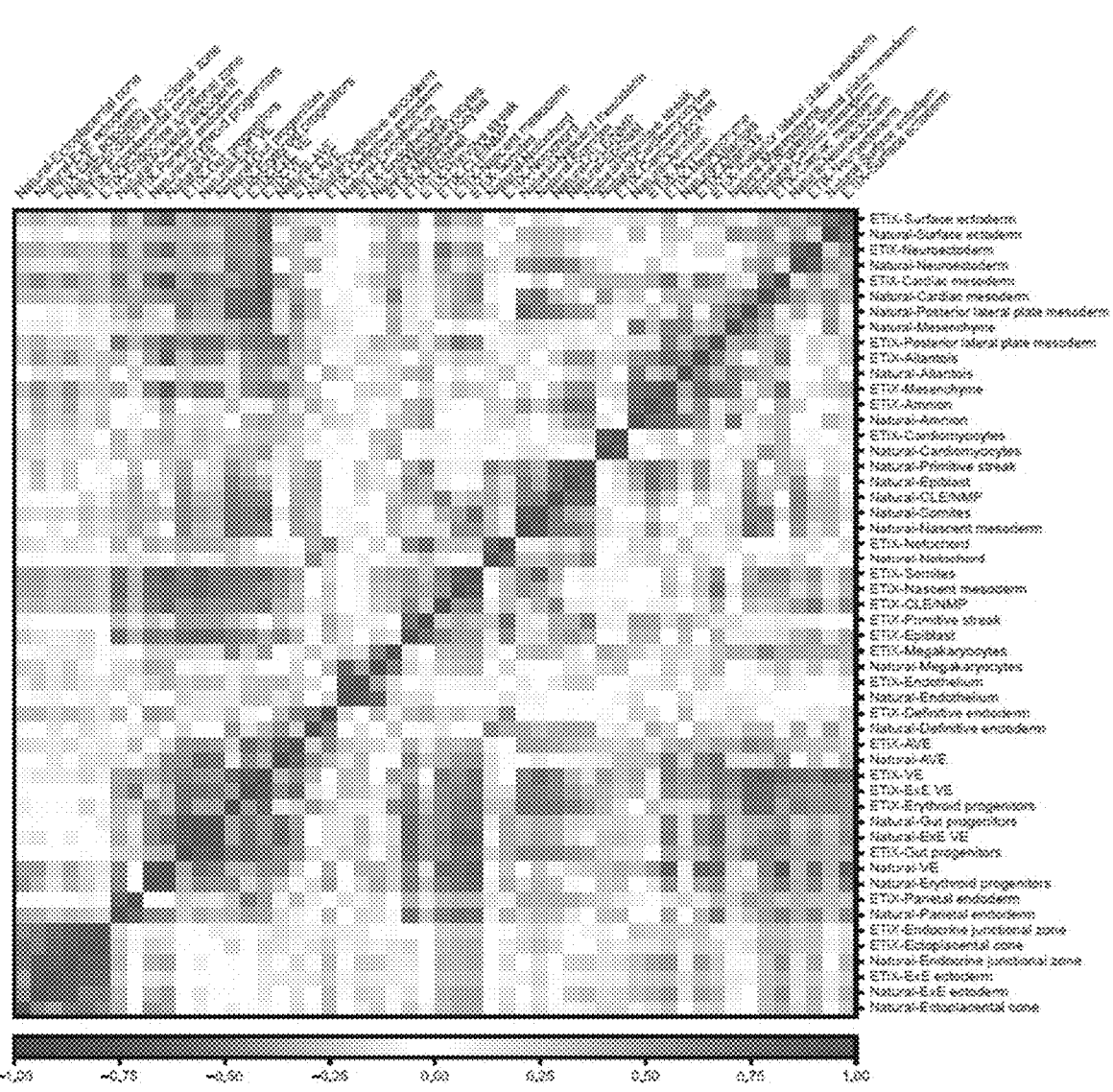

Natural embryos and ETiX embryoids displayed a largely conserved distribution of cells among the different germ layers of the epiblast (ectoderm, mesoderm and endoderm) and among embryonic and extraembryonic lineages (epiblast, ExE, extraembryonic mesoderm and extraembryonic endoderm) (FIG. 7F). As expected, natural embryos exhibited an increase in cell-type complexity over time, corresponding to the formation of differentiated tissues and organs. For instance, cardiomyocytes and neuroectoderm emerged starting from E7.5. This increase in cell-type complexity and spatiotemporal maturation of all the identified populations was similar between natural and ETiX embryoids, indicating that the neurulating embryoids followed a similar developmental timeline (FIG. 7G and FIG. 1H). For example, both systems showed the development of the three germ layers and their derivatives (neuroectoderm, surface ectoderm and gut tube progenitors), the beginning of organogenesis (cardiomyocytes), and the formation of extraembryonic tissues such as amnion and allantois (FIG. 1E and FIG. 1H). A Pearson correlation matrix indicated a high degree of similarity of gene expression between the cell-type clusters of natural embryos and those of ETiX embryoids (FIG. 7H and FIG. 7J). Cell-type proportion comparisons at different time points between natural embryos and ETiX embryoids showed gross similarity in individual clusters, although some variability was also observed (FIG. 7I). Thus, neurulating embryoids recapitulated the generation of the multiple tissues of the neurulating embryo, as evident from both their morphology and their pattern of cell-type-specific gene expression.

Figure 8A:
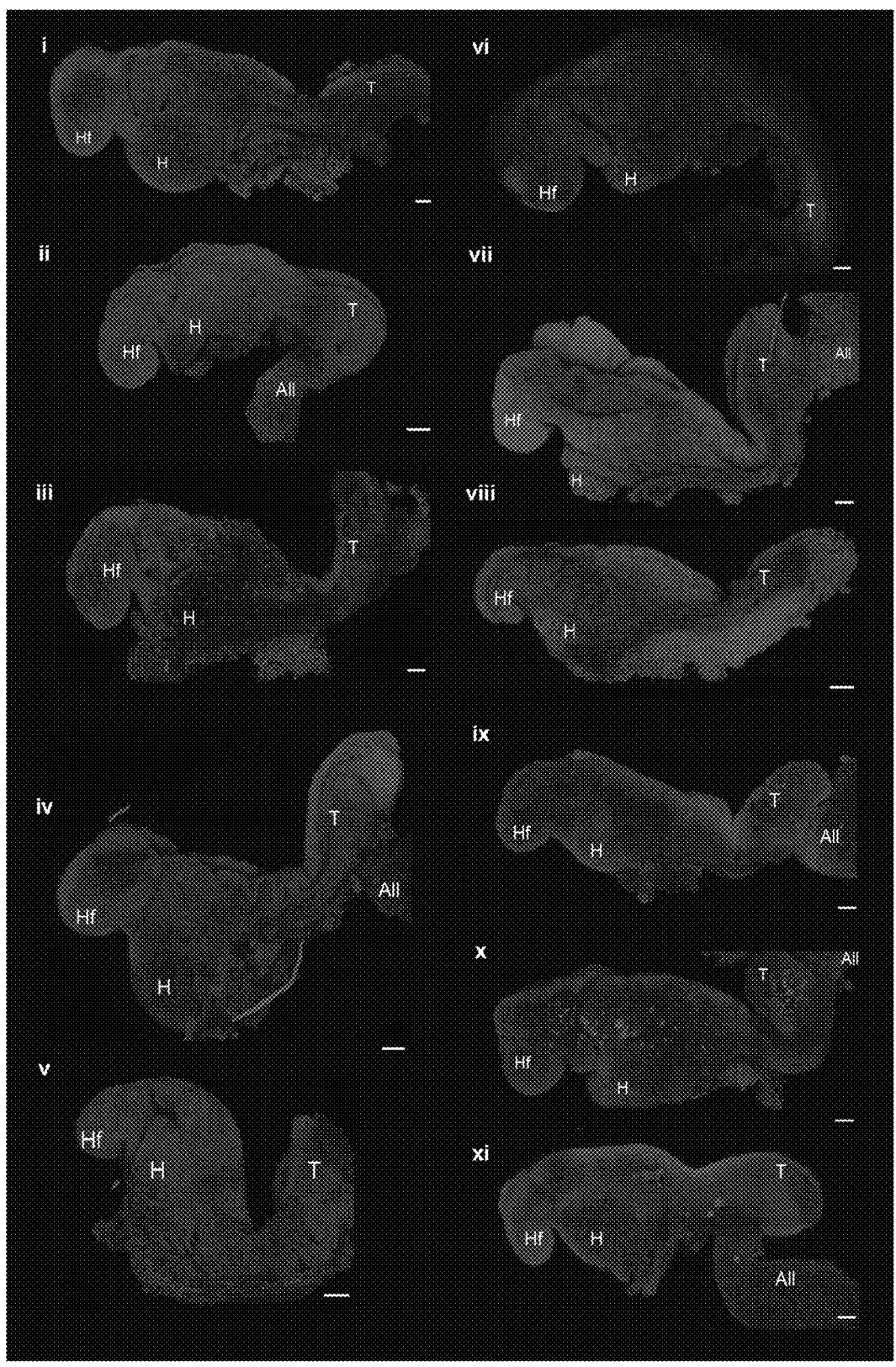
FIG. 8A-FIG. 8C depict non-limiting exemplary embodiments and data related to examples of well-formed ETiX embryoids, failed ETiX embryoids and cultured natural embryos.
Figure 8B:
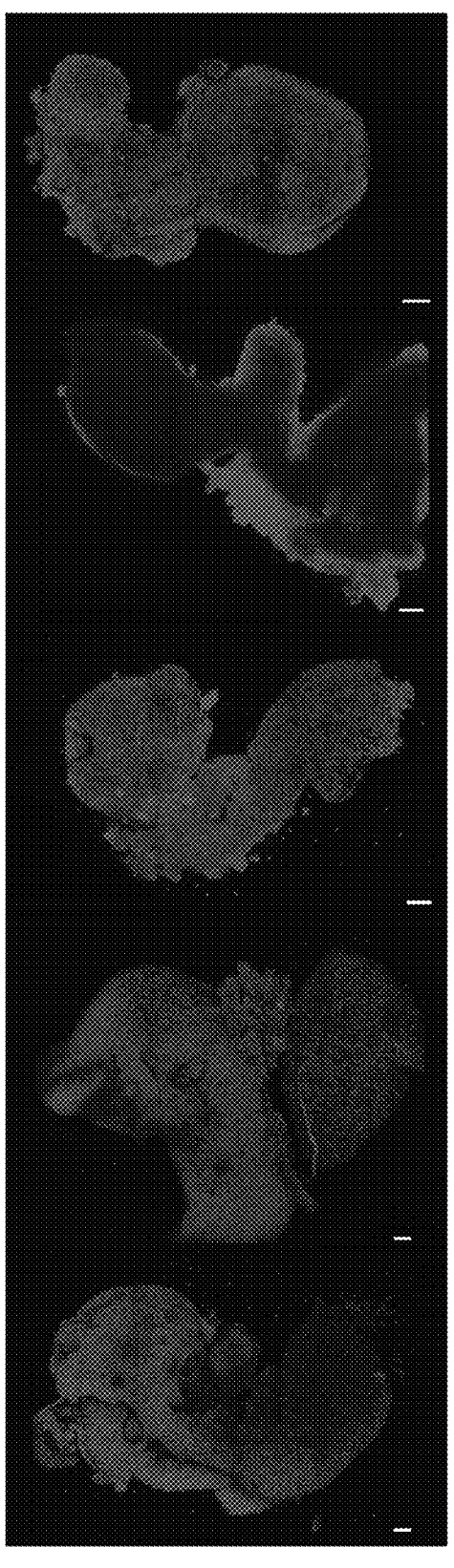
Figure 8C:
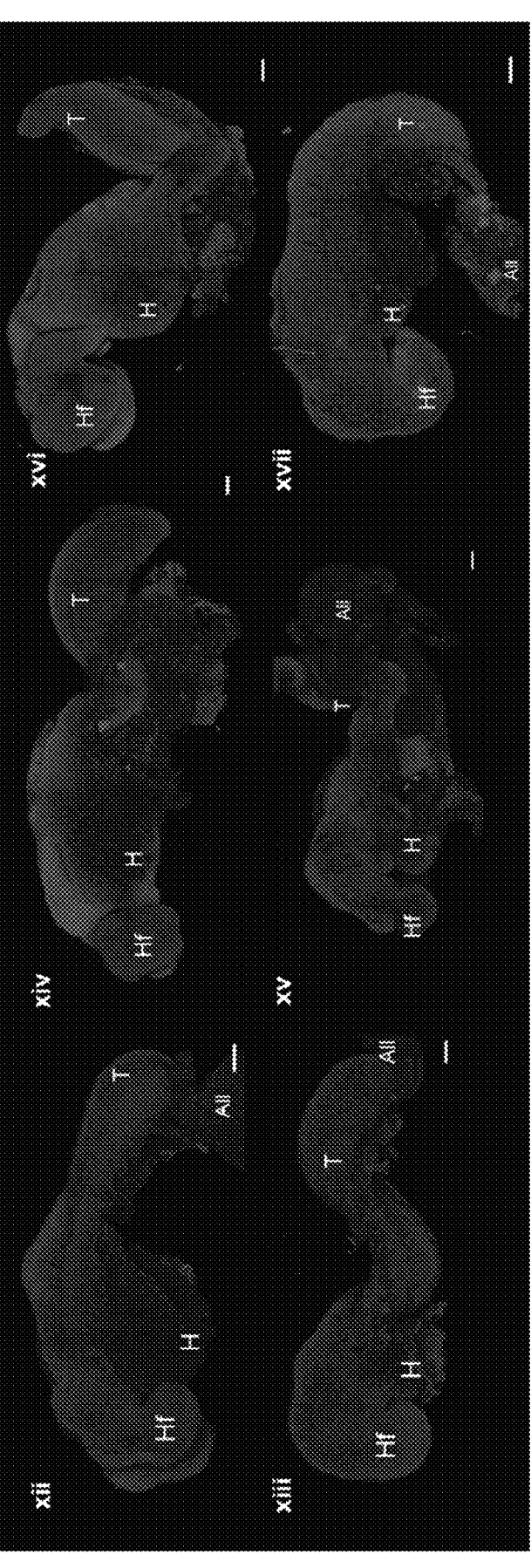

To further assess the reproducibility of neurulating embryoid formation, an additional round of single-cell sequencing was performed, in which individual ETiX embryoids of apparently correct morphology, as well as individual natural embryos cultured in vitro from E6.5 collected at different times in development were individually barcoded and analyzed by tiny-sci-RNA-seq (hereafter referred to as 'tiny-sci'; Example 1 General Methods above), a combinatorial indexing-based method for single-nucleus RNA-sequencing profiling from small amounts of starting material. Furthermore, to understand why some ETiX embryoids did not develop well, individual examples of morphologically aberrant embryoid development on day 6 and day 8 (examples of 'failed' embryoids, well-formed ETiX embryoids and natural embryos cultured in vitro (FIG. 8A-FIG. 8C)) were also included.

Figure 9A:
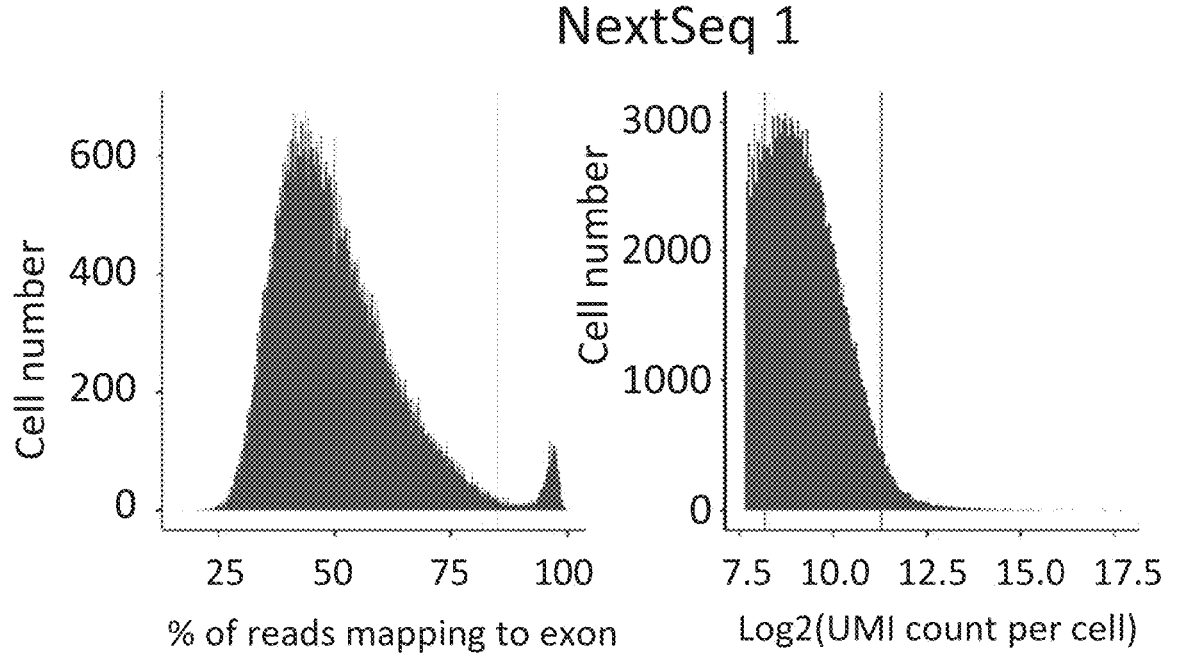
Figure 9B:
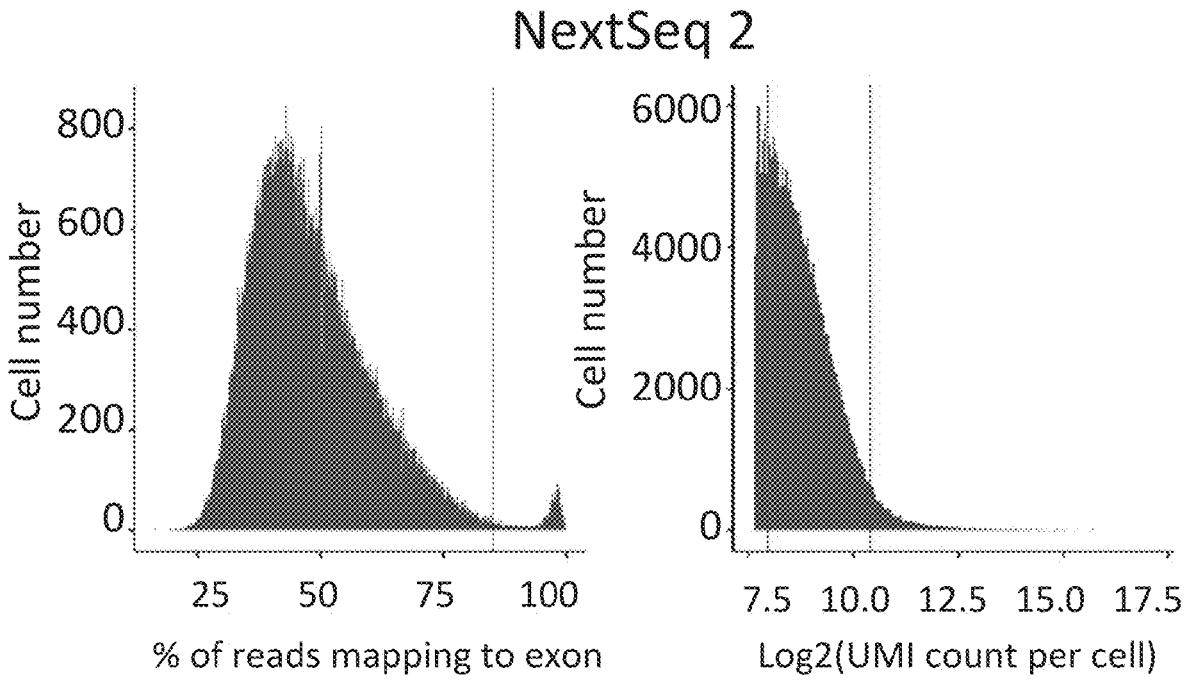
Figure 9D:
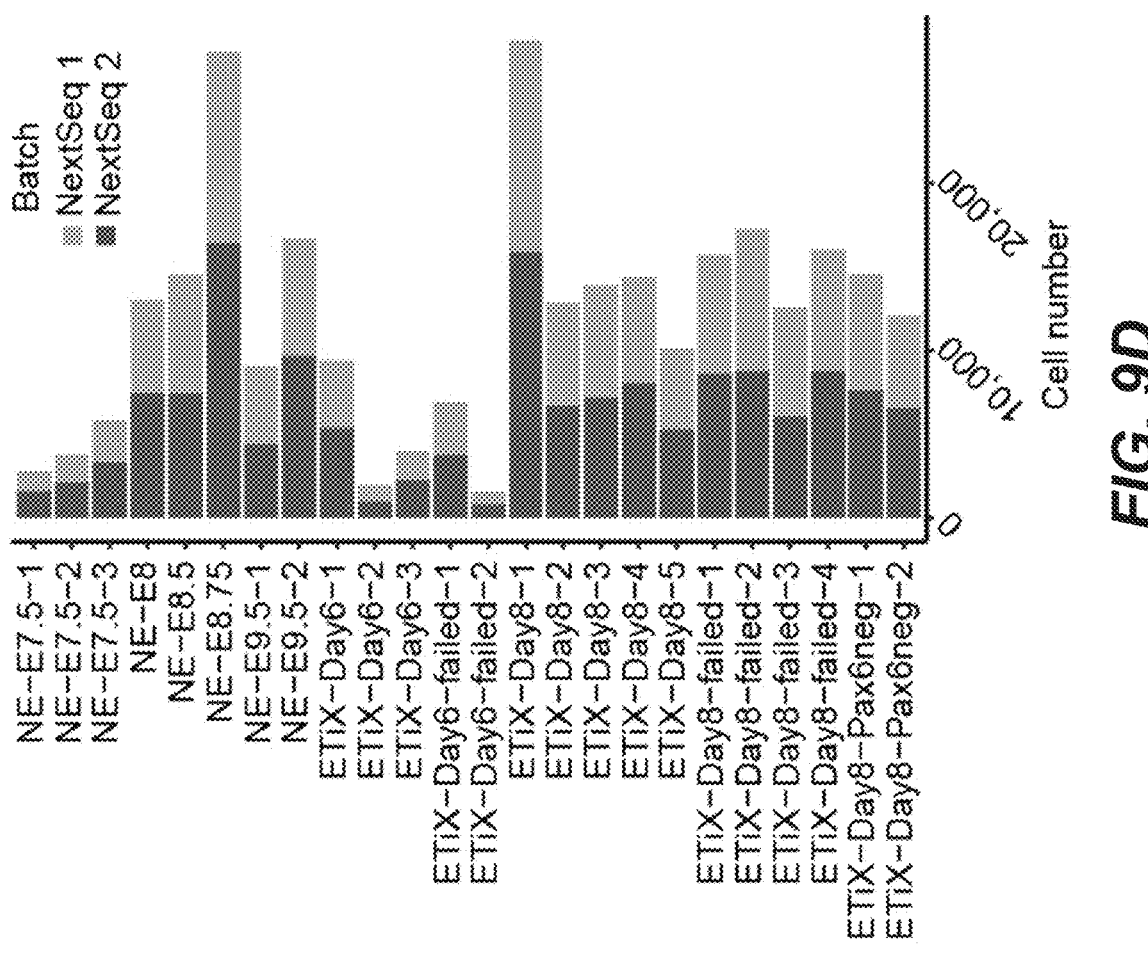
Figure 9C:
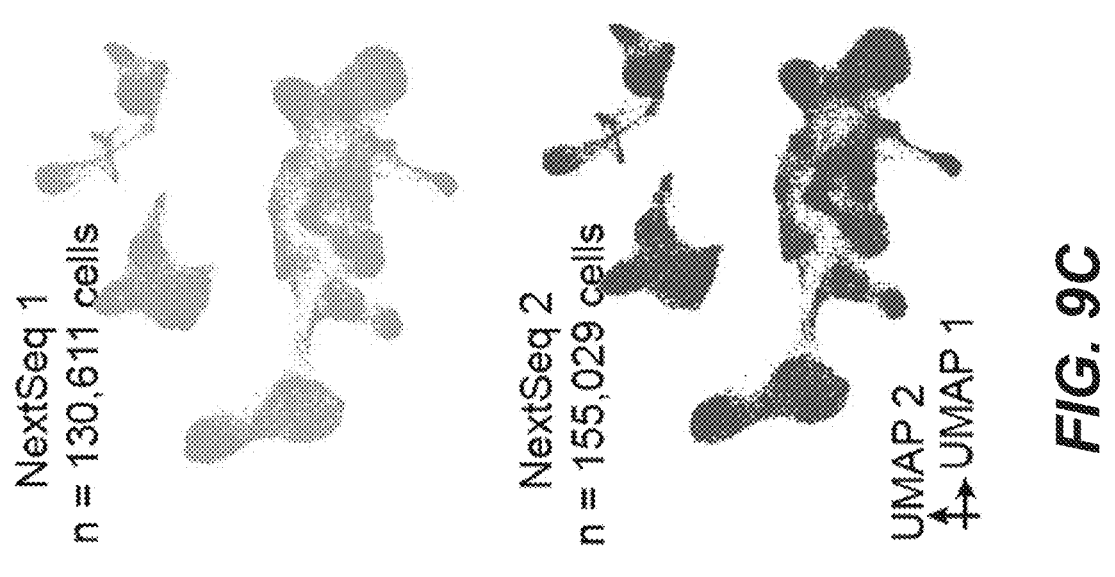
Figures 9E, 9F:
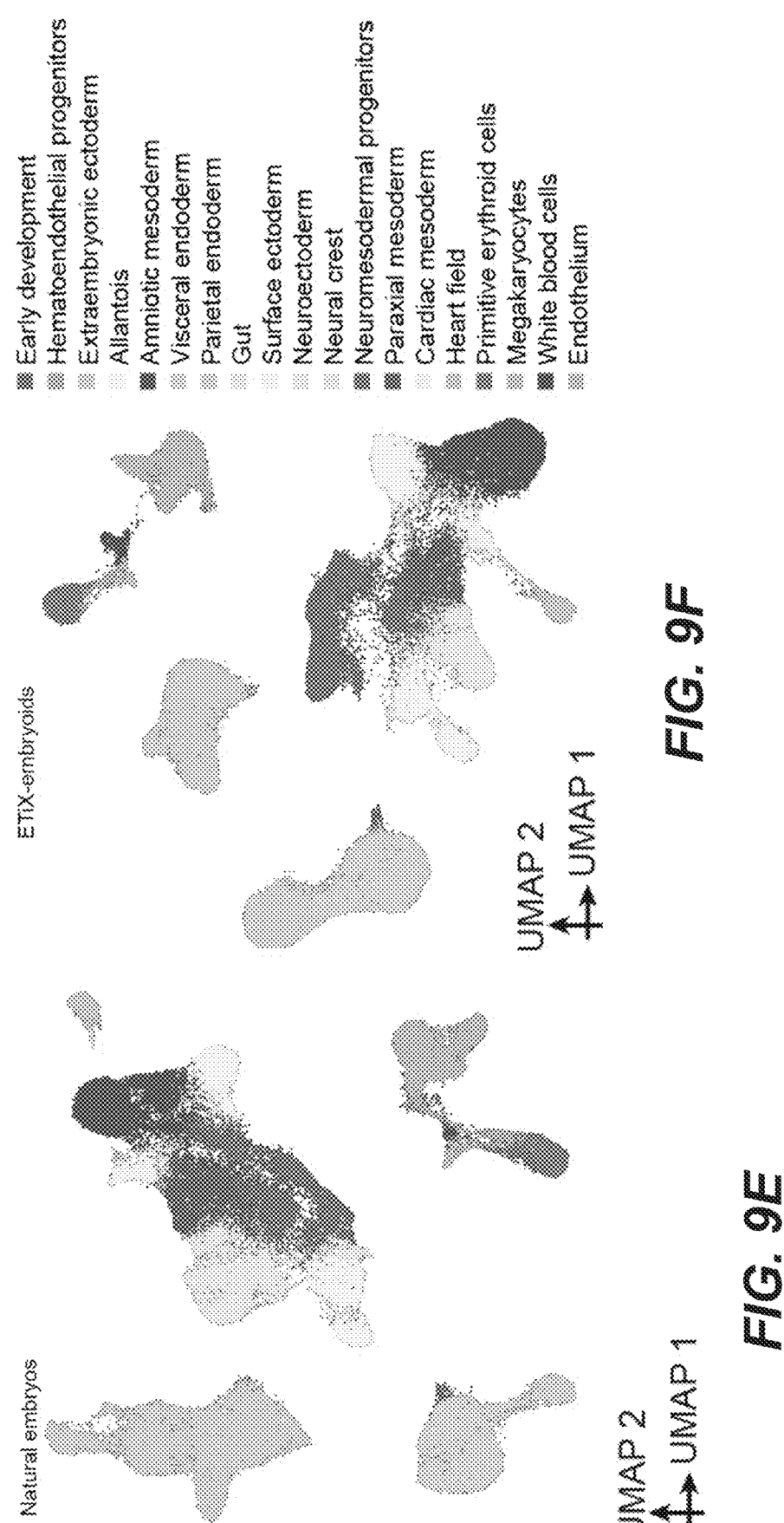
Figure 9G:
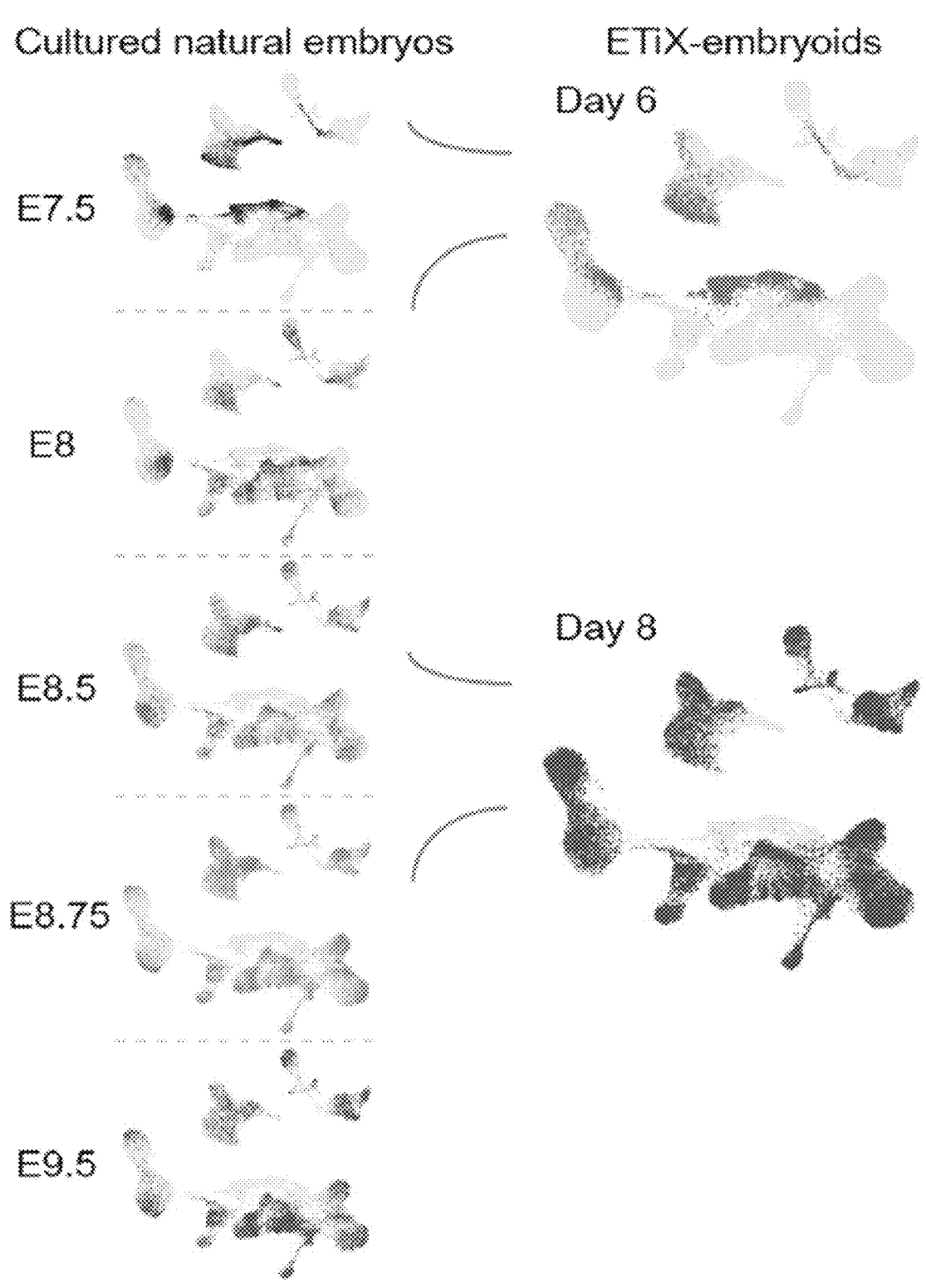
Figure 9H:
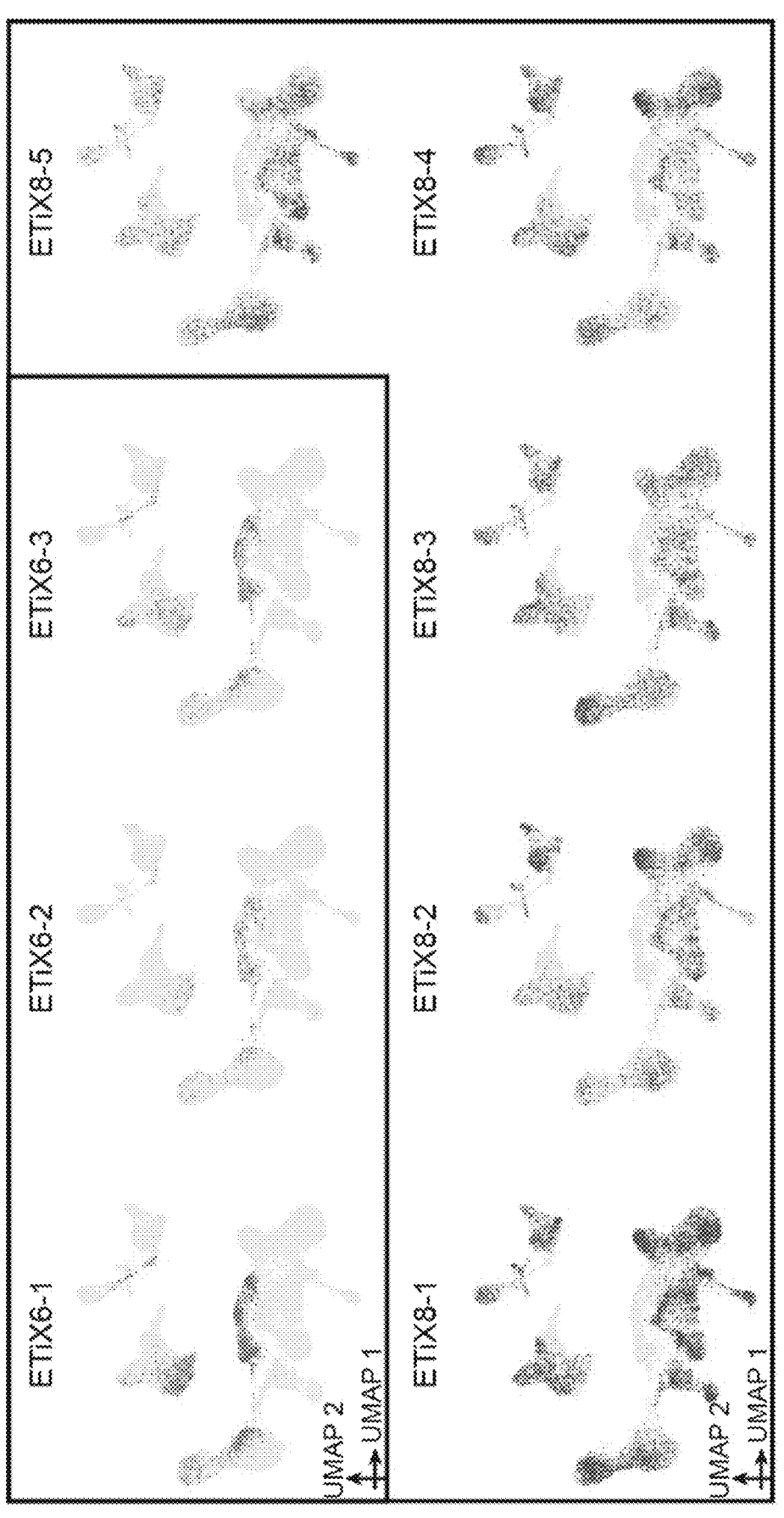
Figure 9I:
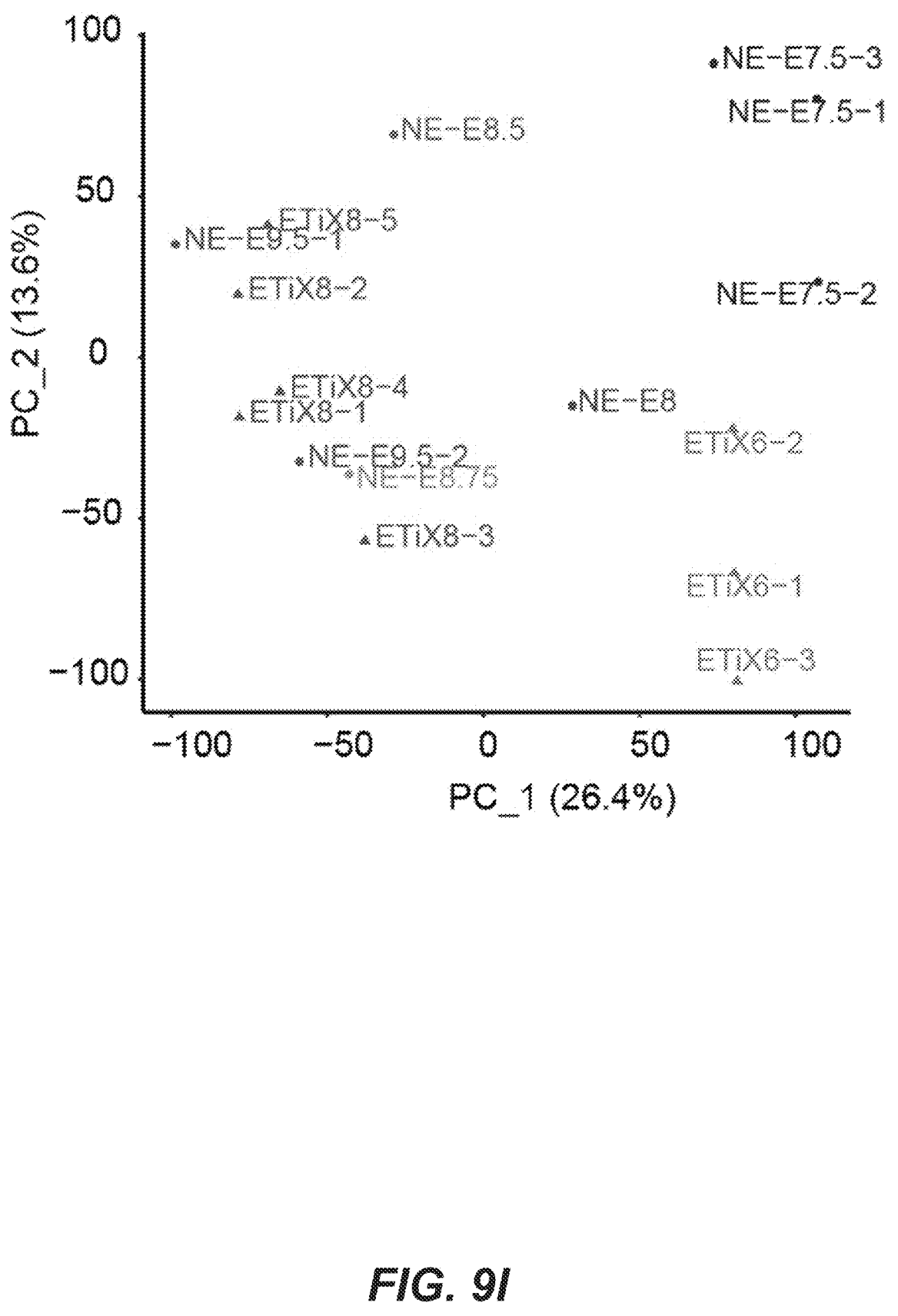
Figure 9J:
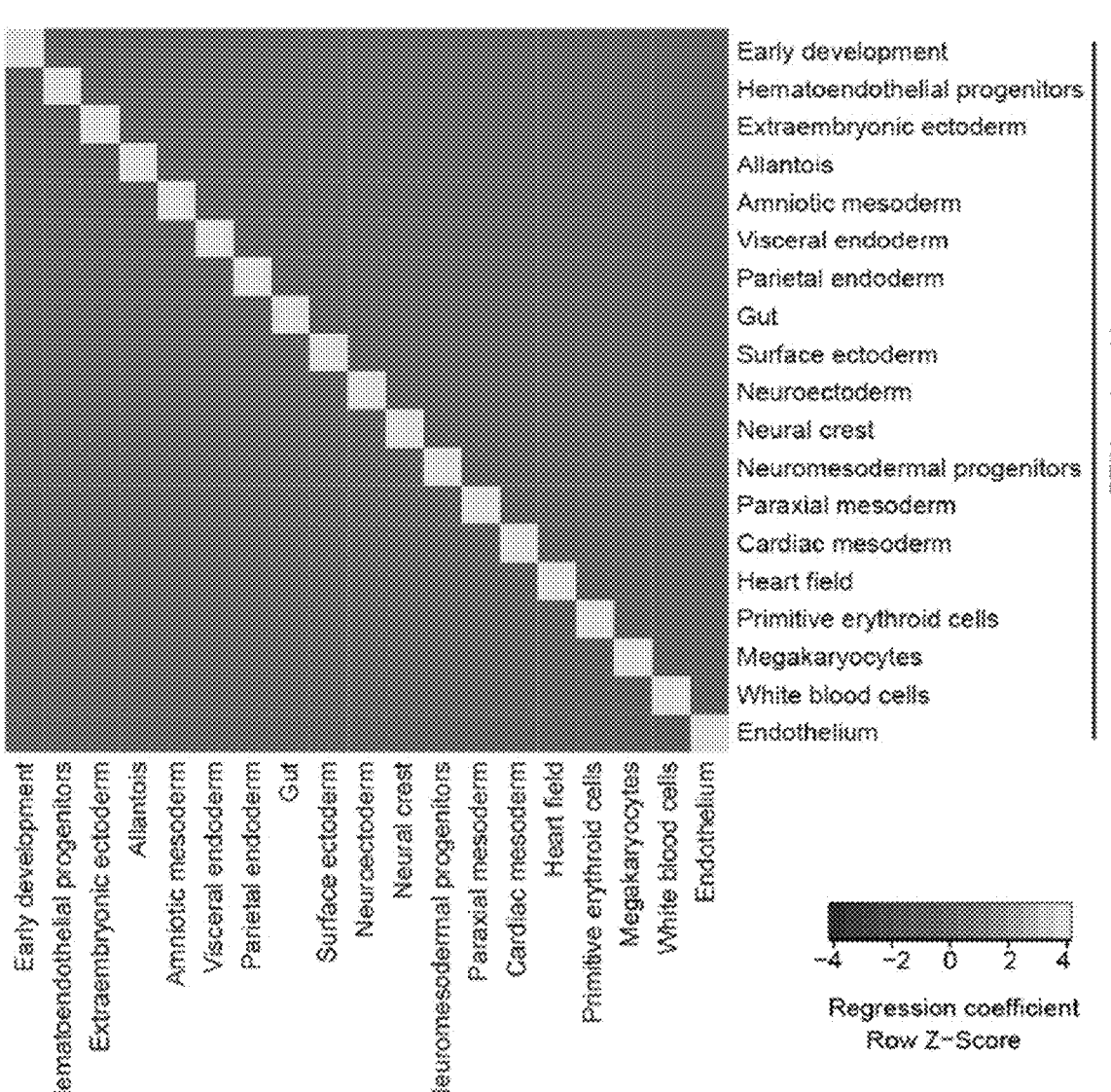
Figures 10A, 10B, 10C:
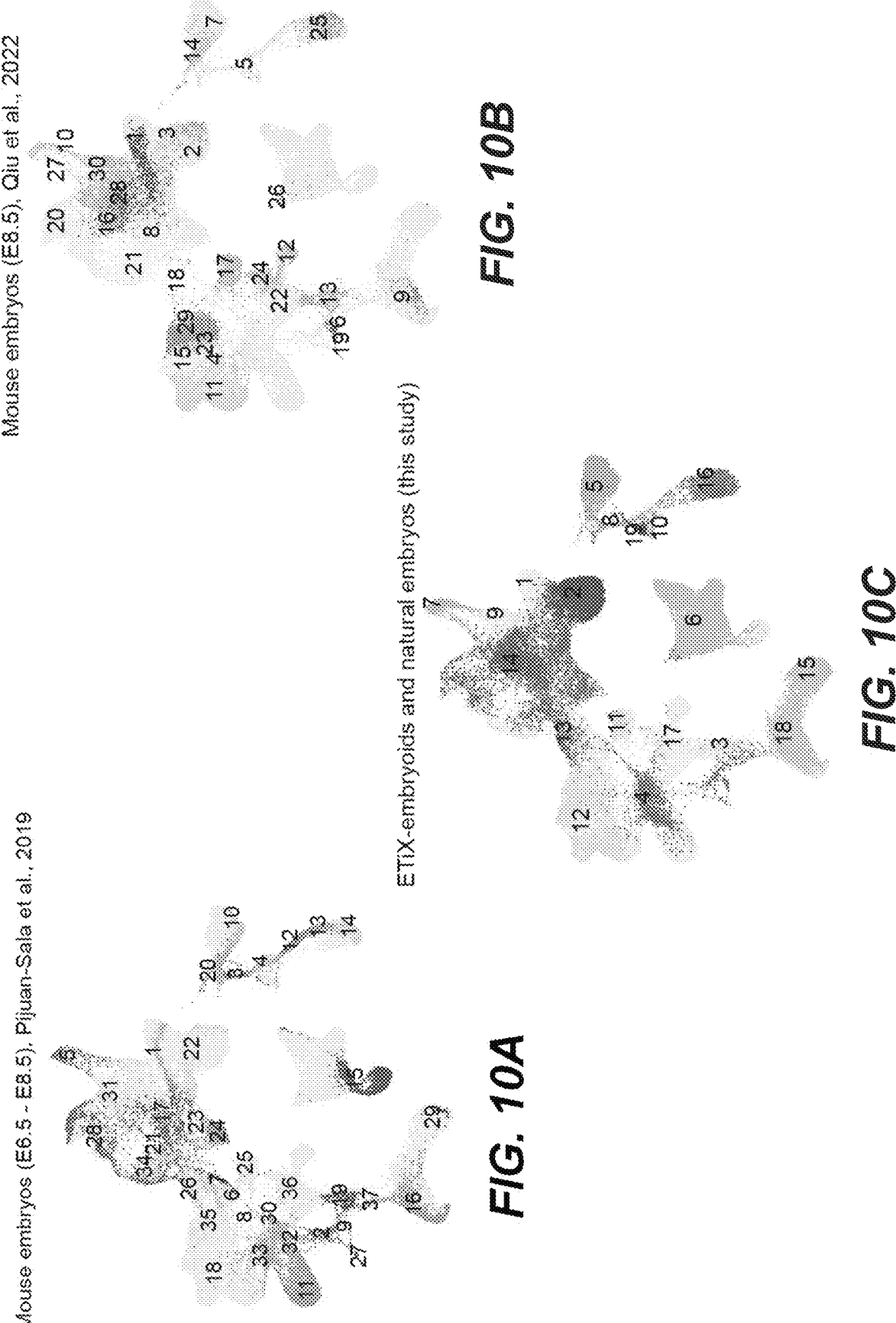
FIG. 10A-FIG. 10E depict non-limiting exemplary embodiments and data related to the tiny sci-RNA-seq dataset of exemplary ETiX embryoids described herein. The tiny sci-RNA-seq dataset integrated seamlessly with published single-cell sequencing datasets and highlighted differences between well-formed and failed ETiX embryoids.
Figure 10D:
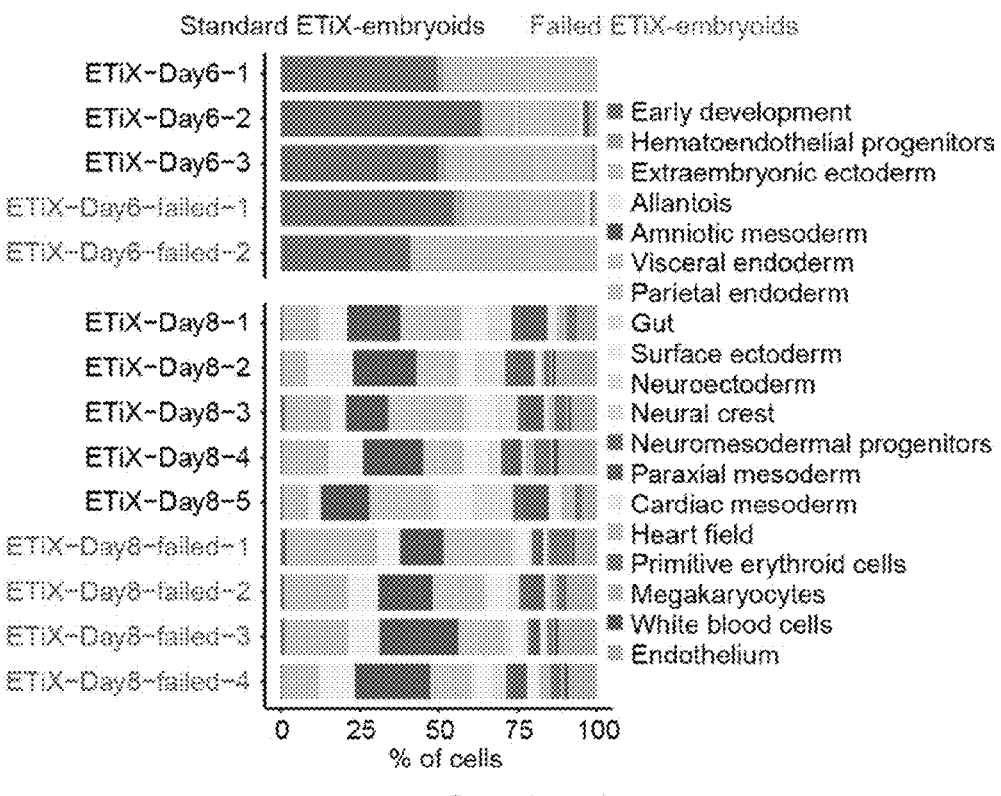

After data processing and quality control, this new dataset contained profiles of 285,640 cells and showed no discernible batch effect between sequencing rounds (FIG. 9A-FIG. 9D). Annotation of this dataset yielded 19 clusters that were present both in natural embryos and ETiX embryoids (FIG. 1F). Notably, in contrast to the previous dataset, the presence of a population of neural crest cells could be clearly detected but PGCs were still not detectable. In this dataset, individual clustering of natural embryos versus ETiX embryoids also showed similar local cluster topography in the UMAP (FIG. 9E-FIG. 9F). Individual ETiX embryoids had very similar cell-type composition from sample to sample (FIG. 1G). From the UMAPs at different time points, it was apparent that day 6 and day 8 ETiX embryoids were most similar to E7.5 and E8.5 or E8.75 natural embryos, respectively (FIG. 9G), a finding that was also observed with individual replicates (FIG. 9H). The similarity between natural embryos and ETiX embryoids was also confirmed by principal component analysis, which showed the samples arranged by developmental age along PC1, whereby day 6 ETiX embryoids most closely resembled E7.5 natural embryos and day 8 ETiX embryoids most closely resembled E8.5-E8.75 natural embryos (FIG. 9I). Notably, E9.5 natural embryos intermingled with these samples, suggesting that the natural embryos did not substantially develop ex utero beyond E8.75. Day 6 ETiX embryoids and E7.5 natural embryos separated along PC2, but day 8 ETiX embryoids and E8.5-9.5 natural embryos did not (FIG. 9I). To assess the overall similarity of each specific cluster to all the other clusters in the dataset, dataset with a non-negative least-squares (NNLS) regression matrix (FIG. 9J) (Example 1 General Methods) was analyzed. This revealed that every cluster in the natural embryo dataset showed the highest similarity with its ETiX embryoid counterpart (for example, the natural heart field cluster was most similar to the ETiX embryoid heart field cluster; FIG. 9J). Furthermore, this tiny-sci dataset integrated very well with published datasets, confirming that the same populations as previously reported were captured in the sampling of natural embryos and ETiX embryoids (FIG. 10A-FIG. 10C). Differences between good ETiX embryoids and failed structures were not readily apparent, since the overall cell composition of even the failed embryoids with aberrant morphology appeared very similar to well-formed embryoids and natural embryos (FIG.

Figure 10E:
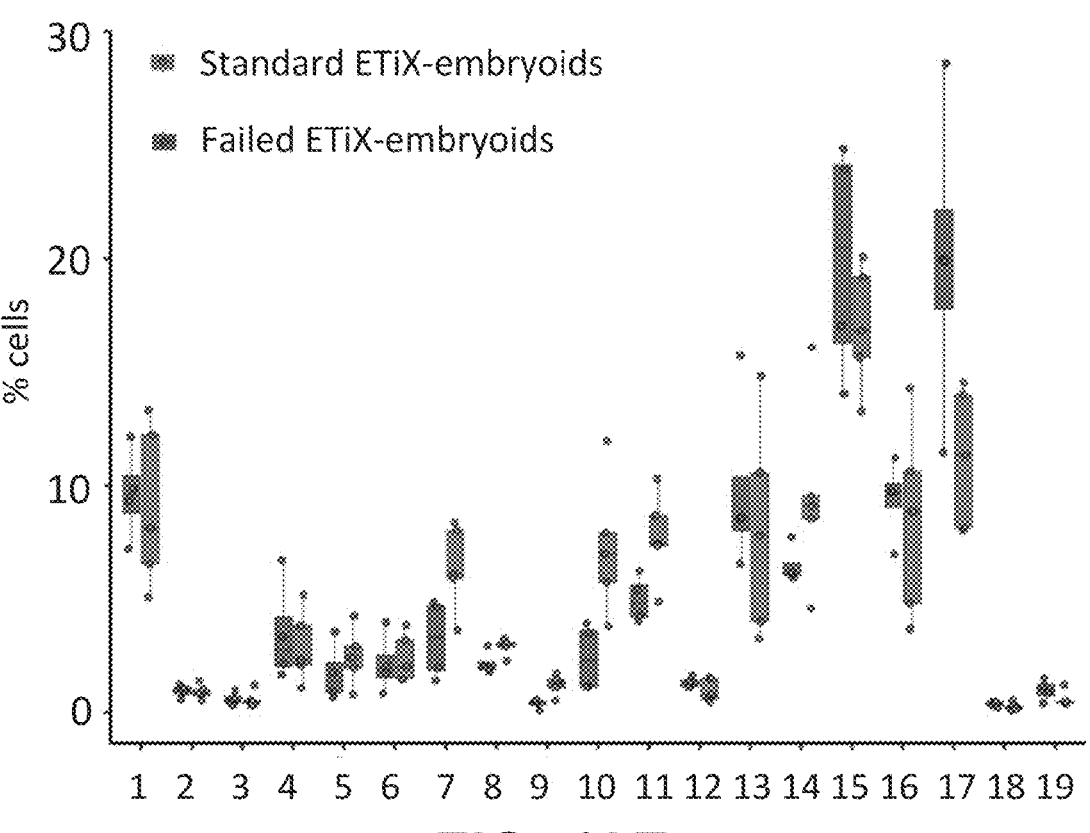

10D), perhaps reflecting some limitations of RNA-sequencing analysis and/or a failure of morphological events despite the continuation of appropriate gene expression. However, the failed structures tended to have a smaller proportion of paraxial mesoderm, neuroectoderm and surface ectoderm at the expense of a larger proportion of ExE cells (FIG. 10E).

Next, to identify global transcriptional differences between natural embryos and ETiX embryoids, GO analysis was performed. Natural embryos showed an enrichment of terms associated with uterine development, implantation and remodulation of the endothelial compartment, whereas ETiX embryoids showed terms associated with embryonic morphogenesis (Tables 2-5). GO analysis did not indicate an obvious stress signature or metabolic differences between natural embryos and ETiX embryoids.

Table 4 lists the differentially expressed genes enriched in natural embryos cultured from E6.5 to E7.5 er utero and analyzed by tiny-sci, according to GO analysis.

TABLE 4

| GENE ONTOLOGY OF E7.5 EMBRYOS Terms enriched in E7.5 natural embryos | | |
| --- | --- | --- |
| GO biological process complete | Fold Enrichment | FDR |
| protection from natural killer cell mediated cytotoxicity (GO: 0042270) | 17.17 | 1.30E−03 |
| regulation of vascular associated smooth muscle contraction (GO: 0003056) | 12.59 | 4.53E−02 |
| lipid phosphorylation (GO: 0046834) | 12.59 | 4.51E−02 |
| positive regulation of lactation (GO: 1903489) | 10.49 | 2.73E−04 |
| regulation of lactation (GO: 1903487) | 10.12 | 3.25E−04 |
| trophoblast giant cell differentiation (GO: 0060707) | 9.94 | 8.95E−03 |
| cell differentiation involved in embryonic placenta development (GO: 0060706) | 7.87 | 3.28E−03 |
| negative regulation of natural killer cell mediated cytotoxicity (GO: 0045953) | 7.87 | 2.11E−02 |
| negative regulation of natural killer cell mediated immunity (GO: 0002716) | 7.55 | 2.39E−02 |
| regulation of actin cytoskeleton reorganization (GO: 2000249) | 7.49 | 6.80E−04 |
| regulation of cardiac muscle cell action potential (GO: 0098901) | 6.99 | 3.12E−02 |
| cell-substrate junction organization (GO: 0150115) | 6.91 | 2.65E−03 |
| homotypic cell-cell adhesion (GO: 0034109) | 6.7 | 1.38E−03 |
| establishment of endothelial barrier (GO: 0061028) | 6.68 | 1.67E−02 |
| negative regulation of leukocyte mediated cytotoxicity (GO: 0001911) | 6.29 | 4.68E−02 |
| cell-substrate junction assembly (GO: 0007044) | 6.29 | 9.55E−03 |
| positive regulation of actin filament polymerization (GO: 0030838) | 5.62 | 3.94E−03 |
| actin filament bundle assembly (GO: 0051017) | 5.24 | 5.99E−03 |
| cell adhesion mediated by integrin (GO: 0033627) | 5.24 | 4.52E−02 |
| regulation of T cell migration (GO: 2000404) | 5.24 | 2.31E−02 |
| negative chemotaxis (GO: 0050919) | 5.12 | 4.98E−02 |
| negative regulation of lymphocyte mediated immunity (GO: 0002707) | 5.08 | 7.20E−03 |
| actin filament bundle organization (GO: 0061572) | 5 | 7.91E−03 |
| leukocyte cell-cell adhesion (GO: 0007159) | 4.72 | 2.08E−02 |
| positive regulation of receptor signaling pathway via STAT (GO: 1904894) | 4.63 | 1.24E−02 |
| negative regulation of endothelial cell proliferation (GO: 0001937) | 4.5 | 1.47E−02 |
| positive regulation of receptor signaling pathway via JAK-STAT (GO: 0046427) | 4.5 | 2.64E−02 |
| regulation of lymphocyte migration (GO: 2000401) | 4.43 | 2.84E−02 |
| positive regulation of smooth muscle cell migration (GO: 0014911) | 4.43 | 2.82E−02 |

Table 5 lists the differentially expressed genes enriched in ETiX-embryoids analyzed at day 6 of development by tiny-sci, according to GO analysis.

TABLE 5

| GENE ONTOLOGY OF ETIX6-EMBRYOIDS Terms enriched in day 6 ETiX-embryoids | | |
| --- | --- | --- |
| GO biological process complete | Fold Enrichment | FDR |
| positive regulation of hepatocyte differentiation (GO: 0070368) | 61.44 | 4.88E−03 |
| regulation of hepatocyte differentiation (GO: 0070366) | 46.08 | 7.41E−03 |
| ascending aorta morphogenesis (GO: 0035910) | 46.08 | 7.39E−03 |
| ascending aorta development (GO: 0035905) | 36.87 | 1.09E−02 |
| atrial septum primum morphogenesis (GO: 0003289) | 36.87 | 1.09E−02 |

TABLE 5-continued

GENE ONTOLOGY OF ETIX6-EMBRYOIDS
Terms enriched in day 6 ETiX-embryoids

| GO biological process complete | Fold Enrichment | FDR |
|---|---|---|
| septum primum development (GO: 0003284) | 30.72 | 1.50E−02 |
| atrioventricular canal development (GO: 0036302) | 27.93 | 3.79E−04 |
| regulation of heart morphogenesis (GO: 2000826) | 23.04 | 2.57E−02 |
| regulation of cardioblast differentiation (GO: 0051890) | 23.04 | 2.56E−02 |
| negative regulation of Wnt signaling pathway involved in heart development (GO: 0003308) | 23.04 | 2.55E−02 |
| epithelial cell proliferation involved in liver morphogenesis (GO: 0072575) | 23.04 | 2.55E−02 |
| hepatocyte proliferation (GO: 0072574) | 23.04 | 2.54E−02 |
| negative regulation of protein sumoylation (GO: 0033234) | 20.48 | 3.19E−02 |
| regulation of Wnt signaling pathway involved in heart development (GO: 0003307) | 20.48 | 3.18E−02 |
| mammary gland formation (GO: 0060592) | 20.48 | 3.17E−02 |
| liver morphogenesis (GO: 0072576) | 18.43 | 3.84E−02 |
| regulation of glucocorticoid metabolic process (GO: 0031943) | 16.76 | 4.61E−02 |
| ectodermal placode morphogenesis (GO: 0071697) | 16.39 | 1.06E−02 |
| ectodermal placode formation (GO: 0060788) | 16.39 | 1.06E−02 |
| ectodermal placode development (GO: 0071696) | 15.36 | 1.26E−02 |
| catecholamine transport (GO: 0051937) | 15.36 | 1.25E−02 |
| atrial septum morphogenesis (GO: 0060413) | 14.46 | 1.49E−02 |
| regulation of cardiocyte differentiation (GO: 1905207) | 13.87 | 2.28E−04 |
| ventricular cardiac muscle cell differentiation (GO: 0055012) | 13.65 | 1.70E−02 |
| cardiac right ventricle morphogenesis (GO: 0003215) | 12.94 | 1.98E−02 |
| cardiac atrium morphogenesis (GO: 0003209) | 12.65 | 3.53E−02 |
| embryonic hindlimb morphogenesis (GO: 0035116) | 12.29 | 4.03E−04 |
| atrial cardiac muscle tissue development (GO: 0003228) | 11.7 | 2.59E−02 |
| signal transduction involved in regulation of gene expression (GO: 0023019) | 11.38 | 7.80E−03 |

Table 6 lists the differentially expressed genes enriched in natural embryos cultured from E6.5 to E8.5 ex utero and analyzed by tiny-sci, according to GO analysis.

TABLE 6

GENE ONTOLOGY OF E8.5 EMBRYOS
Terms enriched in E8.5 natural embryos

| GO biological process complete | Fold Enrichment | FDR |
|---|---|---|
| protection from natural killer cell mediated cytotoxicity (GO: 0042270) | 51.54 | 9.36E−05 |
| positive regulation of lactation (GO: 1903489) | 46.19 | 2.65E−10 |
| regulation of lactation (GO: 1903487) | 44.54 | 1.83E−10 |
| plasminogen activation (GO: 0031639) | 28.35 | 4.16E−02 |
| negative regulation of natural killer cell mediated cytotoxicity (GO: 0045953) | 23.62 | 1.60E−03 |
| negative regulation of natural killer cell mediated immunity (GO: 0002716) | 22.68 | 1.75E−03 |
| positive regulation of miRNA transcription (GO: 1902895) | 20.47 | 1.12E−09 |
| positive regulation of receptor signaling pathway via JAK-STAT (GO: 0046427) | 19.8 | 6.36E−08 |
| negative regulation of endothelial cell proliferation (GO: 0001937) | 19.44 | 1.20E−08 |
| negative regulation of cell killing (GO: 0031342) | 19.44 | 5.41E−04 |
| negative regulation of leukocyte mediated cytotoxicity (GO: 0001911) | 18.9 | 3.40E−03 |
| positive regulation of receptor signaling pathway via STAT (GO: 1904894) | 18.34 | 1.12E−07 |
| regulation of miRNA transcription (GO: 1902893) | 18.04 | 9.08E−10 |
| positive regulation of bone resorption (GO: 0045780) | 17.44 | 2.53E−02 |
| platelet aggregation (GO: 0070527) | 16.8 | 2.78E−02 |
| negative regulation of blood coagulation (GO: 0030195) | 15.12 | 1.73E−03 |
| platelet activation (GO: 0030168) | 14.98 | 3.52E−04 |
| negative regulation of hemostasis (GO: 1900047) | 14.79 | 1.76E−03 |
| negative regulation of endothelial cell apoptotic process (GO: 2000352) | 14.63 | 3.78E−02 |
| negative regulation of coagulation (GO: 0050819) | 14.47 | 1.90E−03 |
| cell differentiation involved in embryonic placenta development (GO: 0060706) | 14.17 | 4.06E−02 |
| regulation of receptor signaling pathway via JAK-STAT (GO: 0046425) | 12.73 | 2.74E−06 |
| female pregnancy (GO: 0007565) | 12.51 | 1.83E−09 |
| homotypic cell-cell adhesion (GO: 0034109) | 12.06 | 1.90E−02 |
| multi-organism reproductive process (GO: 0044703) | 11.83 | 1.07E−09 |
| regulation of receptor signaling pathway via STAT (GO: 1904892) | 11.77 | 4.99E−06 |
| multi-multicellular organism process (GO: 0044706) | 11.53 | 4.74E−10 |
| mammary gland development (GO: 0030879) | 11.26 | 3.07E−08 |
| regulation of blood coagulation (GO: 0030193) | 11.18 | 1.69E−03 |

Table 7 lists the differentially expressed genes enriched in ETiX-embryoids analyzed at day 8 of development by tiny-sci, according to GO analysis.

TABLE 7

GENE ONTOLOGY OF ETIX8-EMBRYOIDS
Terms enriched in day 8 ETiX-embryoids

| GO biological process complete | Fold Enrichment | FDR |
|---|---|---|
| regulation of cardioblast differentiation (GO: 0051890) | 73 | 6.56E−02 |
| protein poly-ADP-ribosylation (GO: 0070212) | 64.89 | 4.84E−02 |
| positive regulation of cytokine-mediated signaling pathway (GO: 0001961) | 17.7 | 5.49E−02 |
| positive regulation of response to cytokine stimulus (GO: 0060760) | 15.96 | 5.84E−02 |
| defense response to virus (GO: 0051607) | 6.66 | 4.59E−02 |
| defense response to symbiont (GO: 0140546) | 6.63 | 4.36E−02 |
| regulation of response to biotic stimulus (GO: 0002831) | 6.4 | 8.42E−03 |
| response to virus (GO: 0009615) | 5.94 | 5.26E−02 |
| blood vessel development (GO: 0001568) | 4.26 | 4.30E−02 |
| regulation of defense response (GO: 0031347) | 3.98 | 4.37E−02 |
| circulatory system development (GO: 0072359) | 3.73 | 1.33E−02 |
| regulation of response to external stimulus (GO: 0032101) | 3.6 | 1.47E−02 |
| regulation of biological process (GO: 0050789) | 1.35 | 5.39E−02 |

Example 3

Embryoid Development of Fore- and Midbrain Regions

This example reports the examination of neural development in the synthetic embryoids described herein.

In natural development, the anterior side of the epiblast retains its epithelial character, up-regulates the neuroectodermal marker Sox1 from E8.0, and begins the formation of the nervous system. The neuroectodermal lineage gives rise to the forebrain, midbrain, hindbrain and the spinal cord.

Figure 2A:
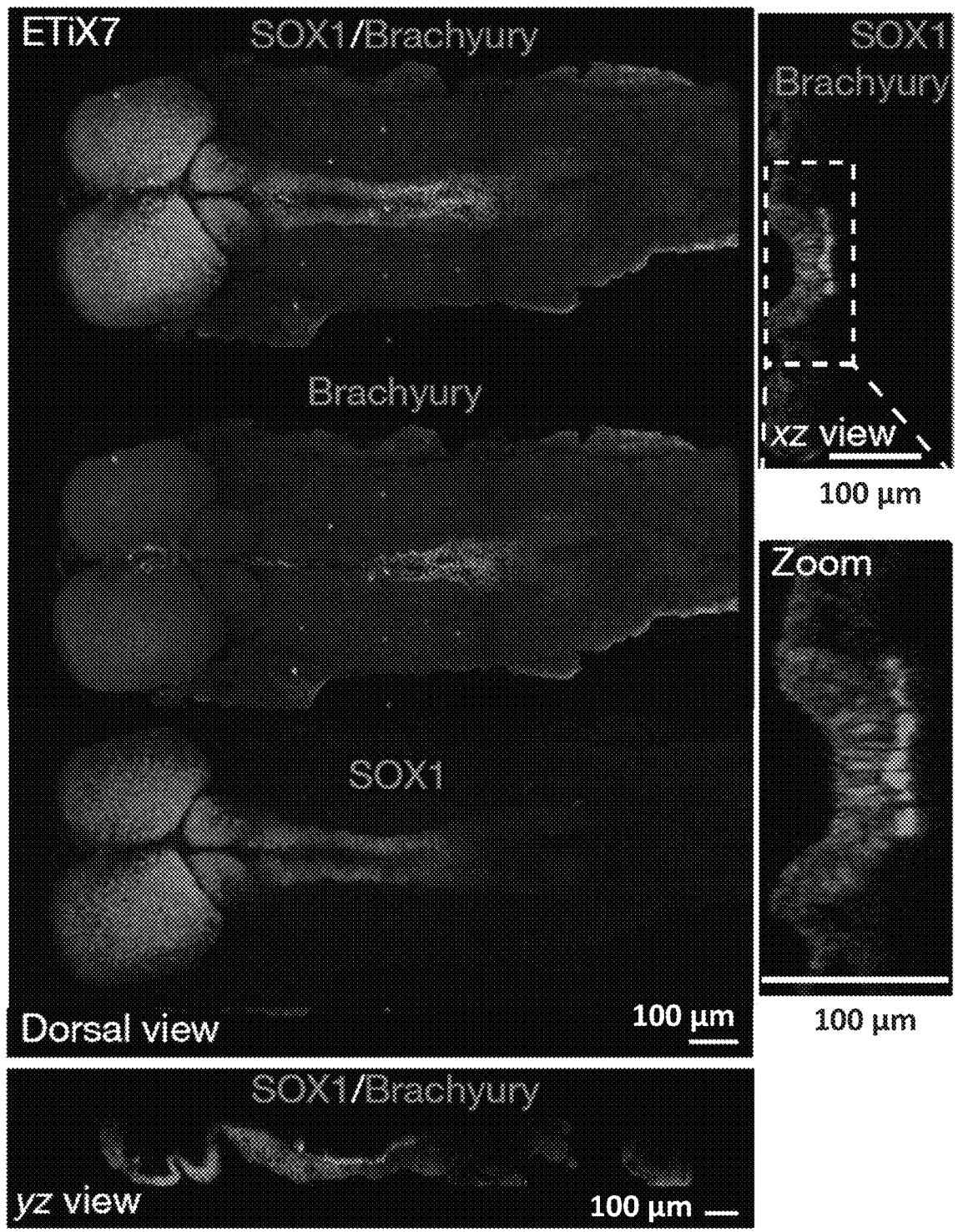
FIG. 2A-FIG. 2J depict non-limiting exemplary embodiments and data related to exemplary ETiX embryoids described herein developing anterior brain and patterned neural tube.
Figure 2B:
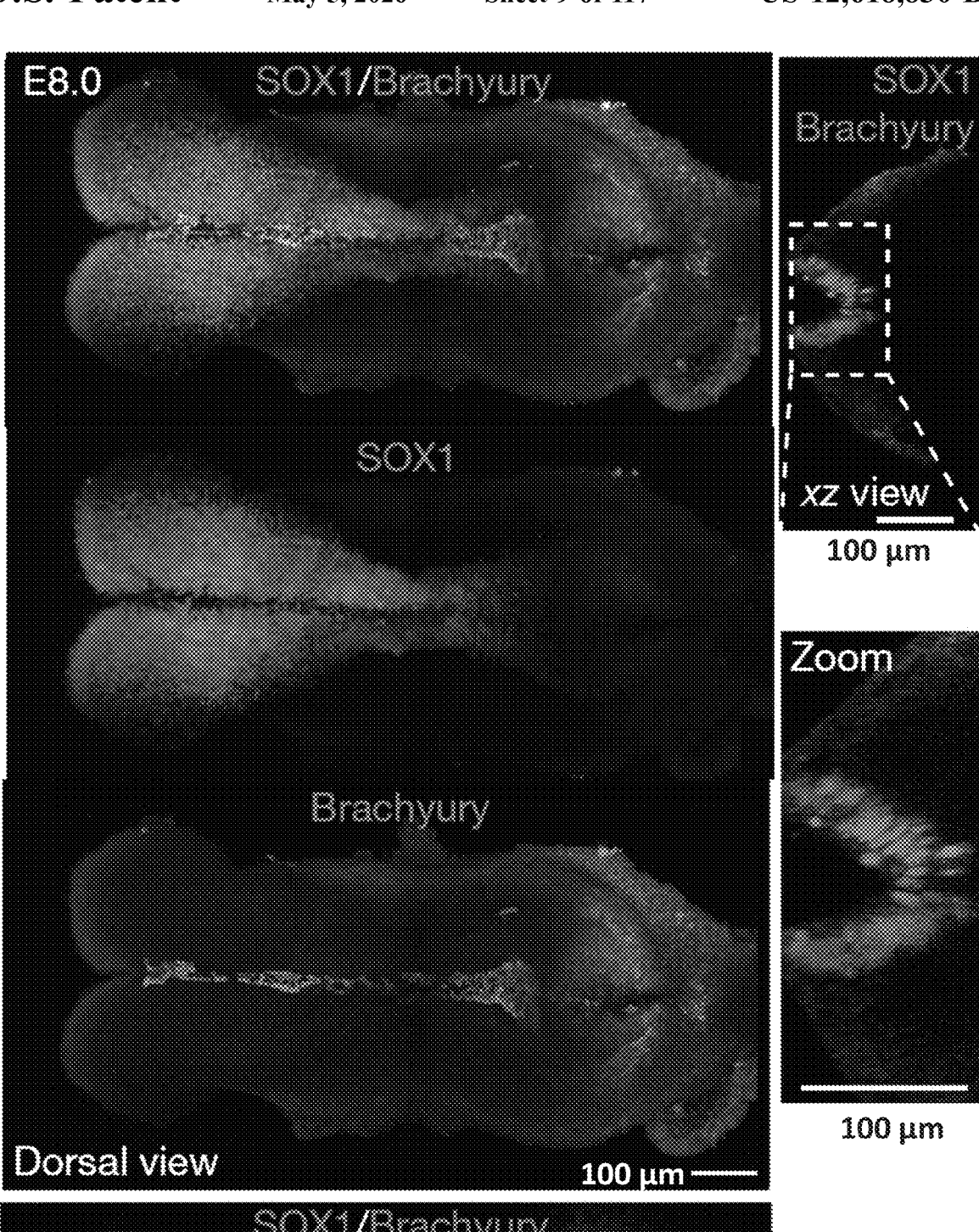

To examine neural development in embryoids, the expression of well-established neuroectodermal markers was analyzed by immunofluorescence. SOX1 and SOX2 were expressed in the neuroepithelial cell population, along the entire anteroposterior axis of neurulating embryoids on day 7 in a pattern similar to the natural E8.0 embryo (FIG. 2A-FIG. 2B and FIG. 11A-FIG. 11B). The SOX1-positive neural tube tissue made up two thirds by length of the neurulating embryoid on day 7 and culminated in two neural folds (FIG. 11A) whereas the SOX1-negative, Brachyury-positive posterior exhibited a tail bud-like morphology (FIG. 2A-FIG. 2B) similar to natural E8.0 embryos. A Brachyury-positive notochord running below the neural tube was readily apparent in both neurulating natural embryos and ETiX embryoids (FIG. 2A-FIG. 2B).

Figure 2C:
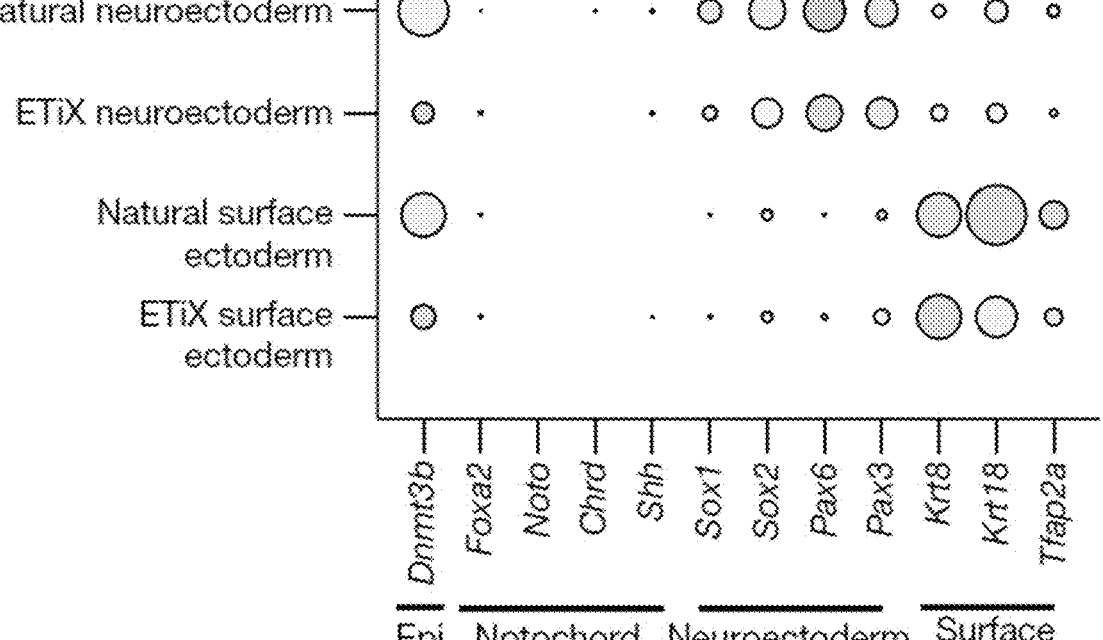
Figure 2C:
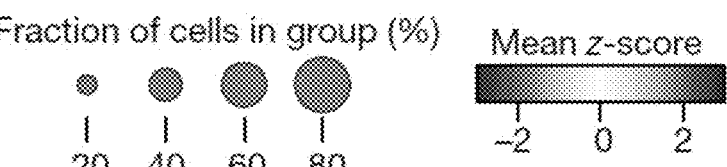

Next, the scRNA-seq data for the expression of key markers of neuroectoderm, surface ectoderm that gave rise to most epithelial tissues, notochord that was important for patterning of the neuroectoderm and neural tube, and epiblast that was the precursor to all these tissues were examined. In the ETiX embryoids and natural embryos, similar expression of Foxa2, Chordin and Shh were observed, marking the notochord (FIG. 2C). Moreover, natural embryos and ETiX embryoids expressed similar levels of Sox1, Sox2, Pax6 and Pax3 in the neuroectoderm, and displayed a similar surface ectoderm signature of keratin gene expression. Thus, tissue-specific gene expression patterns of the neurulating embryoids strongly resembled those of natural embryos.

Figure 2D:
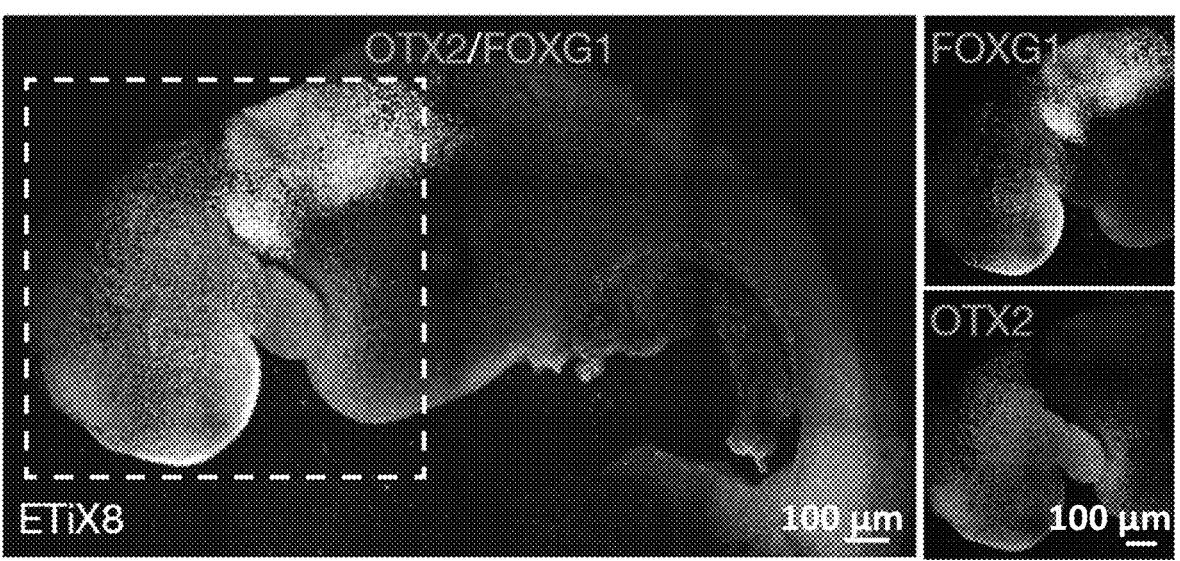
Figure 2E:
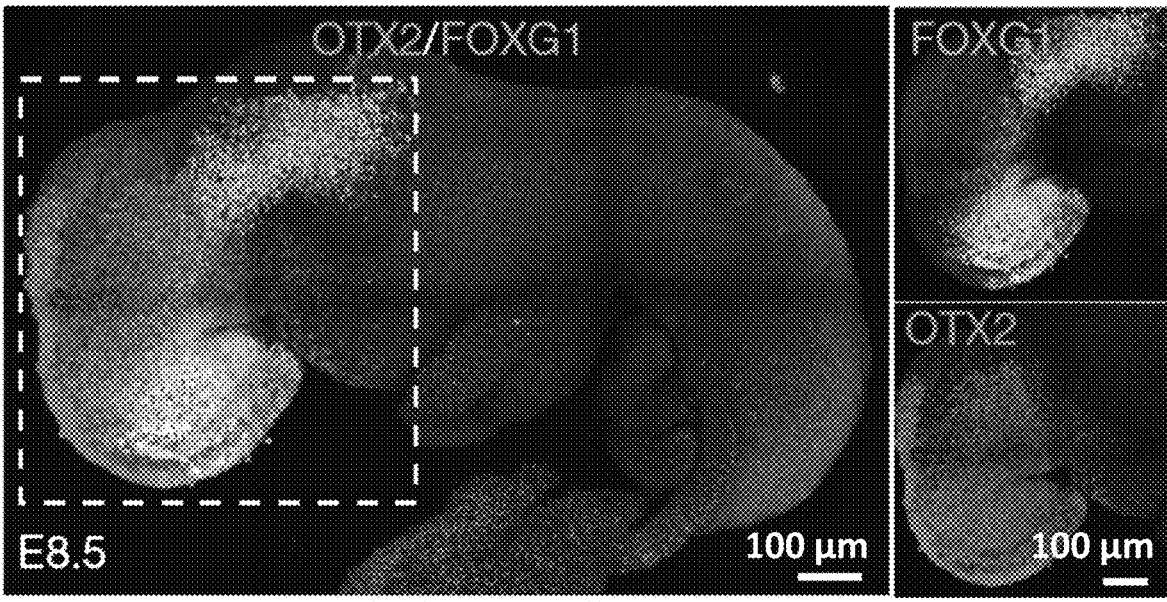
Figure 2F:
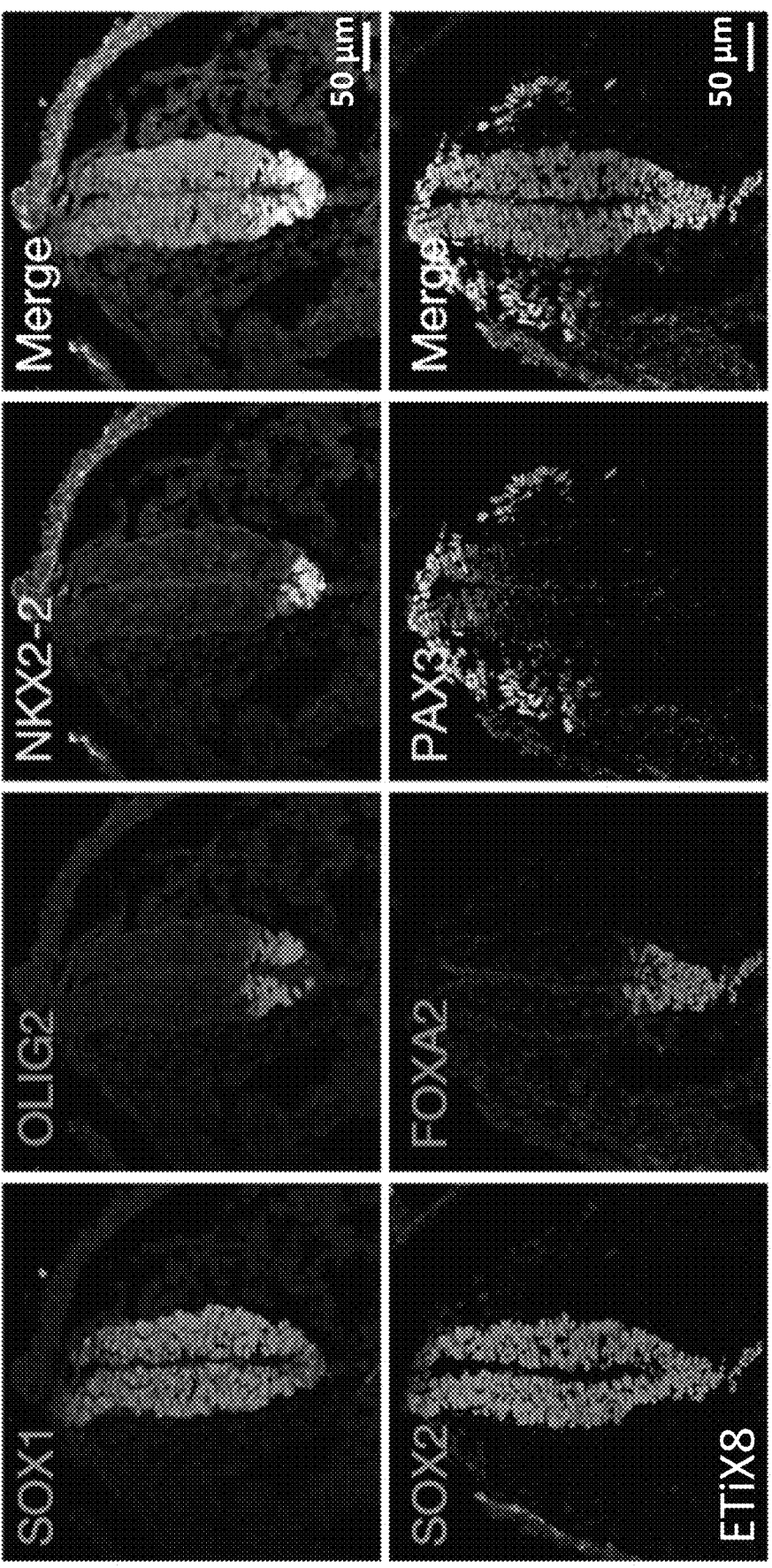
Figure 2F:
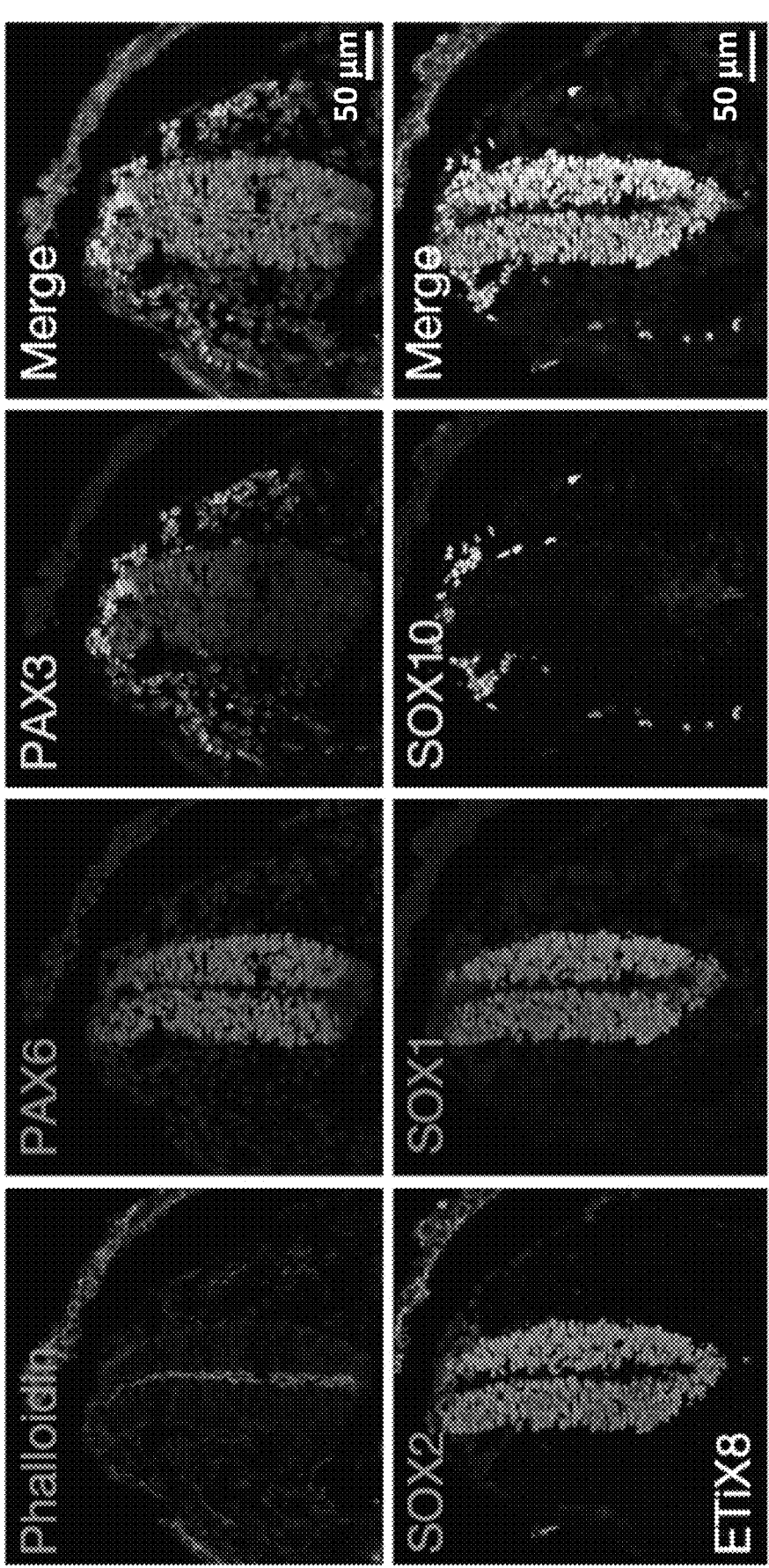
Figure 11B:
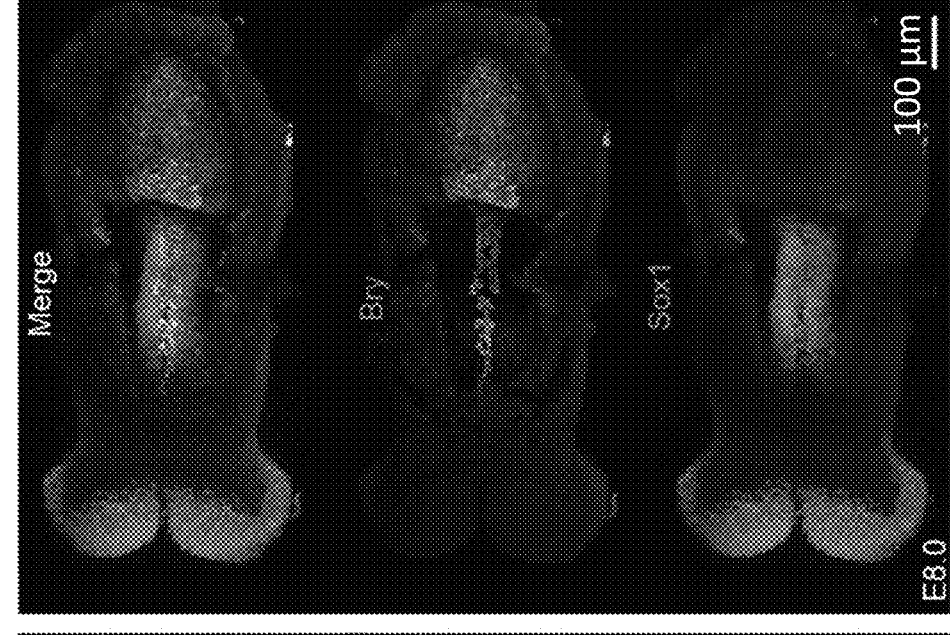
FIG. 11A-FIG. 11G depict non-limiting exemplary embodiments and data related to exemplary ETiX embryoids described herein. The ETiX embryoids show neural folds and a developing tail bud with comparable differentiation trajectory and timing.
Figure 11B:
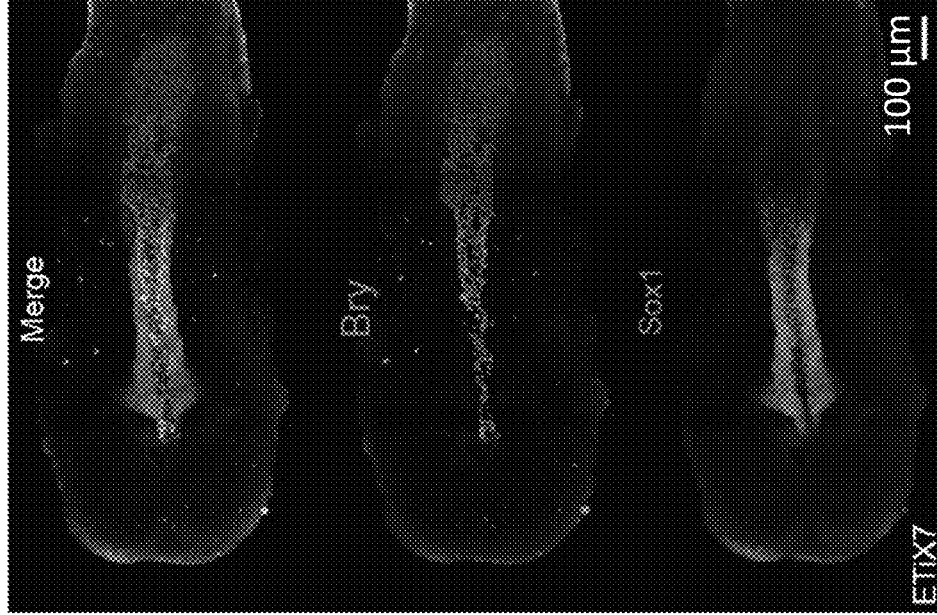
Figure 11A:
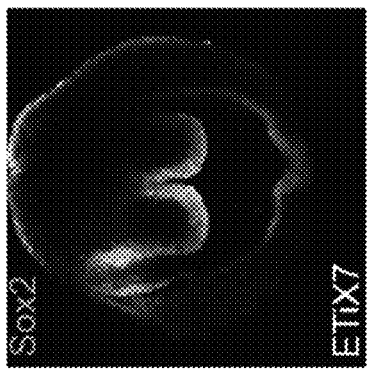
Figure 11A:
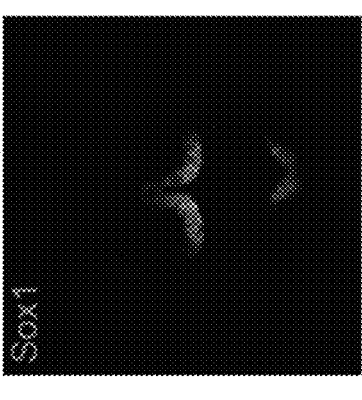
Figure 11A:
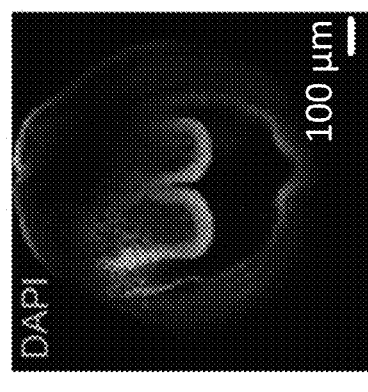
Figure 11C:
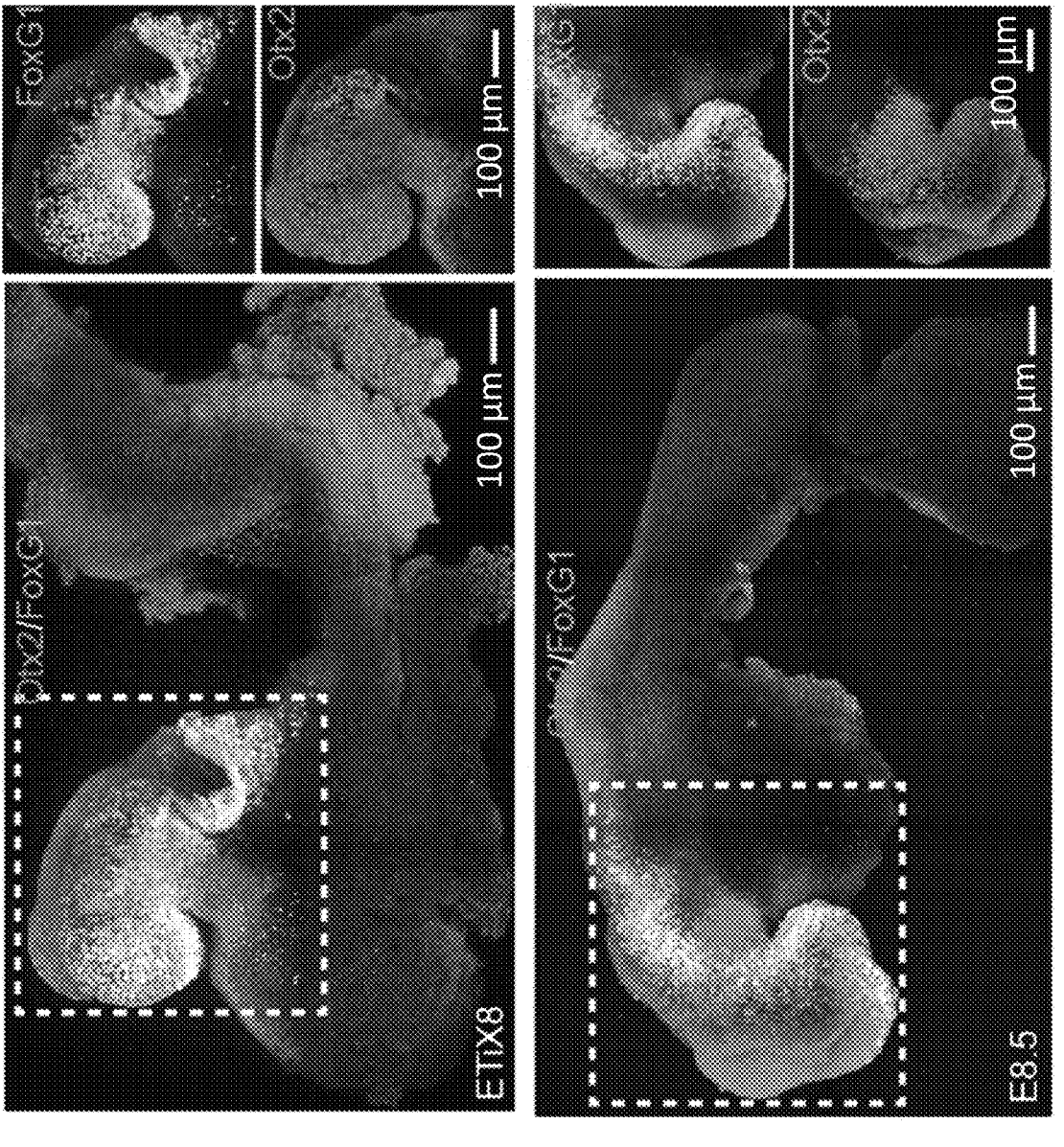
Figures 11D, 11E:
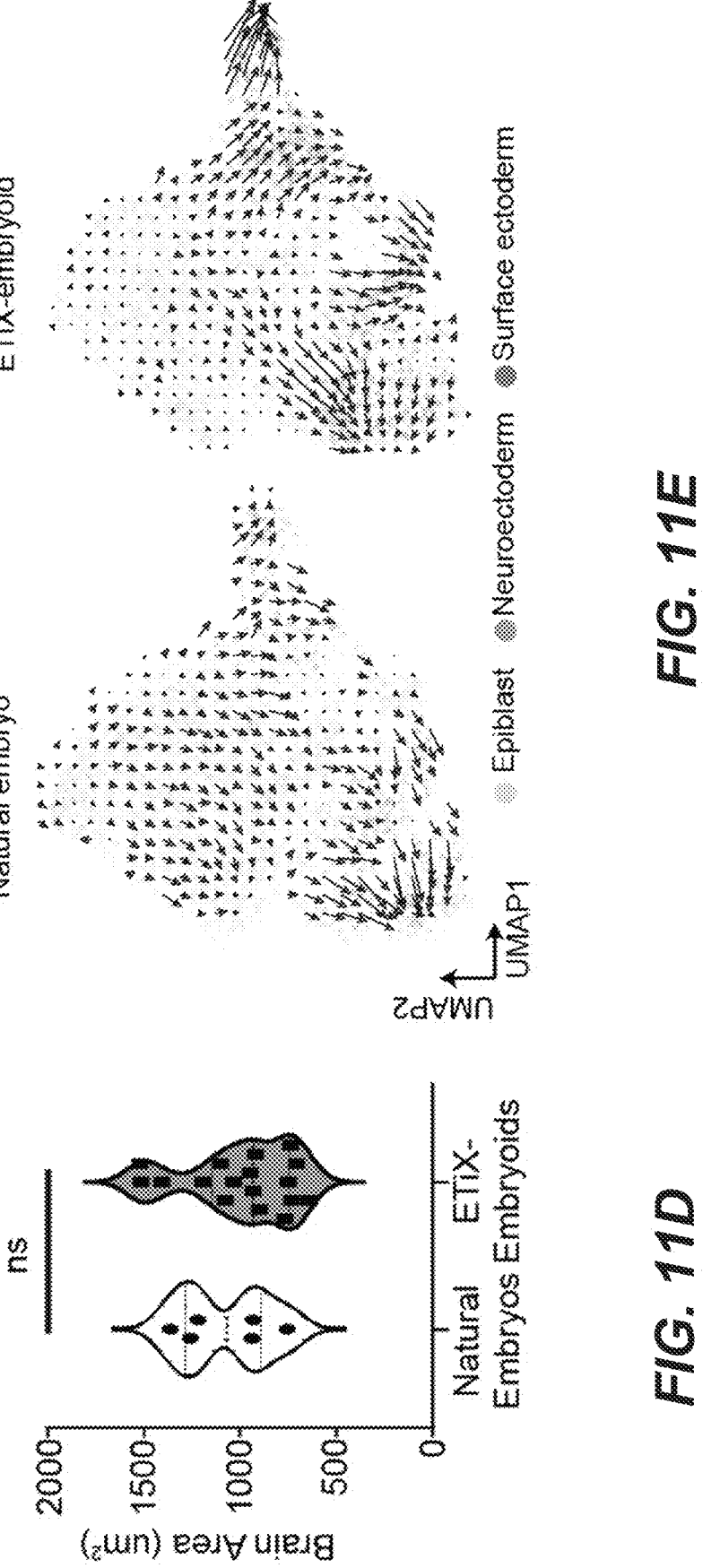
Figure 11F:
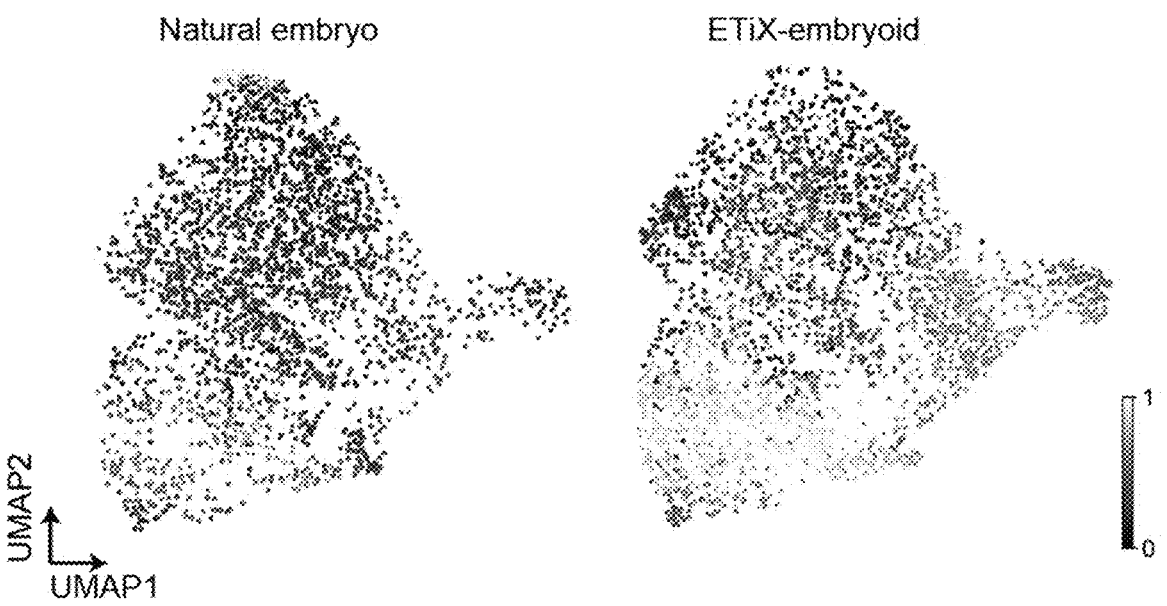
Figure 11G:
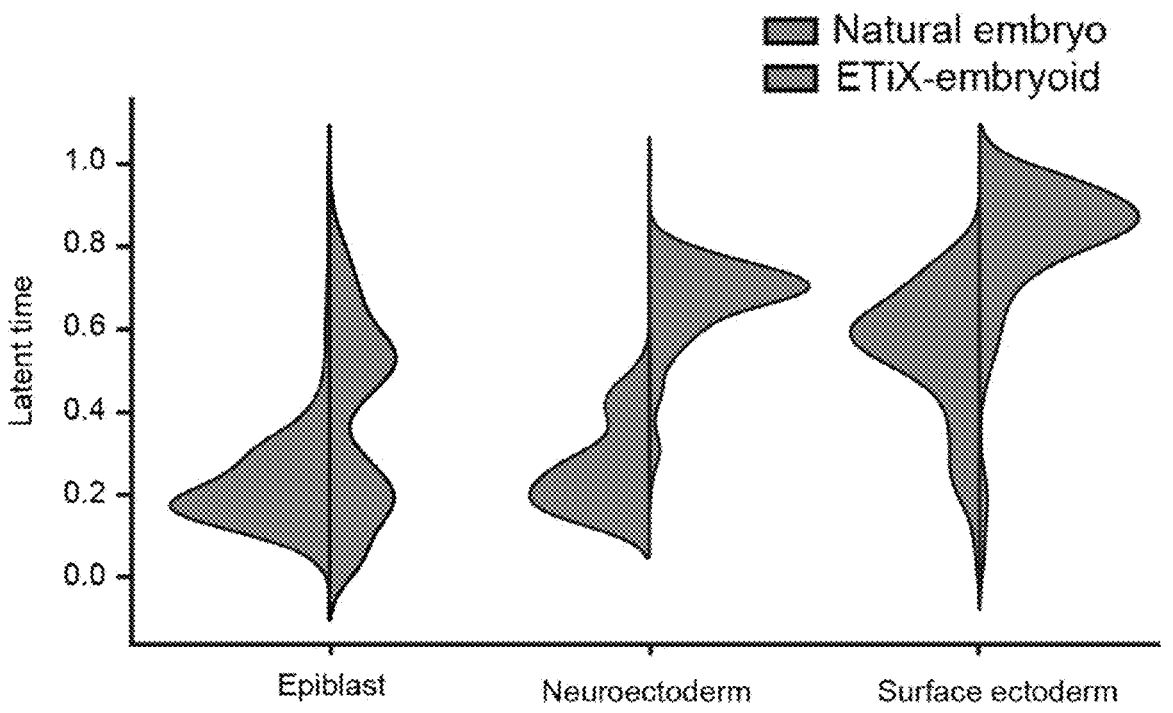

The transcription factor OTX2, which contributes to patterning of the midbrain and forebrain showed restricted expression in the anterior-most third of the headfolds of neurulating day 8 ETiX embryoids (FIG. 2D-FIG. 2E). This region corresponded to the forebrain and midbrain of the natural mouse embryo at E8.5. The neurulating day 8 embryoids also expressed the transcription factor FOXG1, which has a vital role in brain development, in the same region as in natural E8.5 embryos (FIG. 2D-FIG. 2E and FIG. 11C). The area of the brain demarcated by OTX2 expression was similar in natural embryos and ETiX embryoids (FIG. 11D). The neural tube of neurulating day 8 embryoids was closed and showed distinct neural progenitor domains within the neural tube, delineated by the expression of the markers PAX6, OLIG2 and NKX2-2 (FIG. 2F). FOXA2 was expressed in cells lining the ventral midline of the neural tube, marking a floor plate cell population (FIG. 2F), whereas PAX3 was expressed in the dorsal neural tube, in the somatic mesoderm and in neural crest cells (FIG. 2F). SOX10 expression confirmed the identity of neural crest cells, which were displaced from the neural tube, as though undergoing the delamination and migration that occurs during natural brain development (FIG. 2F). Whether formation of neuroectoderm and surface ectoderm occurred in a similar manner in neurulating embryoids in comparison to natural embryos was also determined. To this end, transcriptional trajectories were computed using RNA velocity, which integrated the ratios of spliced and unspliced RNAs over time to infer how a starting population evolved and differentiated. Comparison of RNA velocities between natural embryos and neurulating embryoids indicated similar differentiation trajectories from the epiblast to neuroectoderm and surface ectoderm, suggesting that the specification of these two tissues followed a similar developmental transcription programme in these two systems (FIG. 11E). To determine whether these tissues were forming at comparable times, latent time analysis was performed, which assigned an arbitrary combined pseudotime to give a measure of when specific tissues or subpopulations emerge. Latent time analysis indicated that neuroectoderm appeared to be specified later in neurulating embryoids than in natural embryos. This was also observed with surface ectoderm, although this difference was remarkably smaller (FIG. 11F-FIG. 11G). Together, these findings suggested that neuroectoderm and surface ectoderm were specified with similar transcriptional trajectories in the neurulating ETiX embryoids and natural embryos but with somewhat different timing.

Figure 2G:
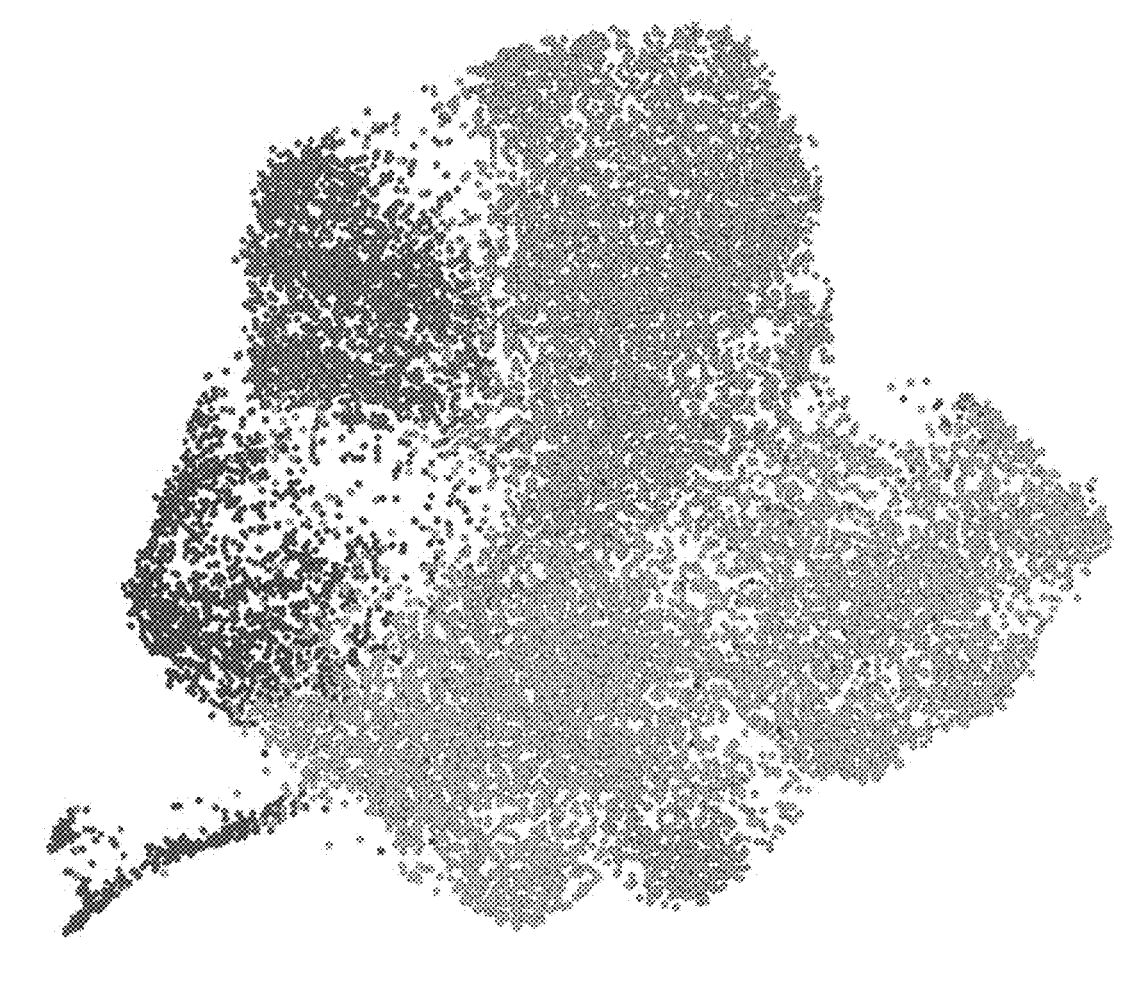
Figure 2H:
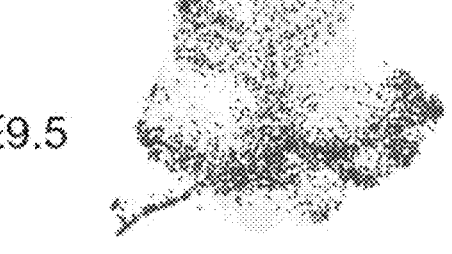
Figure 2I:
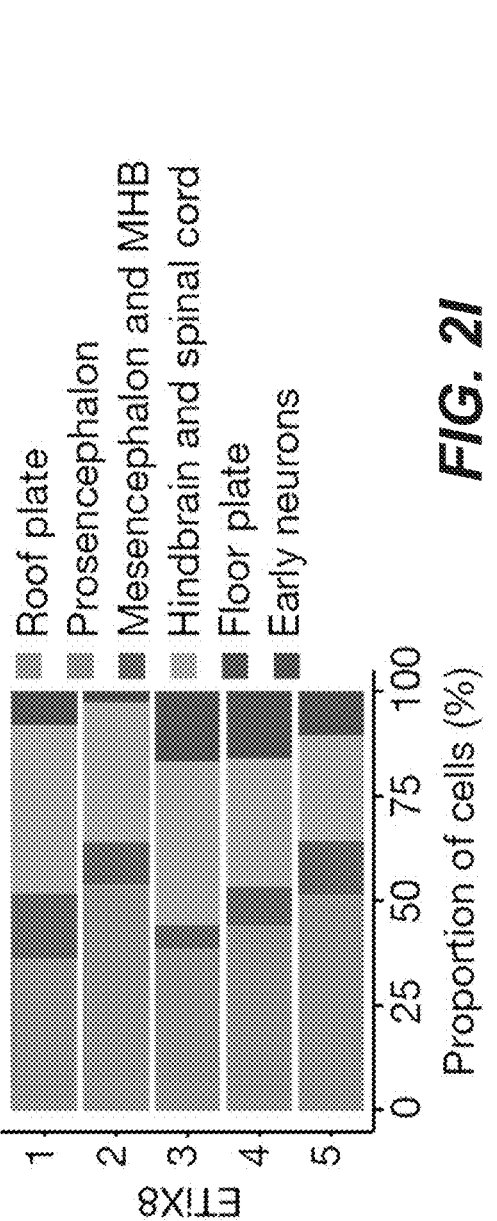
Figure 12A:
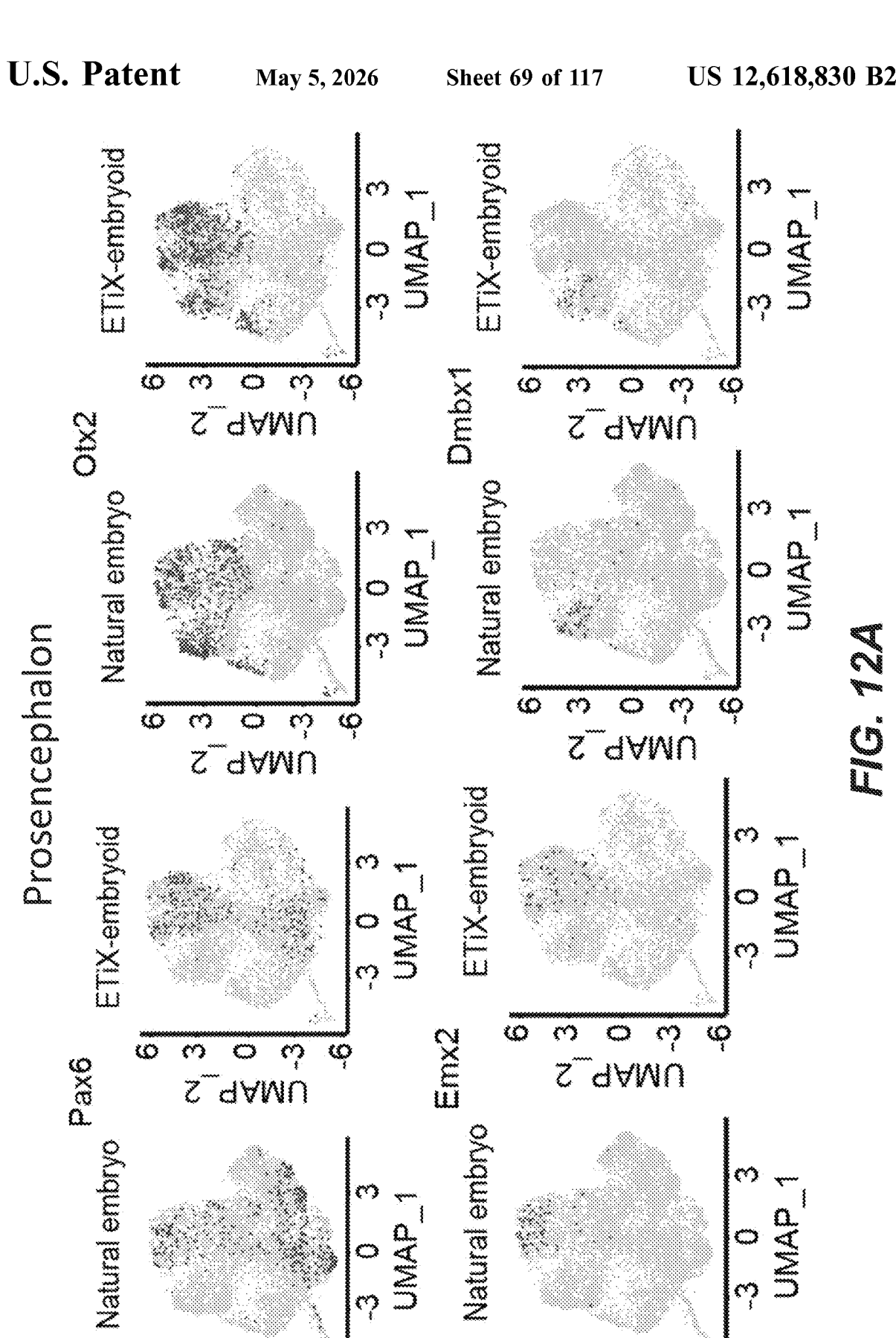
Figure 12B:
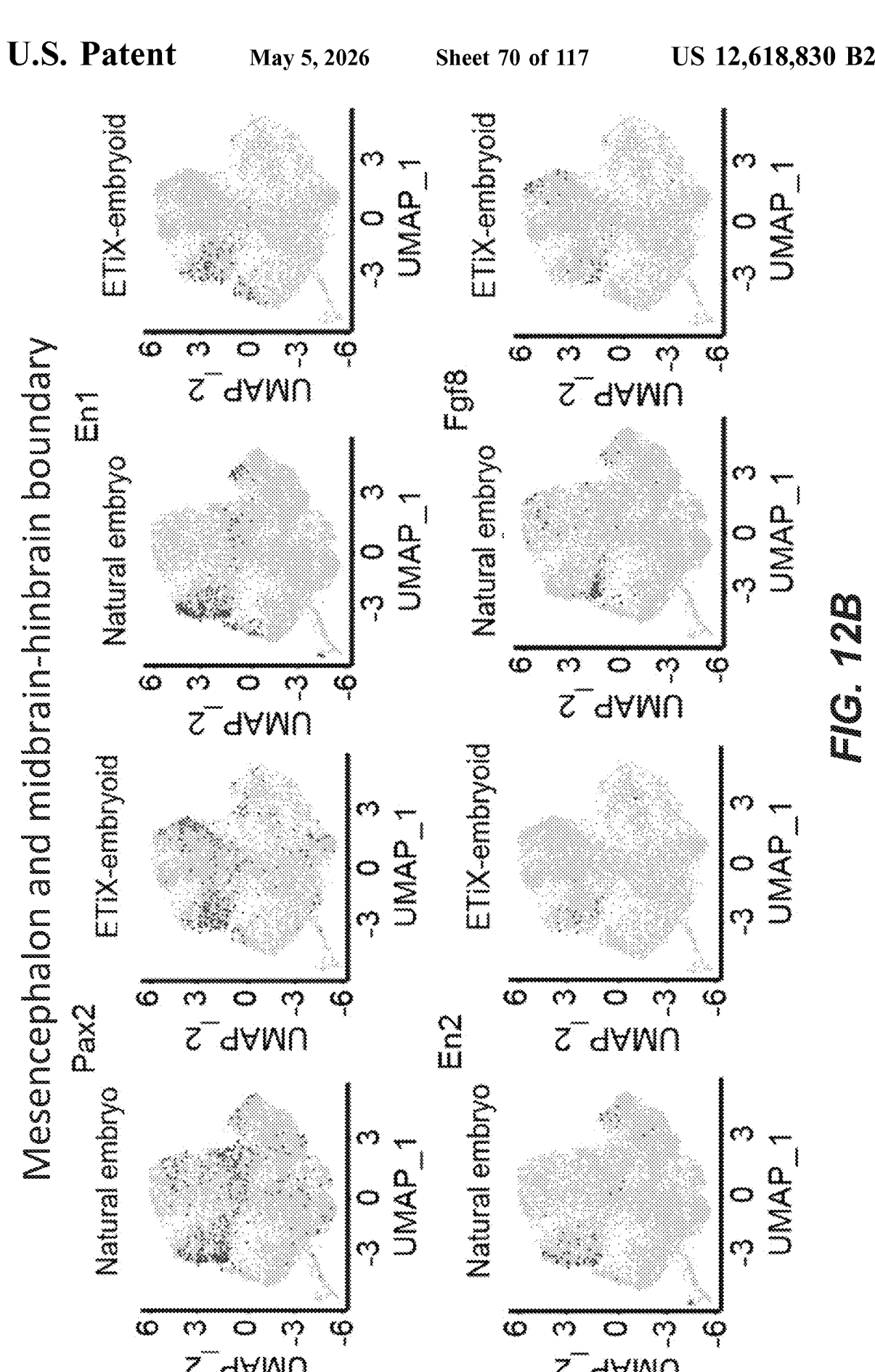
Figure 12C:
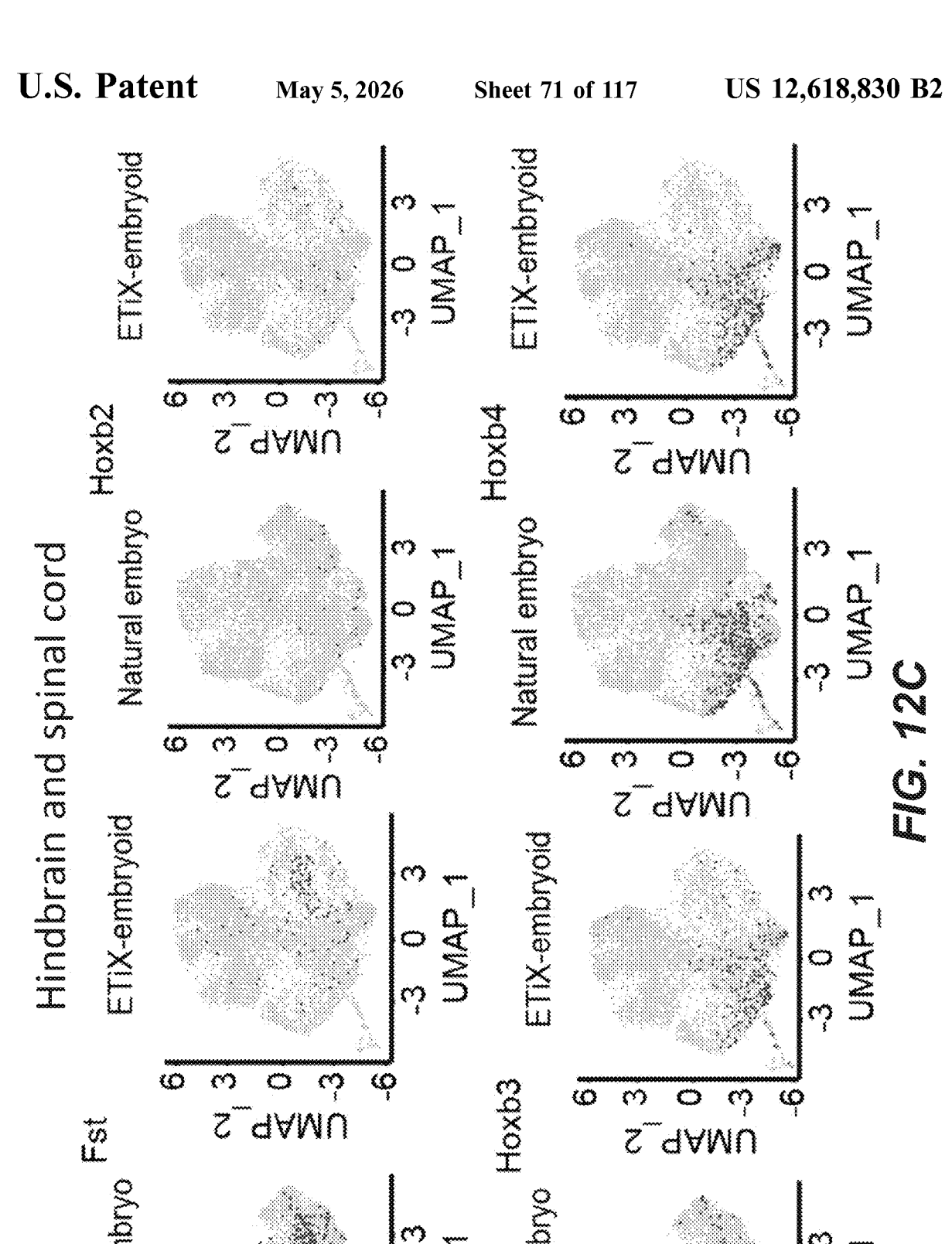
Figure 12D:
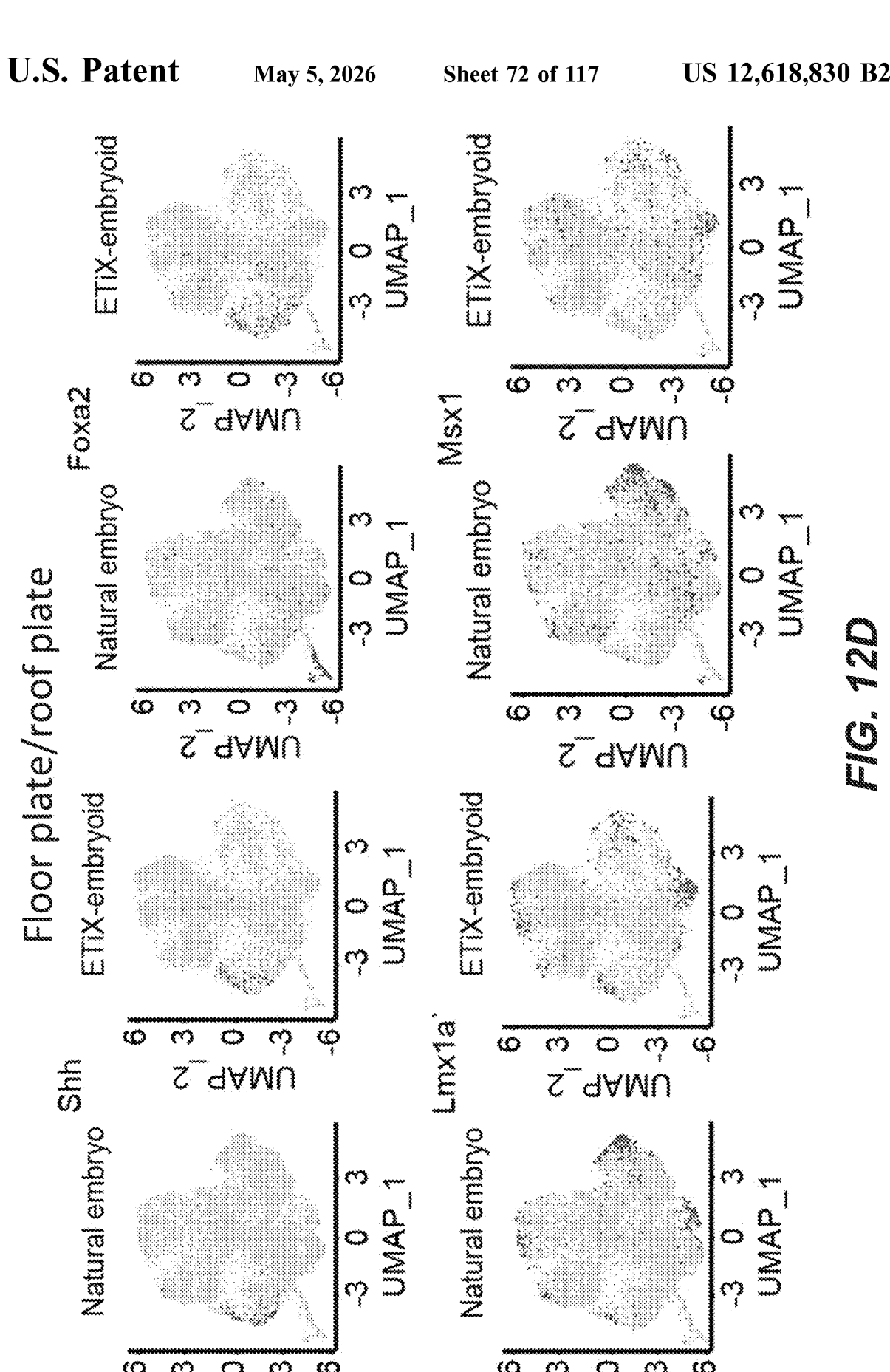
Figure 12E:
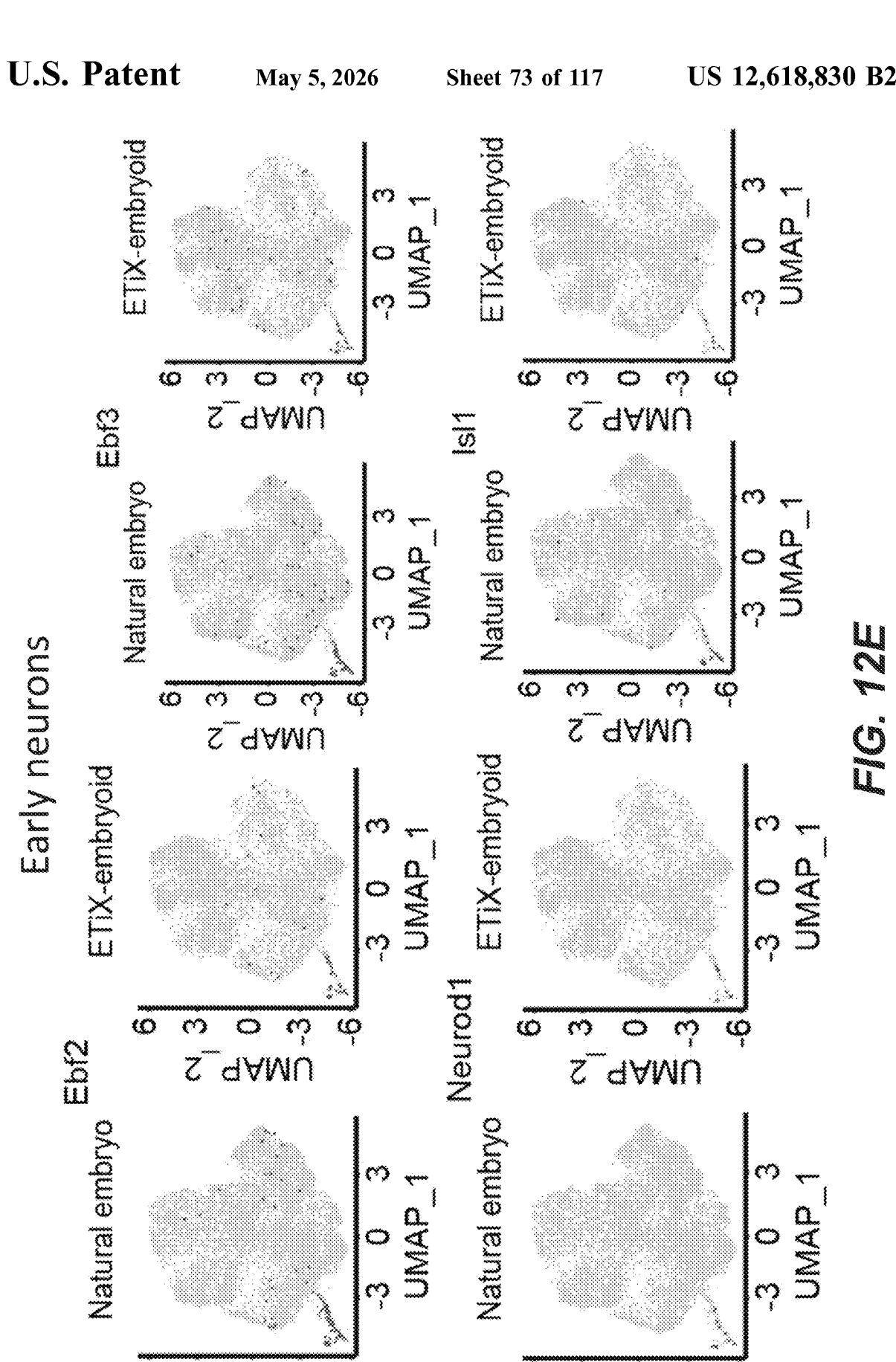
Figure 12F:
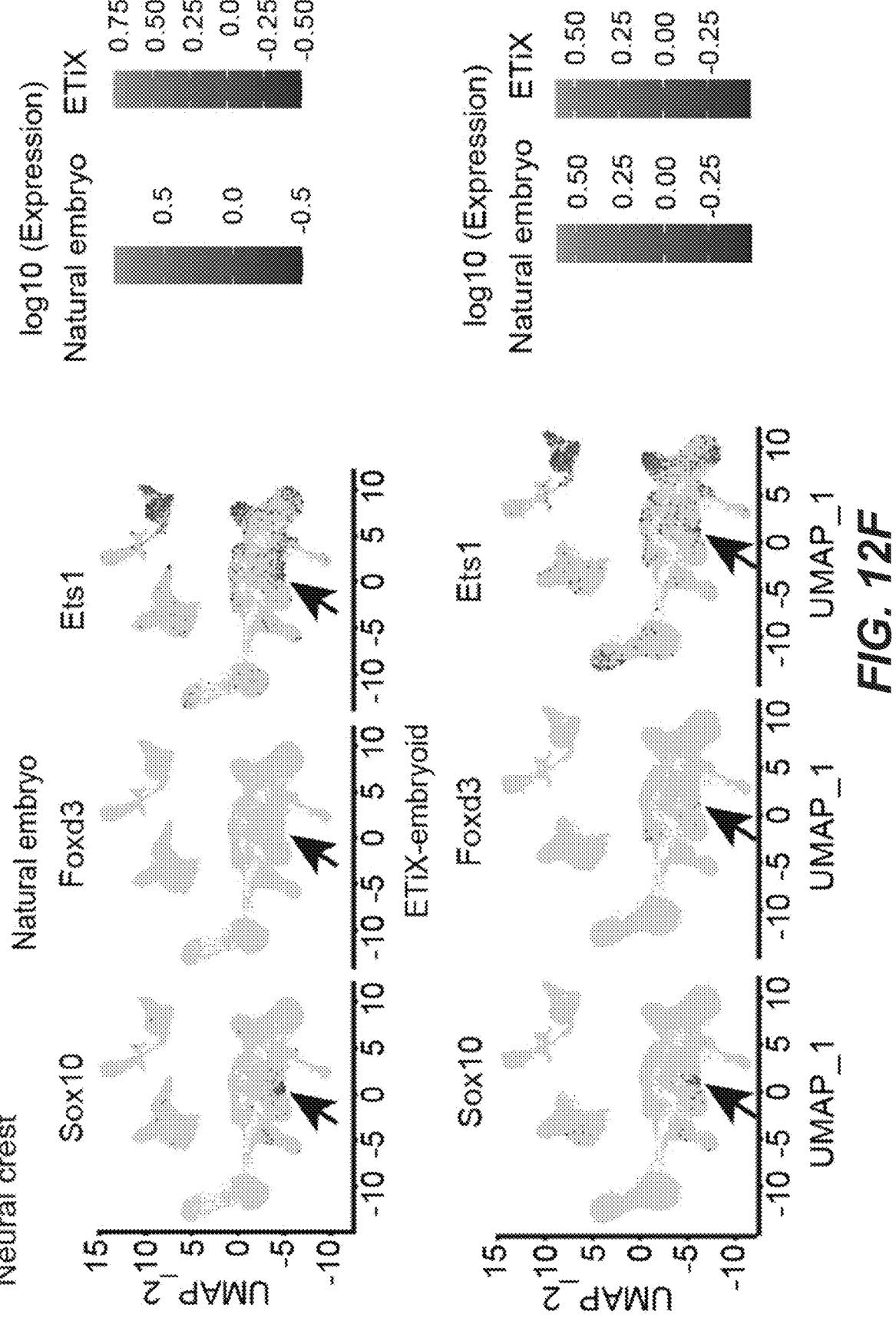
Figure 12G:
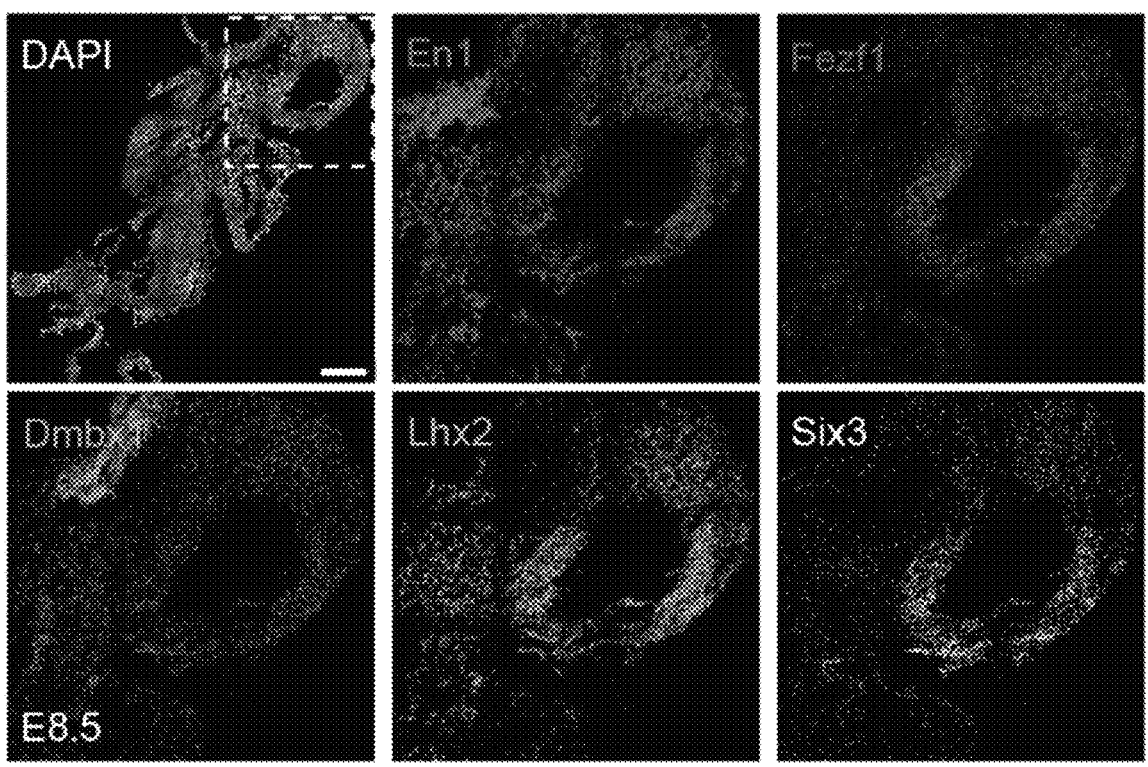
Figure 12H:
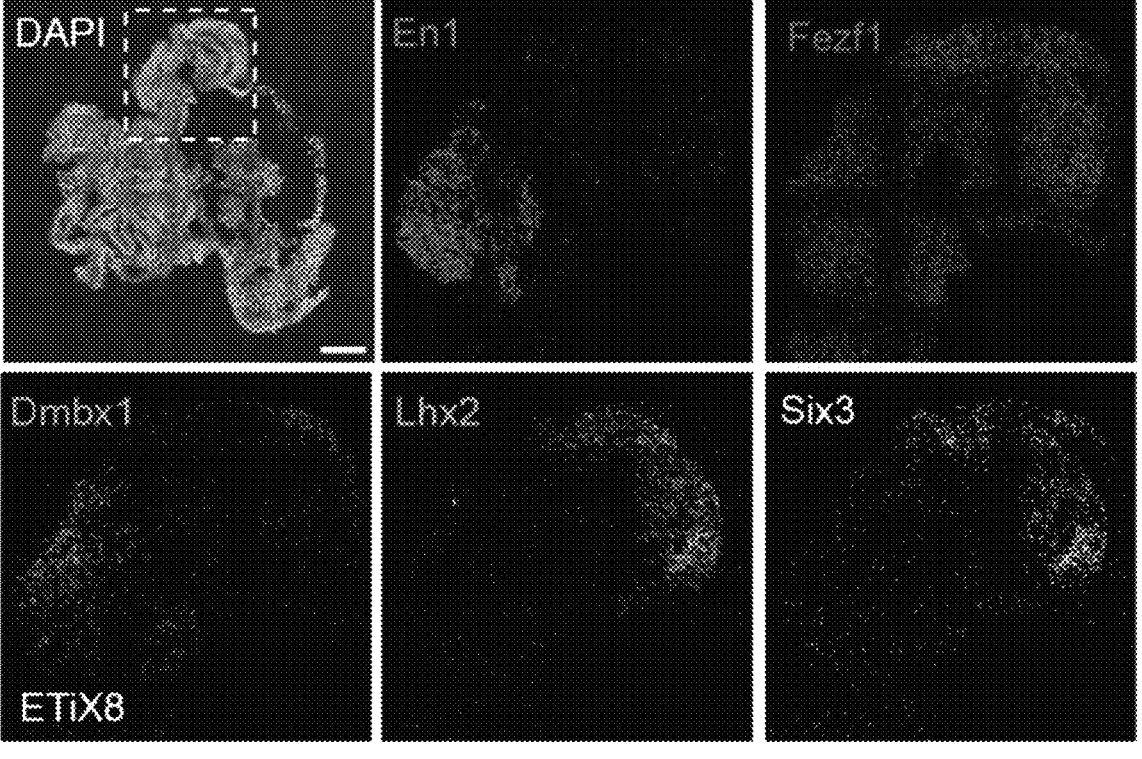
Figures 12I, 12J:
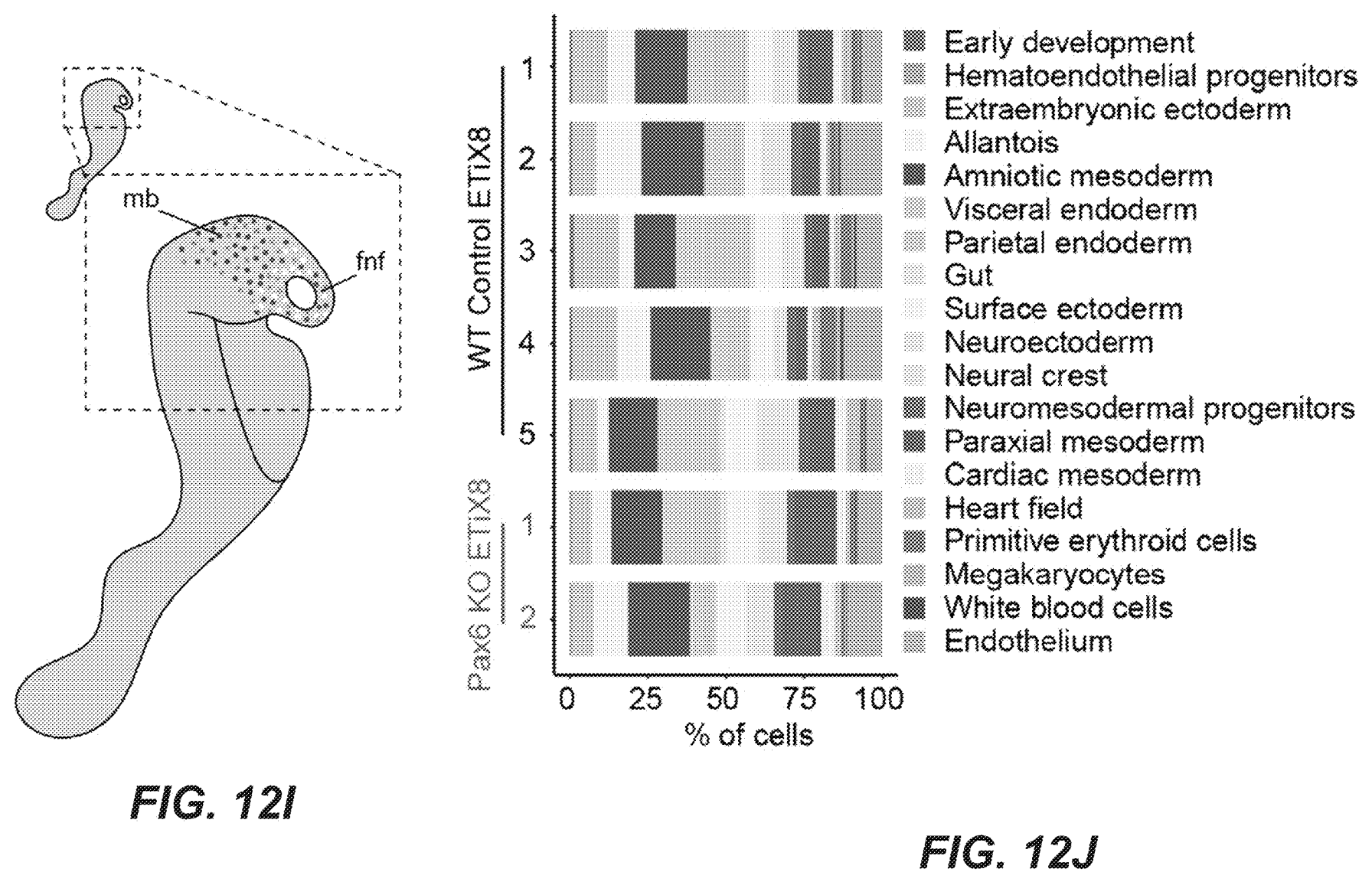

The tiny-sci dataset was further used to explore the different neural cell types present in neurulating ETiX embryoids. Assignment of these subclusters to specific neural identities was performed using well-established markers (FIG. 12A-FIG. 12E). Subclustering and annotation of all neuroectoderm-derived cell types showed the presence of cells expressing markers of the hindbrain and spinal cord, prosencephalon, mesencephalon and midbrain-hindbrain boundary. Cells expressing genes indicative of roof plate and floor plate identity (FIG. 2G-FIG. 2I) were also observed. However, without spatial organization data, it cannot be concluded that there was dorso-ventral patterning in the brain. The presence of similar neural populations were observed in neurulating ETiX embryoids to those observed in embryos at E8.5 (FIG. 2G). These neural types were almost completely absent at E7.5, in line with the major burst of neural induction taking place at E8.0. Accordingly, neural cells in day 6 ETiX embryoids were not observed, which were very similar to E7.5 embryos, whereas in day 8 ETiX embryoids, all these neural subtypes were present, closely matching E8.5 and E8.75 natural embryos (FIG. 2I1). Finally, examination of individual ETiX embryoids on day 8 showed that the presence of these neural subtypes was largely replicated in each structure (FIG. 2I). The early neuron population, however, was presented in 3 out of 5 samples examined, suggesting that the specimens with neurons might have been at a slightly more advanced stage with respect to the onset of neurogenesis. Neural crest cells expressed known marker Ets in addition to Sox10 (FIG. 12F). To confirm that the formation of all these neural subtypes was accompanied by a regionalized pattern of gene expression, sequential smFISH was performed on a sectioned natural embryo and ETiX embryoid (FIG. 12G-FIG. 12I). In both, expression of Fezf1, Lhx2 and Six3 in the forebrain and localized expression of En1 and Dmbx1 in the midbrain were observed, in agreement with published results.

Figure 3A:
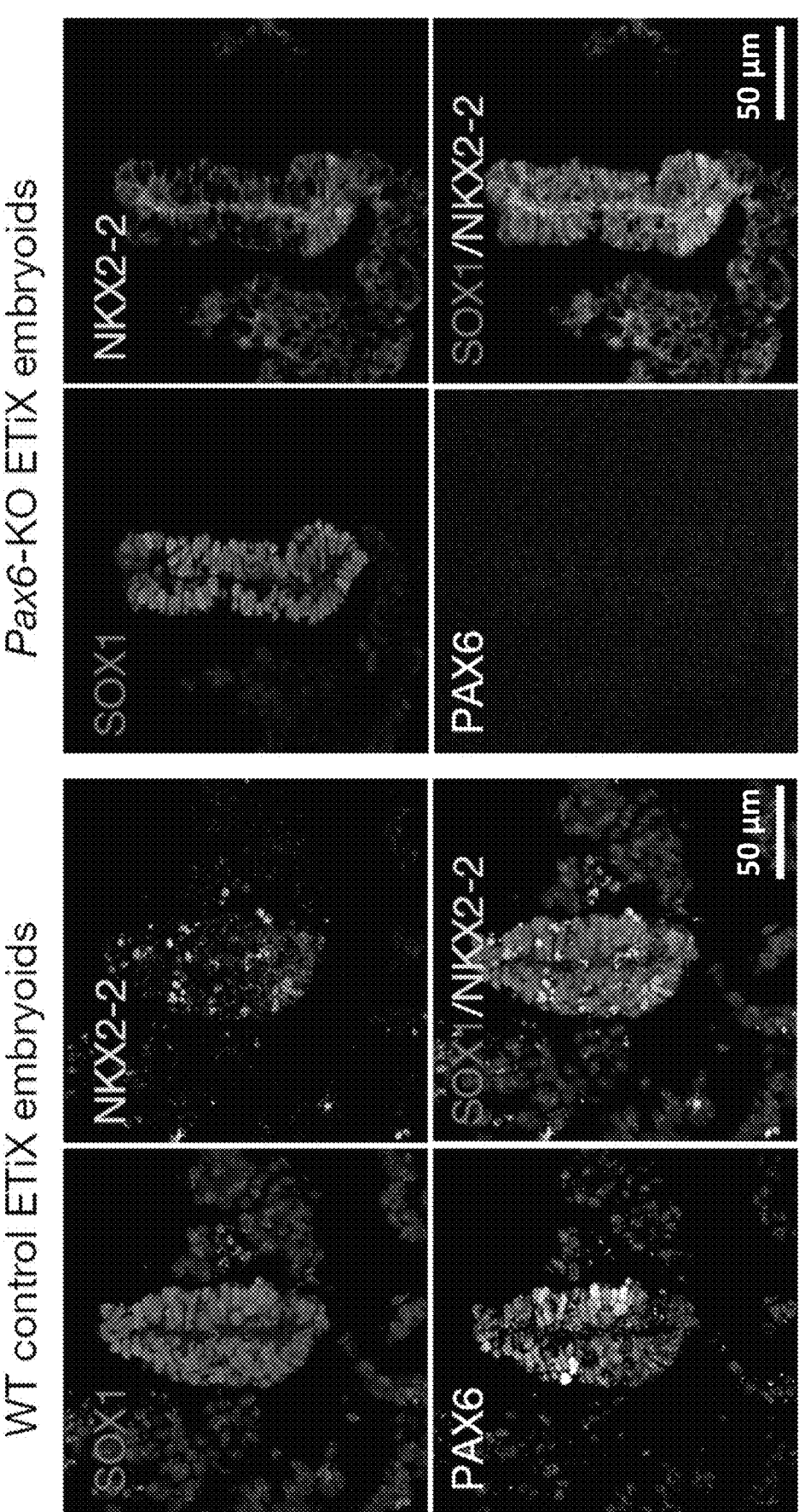
FIG. 3A-FIG. 3C depict non-limiting exemplary embodiments and data related to Pax6 knockout in exemplary ETiX embryoids described herein which recapitulate known mouse embryonic phenotypes.
Figure 3B:
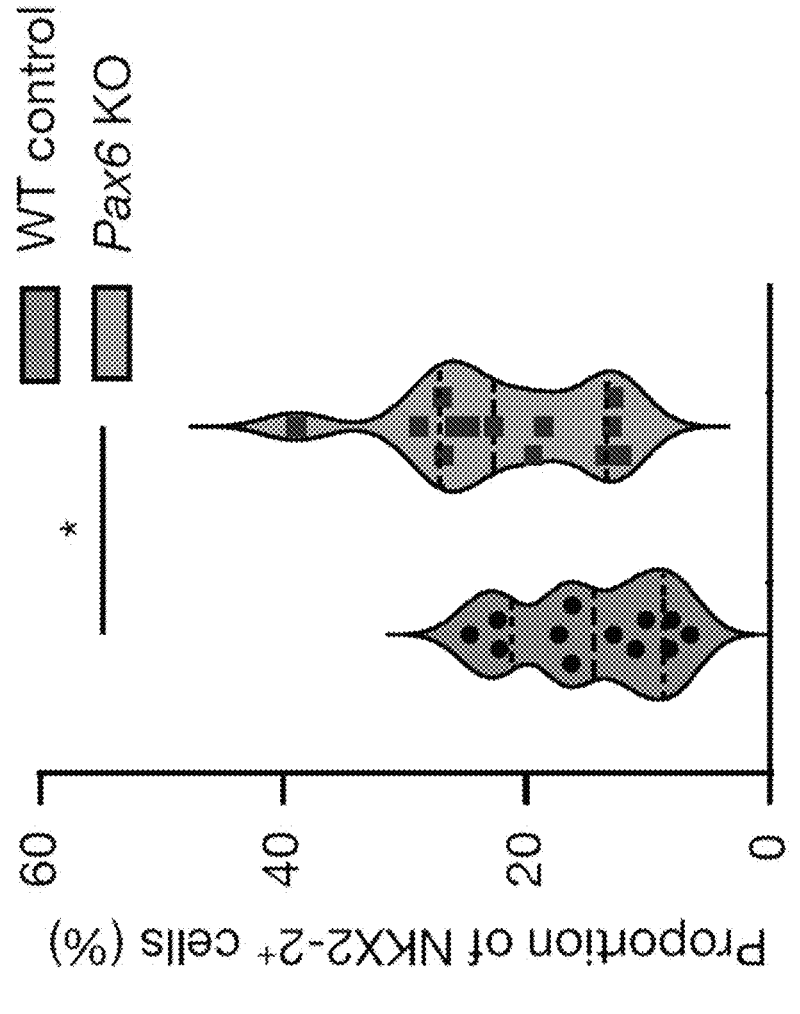
Figure 3B:
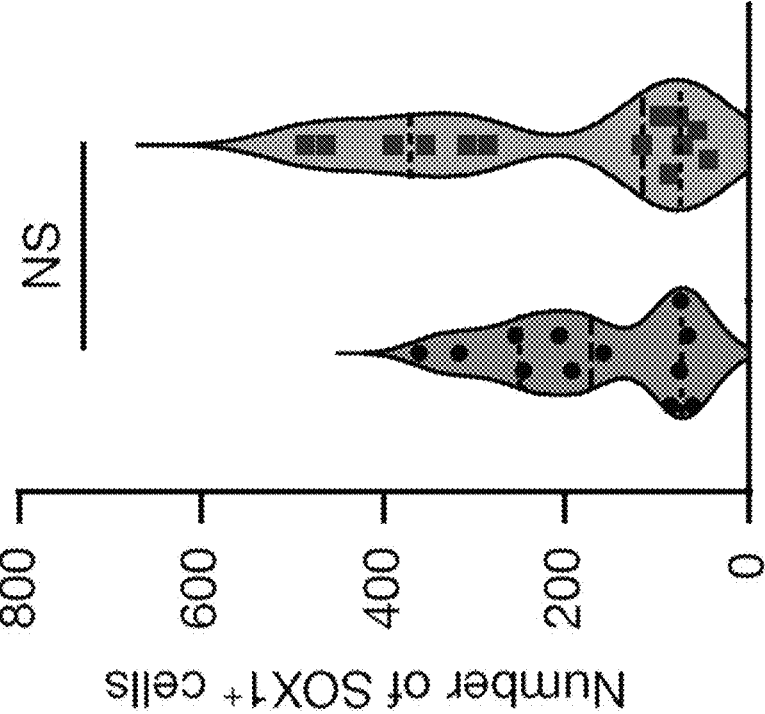
Figure 3C:

To test whether the neural tube of neurulating embryoids responded to a developmental challenge in the same way as the neural tube of natural embryos, embryoids were generated from a transgenic ES cell line that does not express PAX6. PAX6 is a transcription factor required for neural tube patterning as well as brain and eye development. Pax6-knockout ETiX embryoids had similar cell-type proportions as control structures (FIG. 12J). In line with the development of Pax6-knockout natural embryos, the Pax6-knockout embryoids showed no alteration in the total number of SOX1-positive cells in the neurectoderm but showed an increase in the proportion of NKX2-2-positive cells, suggesting an expansion of the ventral domain of the neural tube (FIG. 3A-FIG. 3B). To determine other developmental consequences of the Pax6 deletion, global changes in transcript levels in the absence of Pax6 were examined. Enrichment of transcripts associated with neuron formation and the development and formation of axons (FIG. 3C) was found, consistent with previous results.

Figure 2J:
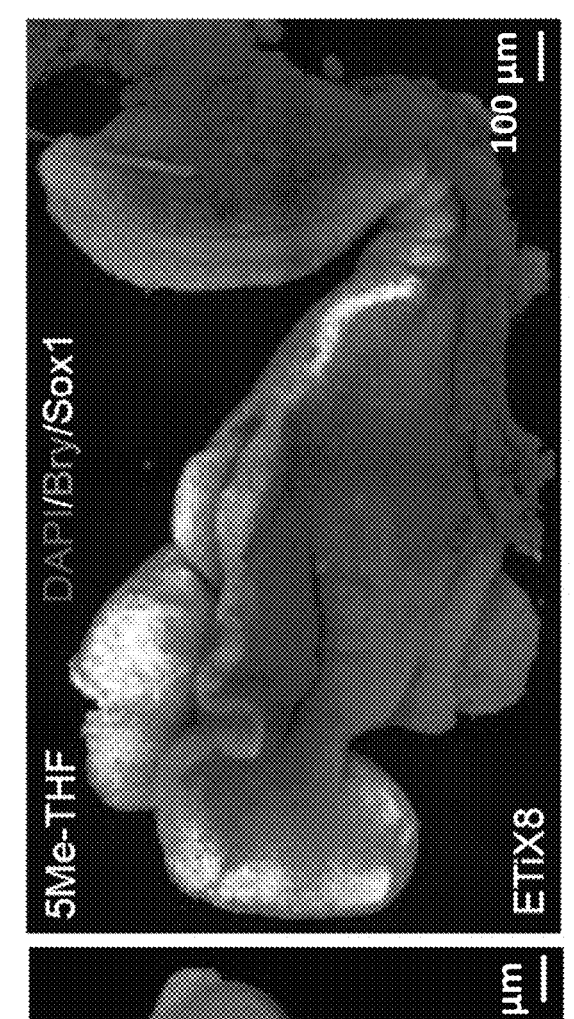
Figure 2J:

Defects associated with nervous system are the second most frequent developmental abnormality in humans, including brain defects such as anencephaly and spine defects such as spina *bifida*. In certain batches of serum, 75-80% of developing ETiX embryos displayed an abnormal twisting or kinking of the neural tube (FIG. 2J). The vast majority of similar neural tube defects in both mouse and humans can be rescued by supplementing the mother's diet with folic acid. To test whether folic acid treatment rescued neural tube defects during ETiX embryo development, the ETiX embryos was cultured in the presence of 5-Methyl-THF (50 ng/ml), the metabolically active form of folic acid. 5-Methyl-THF substantially rescued the neural tube defects of ETiX embryos (FIG. 2J), indicating that ETiX embryos can serve as relevant disease models.

Taken together, the results in this example demonstrate that neurulating embryoids undertook morphogenesis of headfold structures in a manner that closely resembles the natural embryo and can serve as relevant disease models.

Example 4

Somitogenesis and Heart Development in Embryoids

This example reports that neurulating embryoids can undergo somitogenesis to the stage that a beating heart develops. A morphology similar to the natural embryos and the expression of markers associated with somites and heart development were observed.

Figures 4A, 4B:
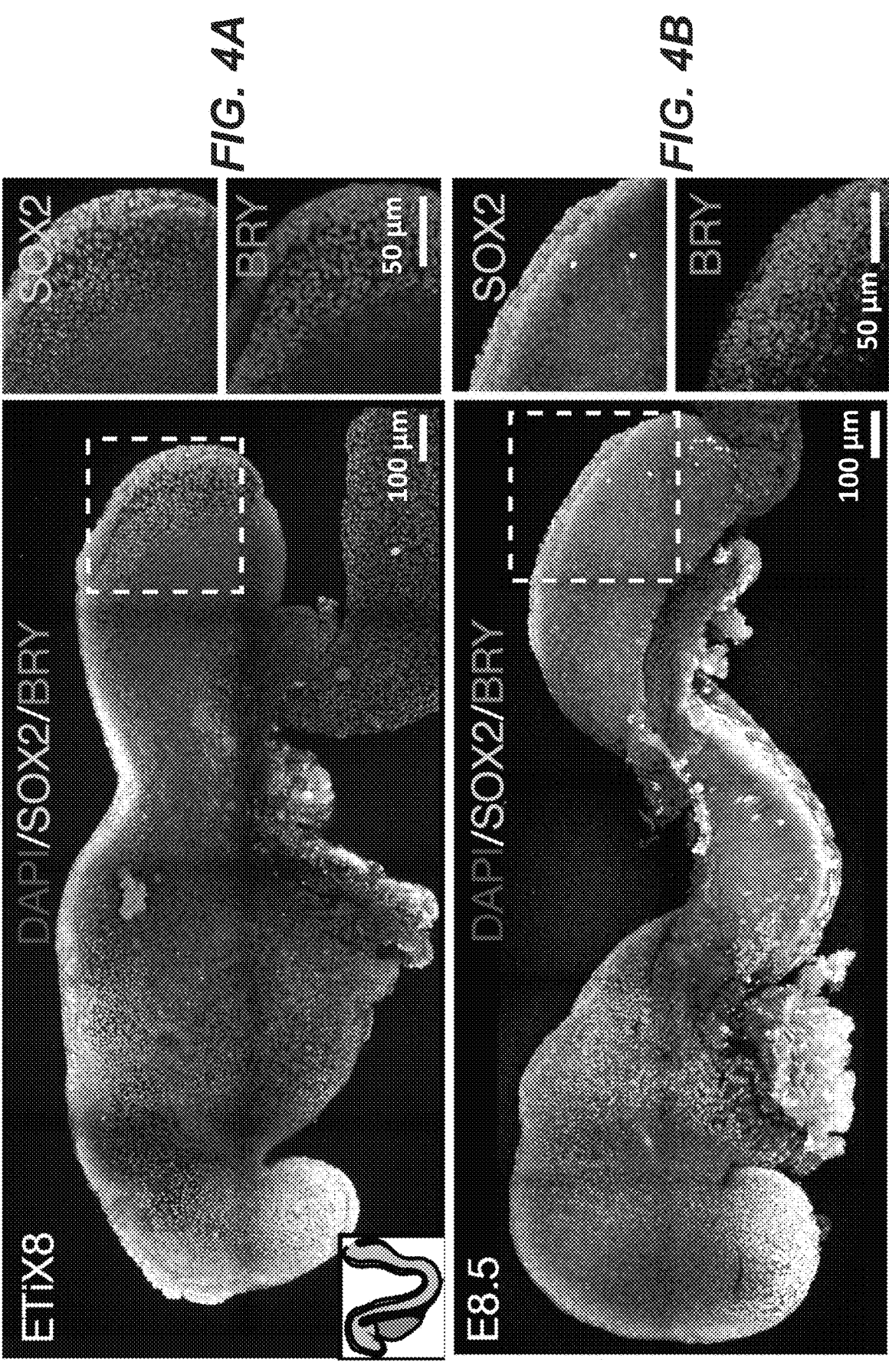
FIG. 4A-FIG. 4L depict non-limiting exemplary embodiments and data related to ETiX embryoids undertaking somitogenesis and heart formation.
Figure 4C:
Figure 4C:
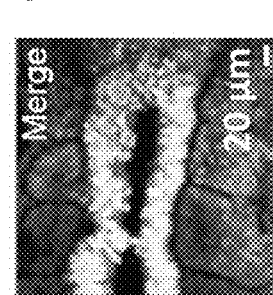
Figure 4C:
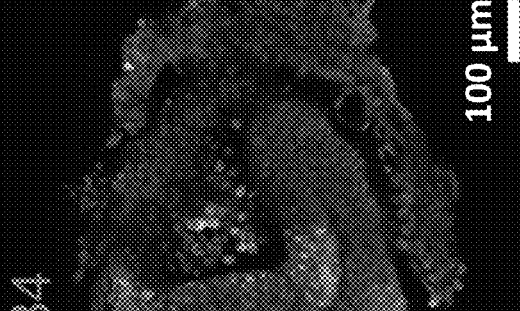
Figure 4C:
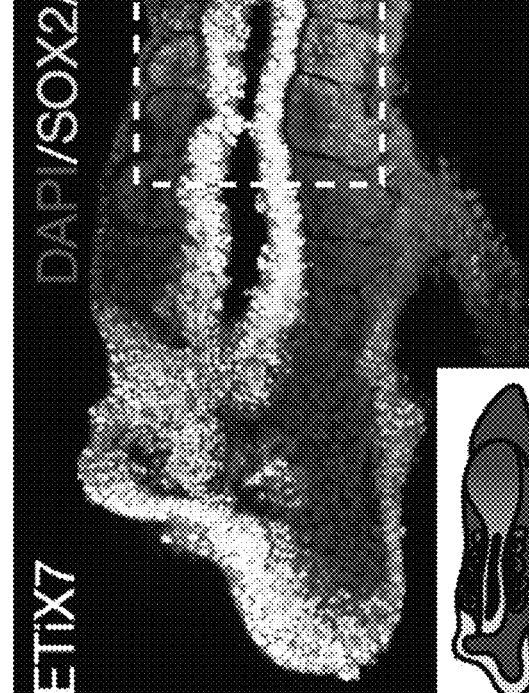
Figure 4D:
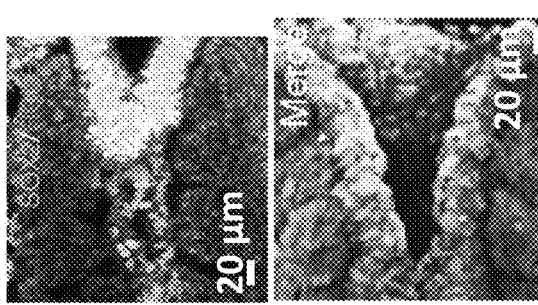
Figure 4D:
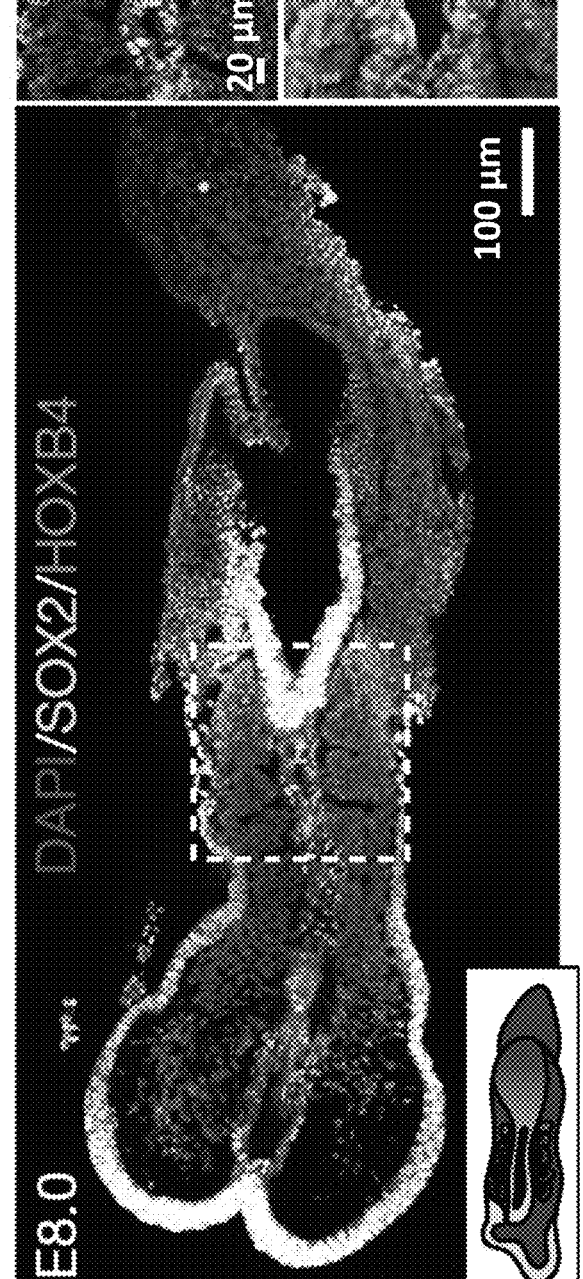
Figure 13A:
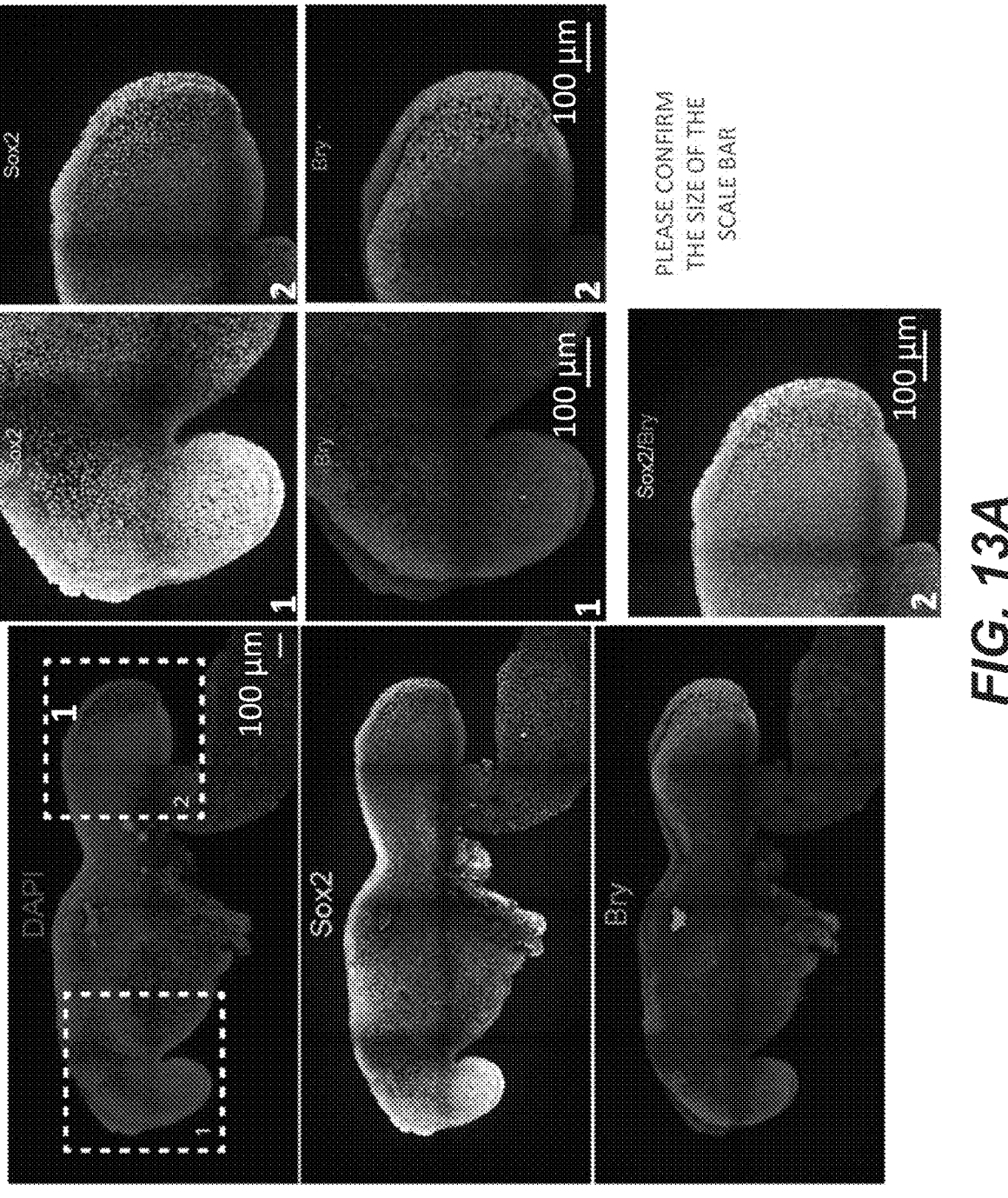
FIG. 13A-FIG. 13J depict non-limiting exemplary embodiments and data related to the development of ETiX embryoids mesoderm into somites and cardiac tissue.
Figure 13B:
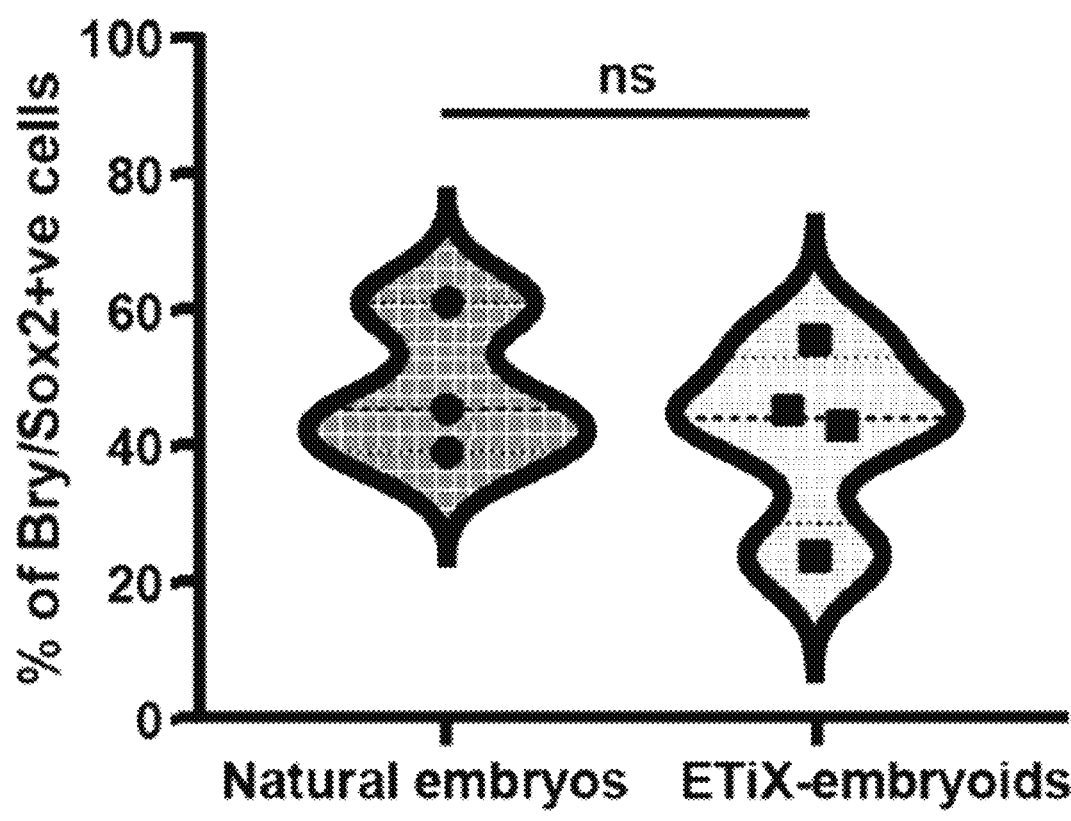
Figure 13C:
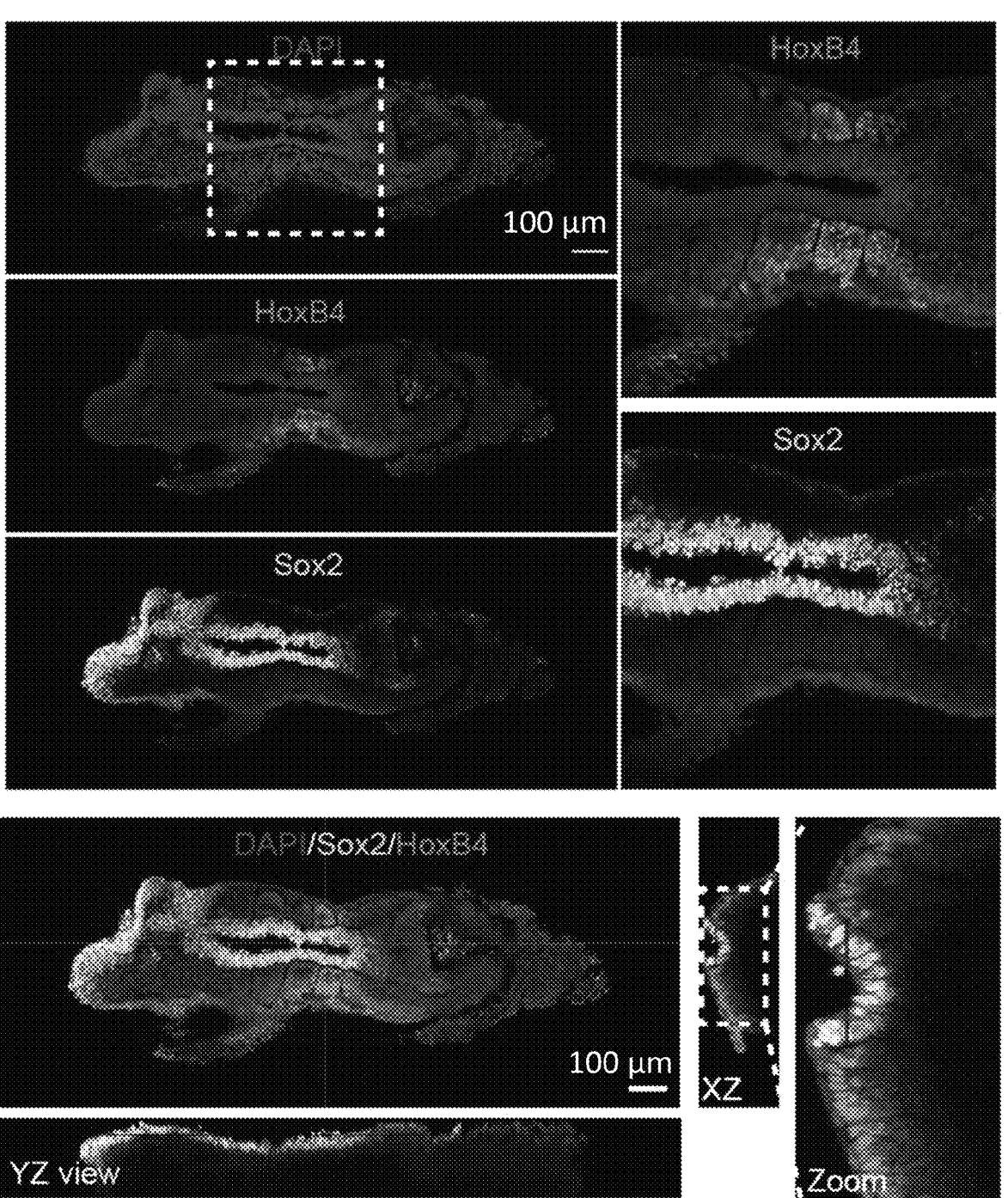
Figure 13D:
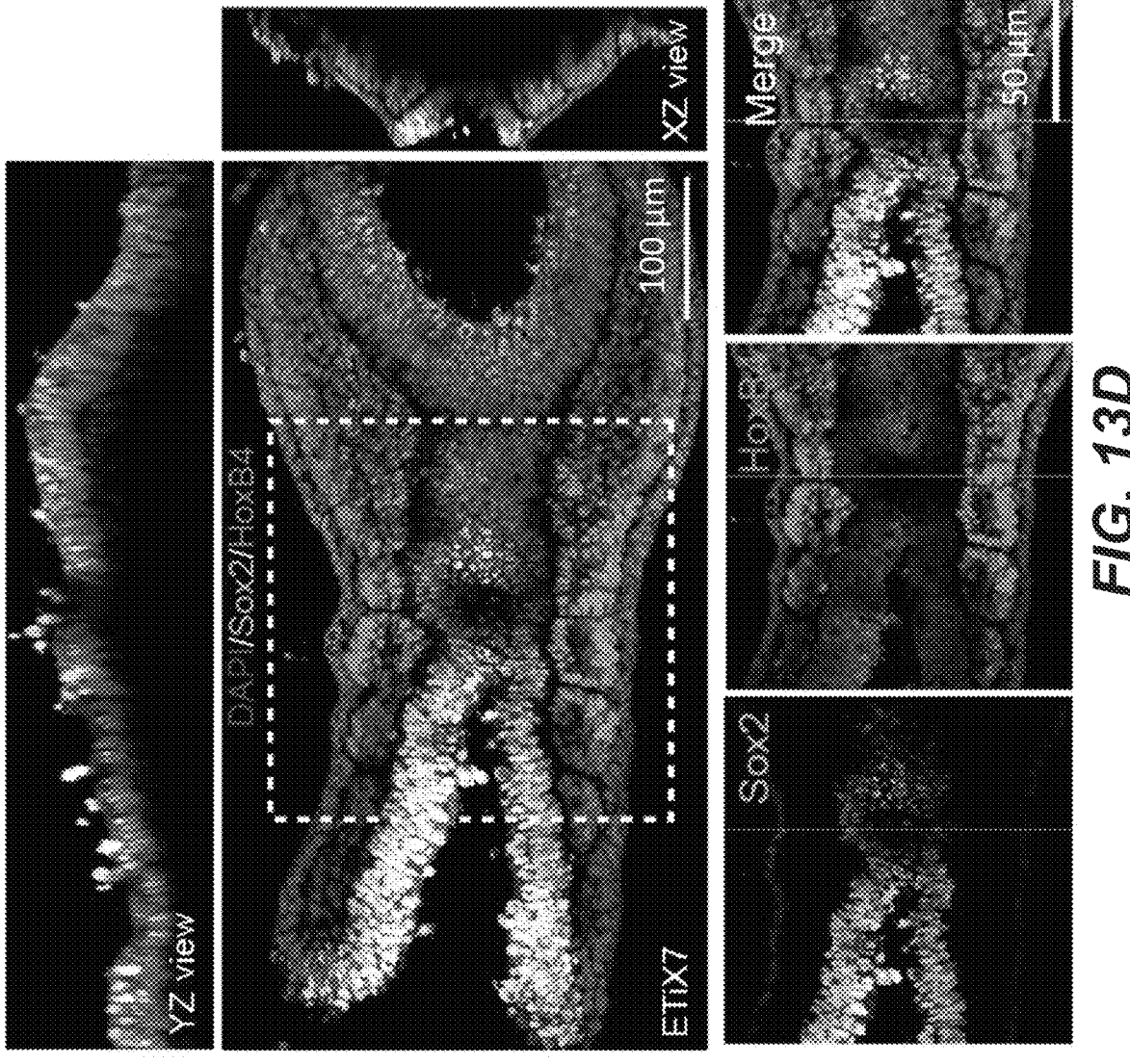
Figure 13E:
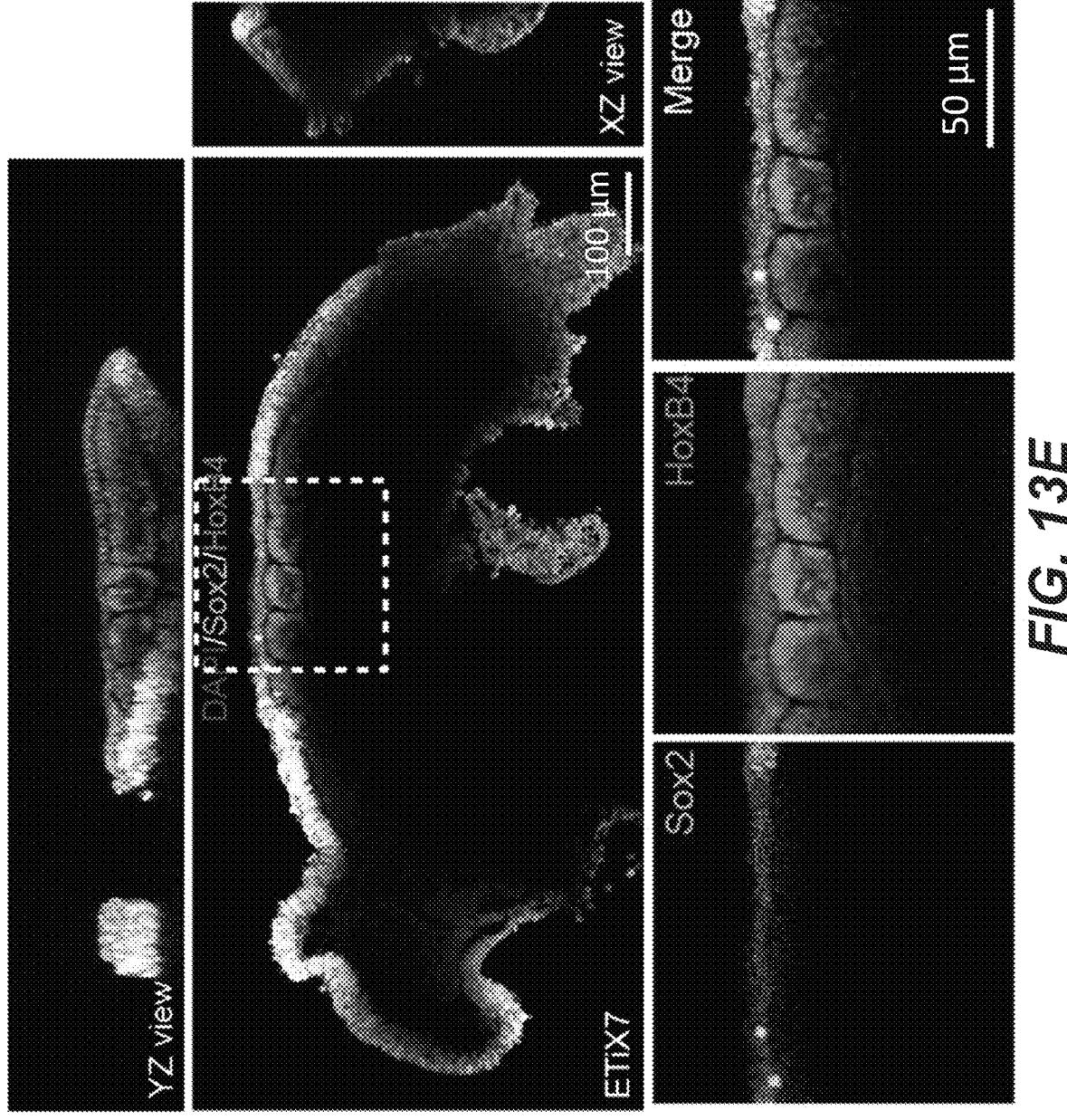
Figure 13F:
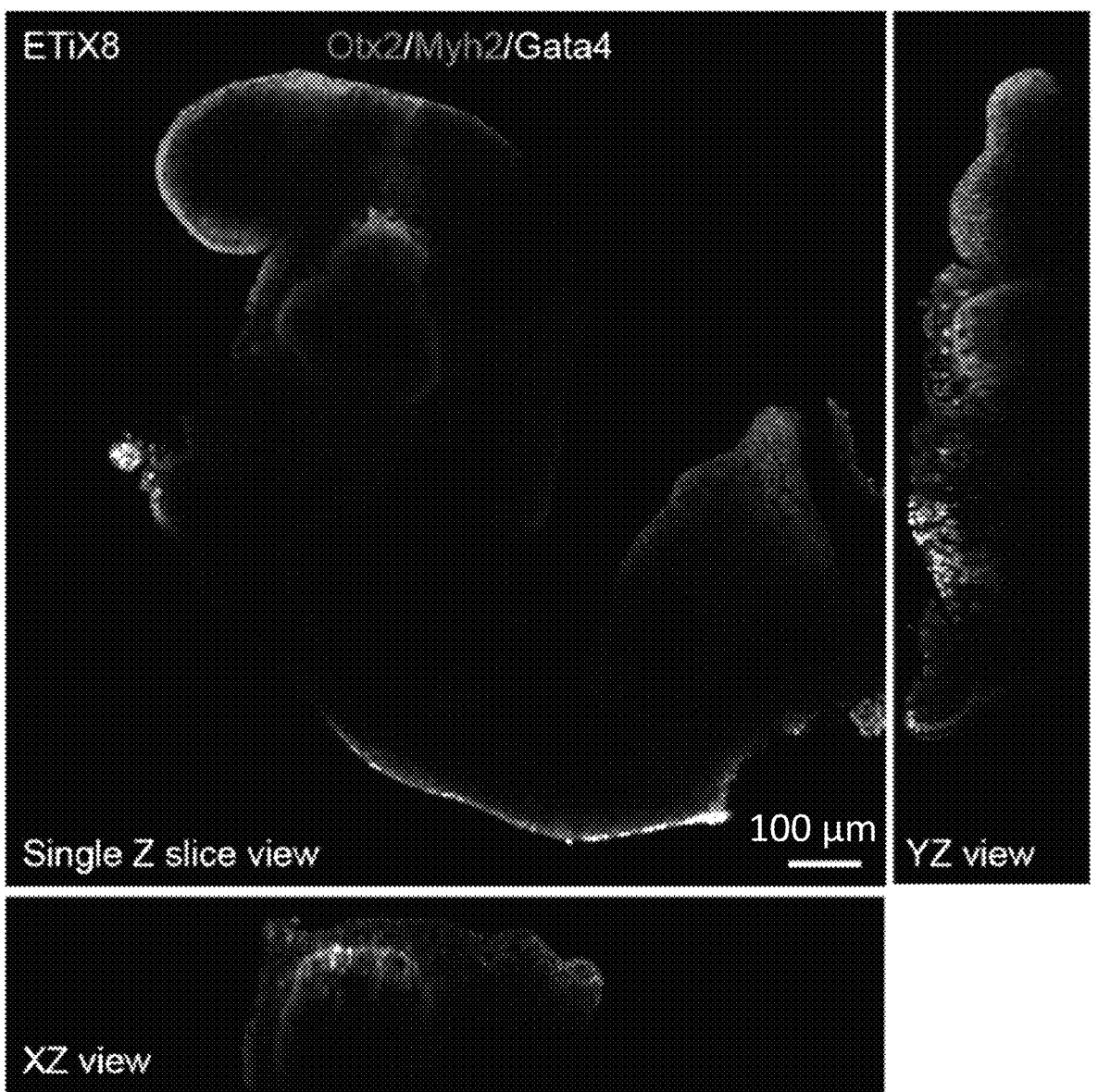
Figure 13G:
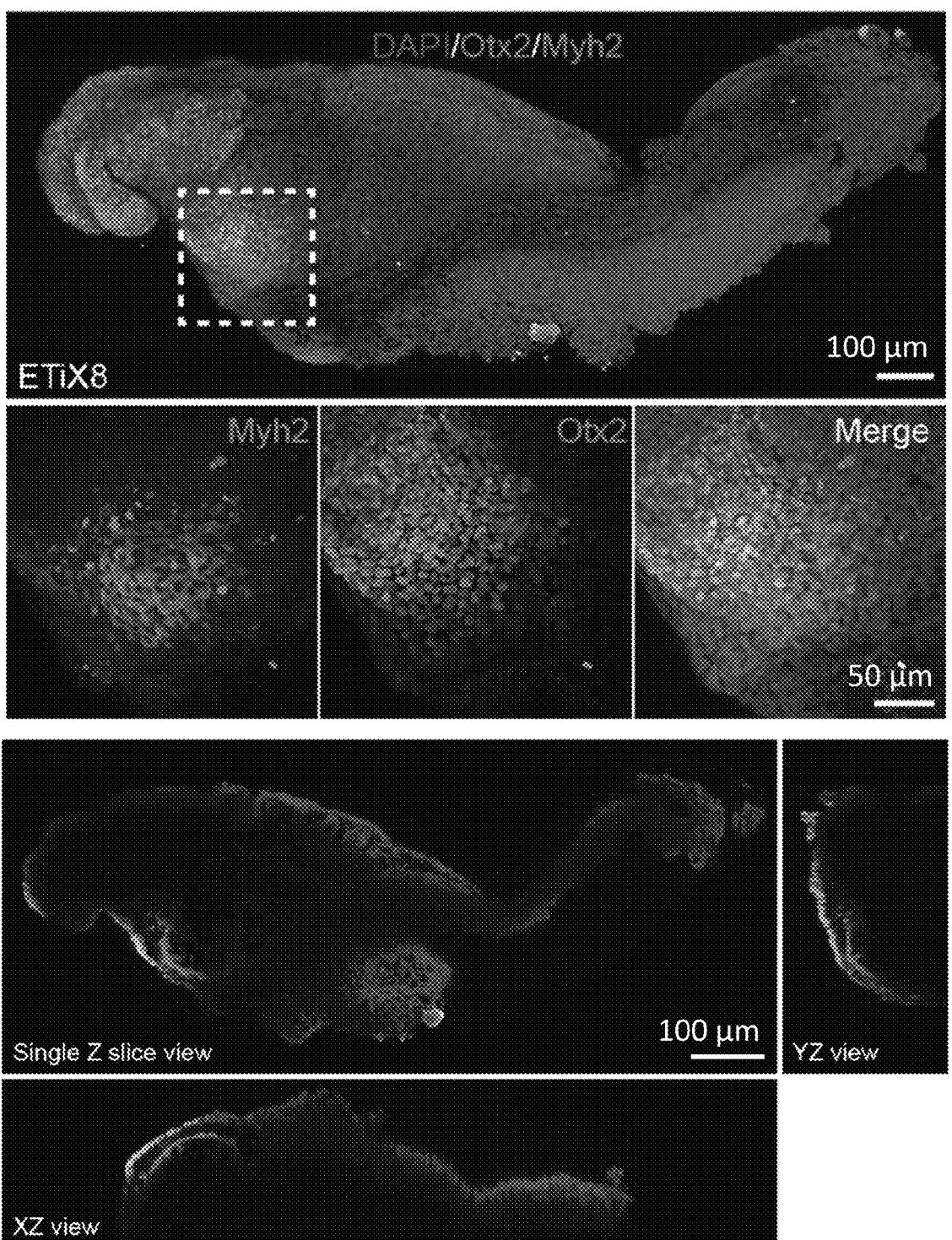

During natural embryogenesis, neuro-mesodermal progenitors (NMPs) contribute to derivatives of the neural tube and the paraxial mesoderm. To determine whether neurulating ETiX embryoids form NMPs, immunofluorescence was performed to detect the expression of the NMP markers SOX2 and Brachyury in a domain spanning the posterior region of the tail bud of neurulating day 8 ETiX embryoids (FIG. 4A). By contrast, the more anterior regions of day 8 ETiX embryoids expressed SOX2 but not Brachyury—marking the neural lineage—or Brachyury but not SOX2—marking the mesodermal lineage (FIG. 4A and FIG. 13A). This pattern of marker expression was similar to that in E8.5 natural embryos (FIG. 4B), consistent with the differentiation trajectory reported for these cells in the embryo. The co-localization of Brachyury and SOX2 in tail bud cells was similar between ETiX embryoids and natural embryos (FIG. 13B). These findings agreed with the differentiation trajectory reported for these cells in the natural embryo.

Figure 4E:
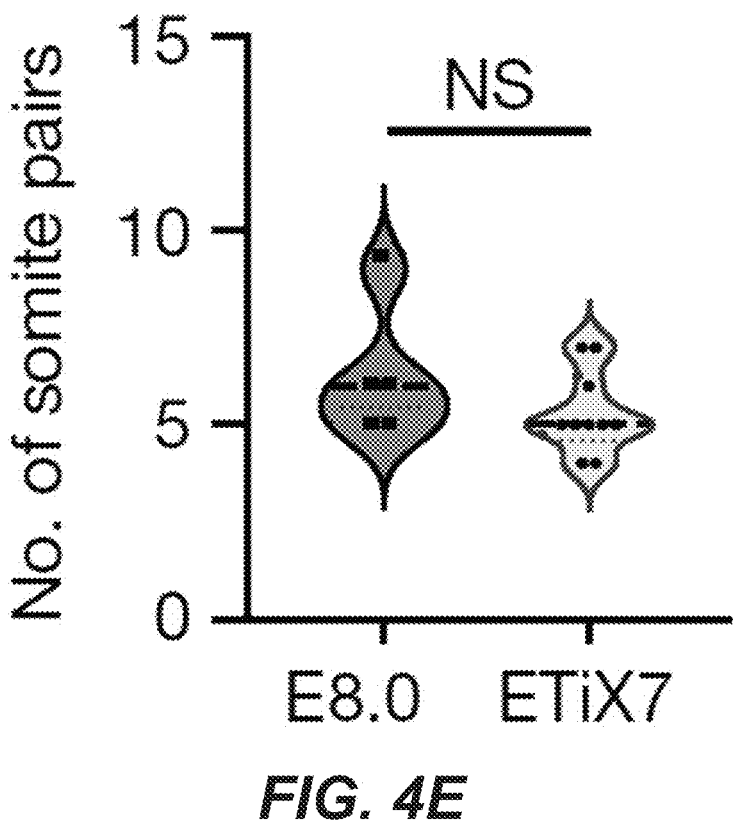
Figure 4F:
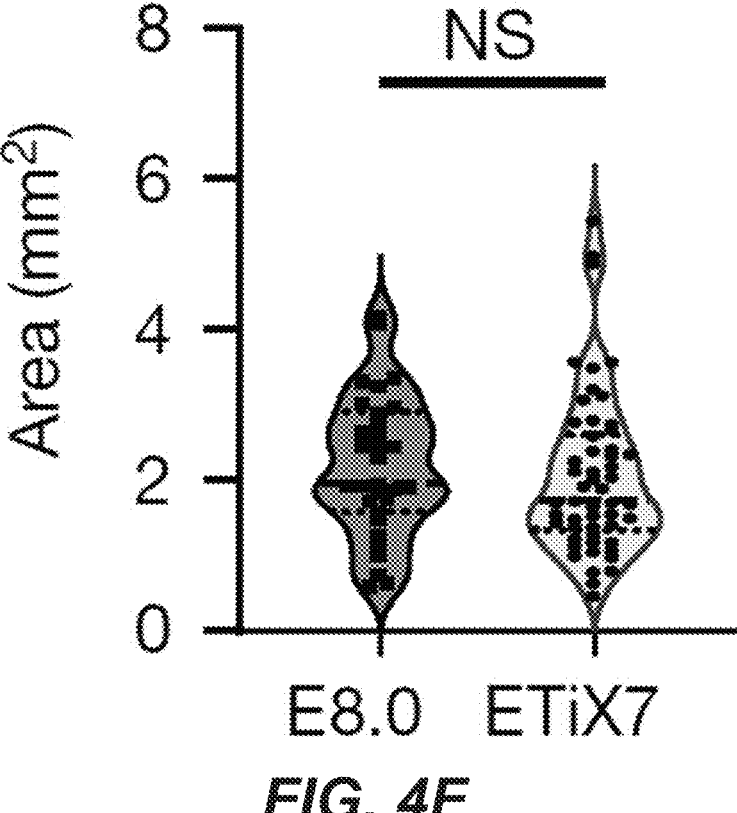
Figure 4G:
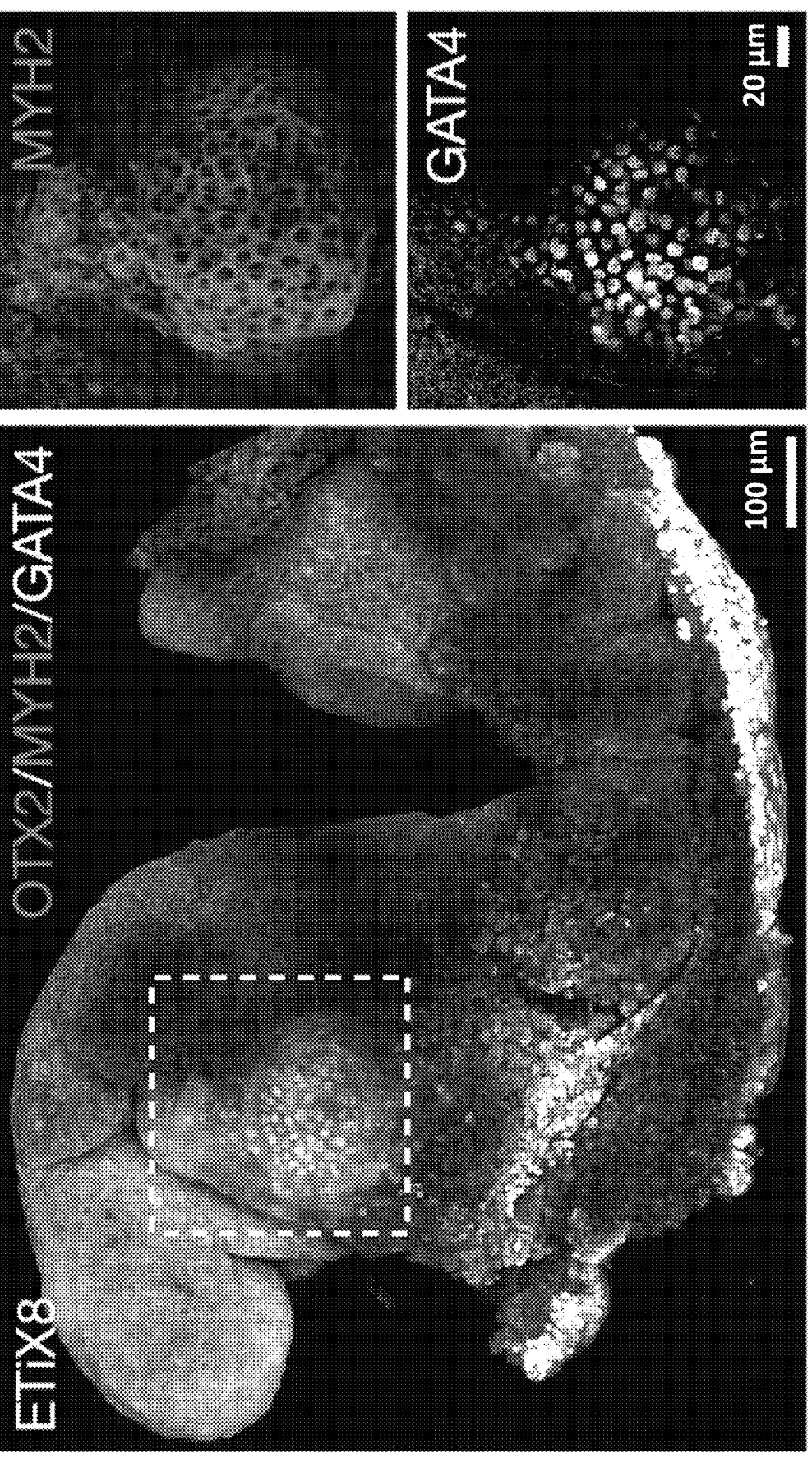
Figure 4H:

The paraxial mesoderm in turn gave rise to somites, which were paired blocks of cells that formed along the anterior-posterior axis of the embryo and were required for segmental formation of skeletal muscle, blood vessels and skin. Pairs of somites expressing the homeobox protein HOXB4 were observed on either side of the SOX1 and SOX2-positive neural tube population in both day 7 ETiX embryoids and natural E8.0 embryos (FIG. 4C-FIG. 4D and FIG. 13C-FIG. 13E). Quantification of the number of somite pairs and the area of somites in ETiX embryoids and natural embryos showed no significant difference (FIG. 4E-FIG. 4F). These expression patterns marked the key features of somitogenesis, which thus recapitulated the corresponding natural process.

Figure 4I:
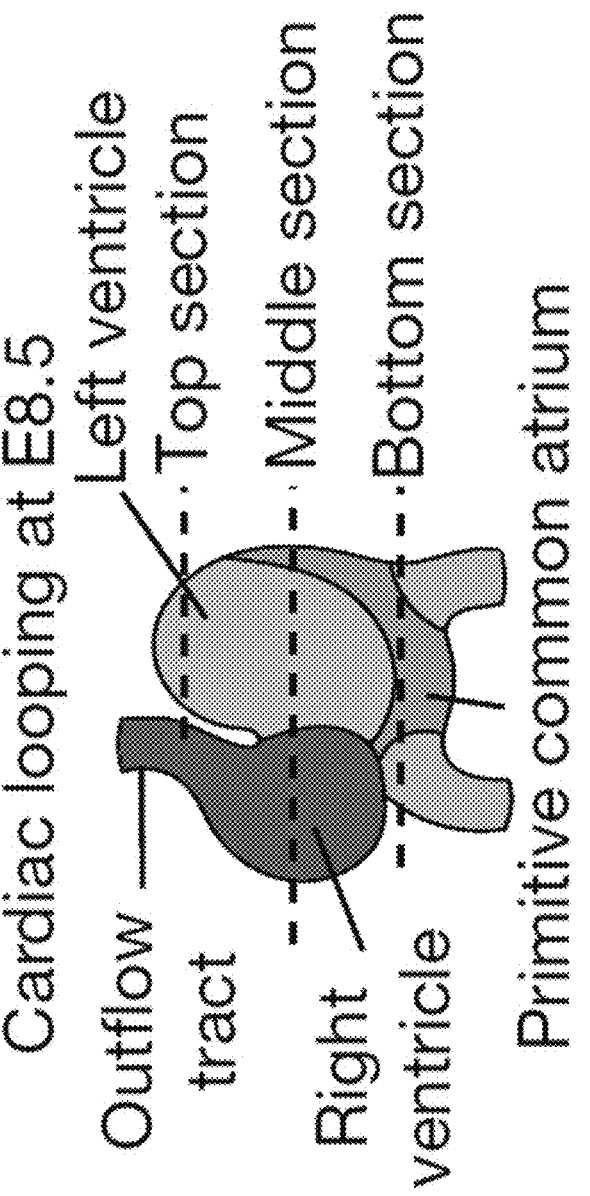
Figure 4J:
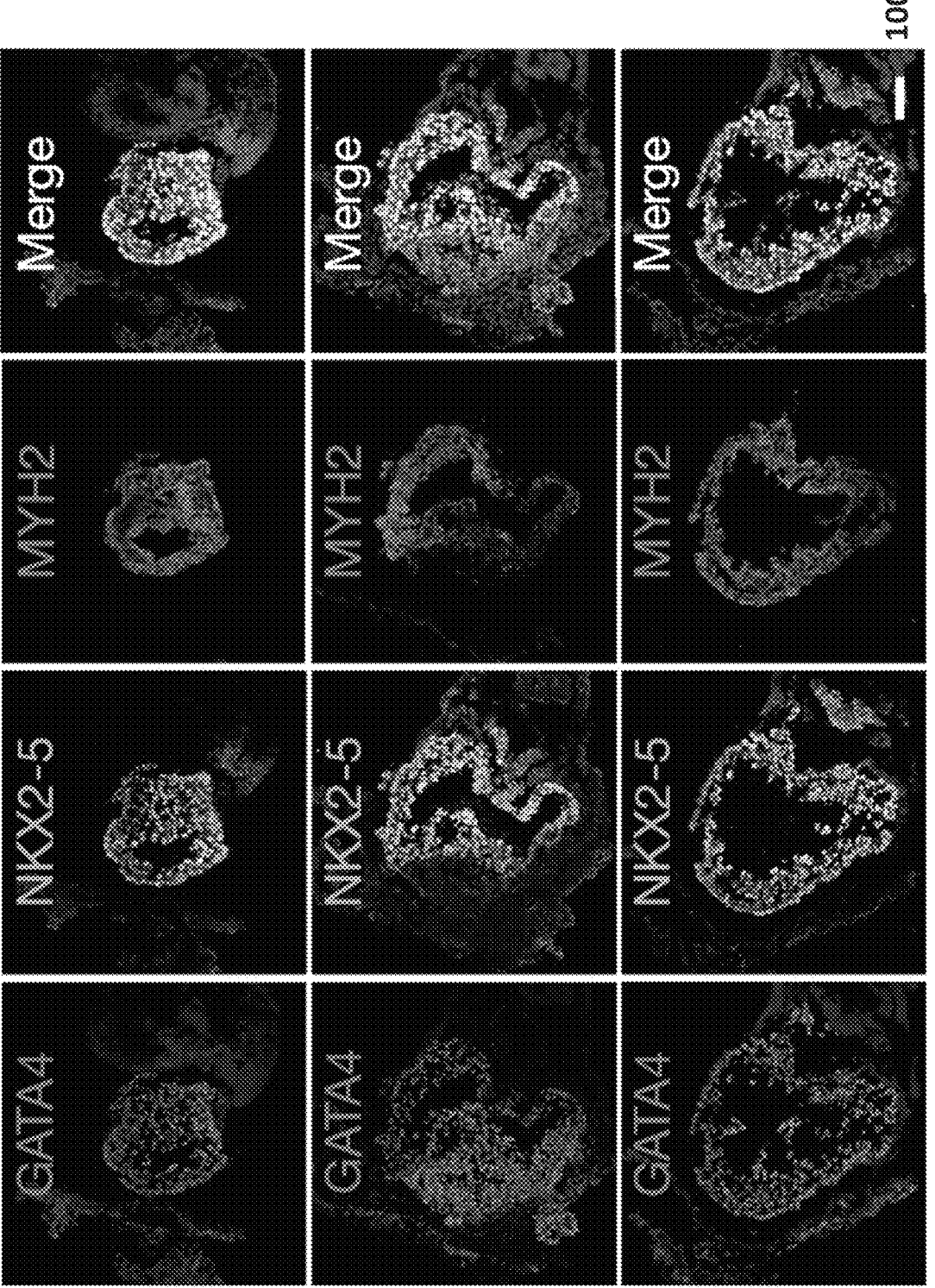
Figure 13H:
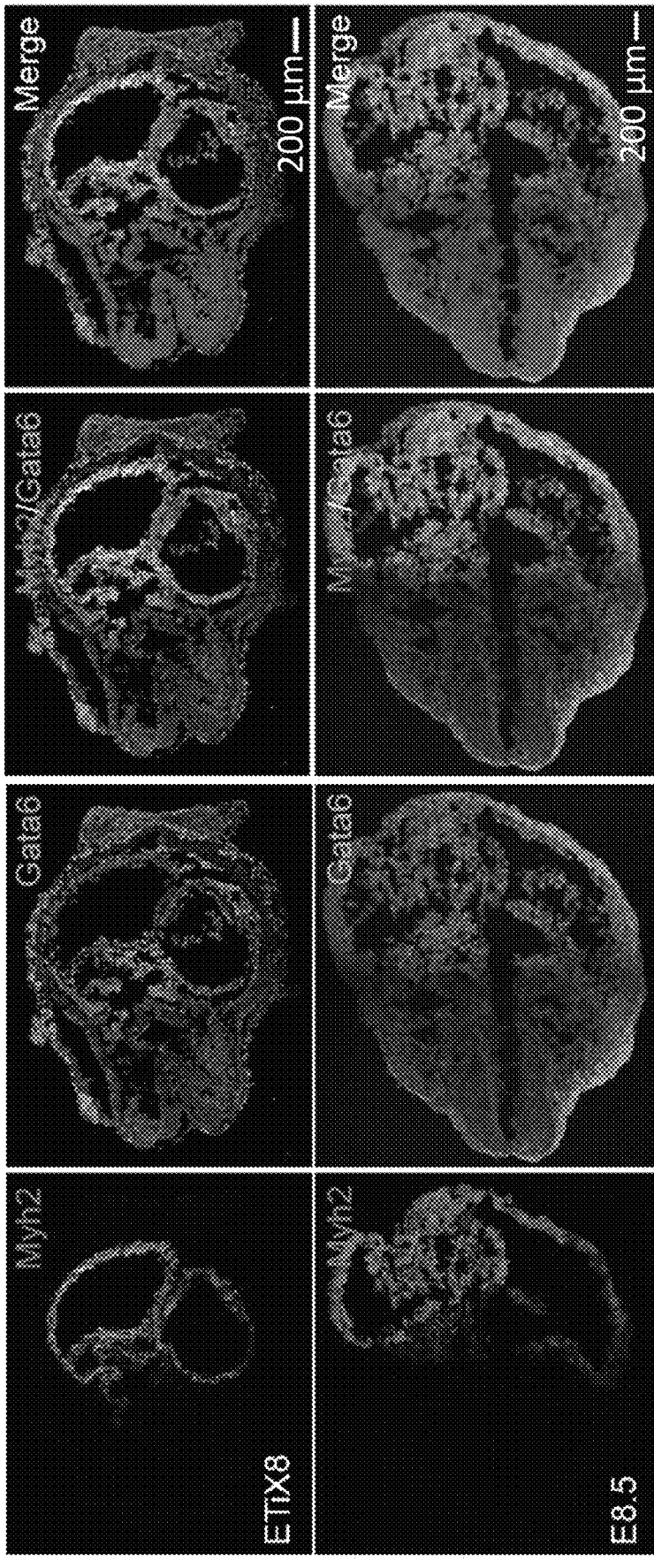
Figure 13I:
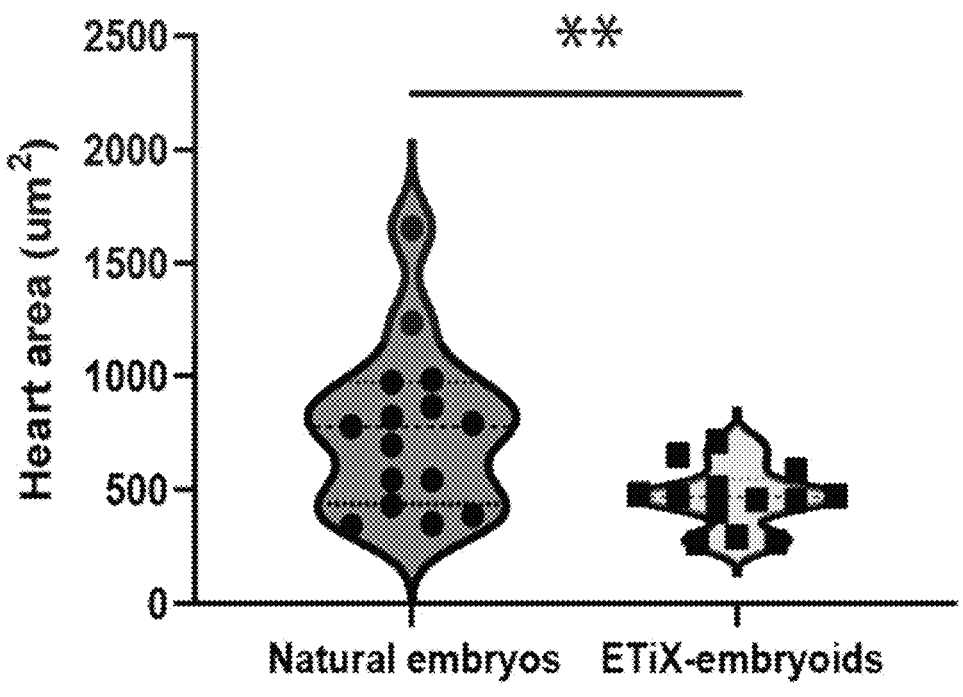
Figure 13J:
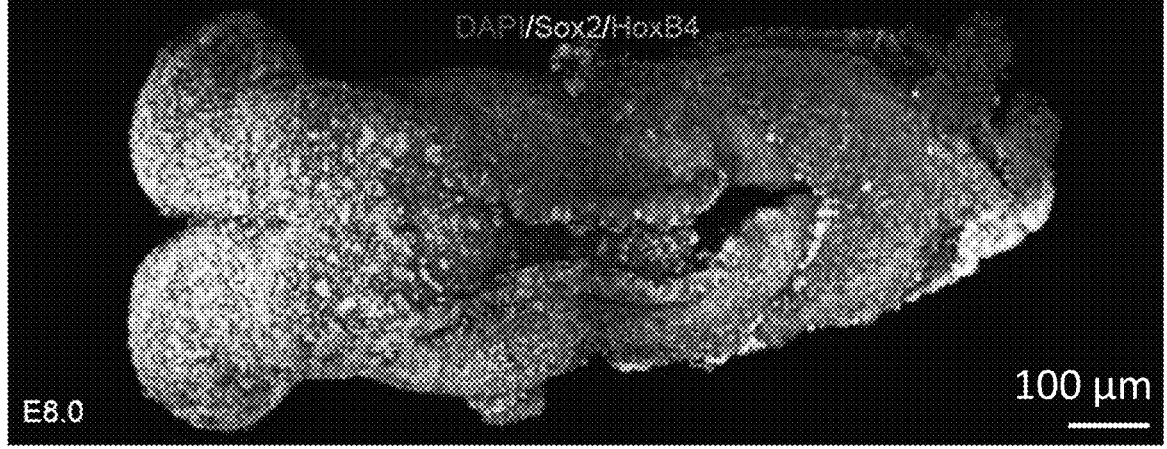

A distinct set of cells destined to form the heart also emerged from the primitive streak at gastrulation. In the natural embryo, this developmental event took place around E8.0. Heartbeat was established as the cardiac mesoderm differentiated into cardiomyocytes. The formation of a beating structure below the encephalon region in day 8 neurulating embryoids was observed. This beating region of the neurulating embryoids expressed myosin heavy chain II (MYH2) and the transcription factor GATA4 (FIG. 4G-FIG. 4H and FIG. 13F-FIG. 13G), which were required for cardiac development, in a similar spatiotemporal profile as the natural embryo. Immunostaining of the indicated sections in day 8 neurulating embryoids showed a NKX2-5, GATA4 and MYH2 triple-positive compartment (FIG. 4I-FIG. 4J). The MHY2-positive region also expressed the transcription factor GATA6 (FIG. 13H). Comparison with an age-matched E8.5 natural embryo heart showed that the abutting cavities observed in the MYH2-positive region of the ETiX embryoid were very similar to the natural embryo heart. However, no clear heart looping was observed. Furthermore, the area of the cardiac domain was decreased in ETiX embryoids compared to natural embryos (FIG. 13I).

Figure 4K:
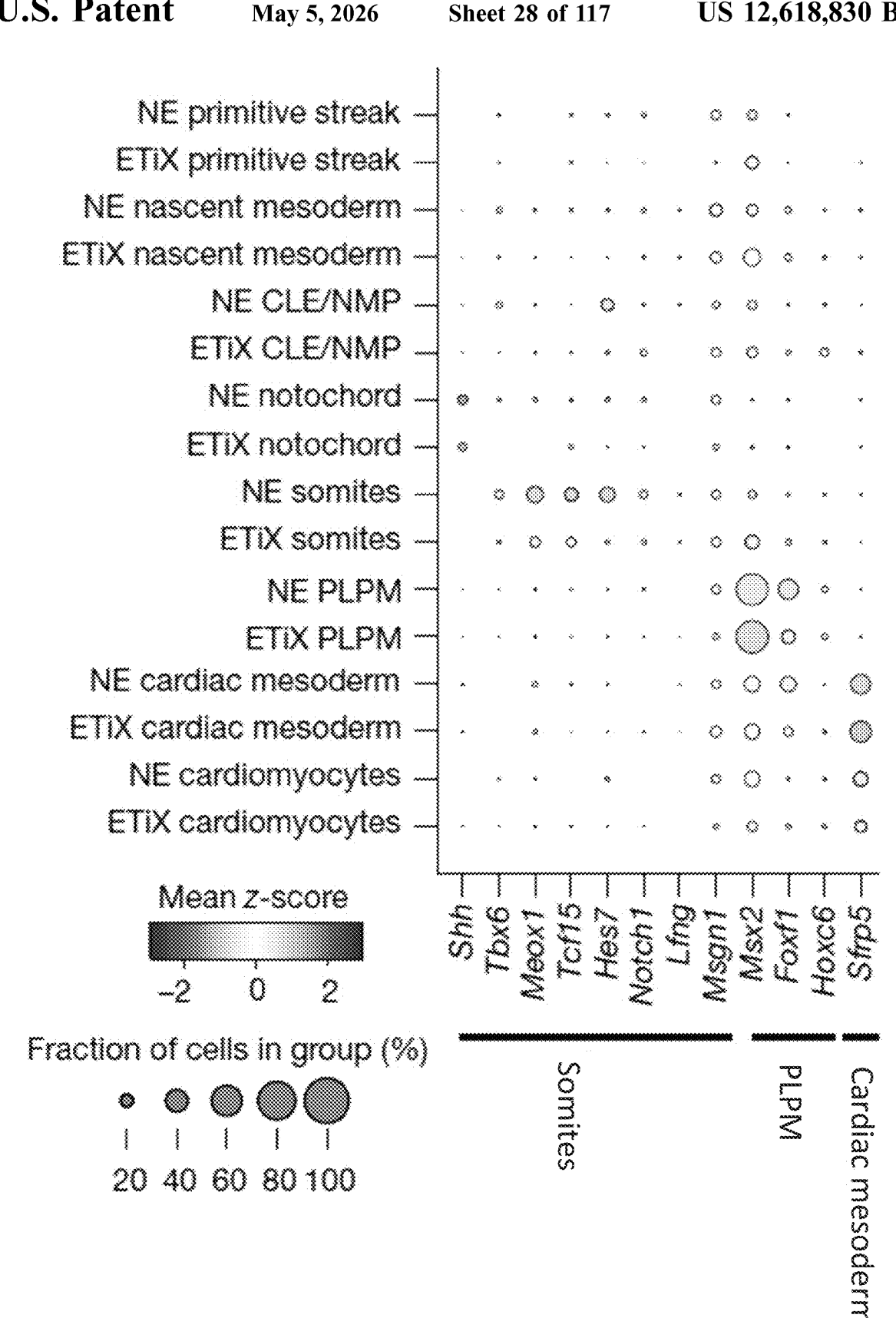
Figure 4K:
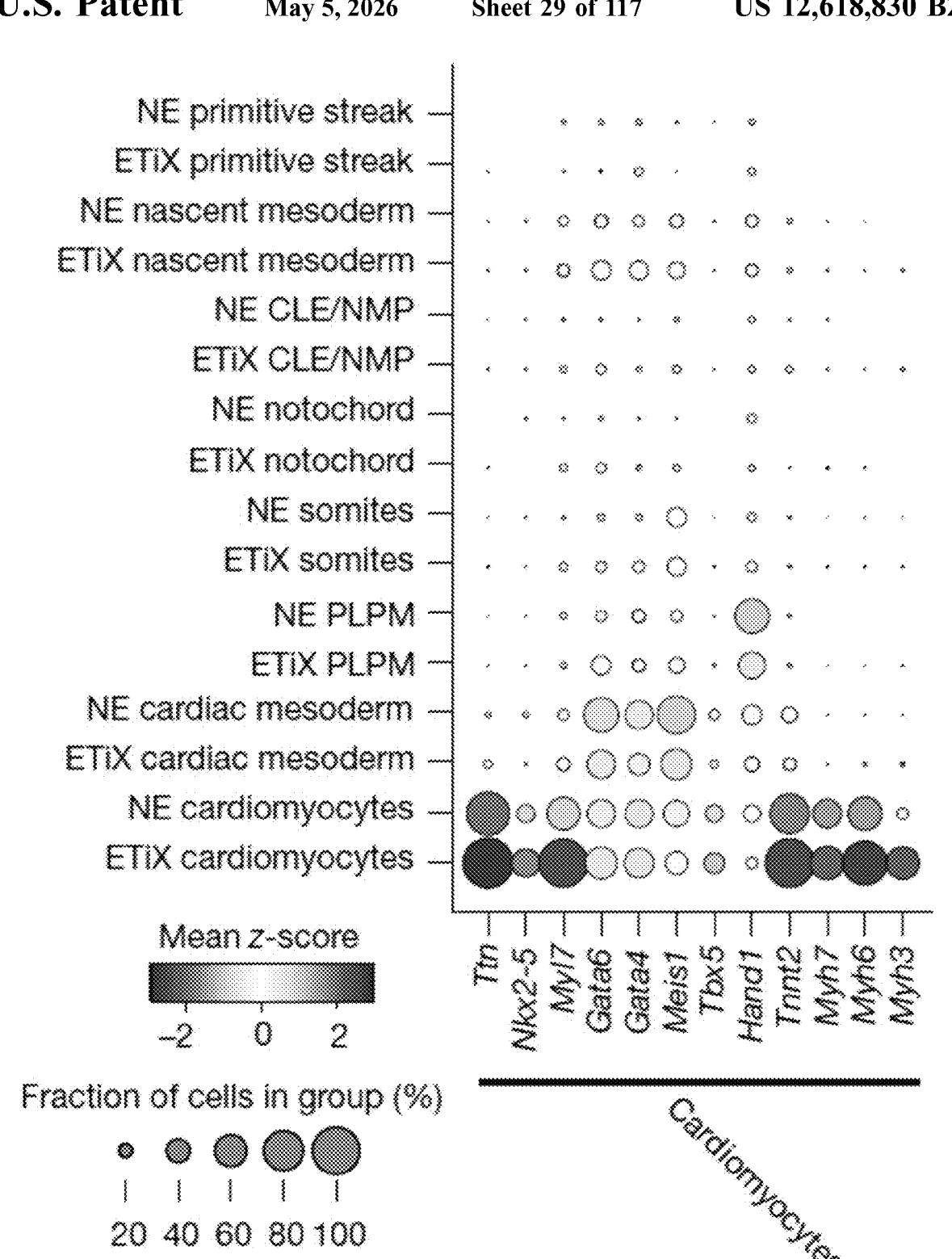
Figure 4L:
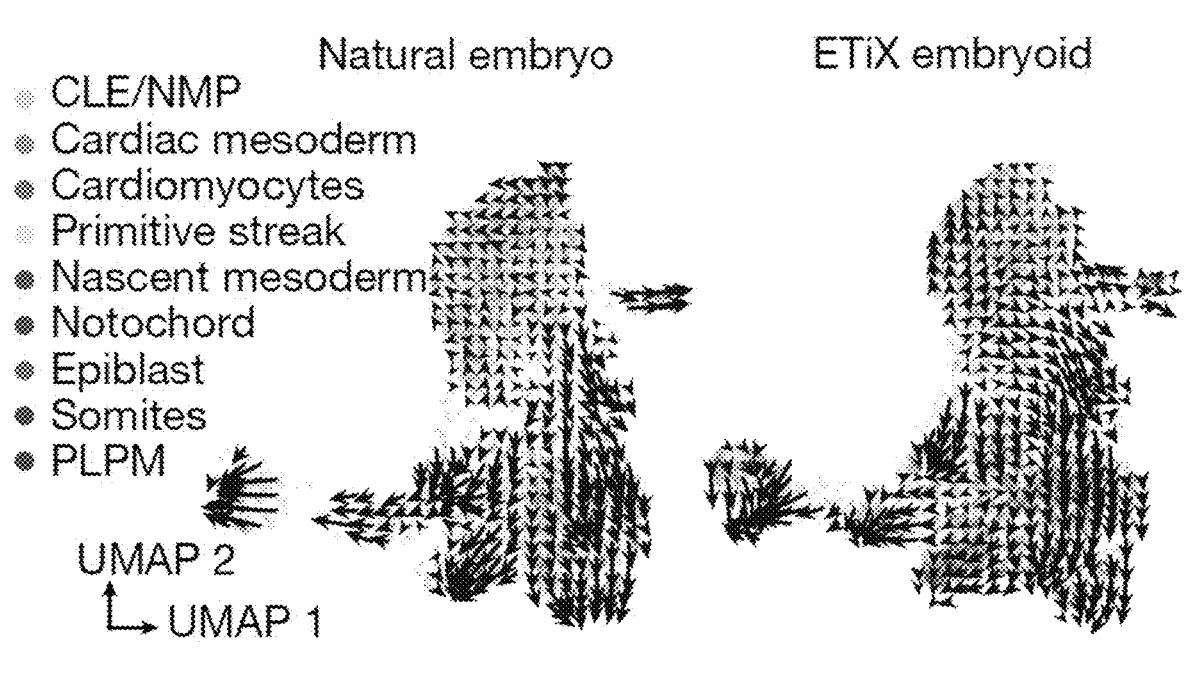
Figure 14A:
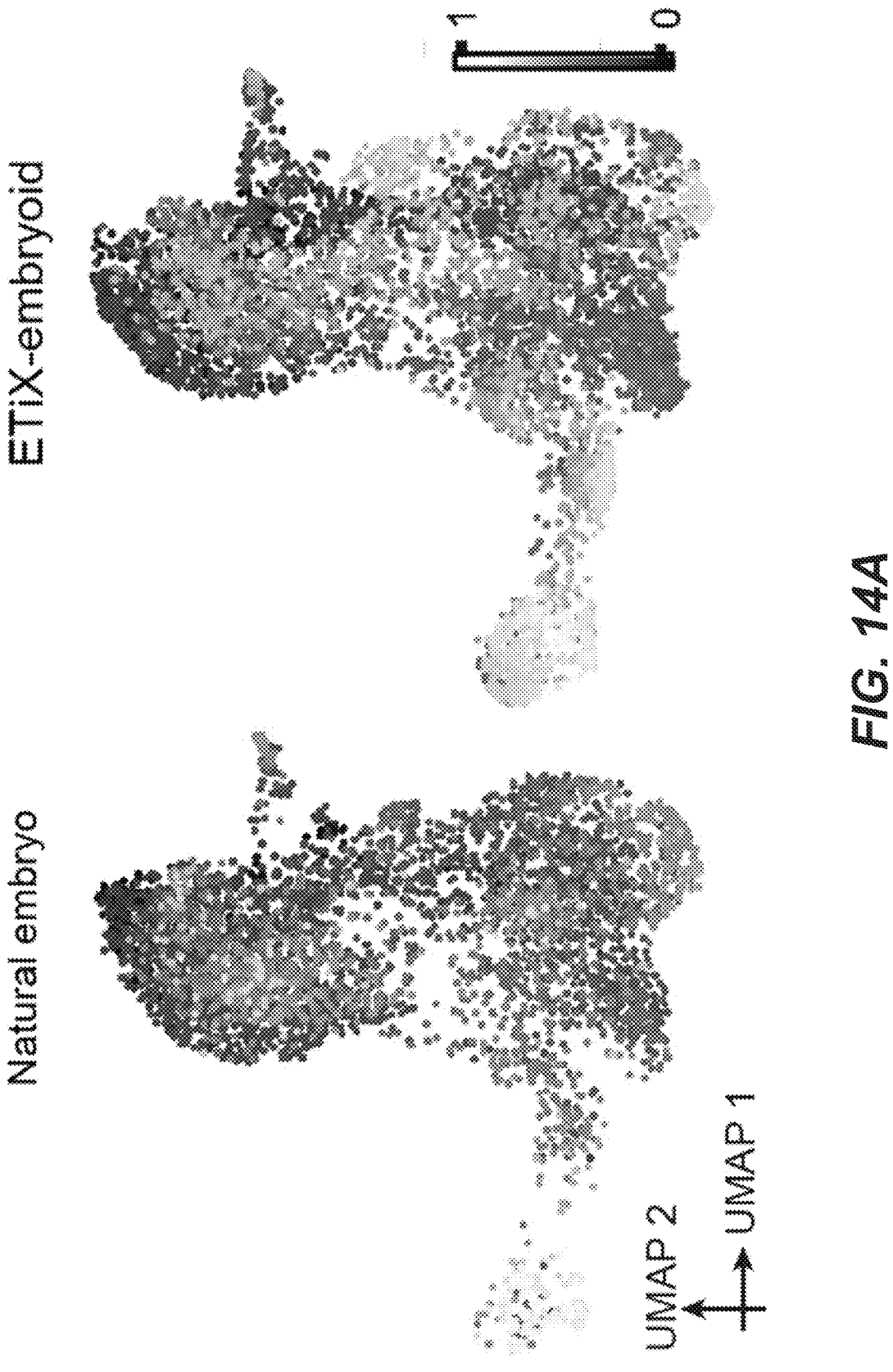
FIG. 14A-FIG. 14F depict non-limiting exemplary embodiments and data related to the developmental trajectories, the timing of mesoderm differentiation and the expression of selected genes.
Figure 14B:
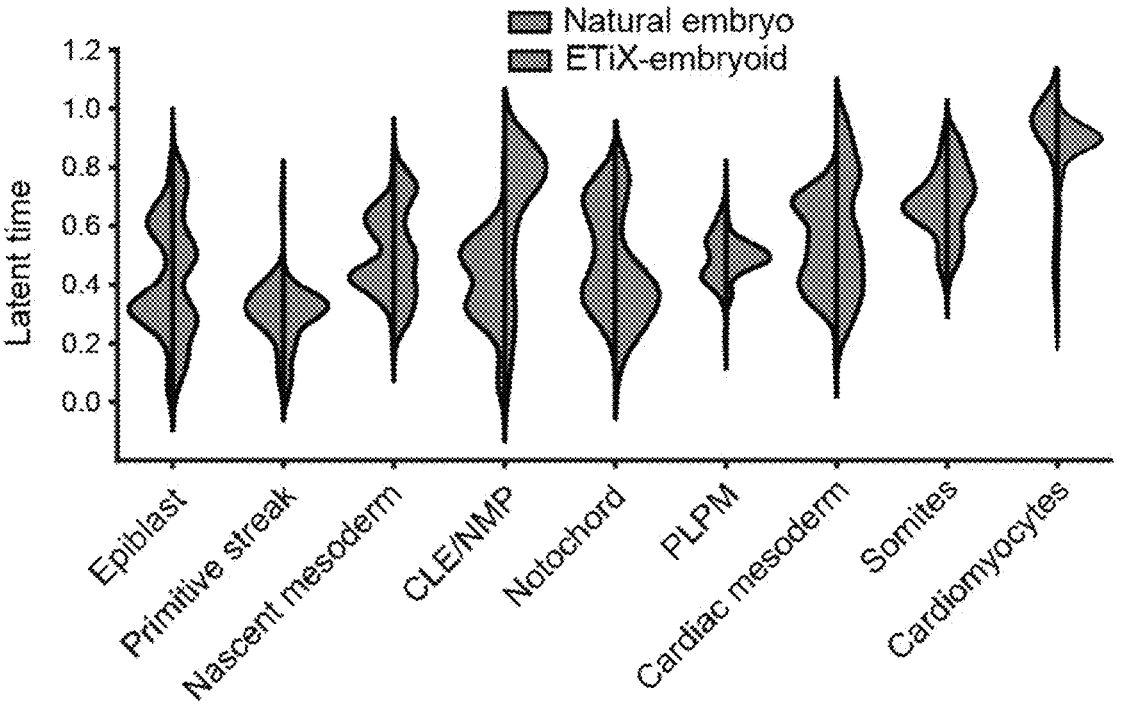
Figure 14C:
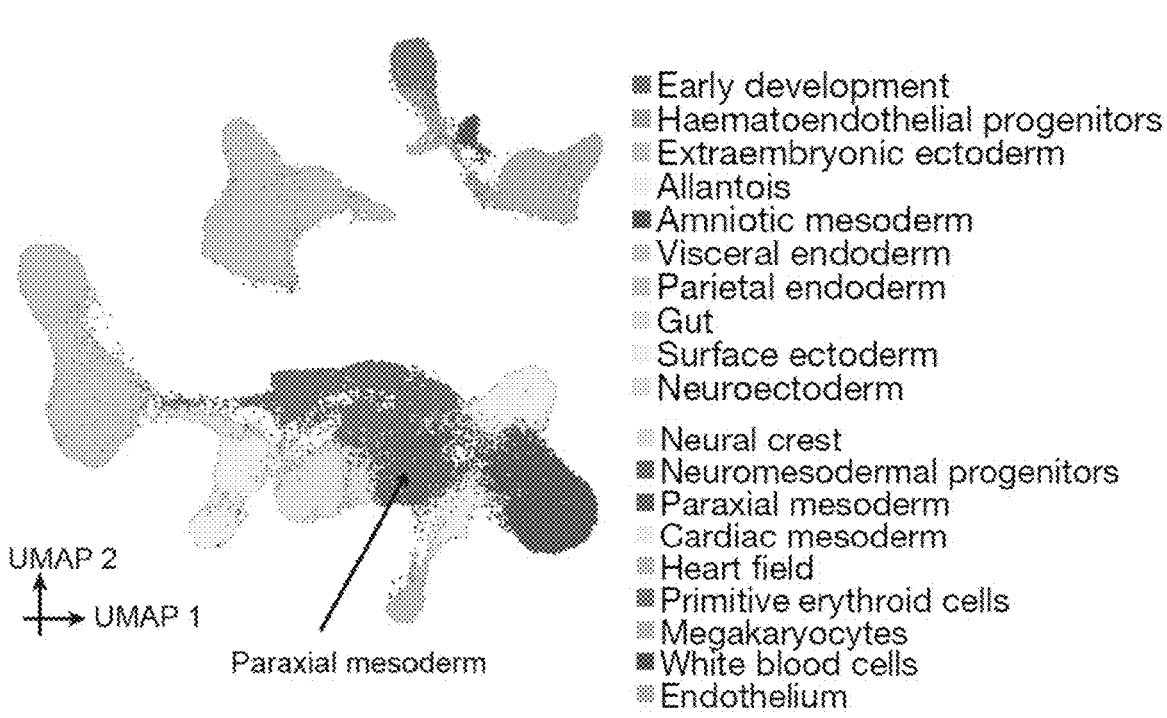
Figure 14D:
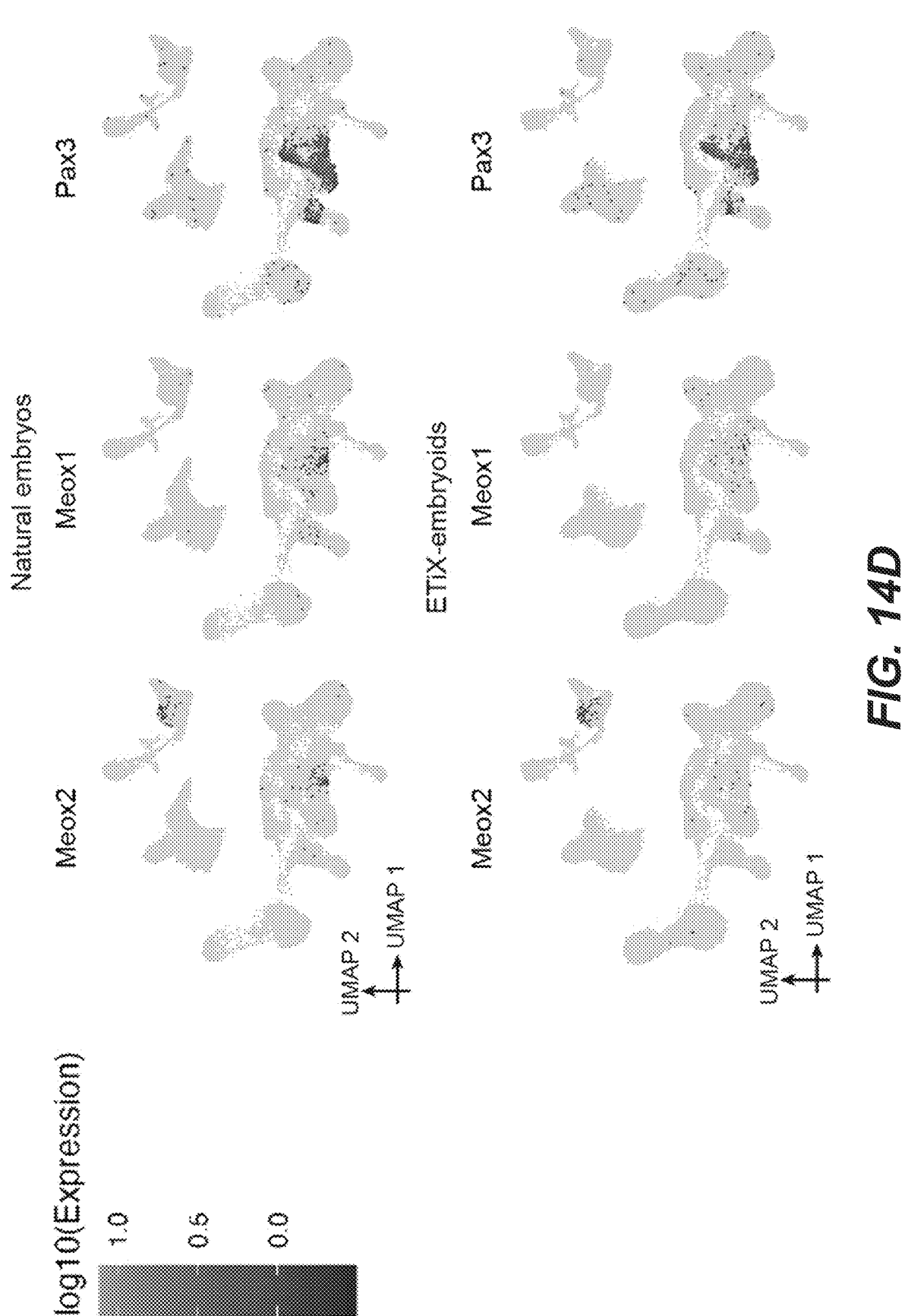

The scRNA-seq data from mesoderm and its derivatives corroborated and extended the findings from immunofluorescence (FIG. 4K). The gene expression signature leading to somite formation was apparent in the neurulating embryoids, although the transcript levels of presomitic identity genes (Tbx6, Hes7 and Msng1), Notch pathway genes (Notch) and Lfng) and a somite marker (Meox1) were lower than in natural embryos. Both natural embryos and neurulating embryoids expressed Gata4 and other important regulators of heart development, including Gata6, Meis), Tbx5 and Hand) (FIG. 4K). Similarly, neurulating embryoids expressed cardiomyocyte markers such as troponin genes (Ttn and Tnnt2) and myosin genes (Myh7, Myh6, Myl3 and Myl7), suggesting that mesoderm development in the neurulating embryoids was remarkably similar to that of natural embryos. To further confirm this, RNA velocity analysis was performed on the epiblast and all of its mesodermal derivatives on both neurulating embryoids and natural embryos. The differentiation trajectories between the two were very similar (FIG. 4L). Similarly, latent time analysis showed that all these mesodermal derivatives emerged in the neurulating embryoids in a temporal order broadly consistent with that of the natural embryo (FIG. 14A). Of the tissues examined, only the caudal lateral epiblast and NMP seemed to emerge at a slightly later time in the neurulating embryoids, whereas notochord formation seemed to occur slightly earlier than in the natural embryo (FIG. 14B). The cell cluster derived of paraxial mesoderm in the tiny-sci dataset was examined. It was found that cultured natural embryos expressed the somite markers Meox1, Meox2 and Pax3, whereas ETiX embryoids expressed Pax3 but instead showed relatively weak Meox1 or no Meox2 expression (FIG. 14C-FIG. 14D), potentially suggesting differences in somitogenesis between natural embryos and ETiX embryoids.

Figure 4M:
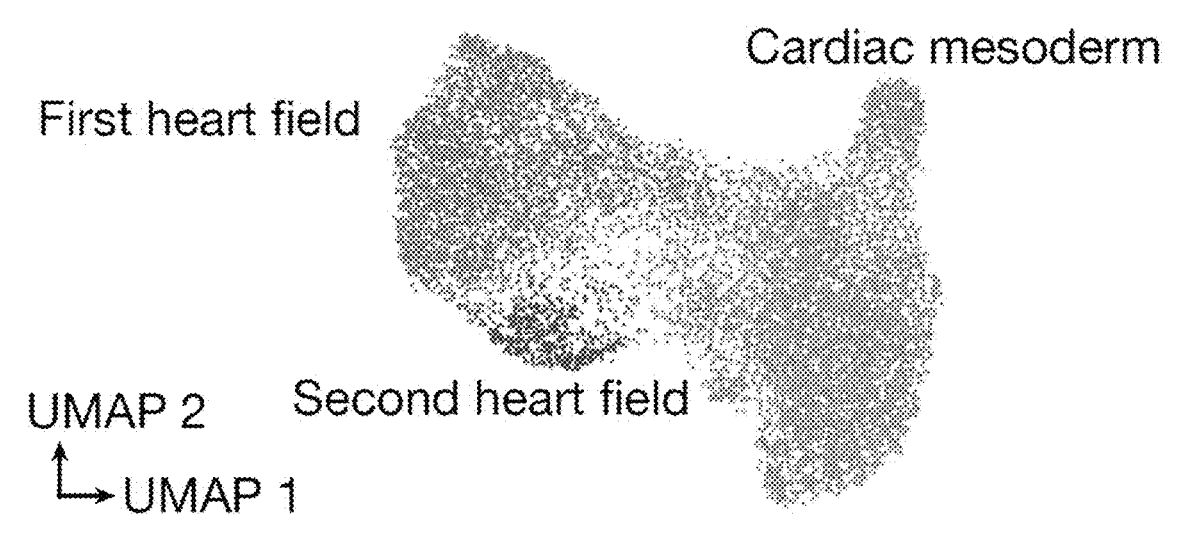
FIG. 4M depicts the UMAP of the tiny-sci-RNA-seq dataset, showing cell types in the subclustered cardiac lineage.
Figure 14E:
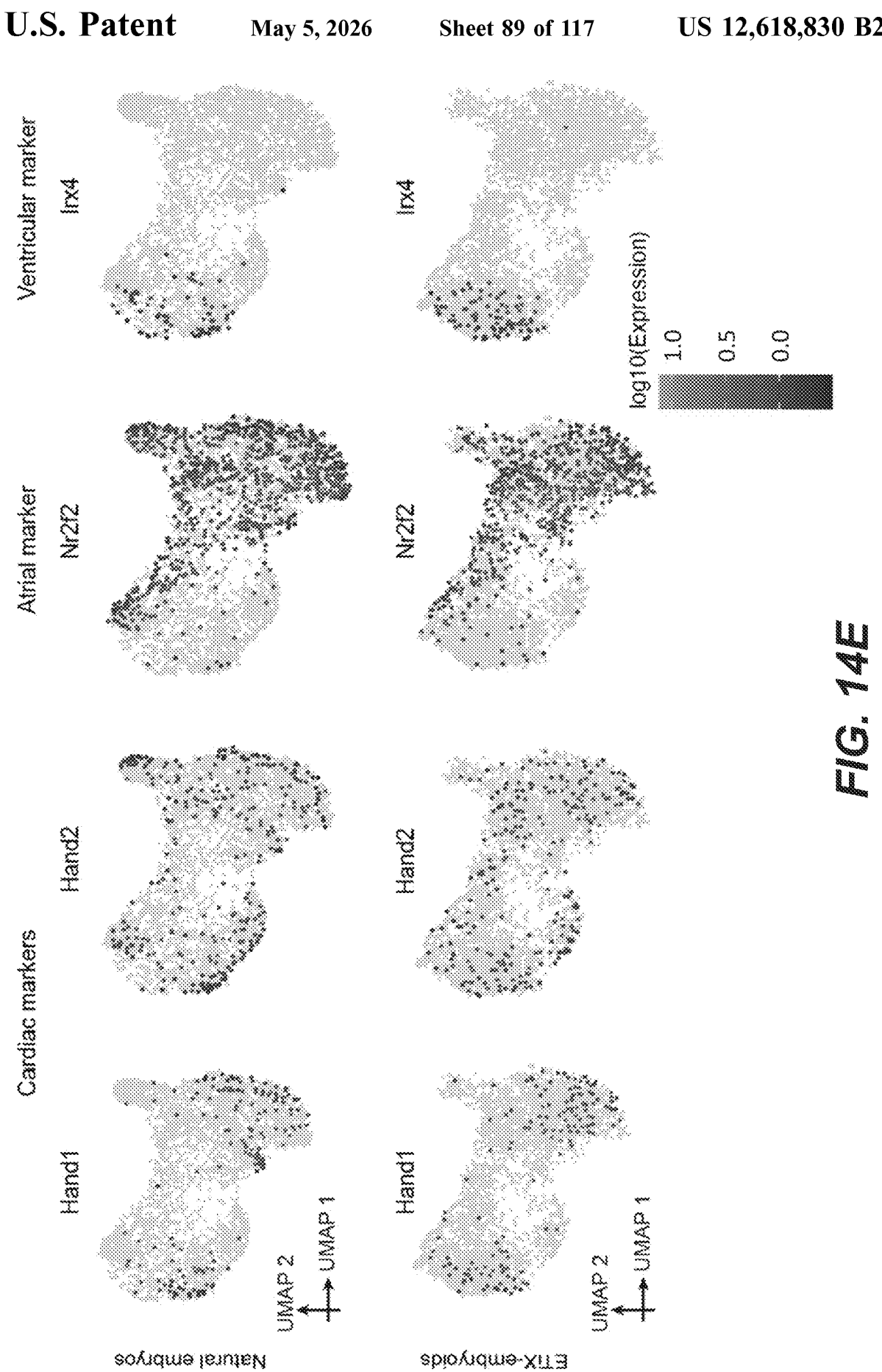
Figure 14E:
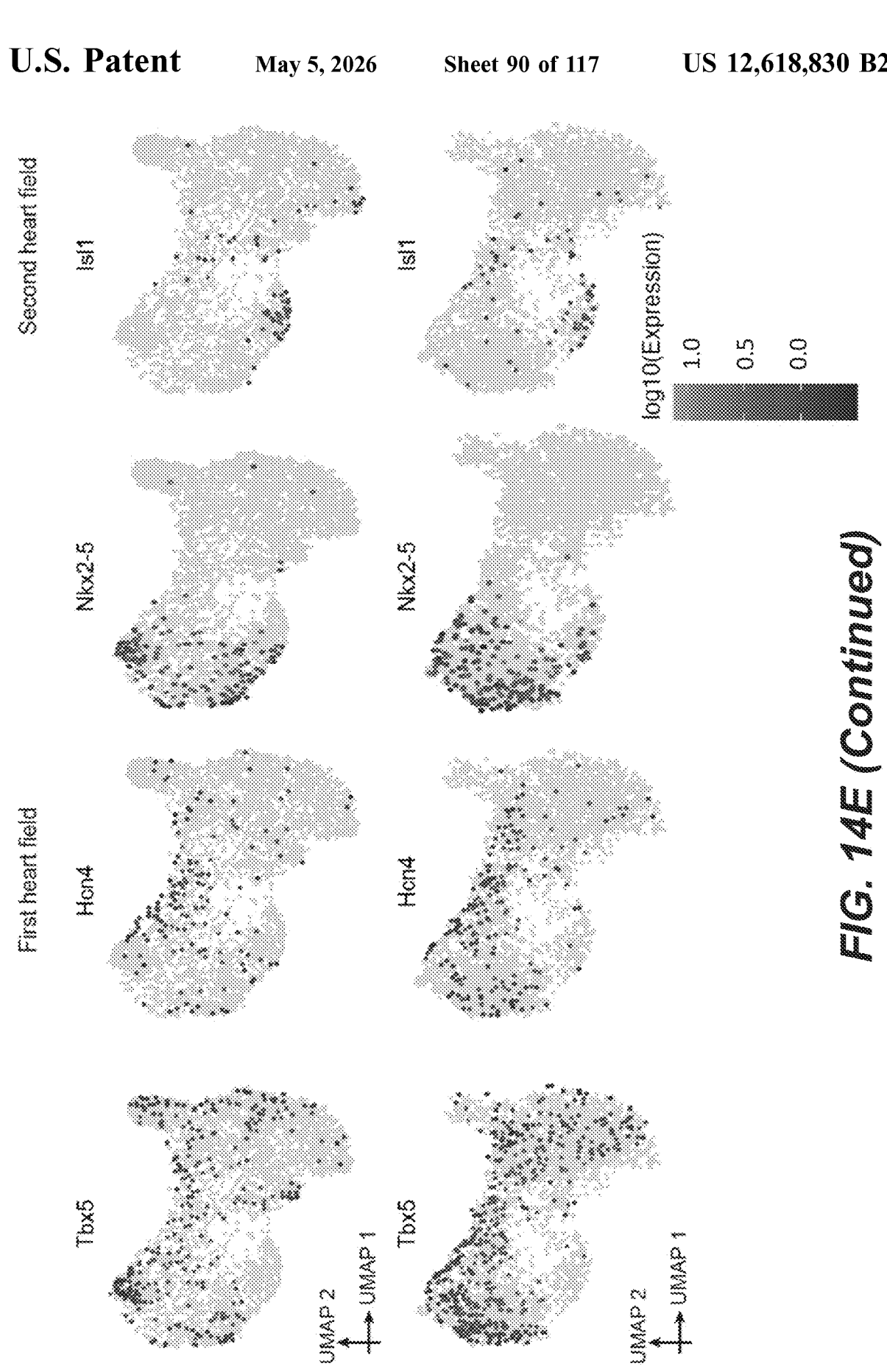
Figure 14F:
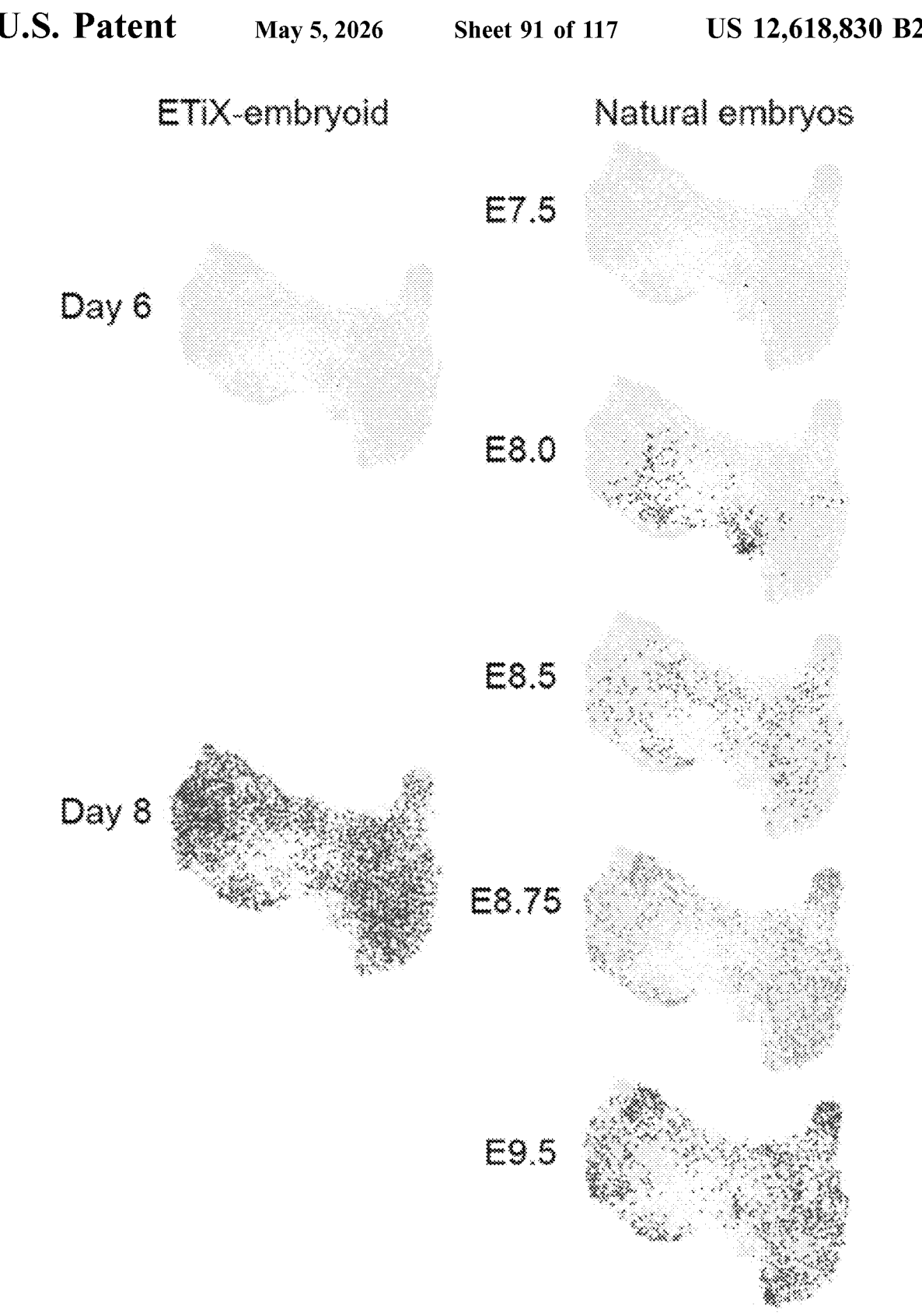

Using the tiny-sci dataset, the cardiac tissue was further analyzed to determine whether additional cell populations could be identified. Subclustering of the cardiac lineage (FIG. 4M), which expressed Hand1 and Hand2 (FIG. 14E), allowed the identification of the first heart field, characterized by robust expression of the canonical markers Tbx5, Nkr2-5 and Hcn4 (FIG. 14E), as well as the second heart field, characterized by localized expression of Isi) (FIG. 14E). The atrial marker Nr2f2 and the ventricular differentiation marker Irx4 were detected in both cultured natural embryos and ETiX embryoids (FIG. 14E). In agreement with the latent time analysis of the pooled data provided by inDrops sequencing, the tiny-sci dataset also confirmed that cardiac cell types emerged in the neurulating embryoids in a conserved temporal fashion reflecting the developmental sequence of the natural embryo. In fact, substantial cardiac lineages were not observed in either day 6 ETiX embryoids or the E7.5 natural embryo. Instead, the cardiac lineage of the natural embryo largely emerged from E8.5 onwards. From this perspective, day 8 of ETiX embryoid development captured cell contributions of the natural embryos on E8.5, E8.75 and E9.5 (FIG. 14F).

The results in this example demonstrate that the ETiX embryoids described herein can proceed to neurulation with the formation of the neural tube, initiation of somitogenesis, and the generation of mesodermal structures including a heart-like structure.

Example 5

Initiation of Gut Development in Synthetic Embryoids

This example reports that the synthetic embryoids described herein can develop definitive endoderm producing gut and associated organs.

Figure 5A:
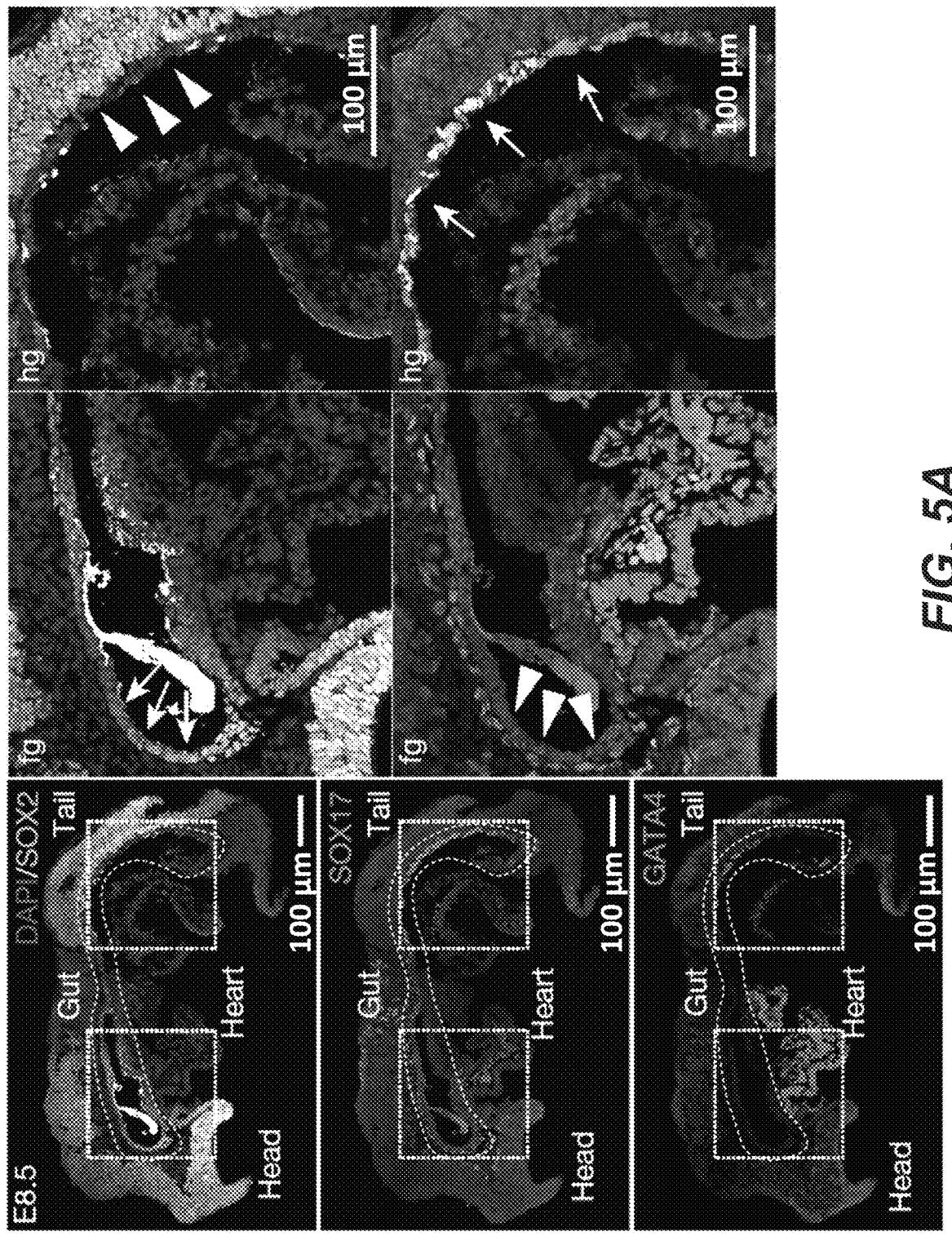
FIG. 5A-FIG. 5I depict non-limiting exemplary embodiments and data related to ETiX embryoids developing a gut pocket and primordial germ cells (PGCs).
Figure 5B:
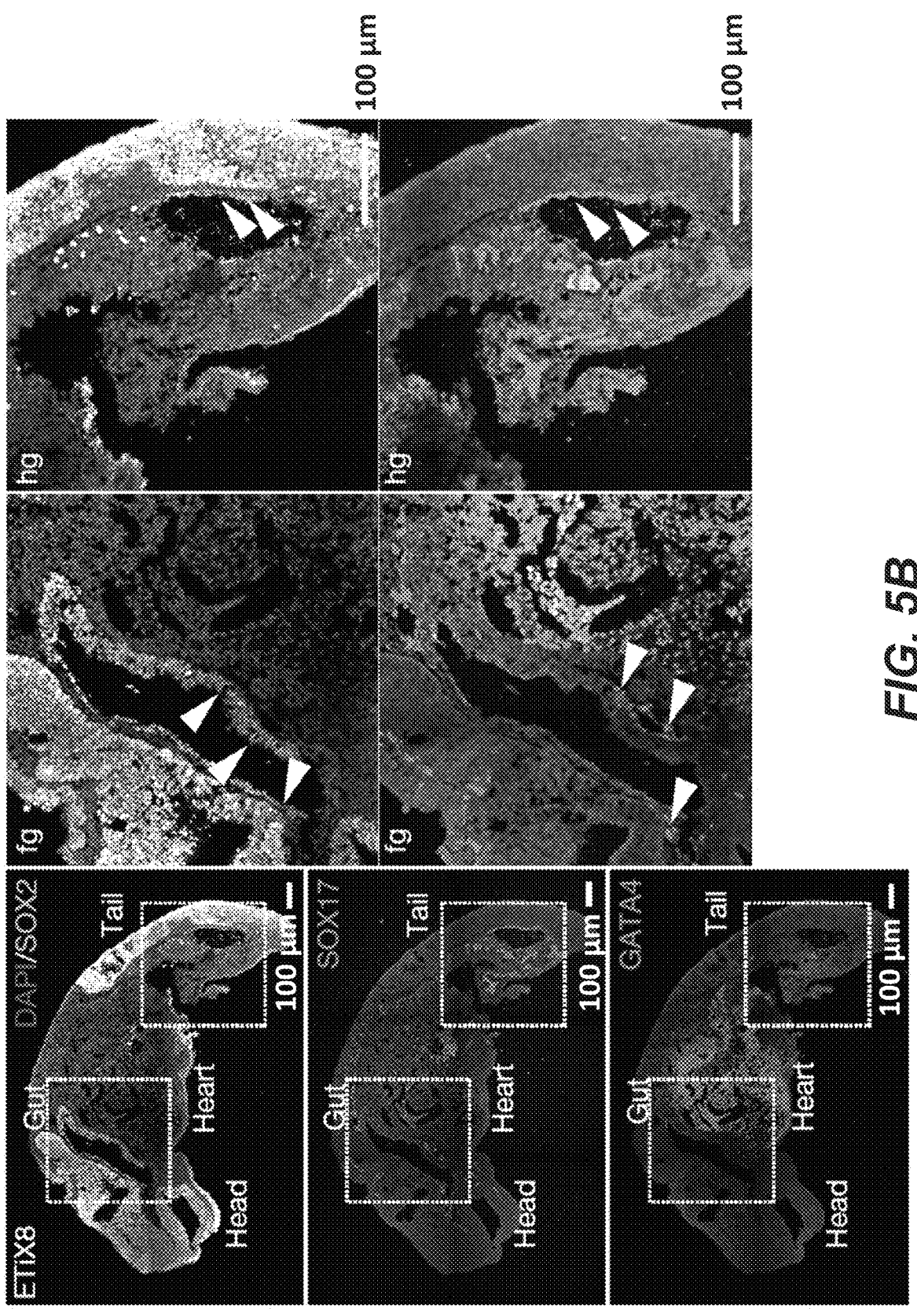
Figures 5C, 5D:
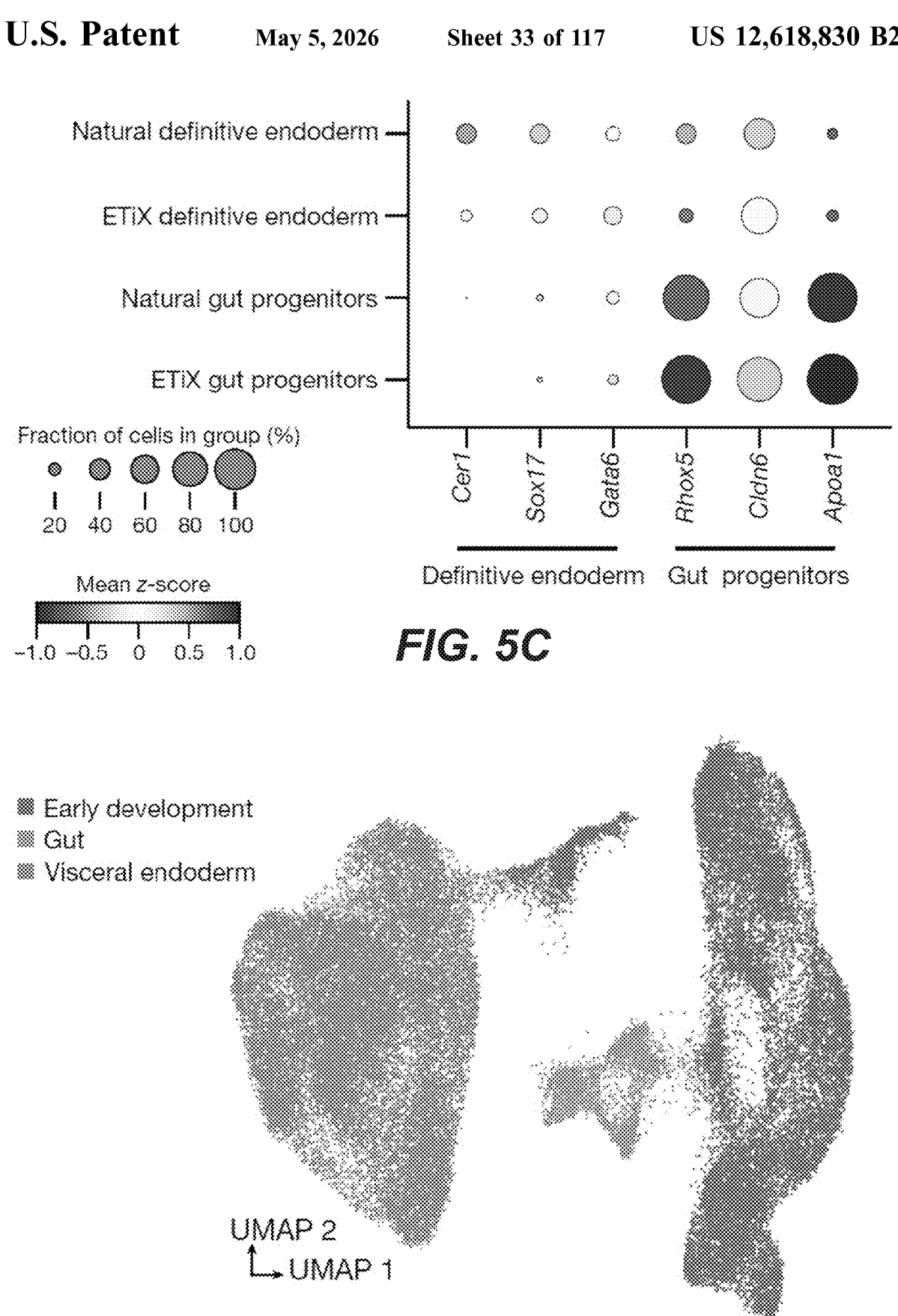
Figure 15A:
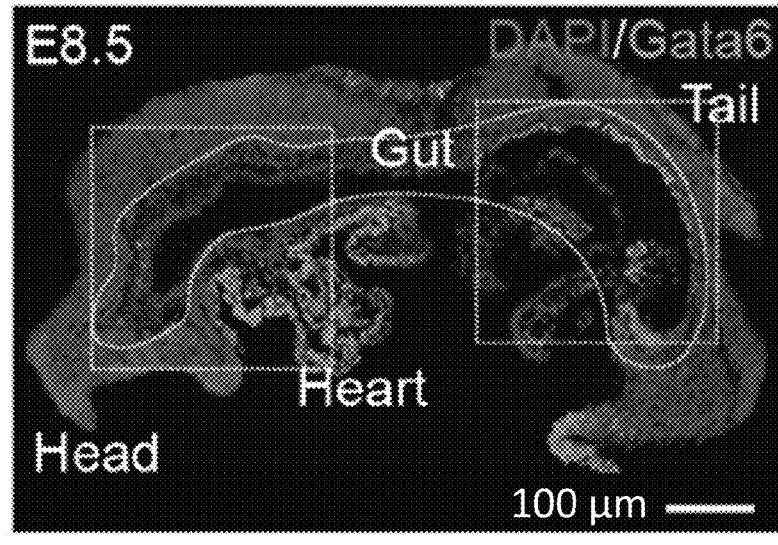
FIG. 15A-FIG. 15F depict non-limiting exemplary embodiments and data related to further characterization of the gut tube of ETiX embryoids revealing similarities and differences in comparison to natural embryos.
Figure 15B:
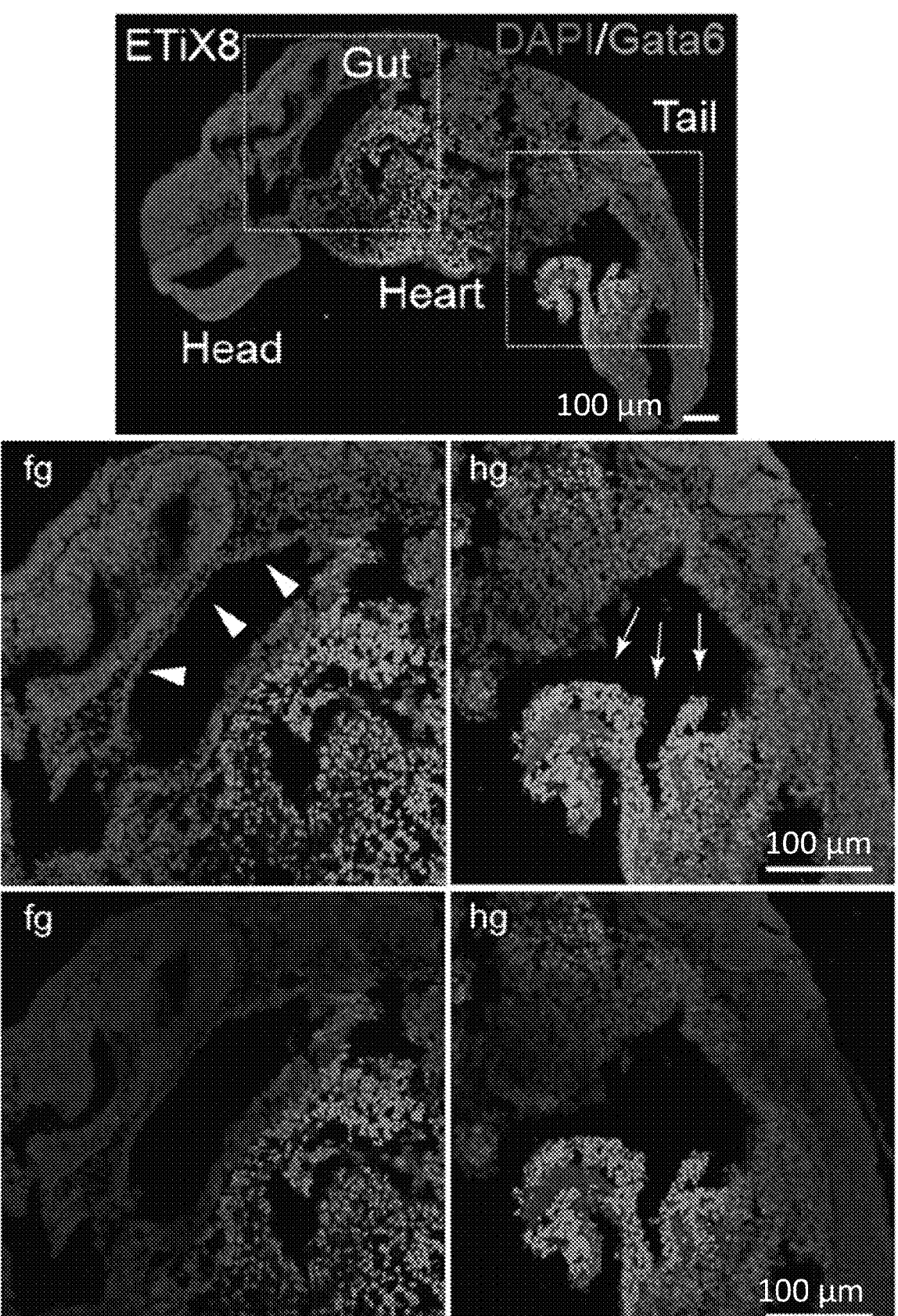
Figure 15C:
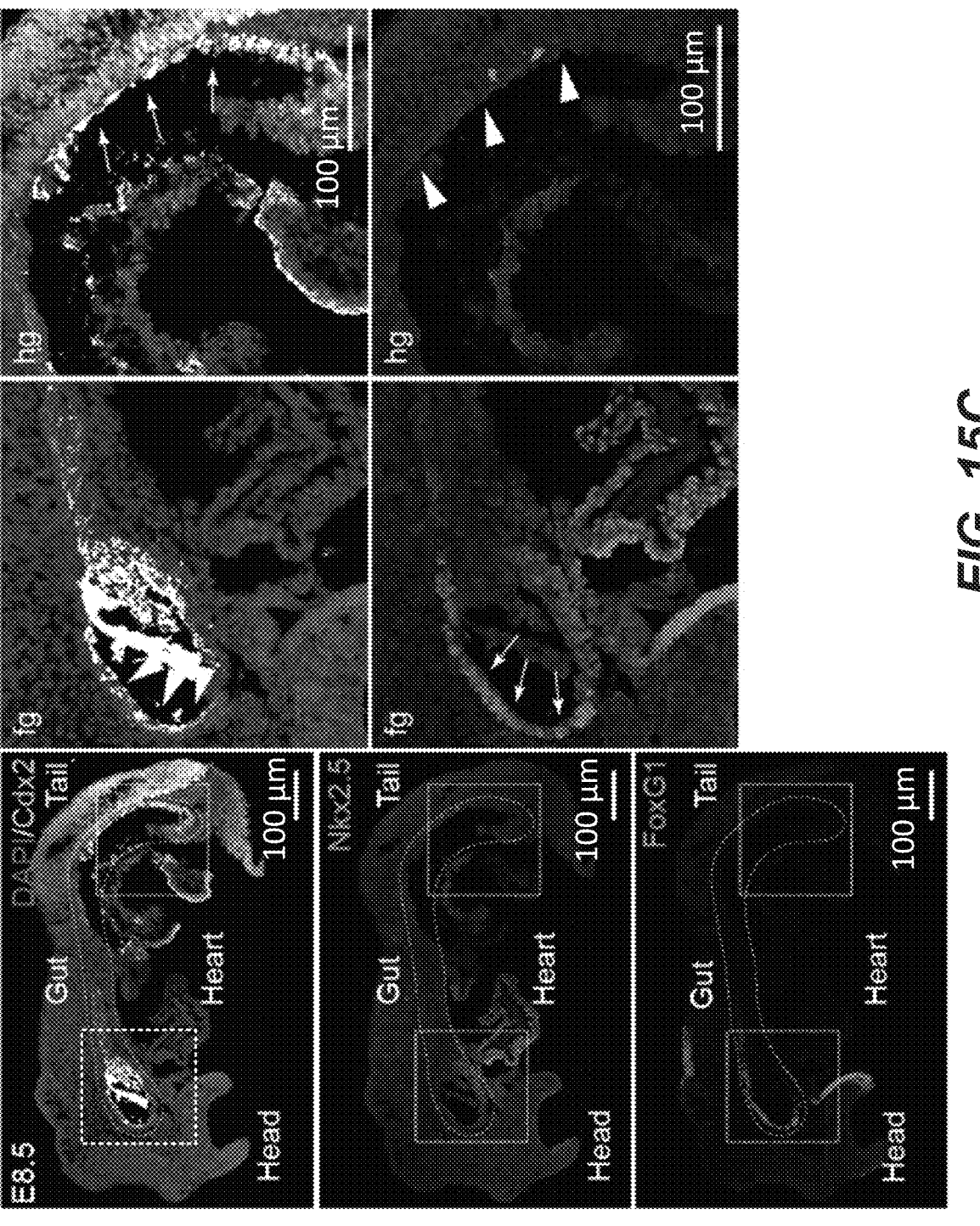
Figure 15D:
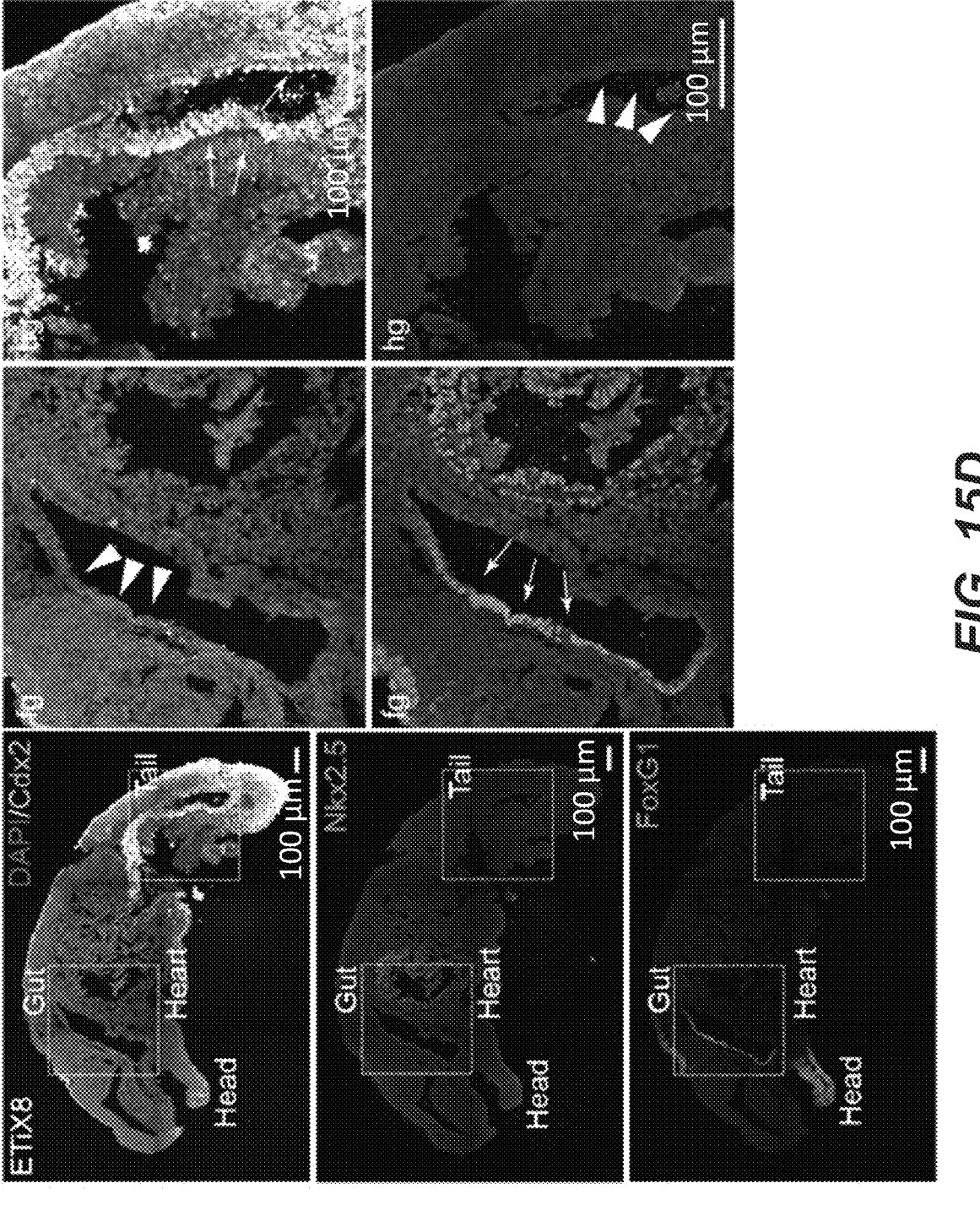
Figure 15E:
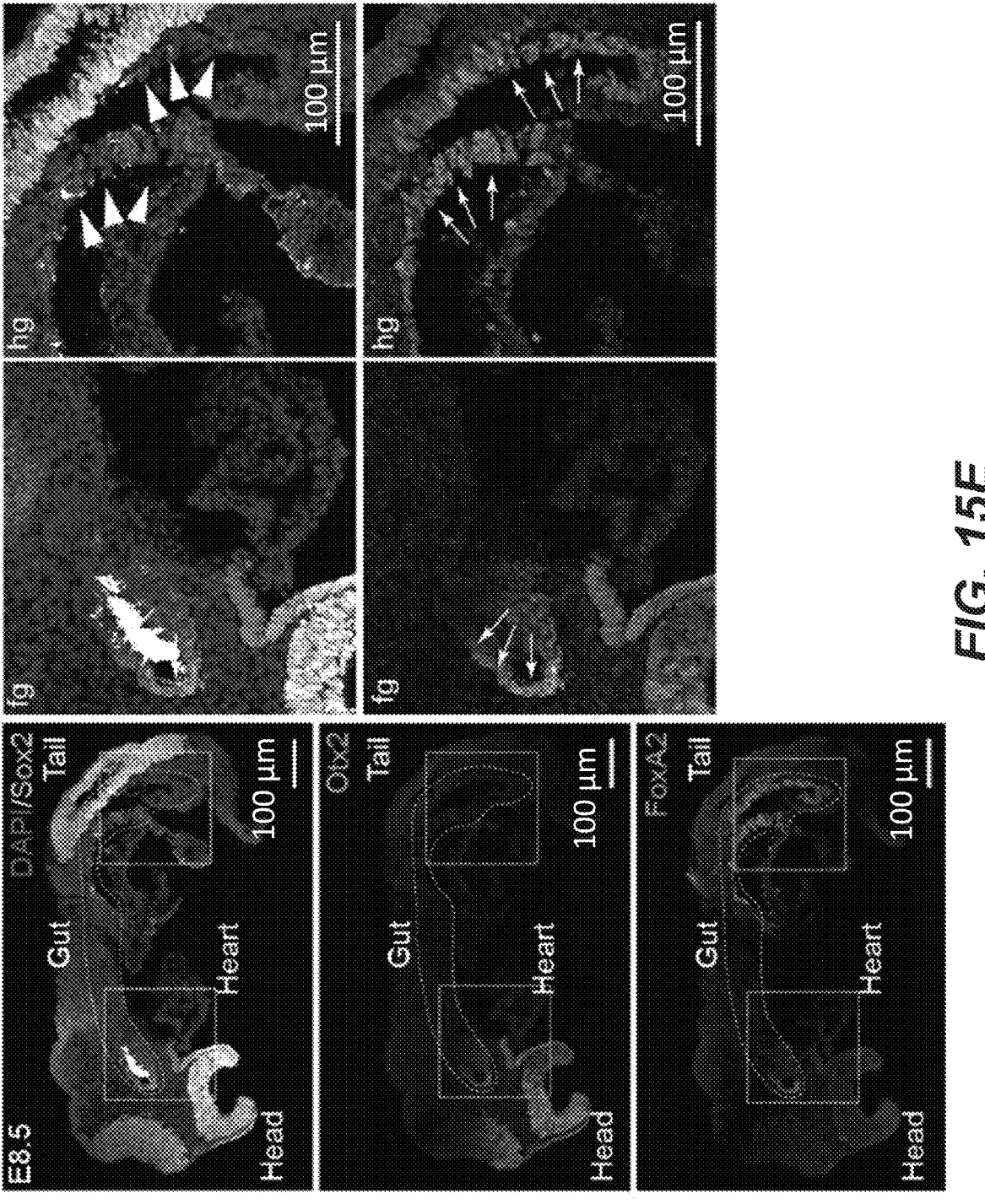
Figure 15F:
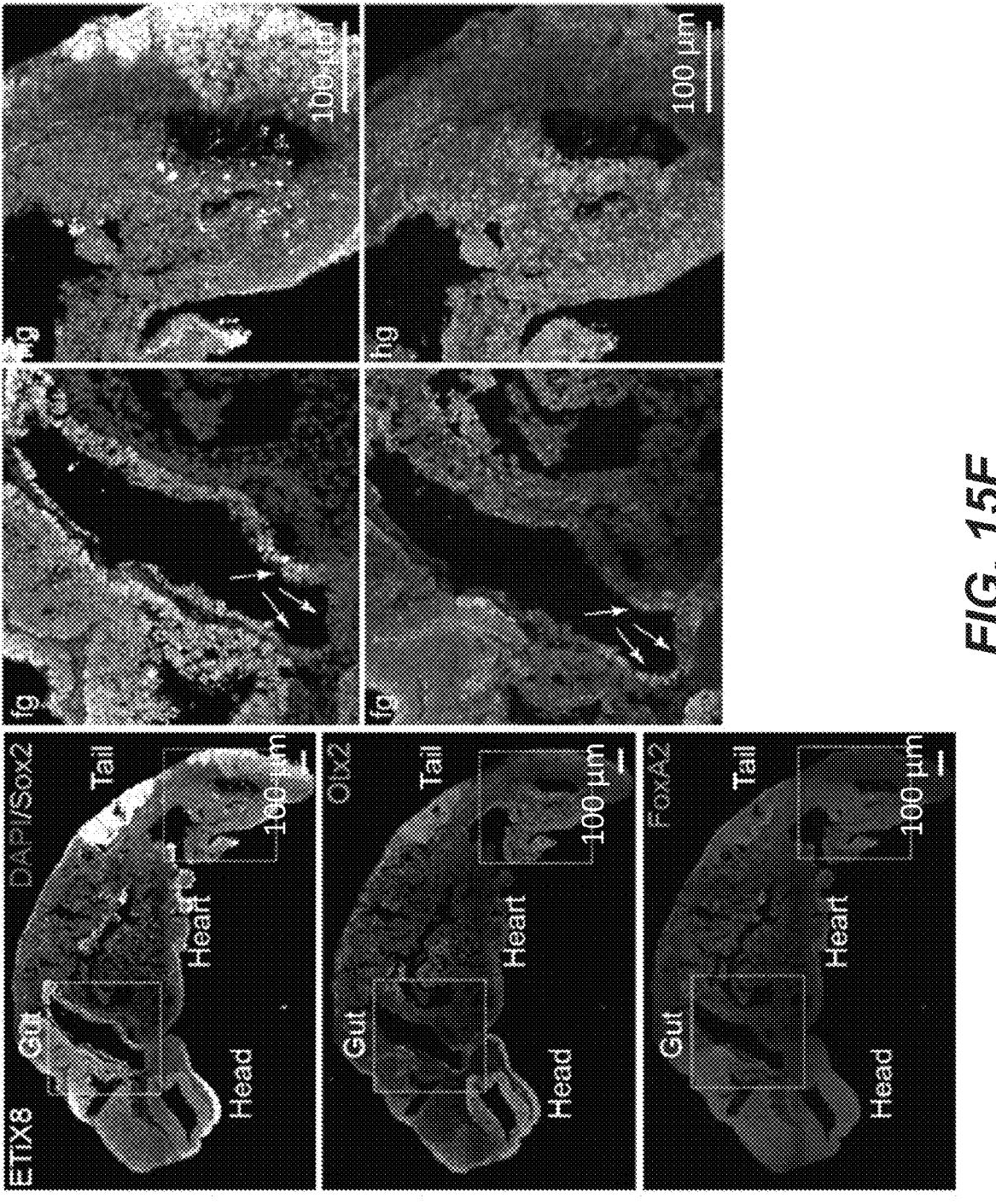

Having observed extensive development and morphogenesis of ectoderm and mesoderm, the extent, to which neurulating embryoids showed development of definitive endoderm that gives rise to the gut and associated organs, was also determined. Sox17 is required for gut endoderm development. Whole mount immunofluorescence of ETiX day 8 embryoids revealed a Sox17-positive region below the heart, indicative of a primitive gut tube population (FIG. 5G-FIG. 5H). By contrast, the heart was Sox17-negative and Gata4-positive, just as in the natural embryo (FIG. 5G-FIG. 5H). Sections of ETiX day 7 embryoids revealed an open gut pocket below the neural tube that expressed the transcription factors Sox2 and FoxA2, both critical for gut development (FIG. 5I). Sagittal sections of E8.5 natural embryos and day 8 ETiX embryoids revealed the presence of foregut and hindgut pockets (FIG. 5A-FIG. 5B). In addition to being expressed in the brain and neural tube, the transcription factor SOX2 was also expressed in the foregut of natural embryos, a pattern of expression that was conserved in neurulating embryoids (FIG. 5A-FIG. 5B). Similarly, SOX17 was expressed in the hindgut of both natural embryos and neurulating embryoids (FIG. 5A-FIG. 5B) and also in a scattered group of cells suggestive of endothelial precursors. However, the gut tube of the ETiX embryoids did not develop as extensively as that of natural embryos within the time frame of the observations. Whereas GATA4 was expressed equally prominently in the heart of natural embryos and ETiX embryoids, it was expressed in the hindgut of natural embryos but not of the ETiX embryoids (FIG. 5A-FIG. 5B). By contrast, GATA6 was expressed in the heart and hindgut of both natural embryos and ETiX embryoids (FIG. 15A-FIG. 15B). Further characterization showed that the foregut of both ETiX embryoids and natural embryos expressed FOXG1 and OTX2 (FIG. 15C-FIG. 15F) and the hindgut of both expressed CDX2 (FIG. 15C-FIG. 15F). However, in contrast to the natural embryo, any expression of the transcription factor FOXA2 in the gut of ETiX embryoids (FIG. 15F) was not observed. Expression of NKX2-5 in natural embryos or in ETiX embryoids was also not detected, despite its mRNA having been shown to be expressed in the gut (FIG. 15C-FIG. 15D).

Figure 16A:
FIG. 16A-FIG. 16L depict non-limiting exemplary embodiments and data related to the developmental trajectories and timing of the endoderm and extraembryonic contribution to gut formation.
Figure 16B:
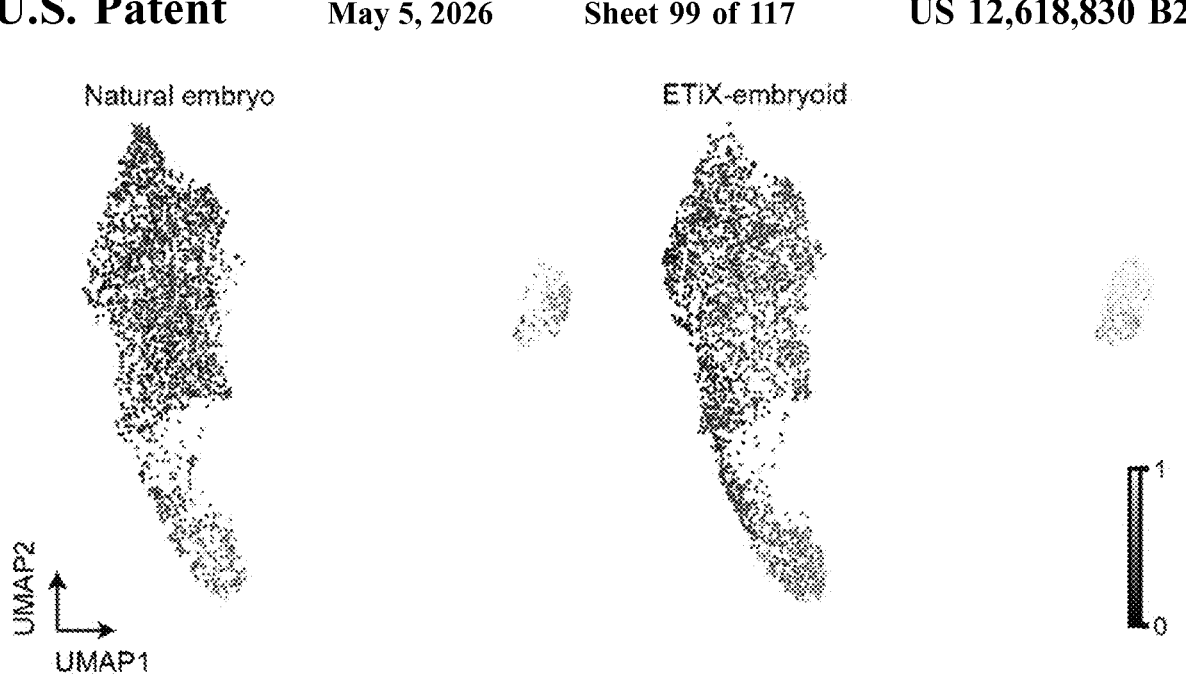
Figure 16C:
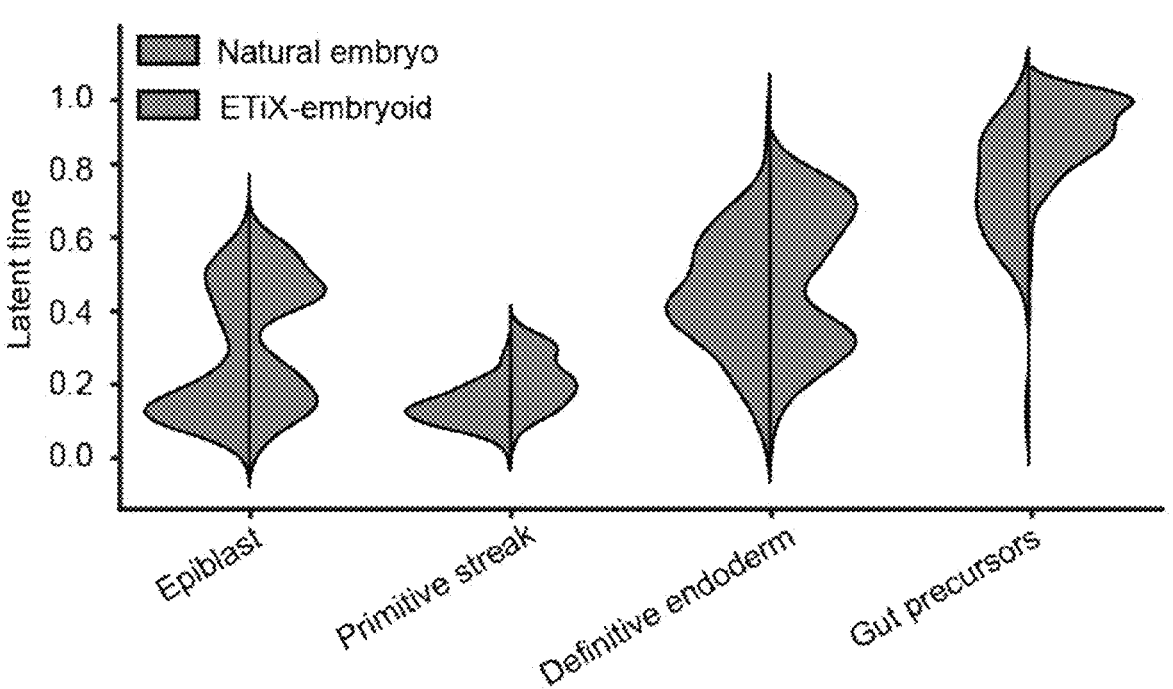
Figures 16D, 16E, 16F, 16G:
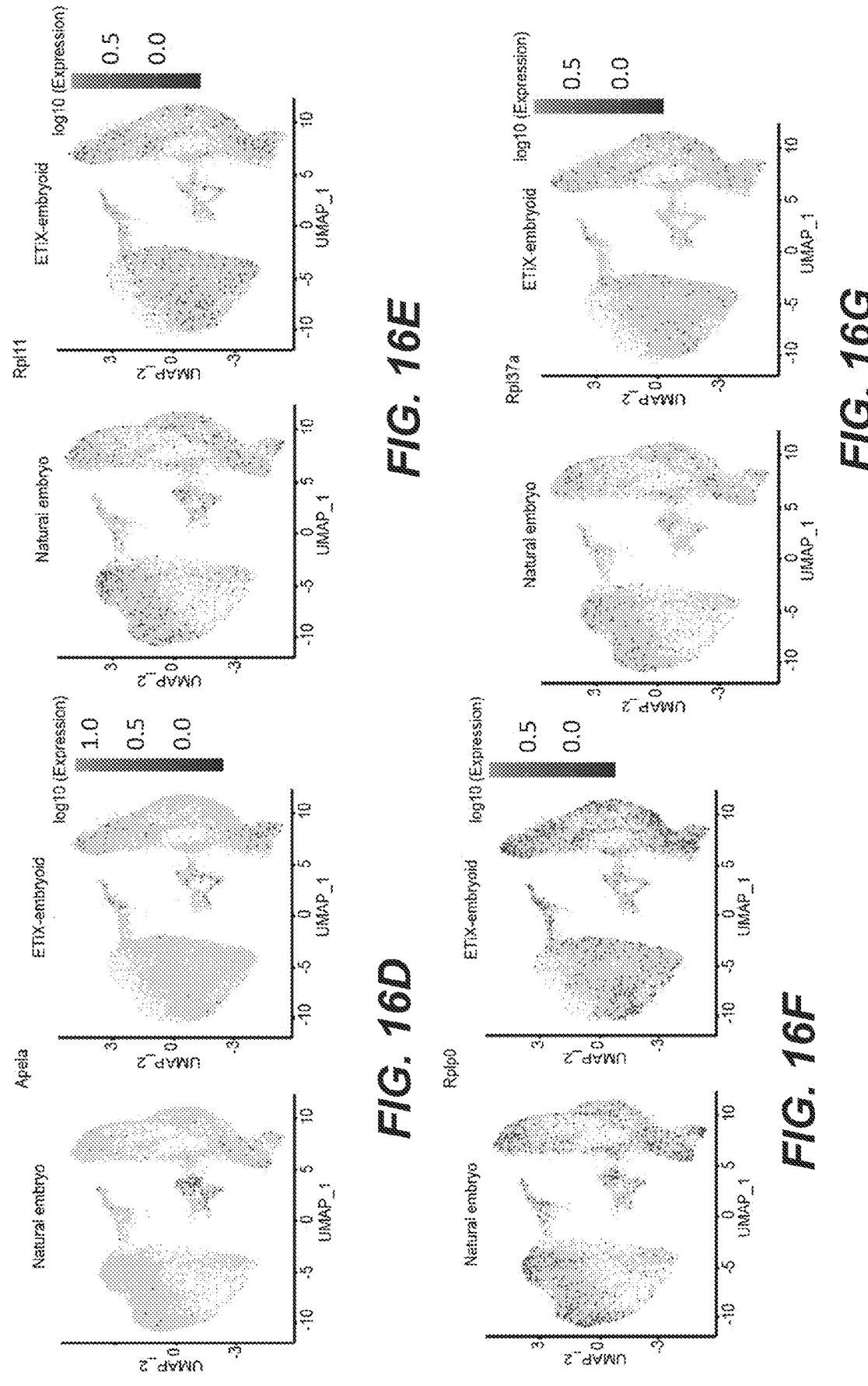
Figures 16H, 16I, 16J, 16K:
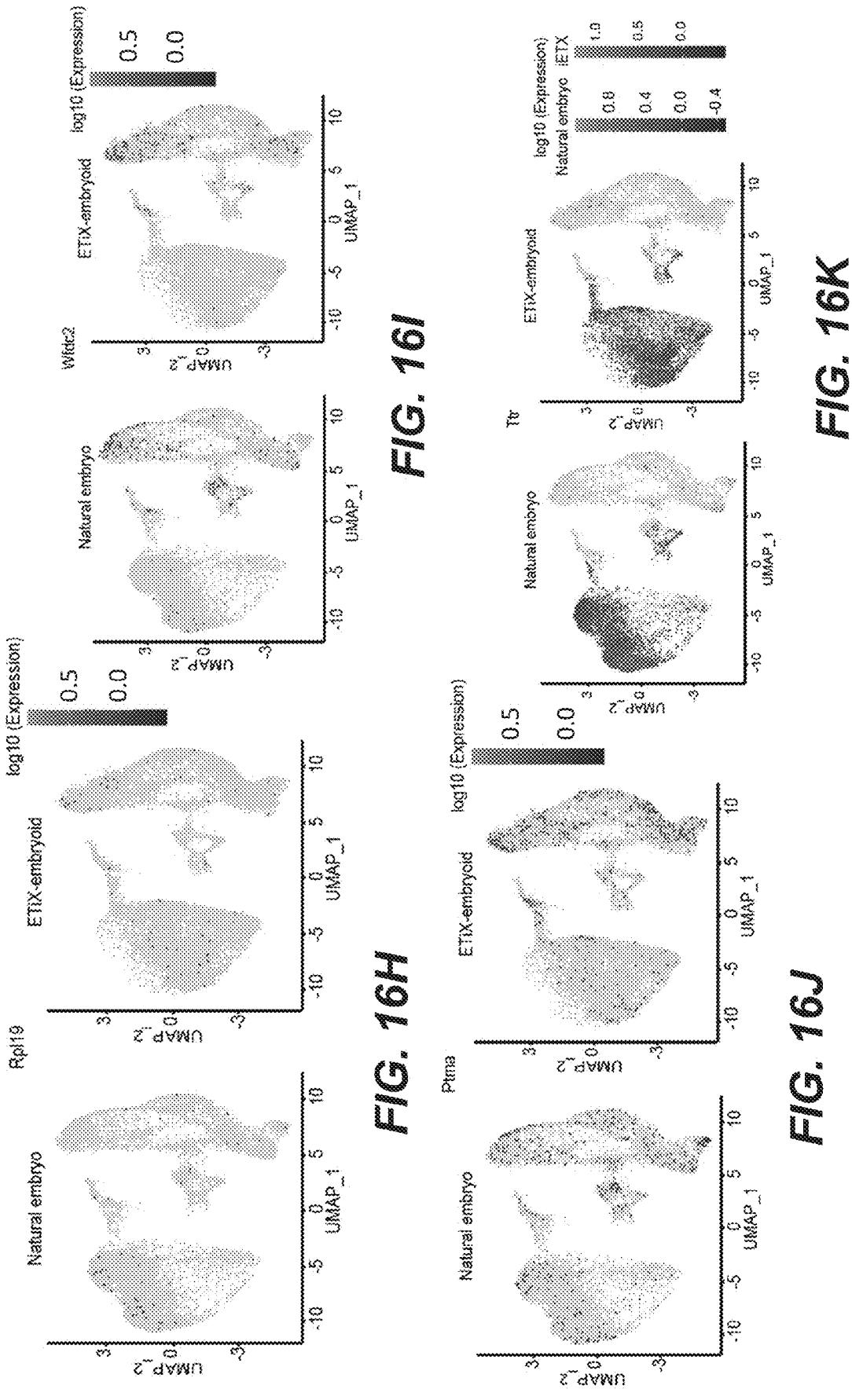
Figure 16L:
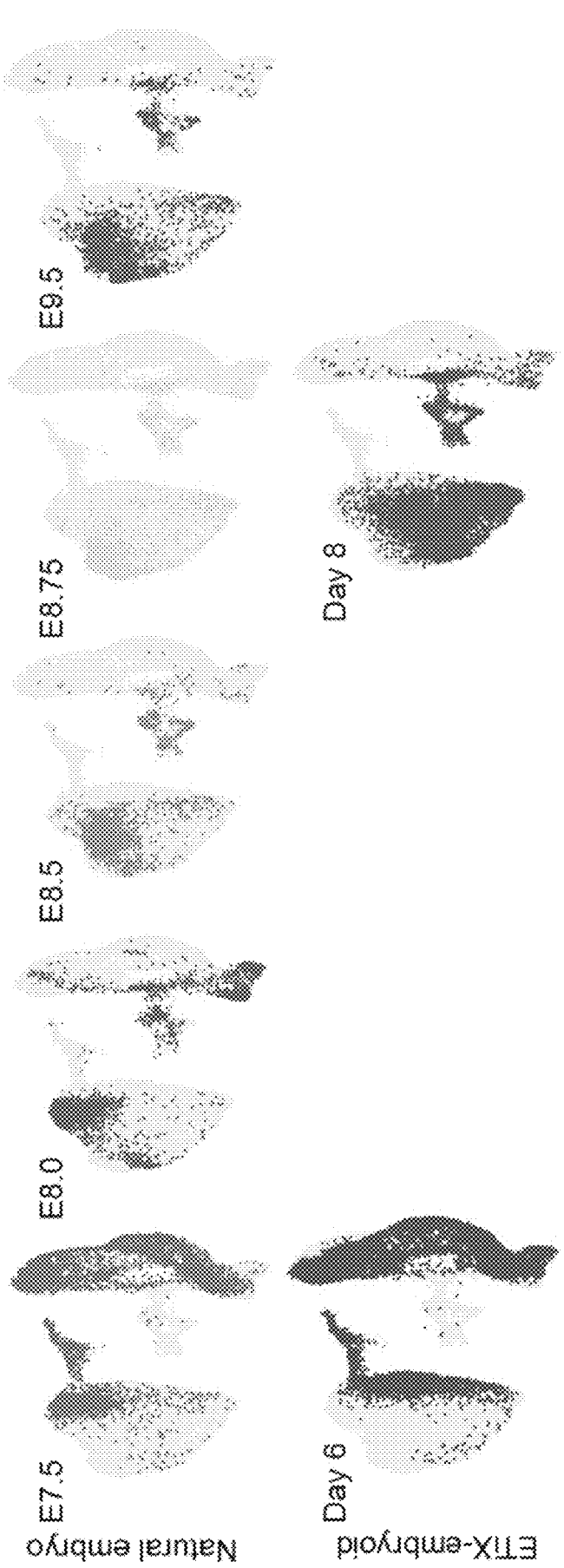
Figure 17A:
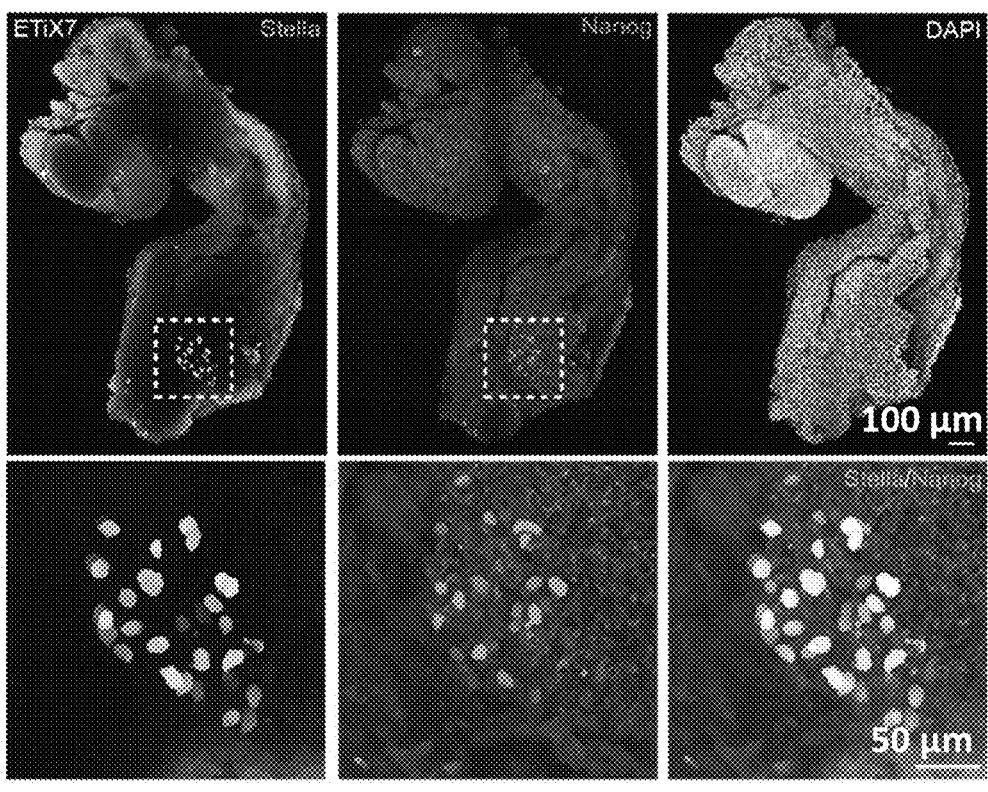
FIG. 17A-FIG. 17D depict non-limiting exemplary embodiments and data related to additional examples of PGC formation in ETiX embryoids.
Figure 17B:
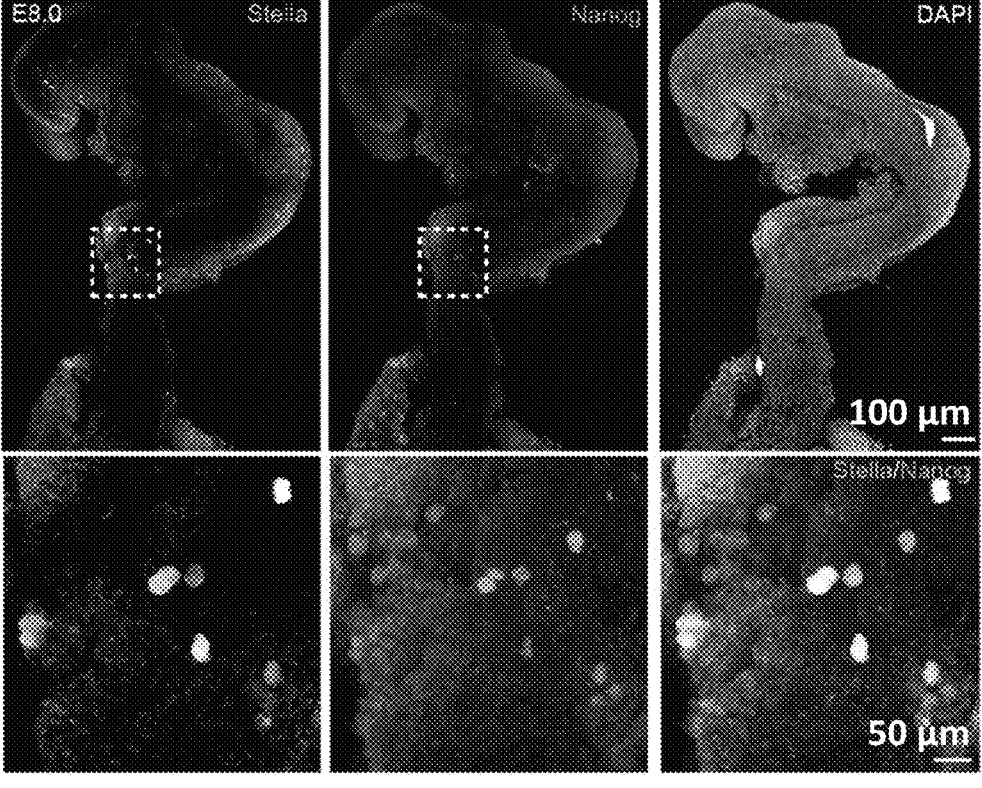
Figure 17C:
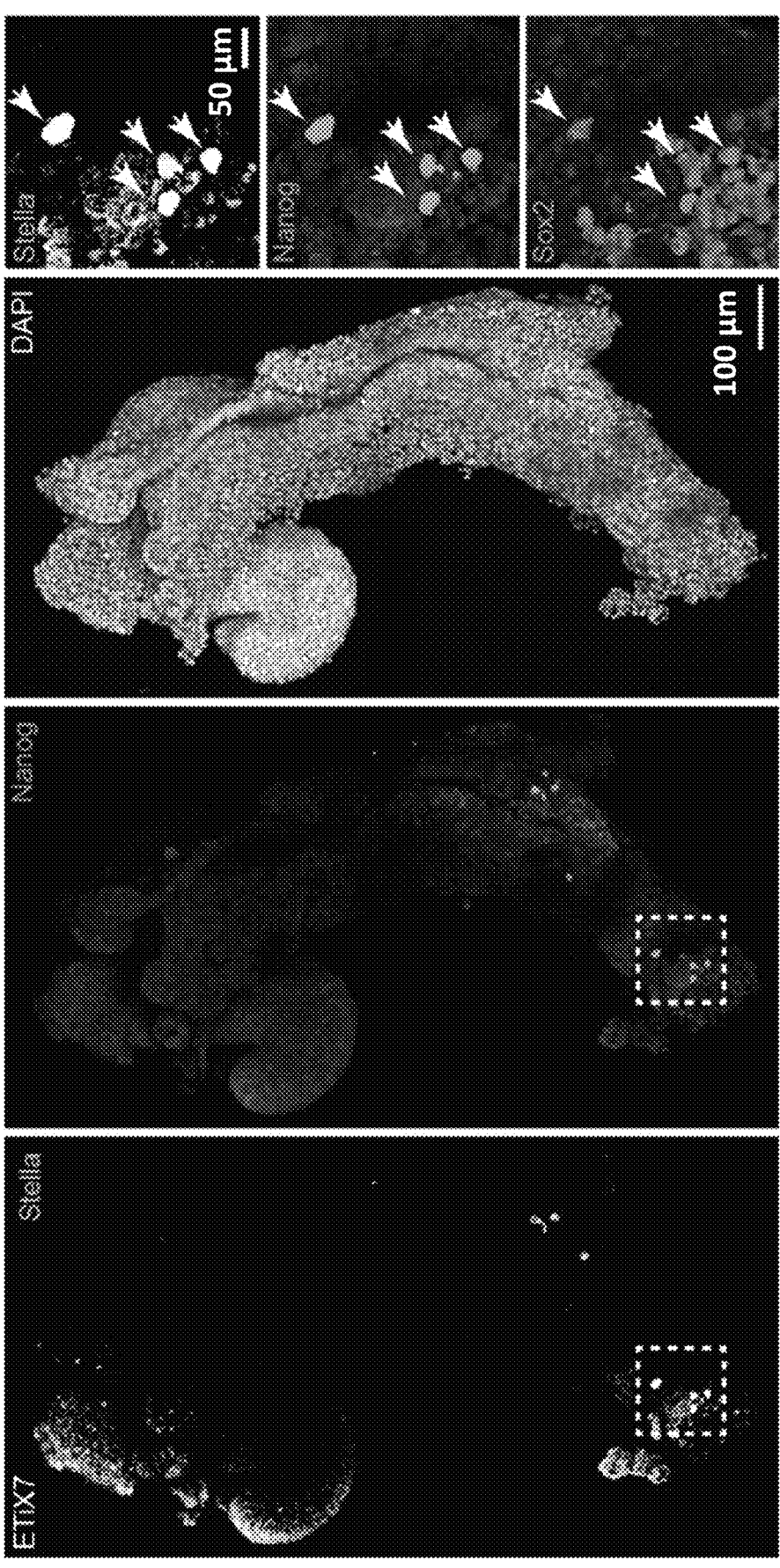
Figure 17D:
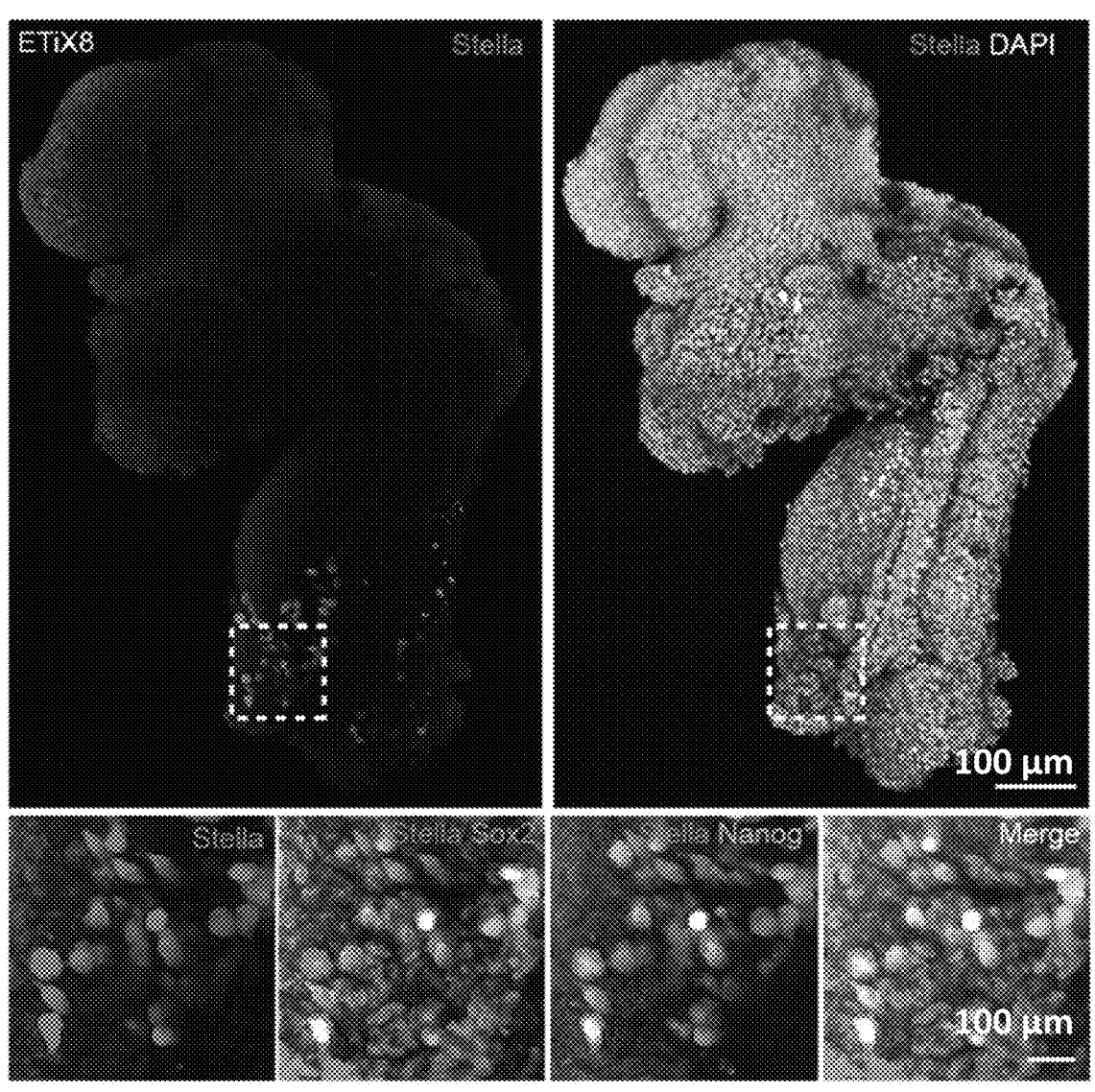

To characterize the gut and associated endodermal tissue further, scRNA-seq datasets were further analyzed. The inDrops scRNA-seq data from natural embryos and ETiX embryoids revealed gene expression signatures corresponding to definitive endoderm (Cer1$^+$Sox17$^+$Gata6$^+$) and VE gut progenitors (Rhox5$^+$Cldn6$^+$Apoa1$^+$) (FIG. 5C). RNA velocity analysis, however, showed that there were likely to be differences in the differentiation trajectories from epiblast to gut between natural embryos and ETiX embryoids (FIG. 16A). By contrast, latent time analysis indicated that the timing of emergence of these lineages was highly similar in embryos and embryoids (FIG. 16B-FIG. 16C). Together, these data indicated that gut formation in ETiX embryoids was likely to proceed with similar timing to that in natural embryos, but with some differences in the developmental trajectory. Analysis of the gut and endodermal clusters in the tiny-sci dataset showed that the gut cluster had both embryonic and extraembryonic contributions (FIG. 5D). Higher expression of genes associated with a definitive endoderm origin in the embryonic portion of the gut cluster (FIG. 5D and FIG. 16D-FIG. 16J) was observed, whereas the presumptive VE-derived portion of the gut cluster (FIG. 5D) expressed higher levels of Tr, which was expressed by gut cells with an extraembryonic origin (FIG. 16K). Cell populations corresponding to precursors of the liver, pancreas, small intestine or colon were not observed in either ETiX embryoids or natural embryos at this stage, suggesting that neither had developed beyond an uncommitted endodermal state under the applied culture conditions, consistent with the onset of organ-specific identities in the gut tube on E8.75. The VE of ETiX embryoids on day 6 was very similar to that of natural embryos at E7.5. However, cells in day 8 ETiX embryoids appeared largely absent in the VE from E8.5 to E9.5 embryos (FIG. 16L).

The development beyond the establishment of the endodermal progenitors for the gut and its associated organs has not been studied, despite observation showing the establishment of the endodermal progenitors for the gut. It may be necessary to optimize culture conditions to achieve this. It is expected that given appropriate culture conditions, ETiX embryoid development would not proceed further in culture.

Example 6

Development of POCs in Synthetic Embryoids

This example reports that PGCs can emerge in the proximo-posterior region of the epiblast, around the same time as Brachyury expression commences in the E6.5 mouse embryo.

Figure 5E:
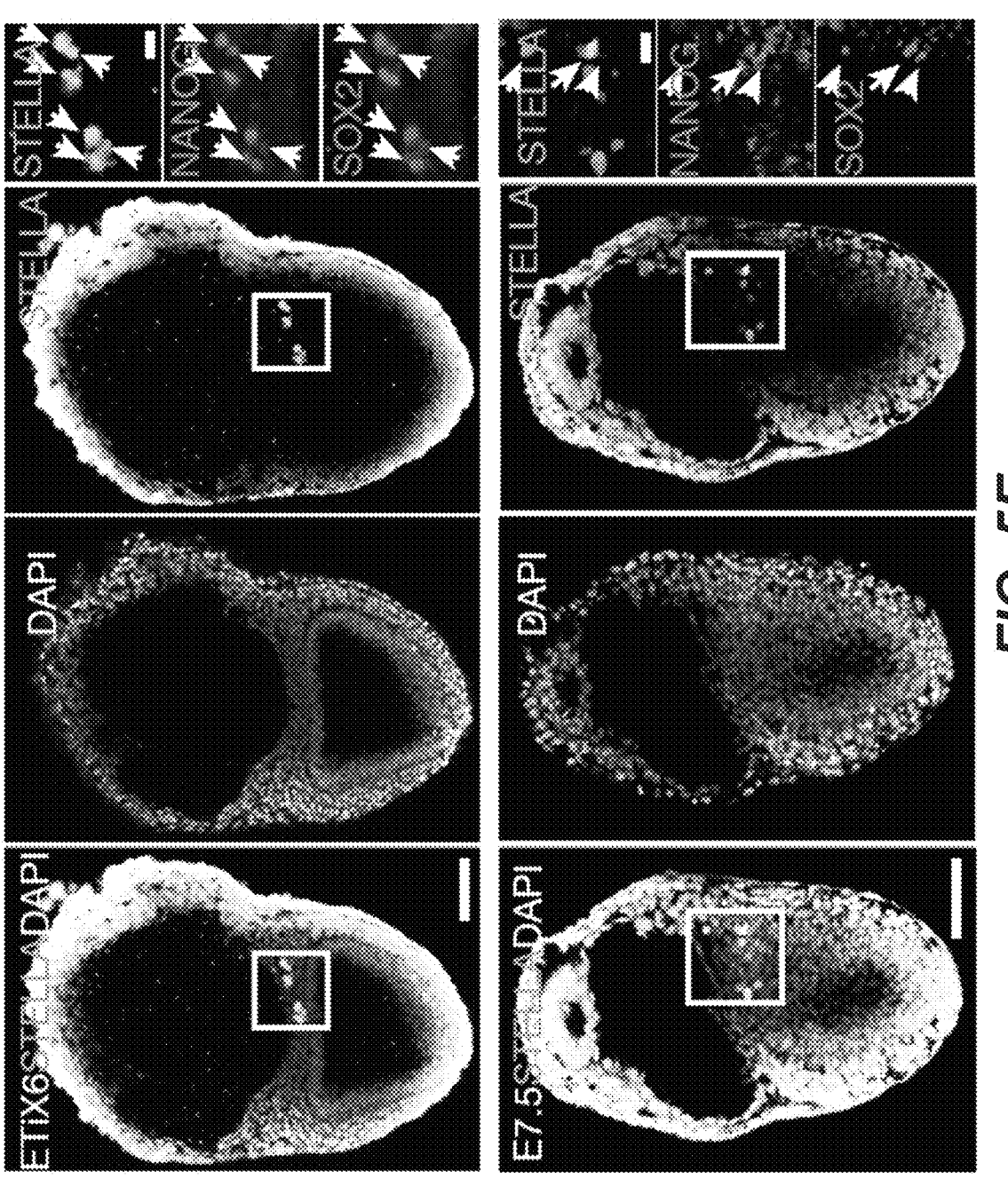
Figure 5F:
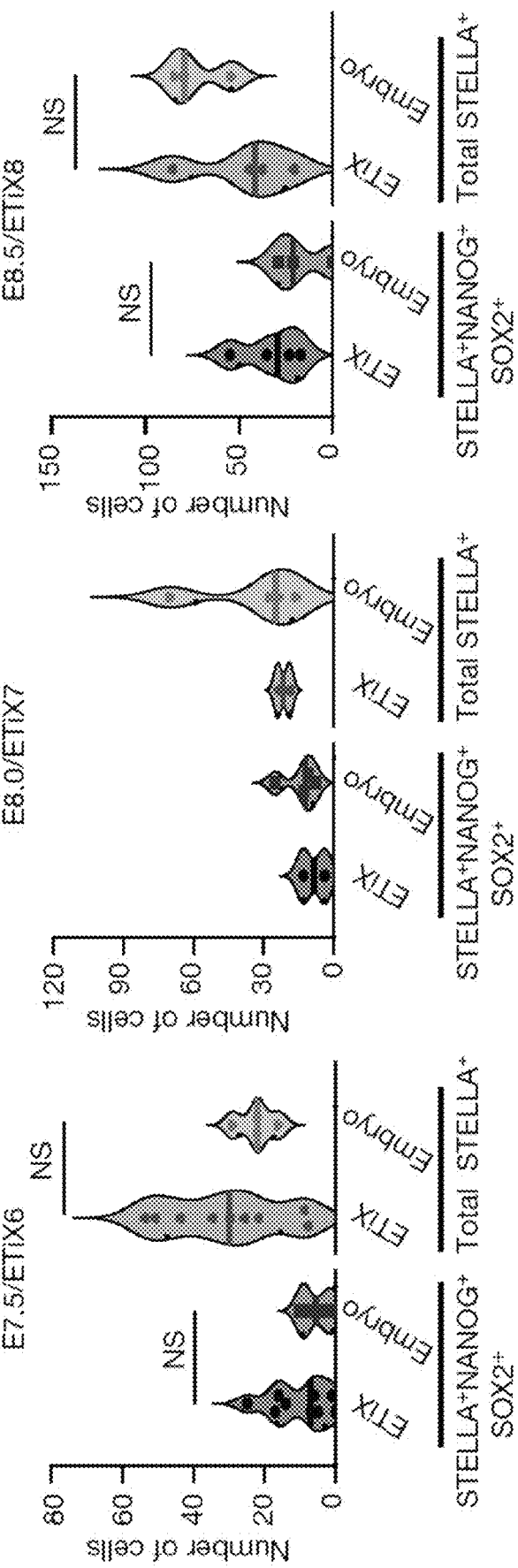
Figure 5G:
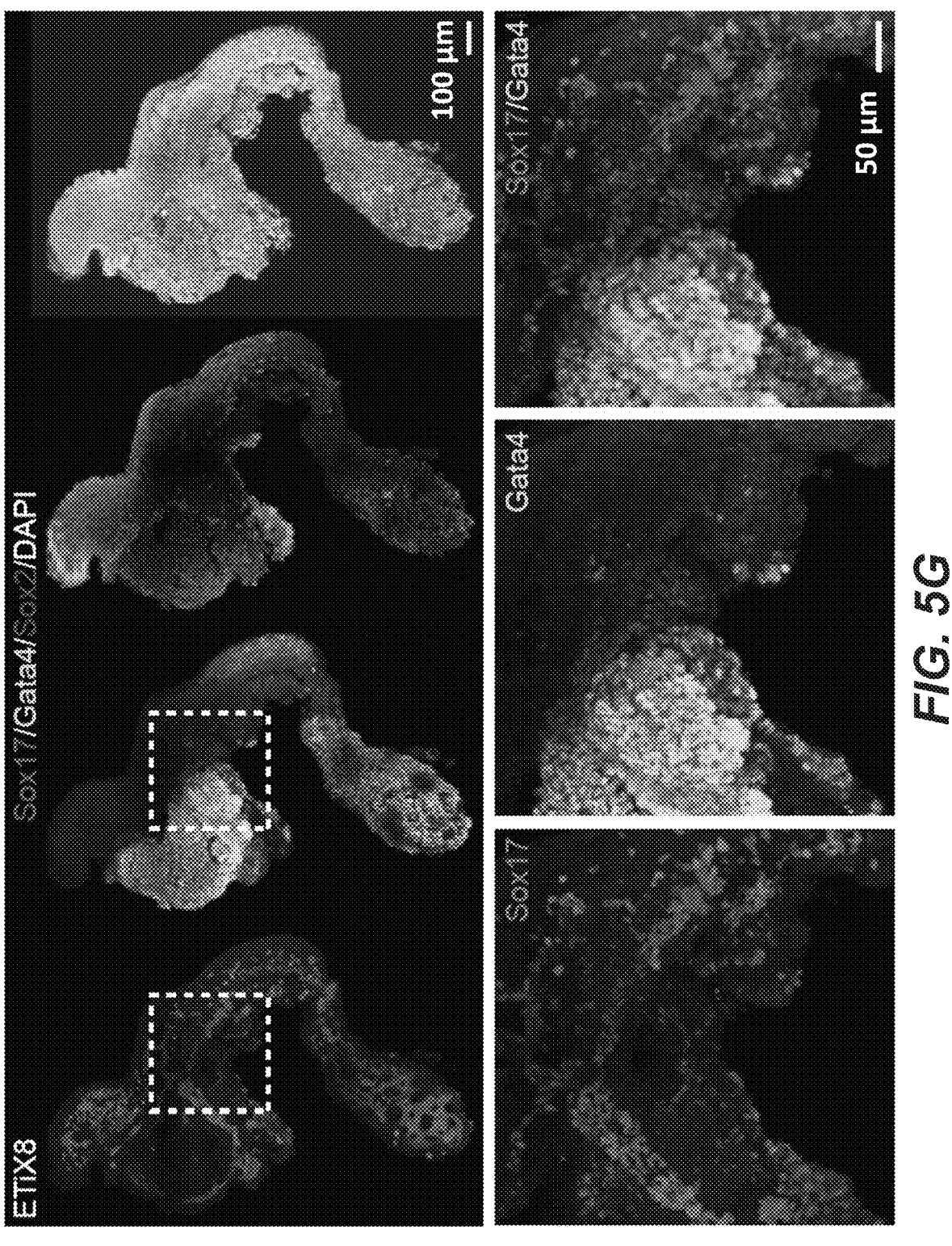
Figure 5H:
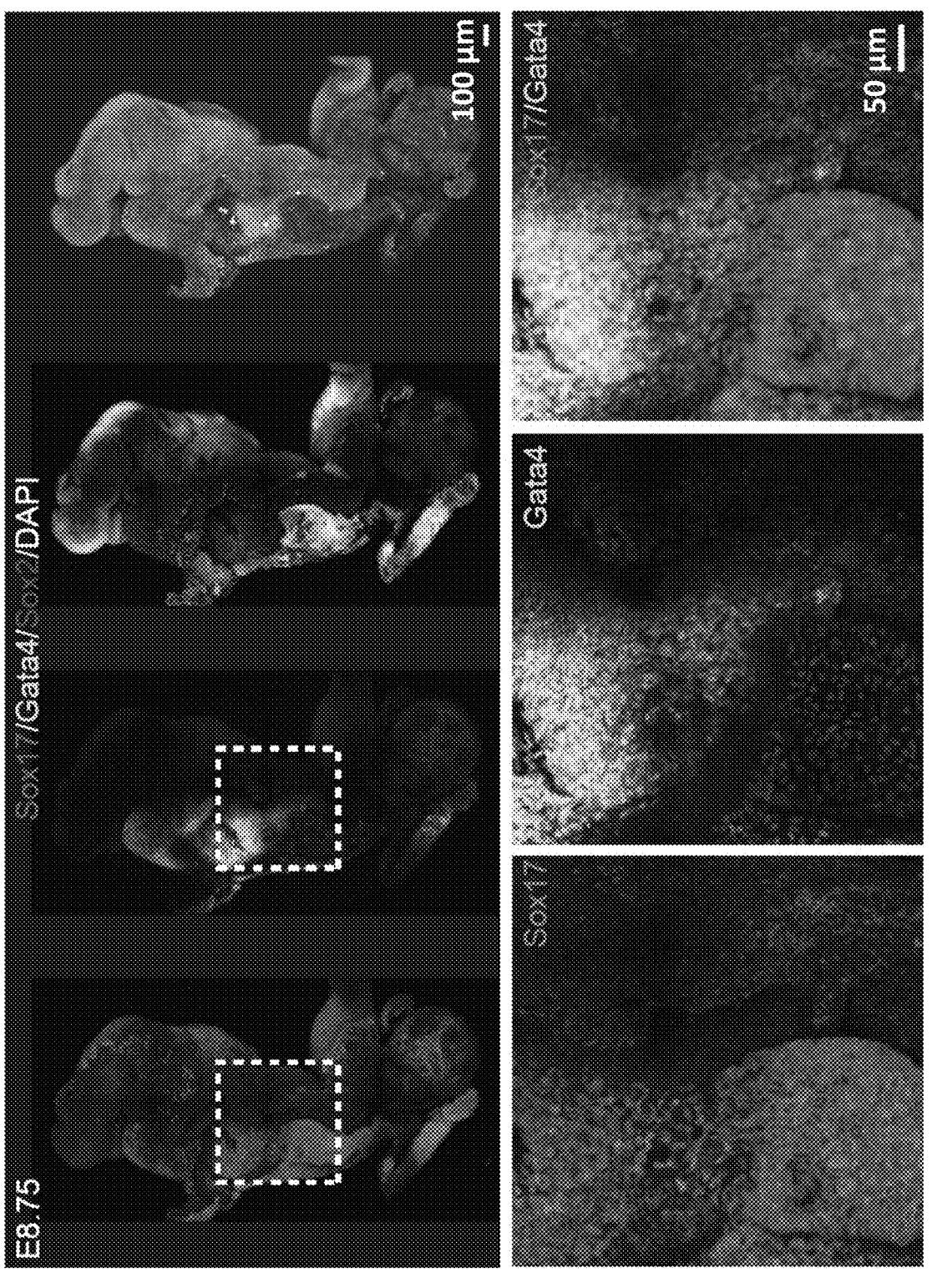
Figure 5I:
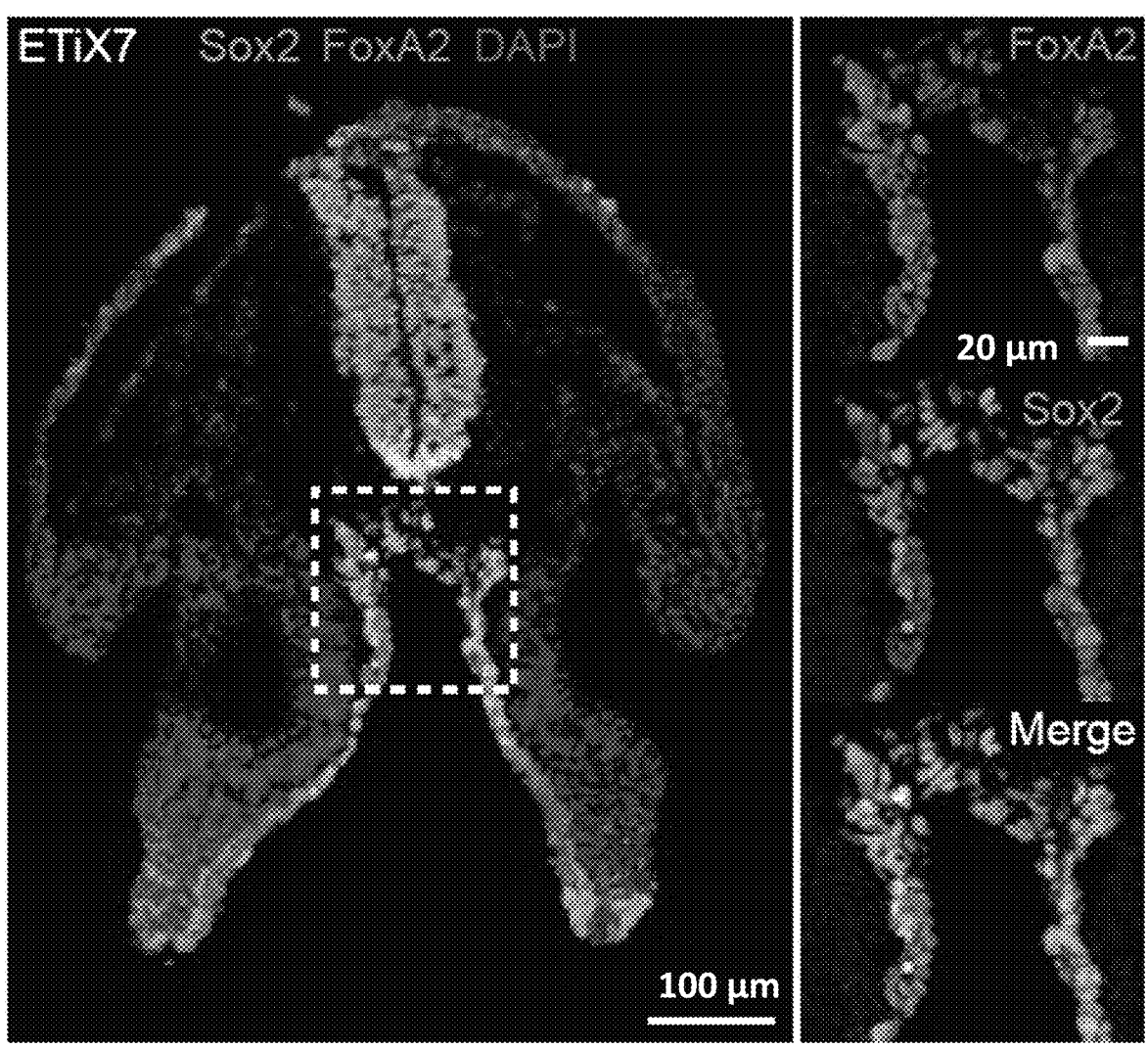
Figure 19A:
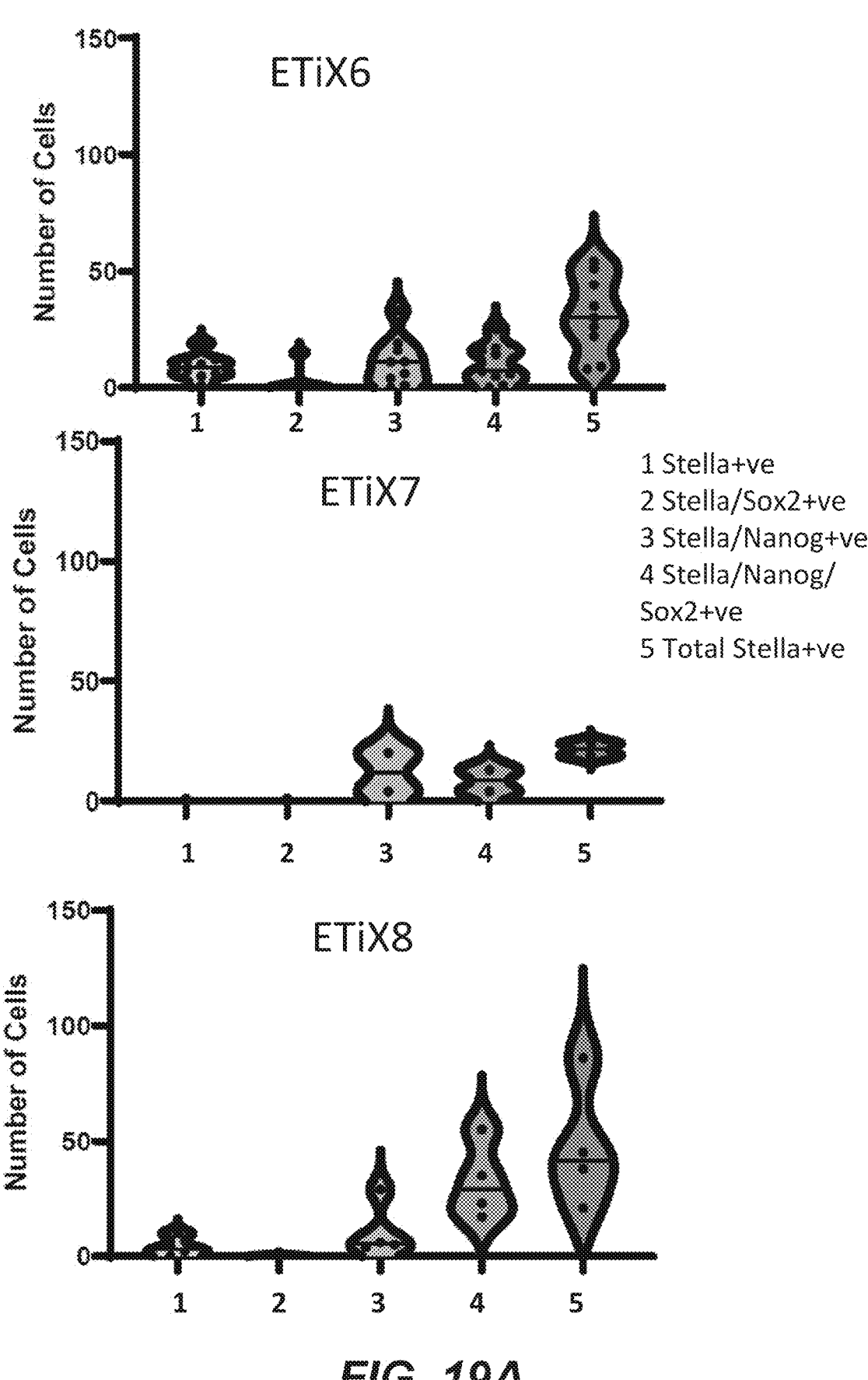
FIG. 19A-FIG. 19B depict non-limiting exemplary embodiments and data related to primordial germ cell (PGC) numbers in ETiX embryos and the development of extraembryonic tissues.

Committed PGCs were characterized by the expression of STELLA, which was detected at the ES cell-TS cell boundary in ETiX embryoids on day 6, similar to the E7.5 natural embryo (FIG. 5E). PGCs were also detectable at later time points of ETiX embryoid development (FIG. 17A-FIG. 17D). During development, PGCs reactivated the pluripotency markers SOX2 and NANOG as observed to occur in ETiX embryoids (FIG. 5E and FIG. 17A-FIG. 17D). PGCs were found in proximity to the allantois in ETiX embryoids on days 7 and 8, similar to the natural embryo on E8.0 (FIG. 17A-FIG. 17D). Quantification of PGC numbers in natural embryos on E7.5 and E8.5 and ETiX embryoids on day 6 and day 8 indicated that there were no significant differences between the total number of STELLA$^+$ or STELLA$^+$ NANOG$^+$SOX2$^+$ cells (FIG. 5F). Quantification of PGC numbers also indicated that day 8 ETiX embryos had 30-100 PGCs, similar to the reported number of PGCs in natural E8.5 embryos (FIG. 19A). Thus, the inability to detect PGCs in the single-cell datasets probably reflected their very low numbers.

Example 7

Yolk Sac and Blood Island Development in Synthetic Embryoids

This example reports the establishment of yolk sac and blood island around the ETiX embryoids described herein. The development of yolk sac and blood island was also confirmed by the expression of amnion and amniotic mesoderm markers.

Figure 6A:
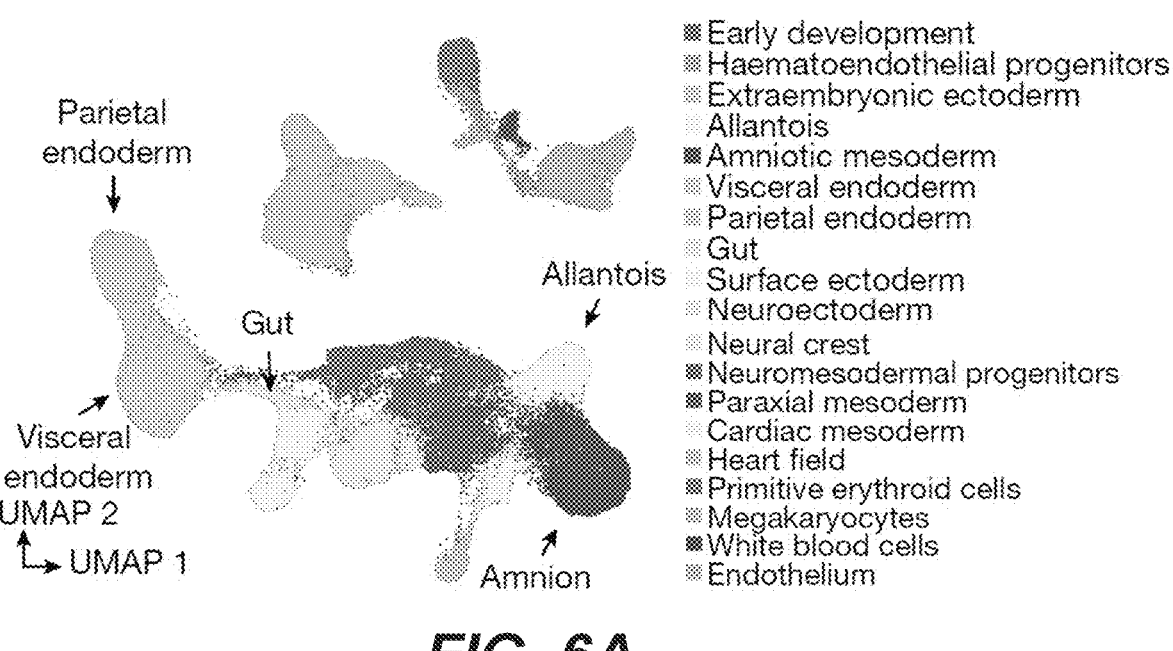
FIG. 6A-FIG. 6J depict non-limiting exemplary embodiments and data related to the characterization of extraembryonic lineages in ETiX embryoids.
Figure 6B:
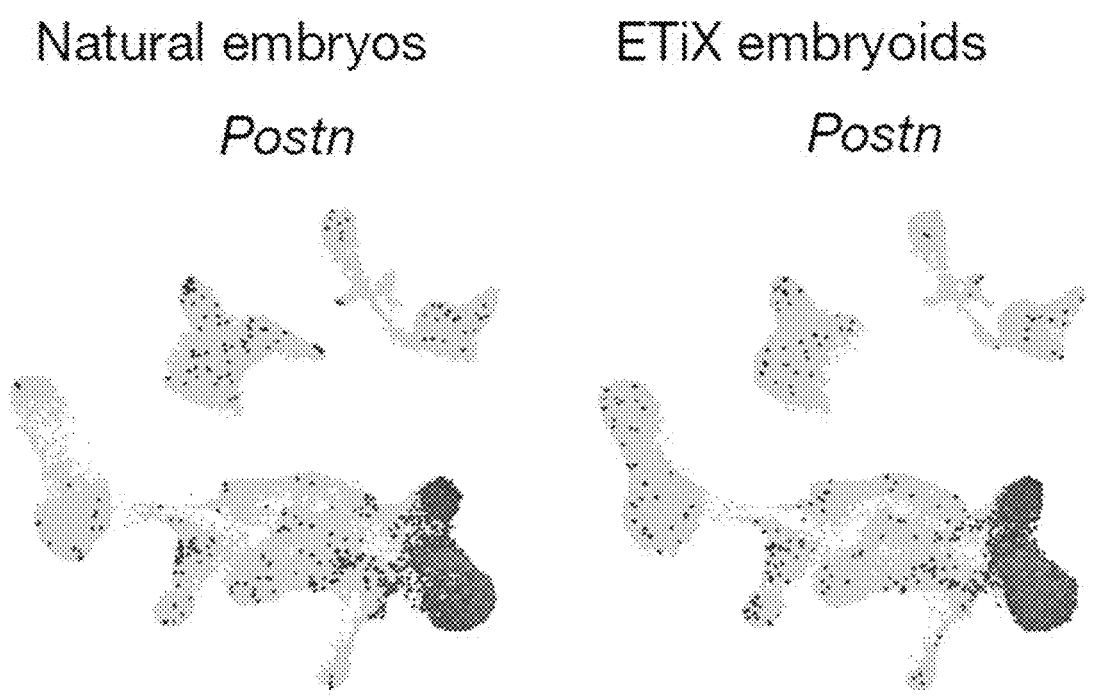
Figure 6C:
Figure 6C:
Figure 6C:
Figure 18A:
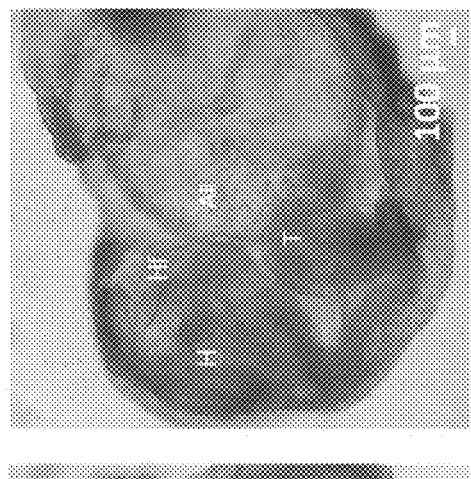
Figure 18A:
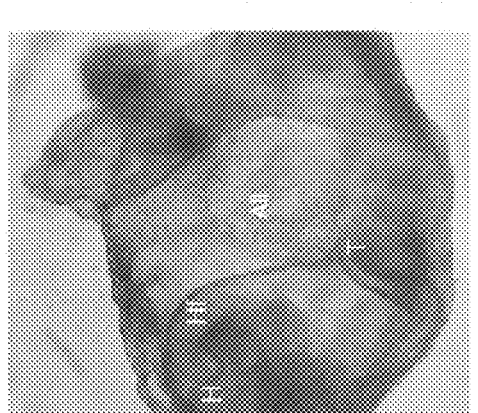
Figure 18A:
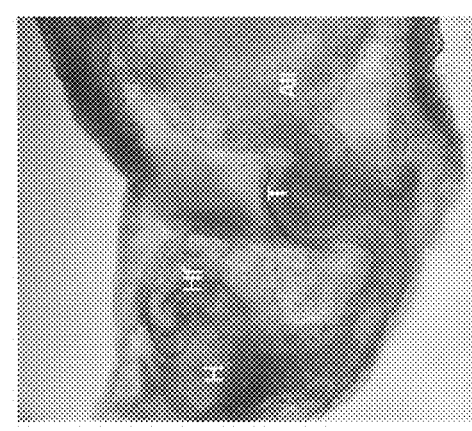
Figure 18A:
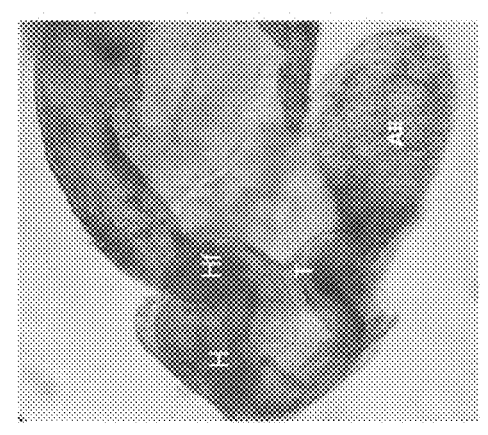
Figure 18B:
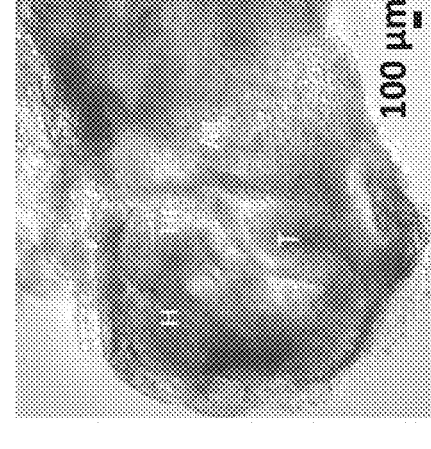
Figure 18B:
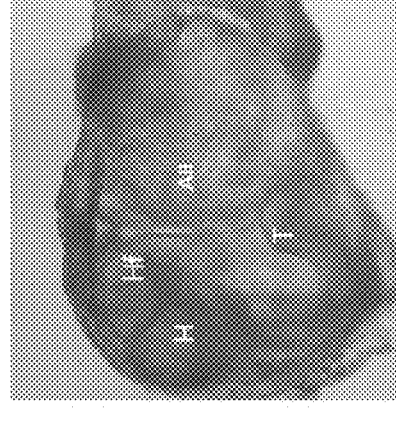
Figure 18B:
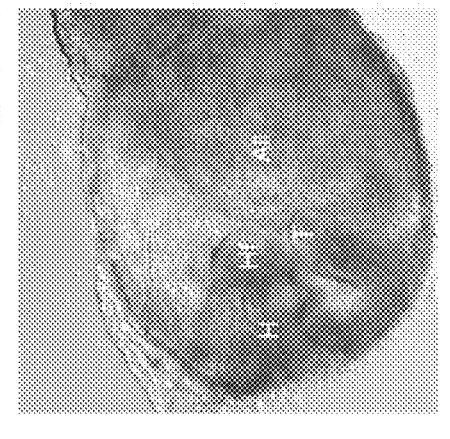
Figure 18B:
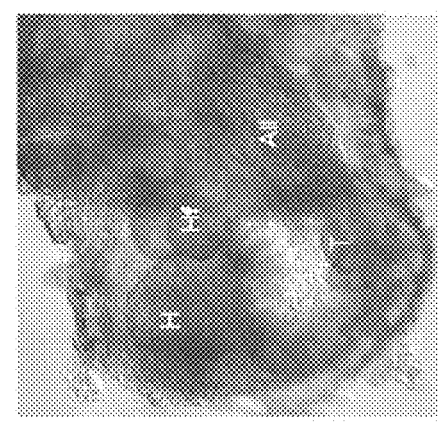

ETiX embryoids developed inside membranes that resemble the amnion and yolk sac, which provided nourishment to the embryo until the establishment of the fetal-maternal circulation. Both cultured embryos and ETiX embryoids had to be dissected from their yolk sacs (FIG. 18A-FIG. 18B) for immunostaining. In both of the sequencing datasets, the amnion and amniotic mesoderm constituted a cluster of cells that expressed the amnion marker Postn (FIG. 6A-FIG. 6B). Additionally, a cluster of cells representative of the allantois tissue marked by the expression of Tbx4 and Hoxa13 in both cultured natural embryos and ETiX embryoids (FIG. 6C) was detected.

Figure 6D:
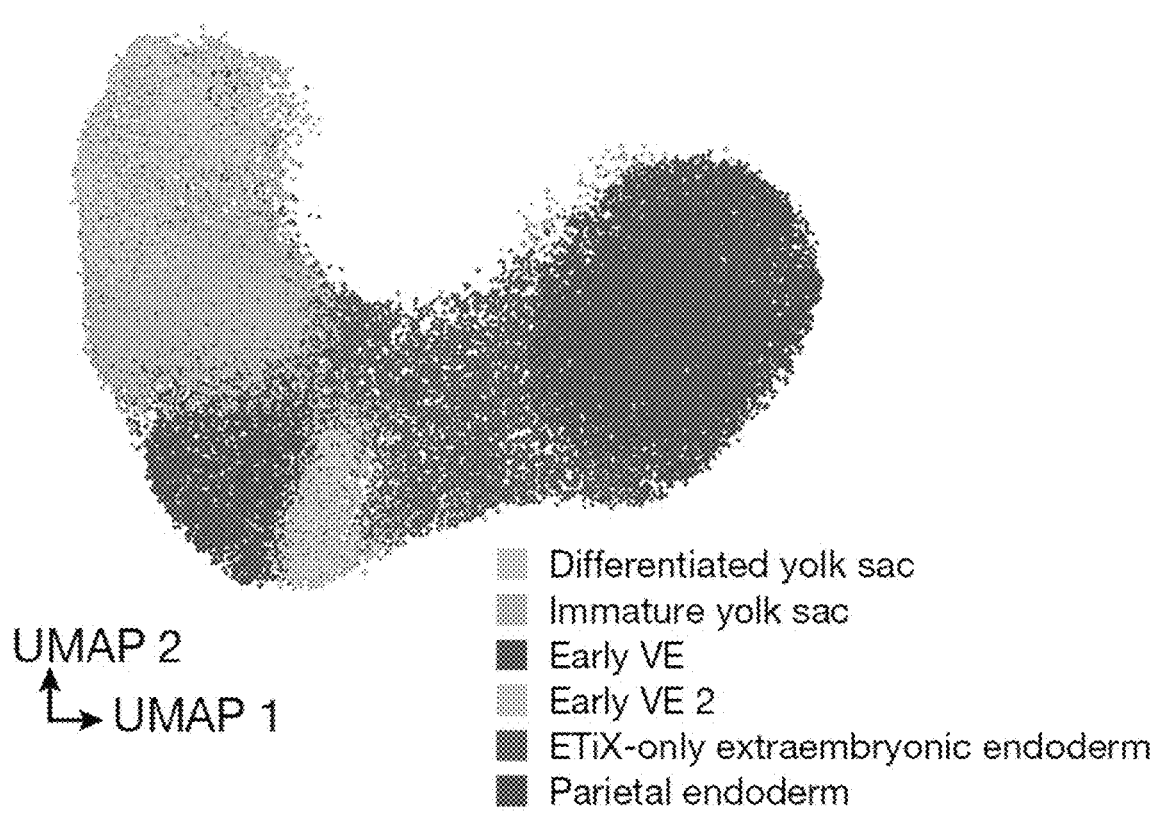
Figure 18C:
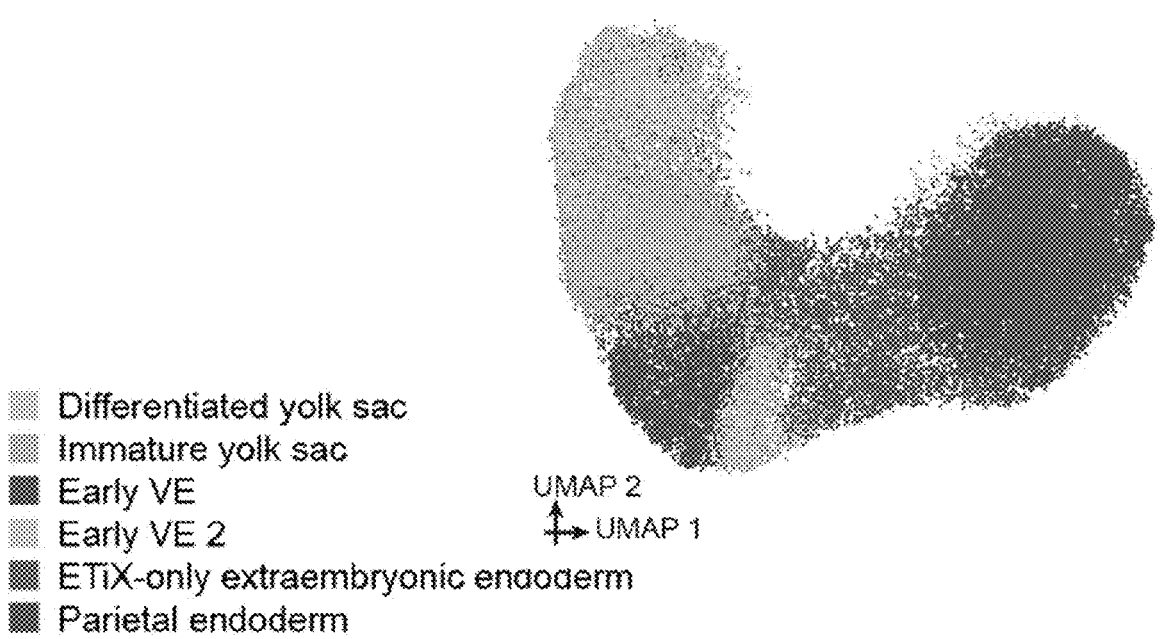
FIG. 18C depicts the subclustered UMAP of extraembryonic endoderm in the tiny sci-RNA-seq dataset and contribution of each individual time point to the subclustered UMAP of the extraembryonic endoderm.
Figure 18C:
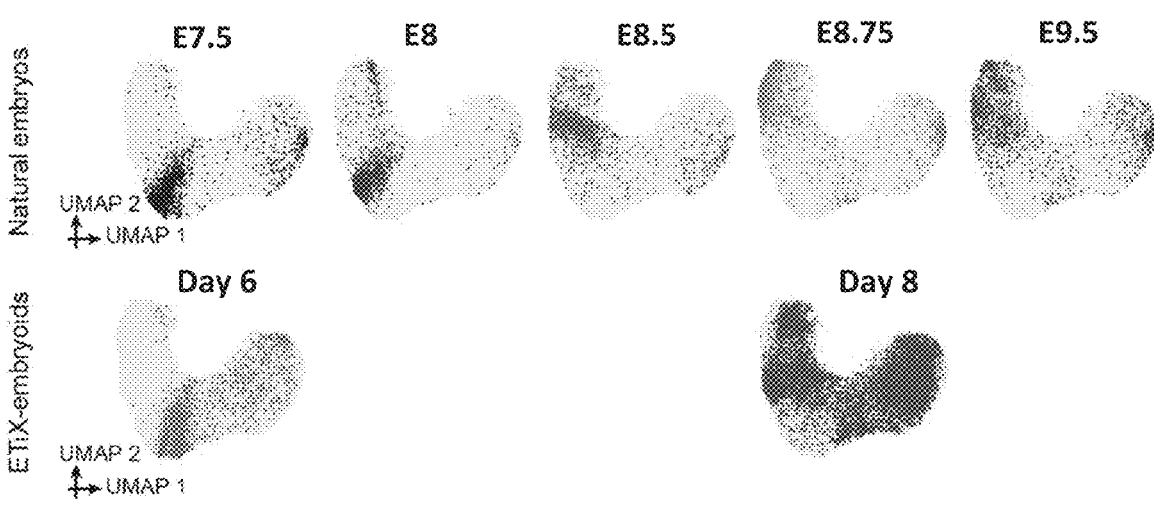
Figures 18D, 18E:
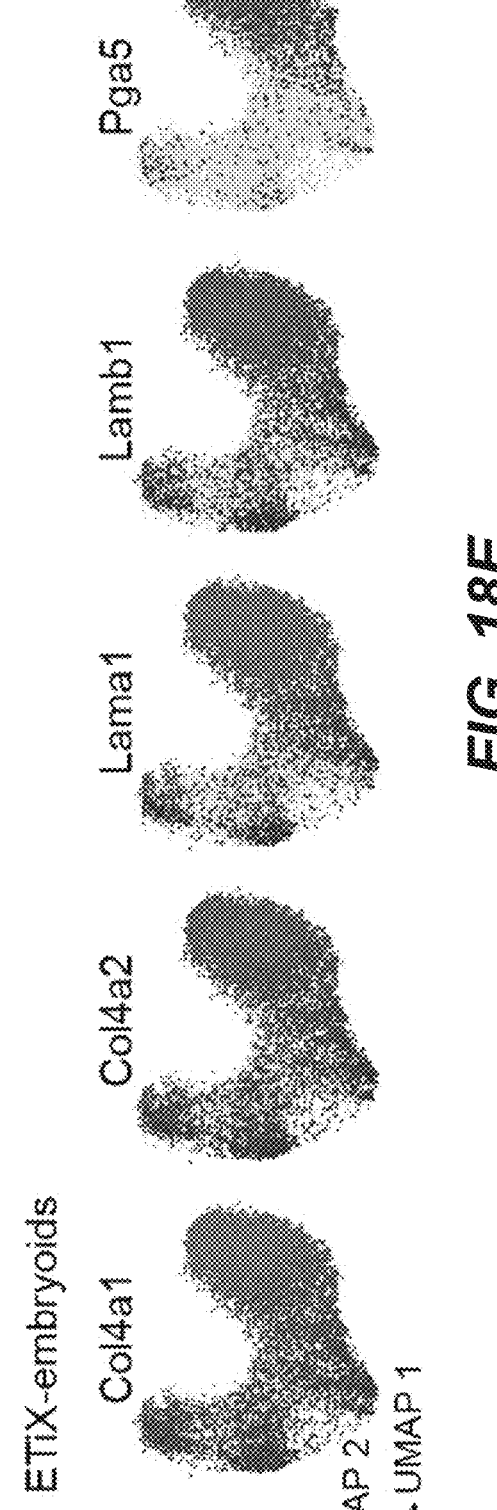
FIG. 18D-FIG. 18E depict the expression of selected parietal endoderm genes in the subclustered UMAP of extraembryonic endoderm shown separately for natural embryos (FIG. 18D) and ETiX embryoids (FIG. 18E).
Figures 18F, 18G:
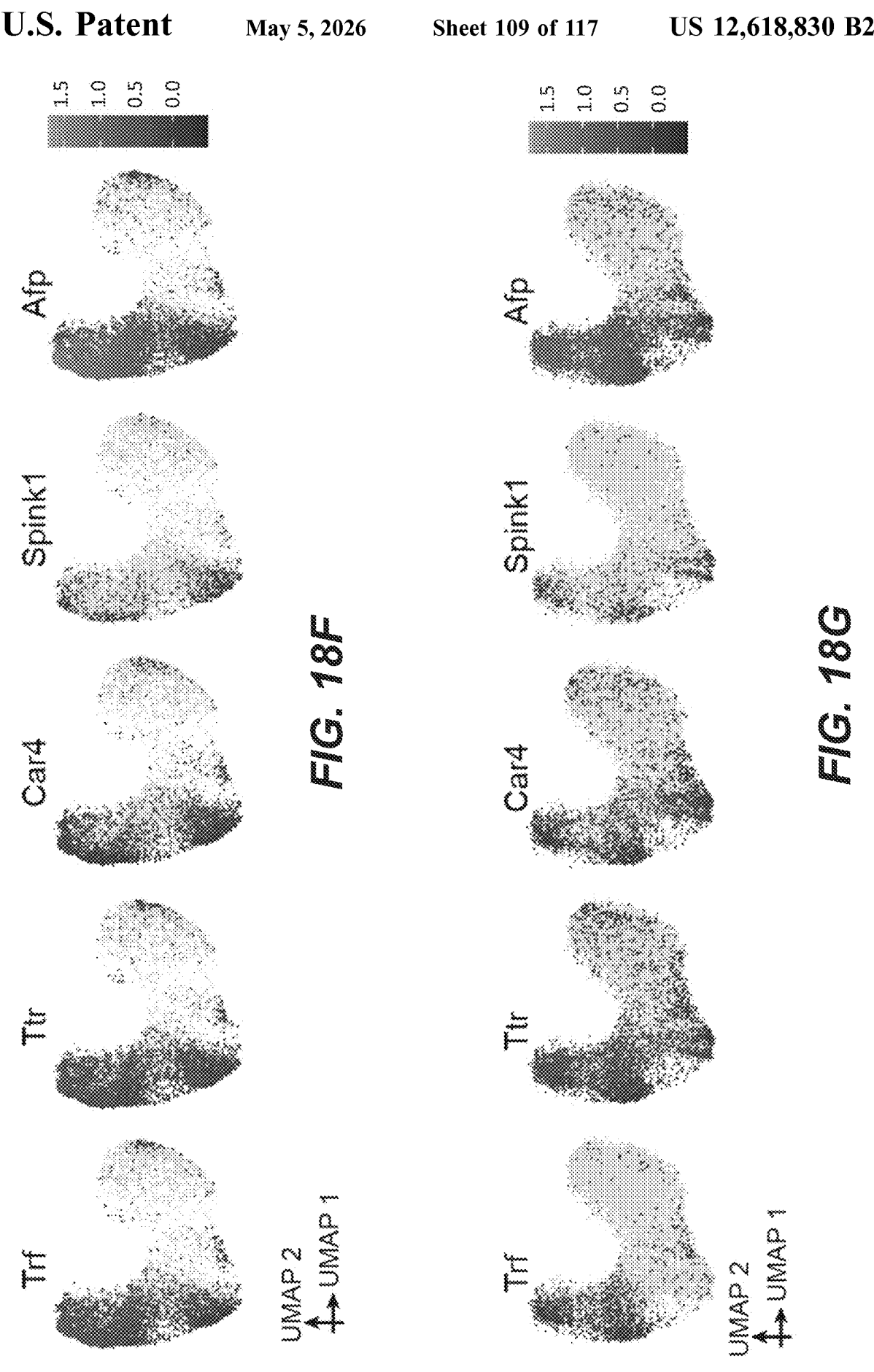
FIG. 18F-FIG. 18G depict the expression of selected extraembryonic visceral endoderm genes in the subclustered UMAP of extraembryonic endoderm shown separately for natural embryos (FIG. 18F) and ETiX embryoids (FIG. 18G).

During development, the yolk sac originated from cells derived from parietal endoderm and VE, respectively. These populations were both present in the datasets disclosed herein (FIG. 6A). To gain further insight into the diversity of cell types present in these two extraembryonic endoderm lineages, a subclustering analysis was performed (FIG. 6D and FIG. 18C). Although the extraembryonic endoderm of ETiX embryoids integrated well with natural embryos (left and far right sides of the UMAP), it also contained cells that were largely absent in natural embryos (ETiX-only extraembryonic endoderm) (FIG. 6D and FIG. 18C). These cells had begun to appear in the day 6 embryoids, but the vast majority appeared on day 8 (FIG. 18C). In the subclustered UMAP, the parietal endoderm cluster expressed high levels of collagen (Col4a1 and Col4a2) and laminin (Lama1 and Lamb1) genes, as reported previously and as found in ETiX embryoids at earlier stages (FIG. 18D-FIG. 18E). Consistently, this cluster also expressed the parietal yolk sac marker Pga5 (FIG. 18D-FIG. 18E). The youngest cluster in the dataset, 'early VE' and 'early VE 2', expressed genes enriched in the embryonic VE at E7.5 (such as Spink1), as well as genes associated with the extraembryonic YE (ExVE) (Afp, Trf, Ttr and Car4) (FIG. 18F-FIG. 18G). Together, this suggested a prevailing ExVE signature, with these ExVE genes being expressed mostly on the left side of the subclustered UMAP (FIG. 18C). GO analysis of 'early YE' clusters and 'differentiated yolk sac' clusters highlighted terms consistent with the role of the visceral yolk sac in nutrient transport, lysosome function and lipid and cholesterol metabolism (Tables 6 and 7). The 'immature yolk sac' cluster was mostly present in ETiX embryoids and lacked a clear expression pattern, suggesting that they might be an aberrant population. The 'early YE 2' cluster was present both in natural embryos and in ETiX embryoids and showed expression of the pro-haematopoietic factor Runx1, which is known to be restricted to the YE at the boundary of the embryo and ExE. Together, subclustering of the extraembryonic endoderm cells suggested that ETiX embryoids developed parietal yolk sac cells and could acquire mature visceral yolk sac identity, but it also identified cells that were insufficiently mature to undergo the correct developmental programme.

Table 8 lists the genes enriched in "Early YE" cell populations in the extraembryonic endoderm subcluster of ETiX-embryoids, according to GO analysis.

TABLE 8

| Gene Ontology of Extraembryonic endoderm Early Visceral Endoderm | | |
| --- | --- | --- |
| Cluster | Term | Enrichment Score |
| 1 | GO: 0005764~lysosome | 6.6 |
| 2 | GO: 0005768~endosome | 5.81 |
| 3 | GO: 0030054~cell junction | 4.55 |
| 4 | GO: 0005905~clathrin-coated pit | 4.53 |
| 5 | GO: 0016020-membrane | 3.03 |
| 6 | GO: 0022857~transmembrane transporter activity | 2.89 |
| 7 | GO: 0003333~amino acid transmembrane transport | 2.53 |
| 8 | GO: 0005783~endoplasmic reticulum | 2.5 |
| 9 | CROSSLNK: Glycyl lysine isopeptide (Lys-Gly) (interchain with G-Cter in SUMO2) | 2.4 |
| 10 | GO: 0008092~cytoskeletal protein binding | 2.38 |

TABLE 8-continued

Gene Ontology of Extraembryonic endoderm
Early Visceral Endoderm

| Cluster | Term | Enrichment Score |
|---|---|---|
| 11 | GO: 0033344~cholesterol efflux | 2.38 |
| 12 | GO: 0051603~proteolysis involved in cellular protein catabolic process | 2.31 |
| 13 | GO: 0042393~histone binding | 2.09 |
| 14 | GO: 0005524~ATP binding | 1.74 |
| 15 | GO: 0050750~low-density lipoprotein particle receptor binding | 1.49 |
| 16 | IPR005829: Sugar transporter, conserved site | 1.48 |
| 17 | GO: 0070411~I-SMAD binding | 1.45 |
| 18 | IPR000408: Regulator of chromosome condensation, RCC1 | 1.41 |
| 19 | GO: 0006397~mRNA processing | 1.35 |
| 20 | GO: 0007275~multicellular organism development | 1.33 |

Table 9 lists the genes enriched in "Differentiated yolk sac" cell populations of ETiX-embryoids, according to (30 analysis.

TABLE 9

Gene Ontology of older cell clusters in Extraembryonic endoderm
Differentiated yolk sac

| Category | Term | Enrichment Score |
|---|---|---|
| 1 | GO: 0005764~lysosome | 16.13 |
| 2 | GO: 0005783~endoplasmic reticulum | 11.79 |
| 3 | GO: 0006629~lipid metabolic process | 9.19 |
| 4 | GO: 0016020-membrane | 6.85 |
| 5 | CARBOHYD: N-linked (GlcNAc . . . ) asparagine | 6.3 |
| 6 | GO: 0008203~cholesterol metabolic process | 5.71 |
| 7 | KW-0009~Actin-binding | 4.18 |
| 8 | GO: 0030301~cholesterol transport | 3.54 |
| 9 | GO: 0034362~low-density lipoprotein particle | 3.43 |
| 10 | GO: 0042632-cholesterol homeostasis | 3.25 |
| 11 | GO: 0051651~maintenance of location in cell | 2.81 |
| 12 | GO: 0032532~regulation of microvillus length | 2.81 |
| 13 | DOMAIN: PDZ | 2.64 |
| 14 | KW-0117~Actin capping | 2.6 |
| 15 | GO: 0005576~extracellular region | 2.58 |
| 16 | DOMAIN: Calponin-homology (CH) 1 | 2.5 |
| 17 | GO: 0006801~superoxide metabolic process | 2.45 |
| 18 | REPEAT: Spectrin 4 | 2.45 |
| 19 | GO: 0005975~carbohydrate metabolic process | 2.41 |
| 20 | GO: 0006695~cholesterol biosynthetic process | 2.28 |

Figure 6E:
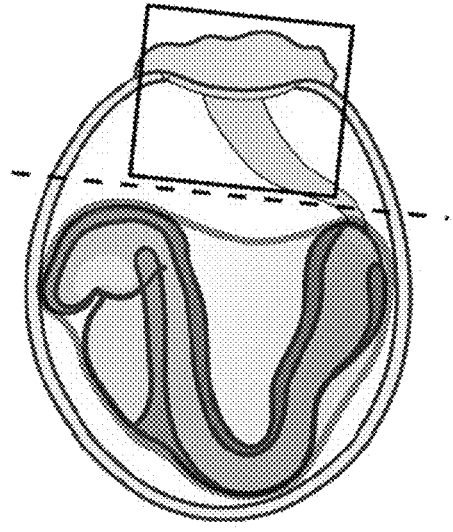
Figure 6F:
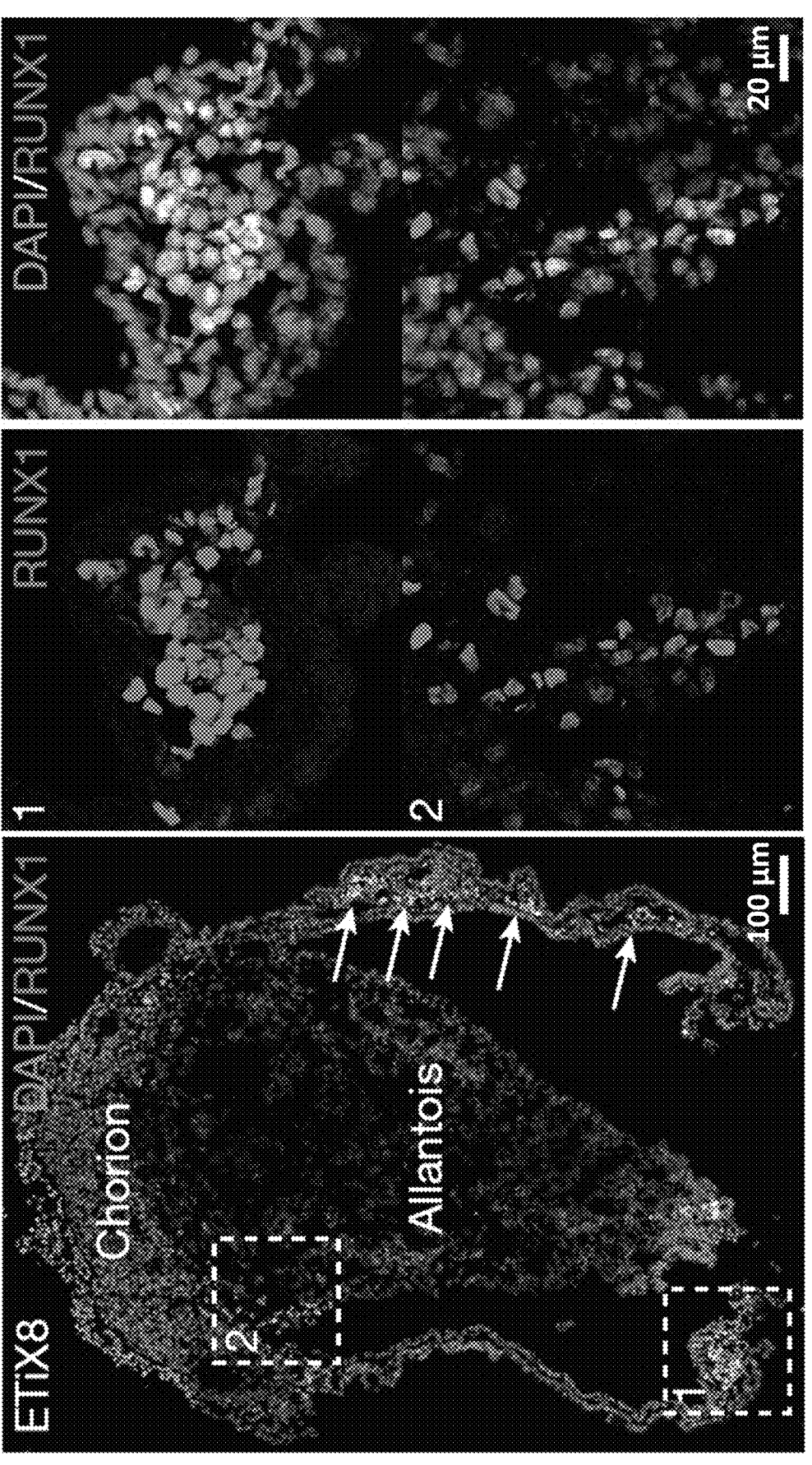
Figure 18H:
FIG. 18H depicts the expression of selected markers of endothelium Pecam1, Cd34, Icam1, Tek, Vegfa and Cdh5 in natural embryos and ETiX embryoids in tiny sci-RNA-seq dataset.
Figure 18H:
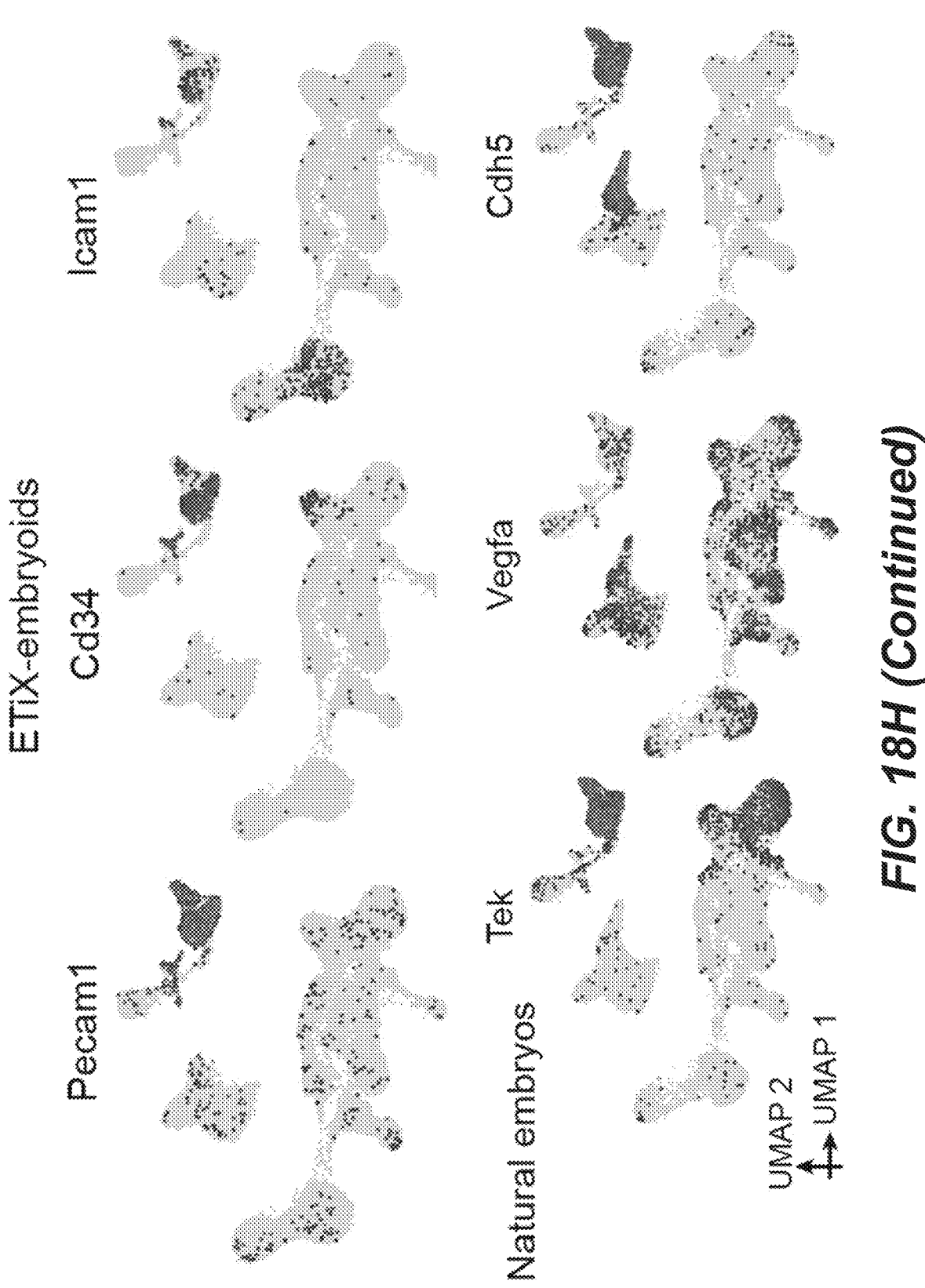
Figures 18H, 18I:
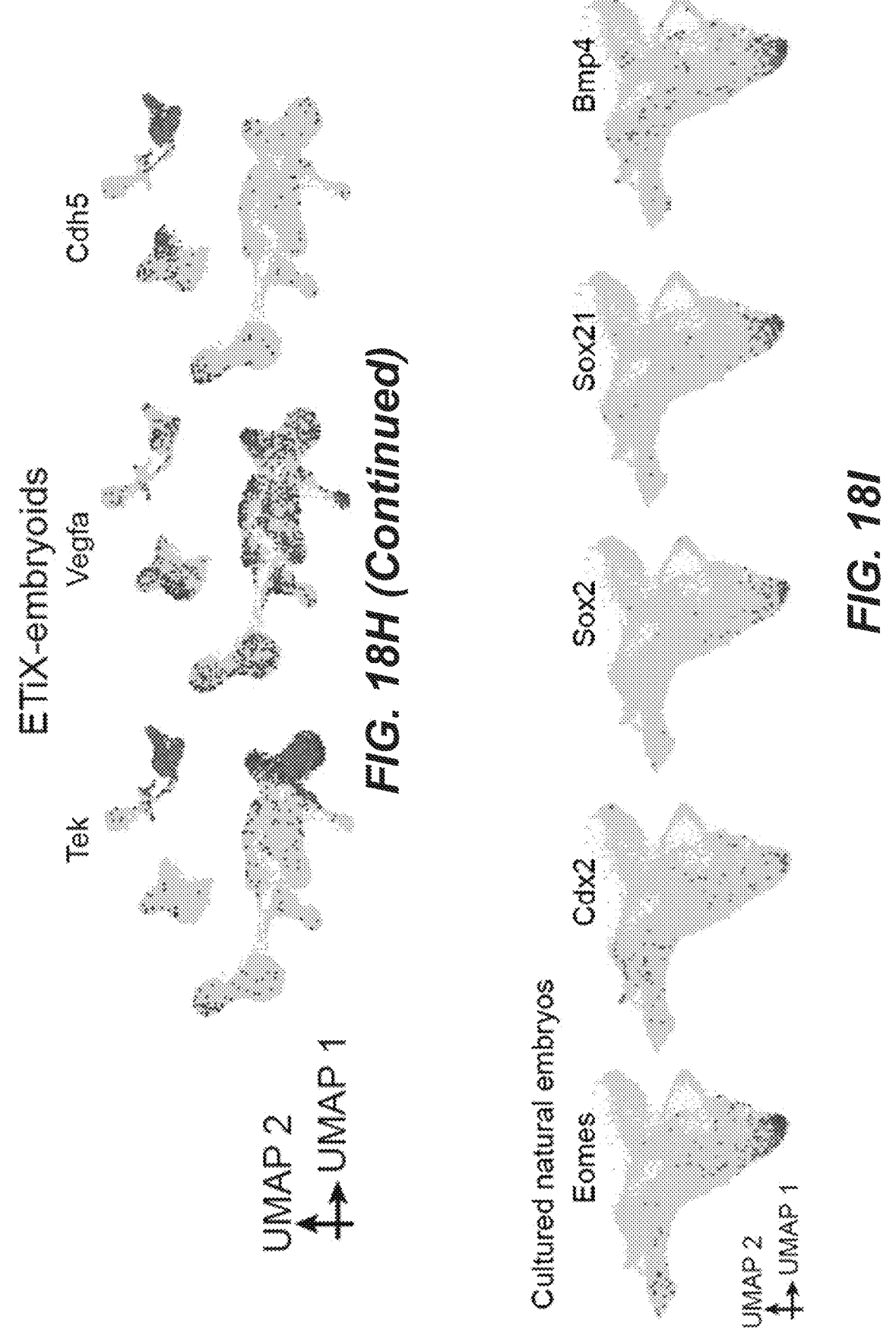
FIG. 18I depicts that Eomes, Cdx2, Sox2, Sox21 and Bmp4 identified a trophoblast progenitor population in natural embryos in the tiny sci-RNA-seq dataset.
Figures 18J, 18K:
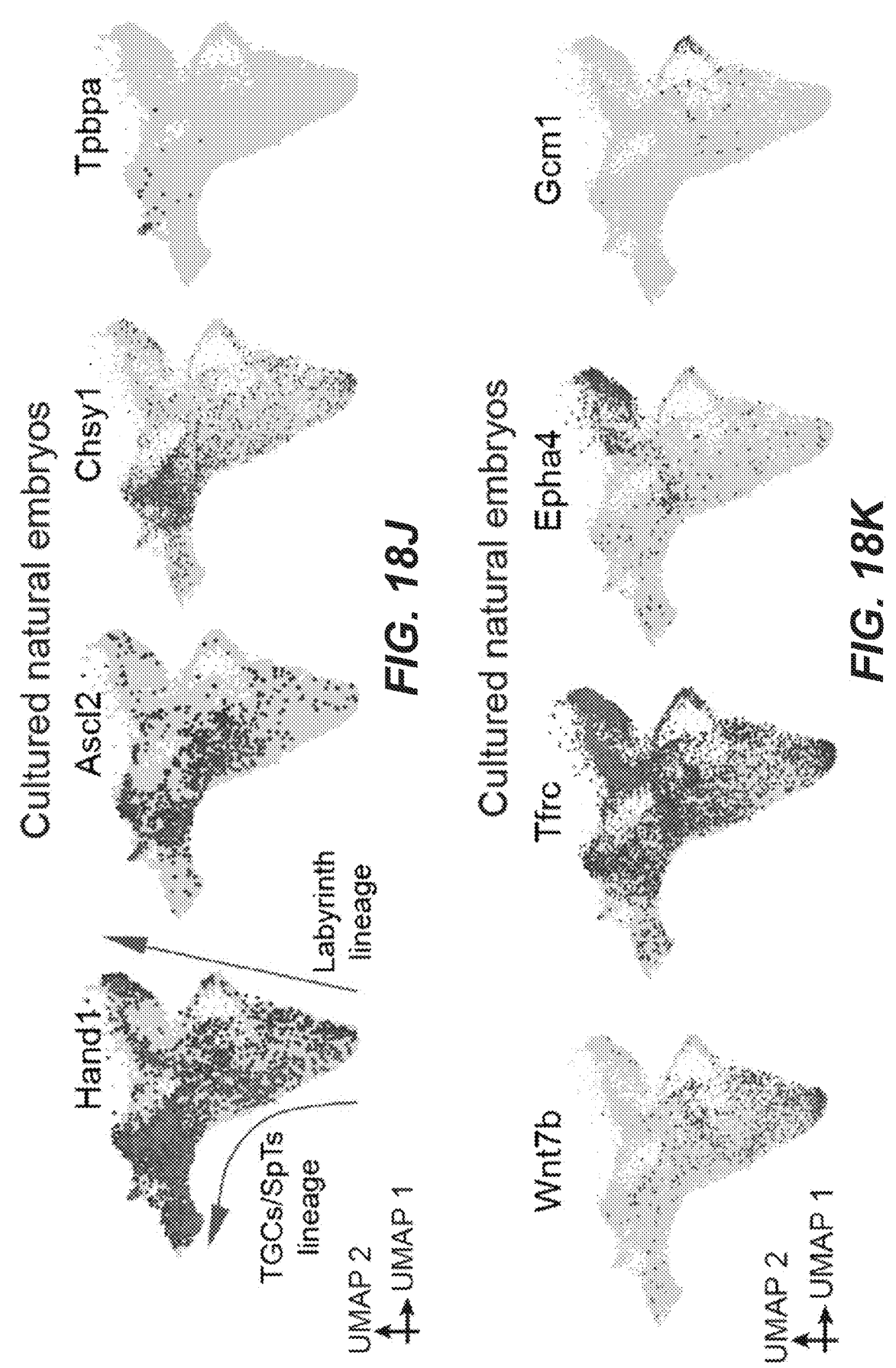
FIG. 18J depicts the expression of selected markers of the ectoplacental cone lineage. High levels of Hand) (left side arrow) showed the developmental progression of the ectoplacental cone (ECP) lineage towards spongiotrophoblast cells and trophoblast giant cells. Co-expression of Ascl2 and Chsy1 indicated committed ECP cells. Tpbpa identified mature spongiotrophoblasts. Expression of Hand) and prolactin genes (FIG. 5I) denoted the trophoblast giant cells.
FIG. 18K depicts the expression of selected markers of chorion progenitors (right side of arrow in Hand1 UMAP in FIG. 18J), chorion and differentiated chorion derivatives in natural embryos. Wnt7b indicated chorion progenitors, Tfrc indicated the chorion cluster, Epha4 identified cells of the syncytiotrophoblast layer I and Gcm1 identified the syncytiotrophoblast layer II.
Figures 18L, 18M:
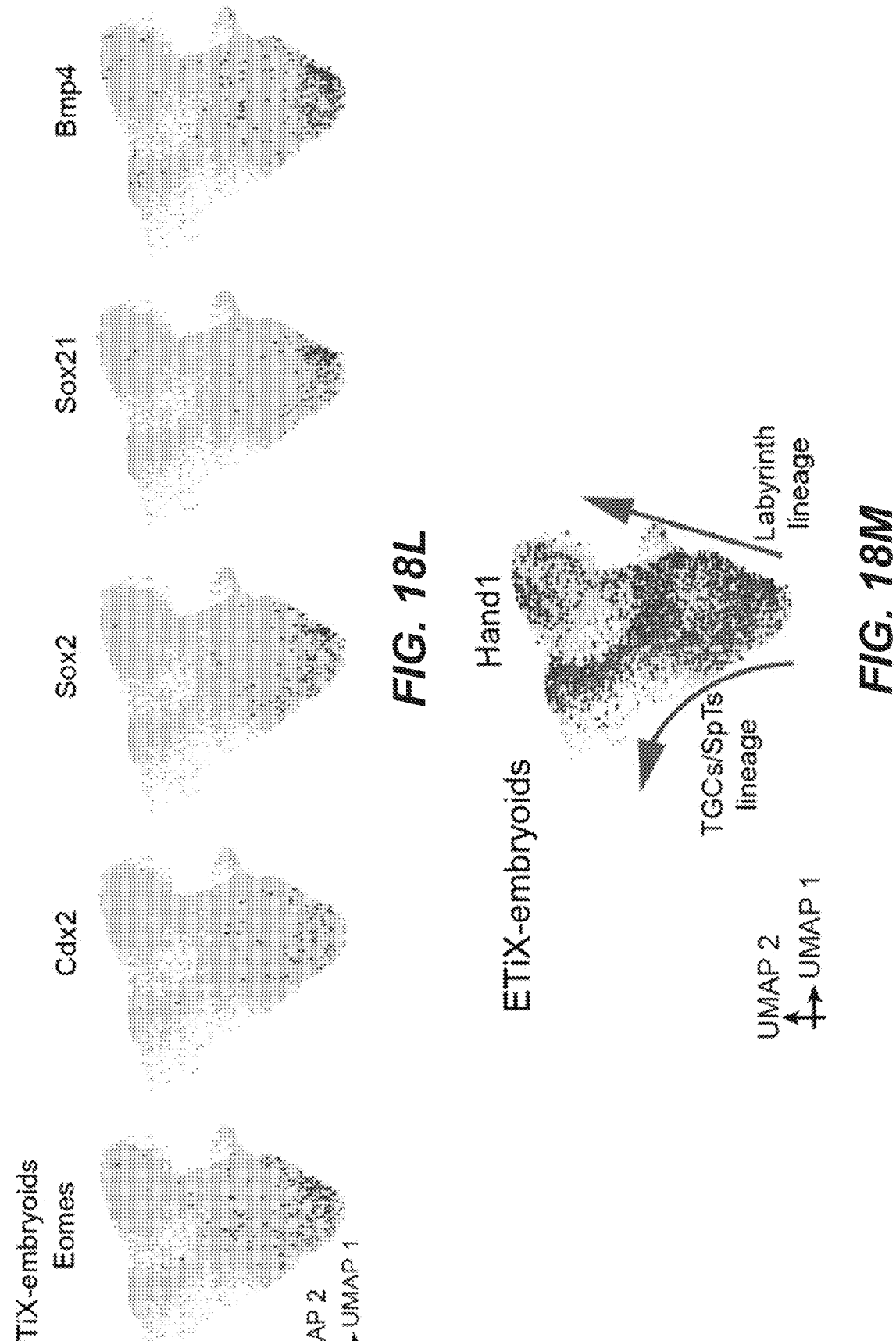
Figures 18N, 18O:
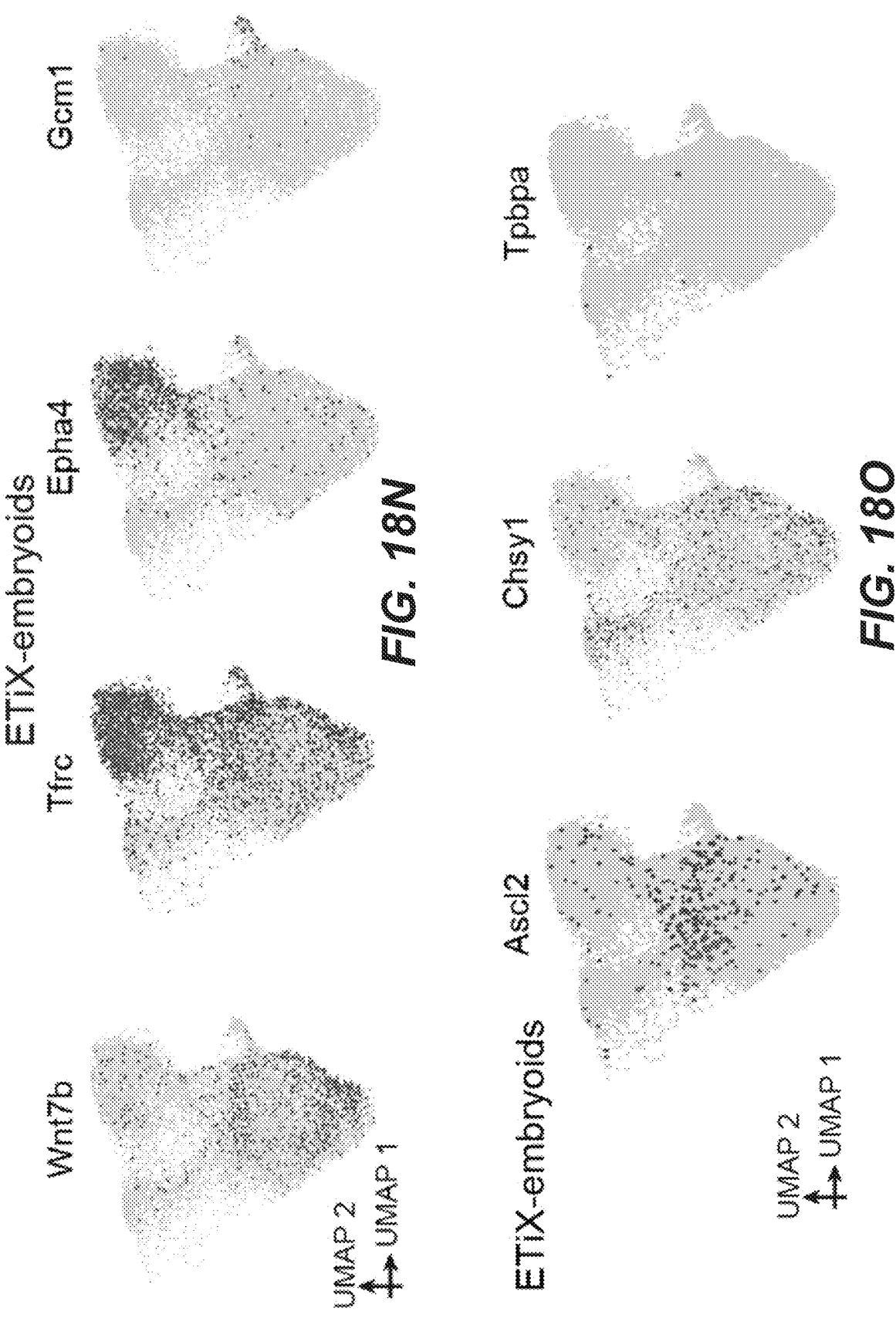
Figure 19B:
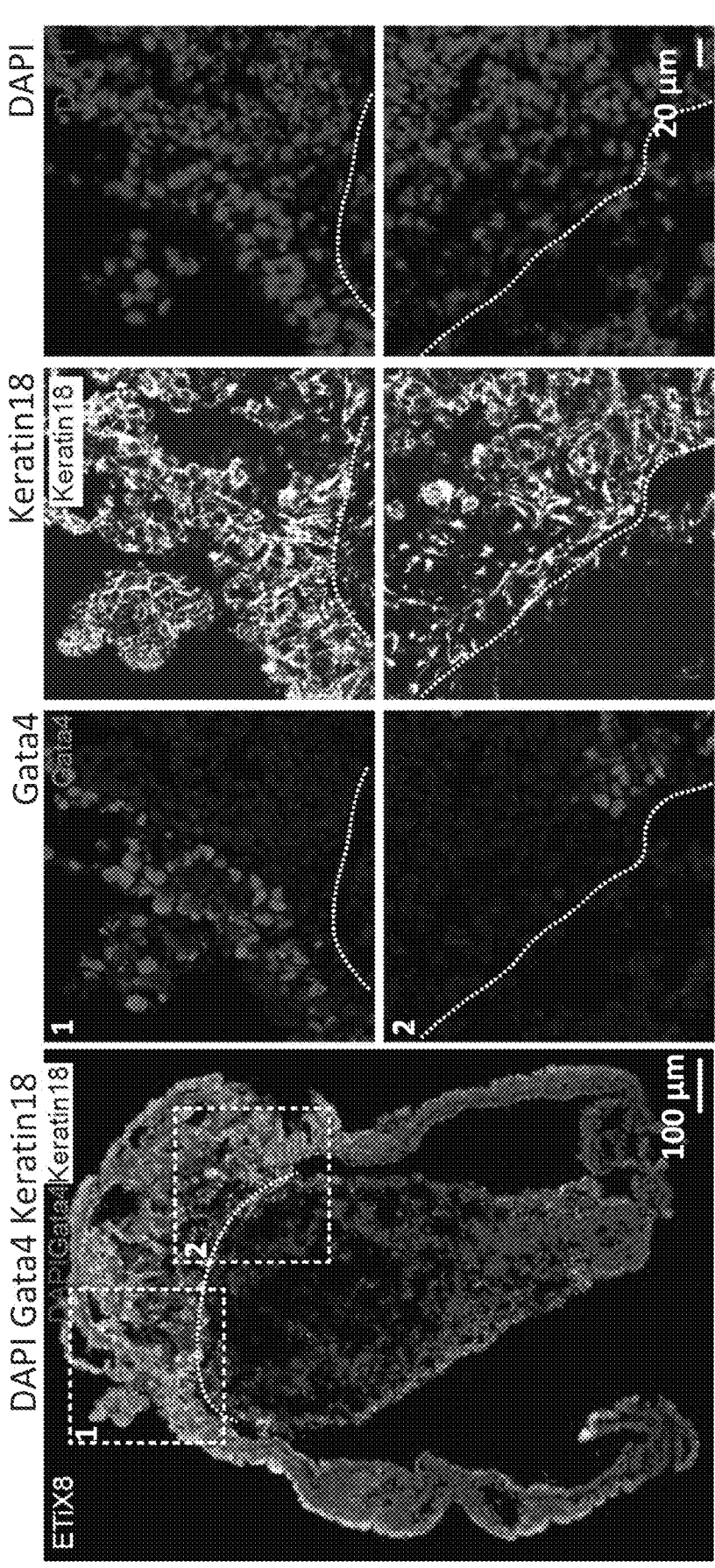

The extraembryonic portion of the yolk sac that developed in ETiX embryoids was attached to a structure resembling the chorion and allantois (FIG. 6E). The yolk sac supported primitive haematopoiesis in the embryo. Notably, RUNX1-positive blood islands were observed in the mesoderm of the yolk sac and at the base of the allantois of neurudating embryoids at day 8 (FIG. 6F). Consistent with the formation of blood islands, genes associated with endothelium were expressed in the tiny-sci dataset (FIG. 18H). Furthermore, the allantois of day 8 ETiX embryoids was connected to a chorion-like tissue, which expressed Gata4 and Keratin 18, unlike the yolk sac in natural embryos, which expressed only Gata4 (FIG. 19B).

Figure 6G:
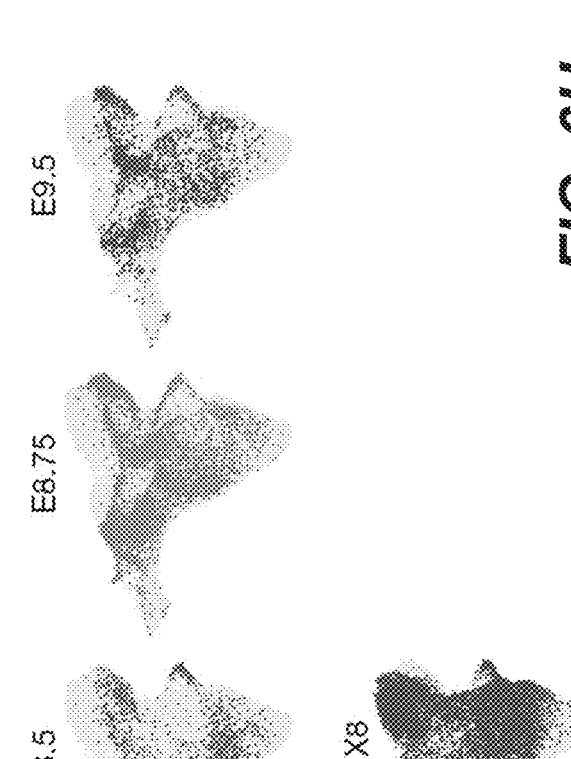

Finally, the trophoblast compartment in natural embryos was characterized to determine whether ETiX embryoids could also develop the cell populations required to form the functional placenta. During development, the proximal portion of the ExE differentiates into the ECP, precursor of trophoblast giant cells and spongiotrophoblasts. The portion of the ExE retaining a stem cell character differentiates into chorion and eventually forms the syncytiotrophoblast layers of the labyrinth, whose surface mediates gas and nutrient exchange between fetus and mother. The ExE subclustered UMAP (FIG. 6G) was annotated using known markers (FIG. 18I-FIG. 18O) and showed the presence of trophoblast precursors, committed and uncommitted ECP, trophoblast giant cells, spongiotrophoblast cells, chorion progenitors, chorion and syncytiotrophoblast cells of layers 1 and 2.

Figure 6H:
Figure 6H:
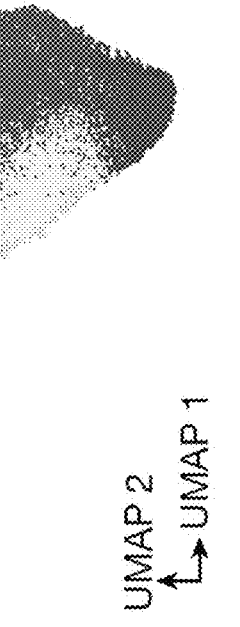
Figure 6H:
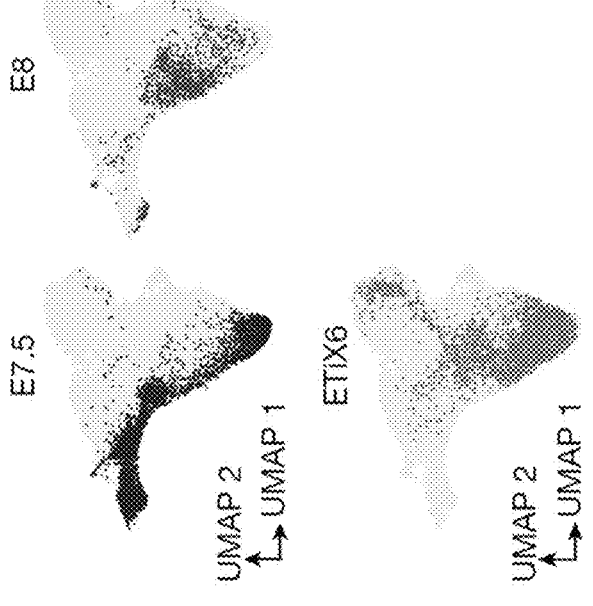
Figure 6I:
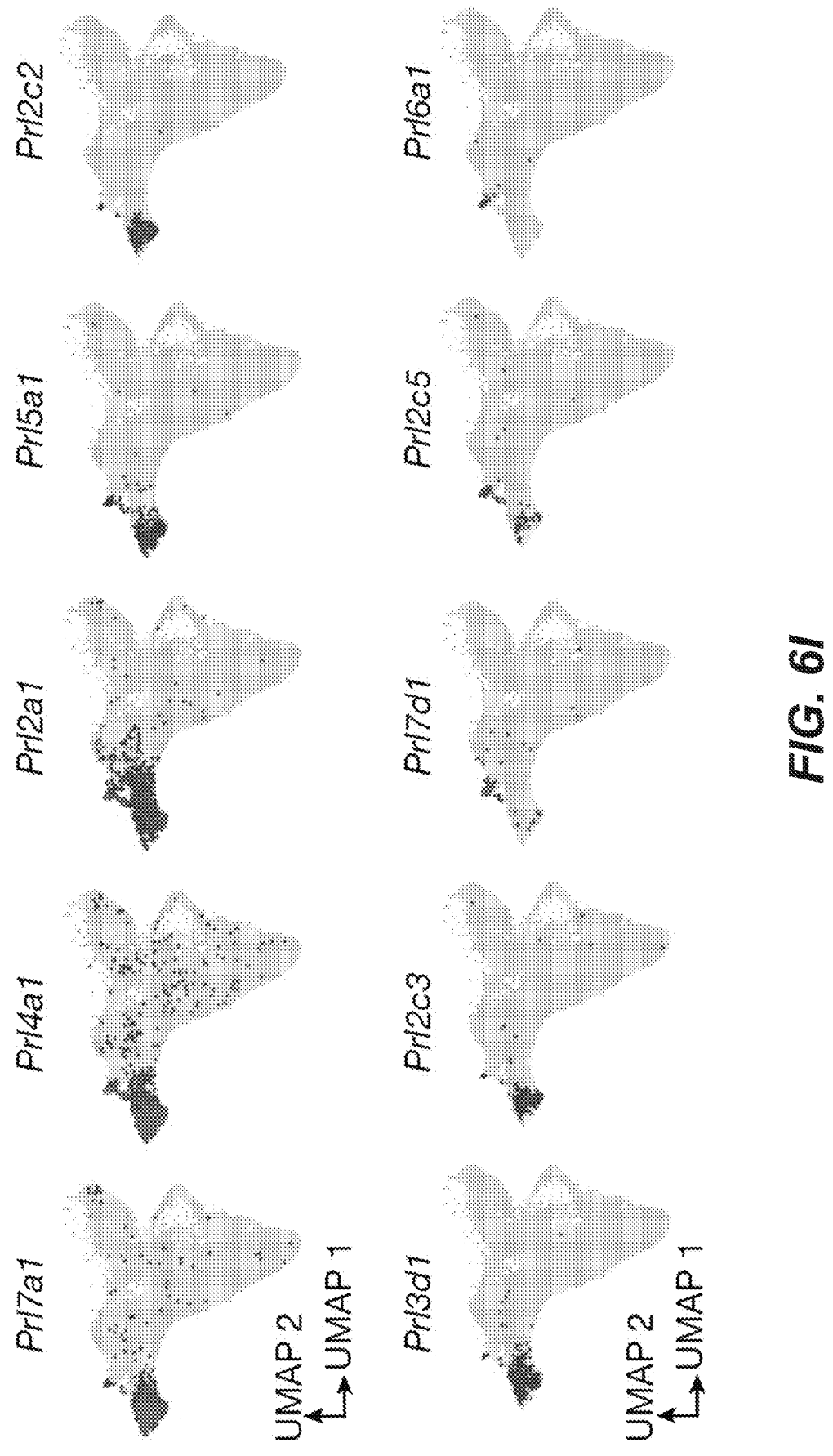
Figure 6J:

The continued presence of trophoblast precursors that split into the ECP and chorionic lineages was observed in ETiX embryoids, similar to that in natural embryos. However, the chorionic lineages in the ETiX embryoids did not perfectly cluster with the chorionic lineages of the natural embryo (FIG. 6G-FIG. 6H, see FIG. 18I-FIG. 18O for specific markers). Moreover, the ECP lineage in ETiX embryoids was not fully developed, as the expression of ECP genes was altered or absent (ETiX-only ECP). Moreover, the lack of prolactin gene expression indicated that trophoblast giant cells and spongiotrophoblast cells were missing (FIG. 6I-FIG. 6J). This analysis showed that whereas development of the chorion lineages had largely taken place, the extraembryonic lineages derived from the ECP were largely absent in ETiX embryoids.

The results in this example demonstrate that the embryonic lineages of ETiX embryoids captured natural development quite closely with deviation observed in the extraembryonic lineages. The deviation might reflect the lack of contact with the maternal environment (natural embryos were recovered when the ECP had already begun developing).

Terminology

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

---

What is claimed is:

1. A method of generating a synthetic embryo in vitro, the method comprising:
   (a) co-culturing at least one mammalian pluripotent stem cell and an extra-embryonic stem cell in a first culture media under a static condition allowing the mammalian pluripotent stem cell and the extra-embryonic stem cell to self-assemble into a post-implantation embryo structure;
   (b) culturing the post-implantation embryo structure in a second culture media under a static condition allowing the post-implantation embryo structure embryo structure to develop into a neurulating embryo structure, wherein the second culture media comprises a basal culture medium, human cord serum, and bicarbonate or HEPES; and
   (c) culturing the neurulating embryo structure for at least one day in the second culture media under a dynamic condition in a culture chamber allowing the neurulating embryo structure to develop into a synthetic embryo of at least early organogenesis stage.

2. The method of claim 1, wherein the at least one mammalian pluripotent stem cell comprises a wild type mammalian embryonic stem cell and a mammalian embryonic stem cells modified to express an inducible GATA transcription factor upon induction.

3. The method of claim 1, wherein the at least one extra-embryonic stem cell comprises a trophoblast stem cell.

4. The method of claim 2, wherein the GATA transcription factor is GATA4.

5. The method of claim 1, wherein the mammalian pluripotent stem cell and the extra-embryonic stem cell are cultured in the first culture media for up to 4 days.

6. The method of claim 1, wherein step (a) is from embryonic day E0-E5.5 of a mouse embryo structure, step (b) is from embryonic day E5.5 to E8.0 of a mouse embryo structure, and/or step (c) is from embryonic day E8.0 to at least E8.5 of a mouse embryo structure.

7. The method of claim 1, wherein the post-implantation embryo structure is a post-implantation pre-gastrulation embryo structure.

8. The method of claim 1, wherein the post-implantation embryo structure resembles an E5.5 natural mouse embryo structure, the neurulating embryo structure resembles an E8.0 natural mouse embryo structure, and/or the generated synthetic embryo resembles an E8.5 natural mouse embryo structure, an E9.0 natural mouse embryo structure or beyond.

9. The method of claim 1, wherein the mammalian pluripotent stem cell and the extra-embryonic stem cell are cultured in a substrate, and wherein the substrate comprises a dish, a U-plate, a flask, a microwell plate, or inverted pyramidal microwells.

10. The method of claim 1, wherein step (a) comprises culturing the mammalian pluripotent stem cell and the extra-embryonic stem cell in a feeder cell (FC) media and culturing the mammalian pluripotent stem cell and the extra-embryonic stem cell in an in vitro culture (IVC) media following culturing the mammalian pluripotent stem cell and the extra-embryonic stem cell in the FC media,
   wherein the FC media and the IVC media comprise a basal culture medium and wherein the basal culture medium comprises Dulbecco's Modified Eagle Media (DMEM), DMEM Nutrient Mixture 12 (DMEM/F12), a non-human serum or serum substitute thereof, a reducing agent, an antibiotic, L-glutamine or an analogue thereof, or any combination thereof.

11. The method of claim 10, wherein the mammalian pluripotent stem cell and the extra-embryonic stem cell are cultured in the FC media for about 2 days and in the IVC media for about 2 days.

12. The method of claim 10, wherein the FC media comprises DMEM, fetal bovine serum, sodium pyruvate, L-glutamine or an analogue thereof, MEM non-essential amino acids, 2-mercaptoethanol, penicillin and/or streptomycin, or any combination thereof.

13. The method of claim 10, wherein the IVC media comprises:

a) insulin, an insulin analogue, or an insulin receptor agonist;

b) estrogen, an estrogen analogue, or an estrogen receptor agonist; and c) progesterone, a progesterone analogue, or a progesterone receptor agonist.

14. The method of claim 10, wherein the IVC media comprises DMEM/F12, fetal bovine serum, L-glutamine or an analogue thereof, ITS-X, β-estradiol, progesterone, N-acetyl-L-cysteine, penicillin and/or streptomycin, or any combination thereof.

15. The method of claim 1, wherein the post-implantation embryo structure is cultured in the second culture media for up to 3 days.

16. The method of claim 1, wherein the second culture media comprises DMEM, rat serum, human cord serum, L-glutamine or an analogue thereof, penicillin and/or streptomycin, HEPES, or any combination thereof.

17. The method of claim 1, wherein step (b) comprising supplying the second culture media with at least 3 mg/ml glucose.

18. The method of claim 1, wherein step (b) comprises culturing the post-implantation embryo structure in a media comprising about 1 mg/ml glucose for two days and culturing the post-implantation embryo structure in a media comprising about 3 mg/ml glucose for one day.

19. The method of claim 1, wherein the second culture media in step (c) comprises at least 30% non-human serum.

20. The method of claim 1, wherein the dynamic condition comprises suspension agitation.

21. The method of claim 1, wherein the culturing the neurulating embryo comprises providing a plurality of gases to the culture chamber at a gas pressure of about 0.5 to 1 psi.

22. The method of claim 1, wherein the culture chamber has an atmosphere comprising an incremental increase of oxygen concentration from about 5% to about 25%.

23. The method of claim 1, wherein the synthetic embryo has established brain regions, a neural tube, a beating heart, a gut tube, developing somites, and/or primordial germ cells.

24. The method of claim 1, wherein the method does not comprise any in vivo step.

25. The method of claim 1, wherein the synthetic embryo is a mouse embryo.

26. A synthetic embryo obtained by the method of claim 1.

27. The method of claim 1, wherein oxygen is supplied to the culture chamber at a constant concentration.

\* \* \* \* \*